US007888492B2

(12) United States Patent
Chenik et al.

(10) Patent No.: US 7,888,492 B2
(45) Date of Patent: Feb. 15, 2011

(54) **POLYPEPTIDES OF *LEISHMANIA MAJOR* AND POLYNUCLEOTIDES ENCODING SAME AND VACCINAL, THERAPEUTICAL AND DIAGNOSTIC APPLICATIONS THEREOF**

(75) Inventors: Mehdi Chenik, La Marsa (TN); Sami Lakhal, Bellevue (TN); Hechmi Louzir, La Marsa (TN); Koussay Dellagi, Tunis (TN)

(73) Assignees: Institut Pasteur, Paris (FR); Institut Pasteur De Tunis, Tunis (TN)

( * ) Notice: Subject to any disclaimer, the term of this patent is extended or adjusted under 35 U.S.C. 154(b) by 0 days.

(21) Appl. No.: 11/887,956

(22) PCT Filed: Apr. 7, 2006

(86) PCT No.: PCT/EP2006/003978

§ 371 (c)(1), (2), (4) Date: Jan. 8, 2009

(87) PCT Pub. No.: WO2006/108720

PCT Pub. Date: Oct. 19, 2006

(65) Prior Publication Data

US 2009/0169554 A1 Jul. 2, 2009

(30) Foreign Application Priority Data

| | | |
|---|---|---|
| Apr. 8, 2005 | (CA) | 2503932 |
| Apr. 5, 2006 | (CA) | 2540736 |

(51) Int. Cl.
*C07H 21/04* (2006.01)

(52) U.S. Cl. ................ 536/23.7; 435/252.3; 435/320.1; 424/269.1

(58) Field of Classification Search ....................... None
See application file for complete search history.

(56) References Cited

FOREIGN PATENT DOCUMENTS

FR 2 826 018 A * 12/2002

OTHER PUBLICATIONS

Chothia et al (The Embo Journal, 1986, 5/4:823-26).*
Greenspan et al (Nature Biotechnology 7: 936-937, 1999).*
Verma et al, (Nature, vol. 389, No. 6648, pp. 239-242, 1997.*
Rochlitz C. F. (Swiss Medicine Weekly, 131:4-9, 2001.*
Vile et al (Gene Therapy, vol. 7, pp. 2-8, 2000).*
Mikayama et al. (Nov.1993. Proc.Natl.Acad.Sci. USA, vol. 90 : 10056-10060).*
Rudinger et al. (Jun. 1976. Peptide Hormones. Biol.Council. pp. 5-7).*

* cited by examiner

*Primary Examiner*—Jennifer E Graser
(74) *Attorney, Agent, or Firm*—Finnegan, Henderson, Farabow, Garrett & Dunner LLP

(57) ABSTRACT

The present invention relates to new proteins of *Leishmania major* and to therapeutical and diagnostic applications thereof. More particularly, the present invention relates to excreted/secreted polypeptides and polynucleotides encoding same, compositions comprising the same, and methods of diagnosis, vaccination and treatment of Leishmaniasis.

10 Claims, 41 Drawing Sheets

Figure 2A (cont'd)

```
M   E   Q   L   R   I   E   H   K   Q   F   S   E   R   M   E   A   K     360
ATG GAG CAG CTG CGC ATC GAG CAC AAG CAG TTT AGC GAG CGC ATG GAG GCC AAG  1080

N   K   E   L   A   E   L   K   G   T   S   T   R   T   V   Q   Q   L     378
AAC AAA GAG CTG GCG GAG CTA AAG GGC ACG TCG ACG CGC ACG GTG CAG CAG CTG  1134

N   H   L   M   G   Q   L   N   E   L   A   S   E   Q   T   R   L   K     396
AAC CAC CTC ATG GGC CAA CTC AAC GAG CTG GCG AGC GAA CAG ACT CGG CTG AAG  1188

R   E   A   K   S   R   S   E   Y   L   S   R   C   G   K   E   I   A     414
CGC GAG GCG AAG AGC CGC TCA GAA TAC TTG TCG CGC TGC GGG AAA GAG ATC GCG  1242

T   A   T   A   E   A   V   Q   A   E   S   K   H   M   T   L   K   A     432
ACG GCG ACG GCG GAG GCT GTG CAG GCG GAG TCG AAG CAC ATG ACA CTC AAG GCA  1296

Q   Q   E   A   V   K   V   P   K   I   E   E   Y   M   A   Q   K   A     450
CAG CAG GAG GCC GTC AAG GTG CCC AAG ATT GAG GAG TAC ATG GCG CAG AAG GCA  1350

E   E   V   E   L   Q   K   A   V   K   N   L   E   R   K   V   Q   I     468
GAG GAG GTG GAG CTC CAG AAG GCA GTG AAG AAC TTG GAG CGC AAG GTG CAG ATC  1404

A   E   G   Q   A   A   V   V   R   Q   Q   S   R   R   L   Q   A   Q     486
GCC GAA GGC CAG GCT GCG GTG GTG CGA CAG CAG TCG CGT CGG TTG CAG GCG CAG  1458

R   A   S   A   I   K   Y   A   N   E   K   H   L   S   R   N   S   T     504
CGC GCA TCT GCC ATA AAA TAC GCA AAT GAG AAG CAC CTG AGT CGC AAT TCC ACC  1512

T   S   R   A   T   A   S   A   G   A   T   A   S   S   R   P   A   A     522
ACG TCG AGG GCC ACA GCC TCA GCA GGA GCG ACA GCA TCT TCG CGG CCT GCA GCT  1566

G   S   A   R   G   L   L   M   Q   R   R   Q   Q   R   E   Q   E   Q     540
GGA AGT GCA CGT GGC CTG TTG ATG CAG CGC CGG CAA CAG CGG GAA CAG GAA CAA  1620

Q   P   P   S   L   P   E   A   S   T   V   E   Q   D   G   S   A   A     558
CAG CCG CCA TCG CTG CCA GAA GCG AGC ACC GTC GAG CAA GAC GGT AGC GCT GCA  1674

A   P   A   A   D   Q   P   A   A   A   A   T   T   A   T   V   S   S     576
GCA CCA GCG GCG GAC CAG CCA GCA GCA GCG GCG ACA ACG GCG ACG GTC TCA TCC  1728

M   *                                                                     578
ATG TAA                                                                  1734
```

CLONE 15 : (SEQ ID No.: 36 / SEQ ID No.: 2) Figure 2B

```
            M   L   F   V   L   Q   C   T   A   H   T   H   T   H   T      15
gttaaacgctt ATG CTG TTT GTC TTG CAG TGC ACT GCA CAC ACA CAC ACG CAC ACA  11648

H   T   C   R   P   Q   H   L   V   A   P   L   A   S   L   C   R   S      33
CAC ACA TGC AGG CCT CAG CAT CTC GTT GCT CCT CTC GCC TCC CTA TGT CGC TCA  11702

L   V   V   V   S   A   S   L   S   P   F   H   R   P   S   L   R   V      51
CTC GTC GTT GTC TCT GCA TCC CTC TCT CCT TTT CAC CGT CCG TCG CTG CGG GTT  11756

G   H   T   V   Q   C   Q   A   R   S   H   V   S   P   L   P   T   H      69
GGG CAC ACG GTG CAA TGC CAG GCA CGC TCG CAC GTG TCC CCT CTC CCC ACA CAC  11810

L   L   F   S   S   L   A   L   A   A   C   A   H   A   R   R   A   C      87
TTG CTC TTC TCT TCT TTG GCC CTC GCC GCA TGC GCA CAC GCA CGG CGC GCG TGT  11864

R   G   A   F   S   Y   L   T   A   T   T   I   T   I   T   V   T   T     105
AGG GGA GCA TTC TCA TAC CTC ACA GCC ACC ACC ATT ACC ATT ACC GTT ACC ACT  11918
```

Figure 2B (cont'd)

```
 T   F   T   T   F   F   L   F   S   V   V   L   H   P   R   F   N   G     123
ACC TTT ACC ACC TTC TTC CTC TTC TCC GTT GTG CTC CAC CCC CGC TTC AAC GGC  11972

 D   R   A   A   K   A   K   T   G   K   K   M   W   R   R   S   C   C     141
GAC AGA GCA GCG AAG GCG AAG ACG GGA AAG AAG ATG TGG CGG CGC AGC TGT TGC  12026

 V   L   A   P   S   I   P   R   S   V   W   D   P   A   H   Y   N   E     159
GTA TTG GCC CCG AGC ATC CCG CGA AGC GTC TGG GAC CCG GCG CAC TAC AAC GAG  12080

 N   W   V   D   S   Y   S   T   S   I   A   D   R   R   H   W   P   A     177
AAC TGG GTG GAC AGC TAC AGC ACC AGC ATT GCC GAC CGC CGA CAC TGG CCA GCG  12134

 K   K   W   S   I   G   L   E   P   R   T   P   R   D   W   L   R   F     195
AAG AAG TGG TCC ATC GGC CTC GAA CCC CGC ACC CCT CGT GAT TGG CTG CGC TTC  12188

 S   Y   R   N   L   A   Y   A   Y   N   G   A   L   R   A   C   A   T     213
TCT TAC CGA AAC CTT GCC TAC GCC TAC AAC GGC GCG CTG CGT GCC TGC GCG ACG  12242

 F   P   E   M   L   V   Y   Y   K   E   M   K   Q   R   G   V   K   V     231
TTT CCG GAG ATG CTC GTC TAC TAC AAG GAG ATG AAG CAG CGC GGG GTC AAG GTG  12296

 D   V   D   T   L   N   A   L   L   S   R   A   A   R   Y   E   H   I     249
GAC GTG GAC ACG CTG AAC GCG CTG CTC TCG CGC GCG GCA CGG TAC GAG CAC ATC  12350

 Q   V   D   D   V   F   L   L   F   D   E   L   T   A   L   G   A   R     267
CAG GTC GAT GAT GTG TTT CTT CTC TTC GAC GAA CTC ACC GCC CTG GGT GCC CGT  12404

 P   D   I   A   S   V   E   T   L   H   T   V   L   E   H   A   A   H     285
CCG GAT ATC GCG TCC GTG GAG ACG CTG CAC ACA GTA CTC GAG CAC GCC GCG CAT  12458

 Q   P   P   E   W   R   E   T   R   R   R   Q   L   V   E   L   Y   Q     303
CAG CCG CCG GAG TGG CGT GAG ACG CGC CGT CGT CAG CTG GTG GAA CTG TAC CAG  12512

 Y   L   A   L   E   E   I   E   R   L   A   P   H   R   V   D   A   L     321
TAC CTT GCG TTG GAG GAG ATC GAG CGC CTC GCC CCG CAT CGC GTC GAT GCA TTG  12566

 L   S   A   Q   I   A   R   L   R   G   N   L   K   Q   L   N   A   S     339
TTG TCT GCG CAG ATC GCG CGT CTG CGA GGA AAC CTC AAG CAA CTC AAC GCG AGC  12620

 L   S   P   S   V   Y   R   R   Y   F   A   A   I   D   L   G   E   T     357
CTC AGC CCA TCC GTG TAC CGG CGC TAC TTT GCG GCT ATC GAC CTC GGT GAG ACA  12674

 L   I   Q   E   V   H   N   F   L   W   E   Y   V   G   A   D   H   A     375
CTG ATC CAG GAA GTC CAC AAC TTT TTG TGG GAG TAC GTC GGC GCC GAT CAC GCT  12728

 A   M   D   V   P   S   L   Q   L   R   I   P   F   V   A   S   V   M     393
GCG ATG GAT GTG CCG TCG CTG CAG CTT CGC ATC CCC TTC GTG GCC TCC GTG ATG  12782

 K   R   P   L   A   T   A   D   P   A   K   V   K   A   T   D   F   E     411
AAG CGG CCG CTG GCG ACG GCA GAC CCT GCC AAG GTG AAG GCG ACC GAC TTT GAG  12836

 D   T   D   V   C   S   V   L   L   A   A   V   E   R   C   V   D   G     429
GAC ACG GAC GTG TGT AGC GTG CTA CTT GCG GCG GTG GAG CGC TGC GTC GAC GGA  12890

 N   F   H   D   R   R   P   V   S   E   R   R   M   Y   L   A   L   L     447
AAC TTC CAC GAC AGG CGG CCT GTG TCT GAG CGG CGC ATG TAT CTC GCC TTG CTG  12944

 T   M   L   T   S   S   G   V   L   Y   T   A   D   L   M   A   Q   M     465
ACC ATG CTC ACC TCC AGT GGC GTC CTG TAT ACA GCC GAT CTC ATG GCG CAG ATG  12998

 M   D   V   V   K   Y   S   R   D   D   R   G   R   D   R   D   A   Q     483
ATG GAT GTT GTG AAG TAC TCG CGC GAC GAT CGC GGA CGT GAC CGC GAT GCG CAG  13052
```

Figure 2B (cont'd)

R L L R Y A L R G S S A A N D A A Y 501
CGG CTG CTG CGG TAC GCC CTG CGC GGG TCC TCG GCA GCC AAC GAC GCC GCT TAC 13106

R E L W R A V A P P V D A R V V G R 519
CGC GAG CTG TGG CGA GCT GTG GCG CCT CCC GTG GAT GCG CGC GTG GTG GGA CGG 13160

Y L A S R D P W S P V H I C Y D R S 537
TAC CTG GCA AGC AGG GAC CCG TGG TCA CCG GTG CAT ATC TGC TAT GAC CGC AGT 13214

F Q F R A F P A L Q Q I T Q S Q C S 555
TTT CAA TTT CGA GCG TTC CCG GCG CTG CAG CAA ATC ACC CAG AGC CAA TGC AGC 13268

S S S S S S S S S S T D A A A V A A 573
AGC AGC AGC AGC AGC AGC AGC AGC AGC AGC ACC GAC GCC GCA GCA GTA GCG GCG 13322

S T A A G A G S S S T A A A A A E P 591
TCG ACG GCT GCC GGG GCA GGA AGC TCC TCT ACT GCG GCG GCG GCC GCC GAG CCG 13376

D E A L E G V S A G P P P G T V A A 609
GAC GAA GCG TTA GAA GGC GTG AGC GCC GGC CCT CCC CCC GGC ACT GTT GCC GCC 13430

K T A E A L Q Q R W D D V R R L I D 627
AAG ACG GCG GAG GCG CTG CAG CAG CGC TGG GAC GAT GTA CGC CGA TTG ATC GAC 13484

I T G V L K P G A G L T S A R T G S 645
ATC ACA GGC GTT CTC AAG CCG GGC GCG GGT CTG ACA AGT GCA AGA ACC GGC TCC 13538

A A P T Q E A A Q Q A M E V F T G A 663
GCC GCG CCA ACA CAG GAG GCG GCG CAG CAG GCG ATG GAG GTC TTC ACC GGC GCG 13592

A A F L R G V A T G C R Y G E L A D 681
GCG GCG TTC CTG CGC GGG GTG GCC ACG GGC TGC CGC TAC GGT GAG TTG GCG GAC 13646

A L A I Q A V G D G Q Q Q H H H A P 699
GCG CTA GCA ATT CAA GCA GTA GGA GAT GGG CAA CAG CAG CAC CAC CAC GCG CCA 13700

R A T P L G G A A A T A G A A R S S 717
CGT GCG ACG CCG CTC GGA GGC GCA GCA GCC ACA GCA GGC GCC GCG CGC AGC AGC 13754

S G N V N T E L Y A G G L D F D V W 735
AGC GGC AAT GTG AAC ACA GAG CTG TAC GCC GGC GGC CTC GAC TTT GAT GTC TGG 13808

Q R L M Q C V Q Q L R Q D M E Q F M 753
CAG CGA CTC ATG CAG TGC GTG CAG CAG CTG CGT CAG GAC ATG GAG CAG TTC ATG 13862

A Q Q Y E A H G L Q V E P E F E C W 771
GCT CAG CAG TAC GAG GCG CAT GGT CTG CAG GTG GAG CCG GAG TTC GAG TGC TGG 13916

E A M L V V L R C I L D F C L V H T 789
GAG GCT ATG CTC GTG GTG CTG CGC TGC ATC TTG GAC TTC TGC CTG GTG CAC ACG 13970

Q Q Y G R T A G G G M A E N L F L E 807
CAG CAG TAC GGC CGT ACG GCT GGT GGT GGC ATG GCG GAG AAT CTG TTC CTG GAG 14024

S A Q L R A Q L V E E S R T R F N G 825
TCG GCG CAG CTG CGC GCG CAG TTG GTG GAG GAA AGT CGC ACC CGC TTC AAT GGC 14078

R M R I L W L Q E V * 836
CGC ATG CGC ATC TTG TGG CTG CAA GAG GTT TAG gctgtcggtctgtaaaaccactgctgc 14138 tgtgctgacaatattgggcccattcacgtgcttgccagggctaccagcagcgcgcgcgcactccaccgccat 14210 tcttcggctccgtttttttgtgtgtctgtccgtctgtgtgtgtgtgtgtttgtgttgataatgtgcgctgaca 14282

Figure 2B (cont'd)

```
atgatgatcttgagtgtgcttaatctctctctctctctgtacgtgtgtgtgtgcgcgcgcacgcgcagggca    14354
catctccgccgcccttgcggaatccttcaccgtgctgcacgacaaaaaaaaaaaaaaaaaaaa              14400
```

CLONE 20.2 $\left(\dfrac{\text{SEQ ID No.:37}}{\text{SEQ ID No.:3}}\right)$  Figure 2C

```
ttccgttgctctgacaccccgcaaaactgctgcgccagtgaagtgcgtcgtgccgcttcatccatcttcgc        936
                                                                M   S   A   N      4
ctttggcacgcgtacttgcattgcttaccaaaggtacacgtacacaggcgagag ATG TCA GCT AAC     1002
 C   A   G   P   A   S   T   P   D   A   K   K   A   R   V   E   A   D       22
TGC GCG GGT CCC GCA TCA ACA CCC GAC GCG AAG AAG GCC CGA GTG GAA GCC GAT      1056
 V   I   T   E   A   D   R   V   P   A   F   P   L   P   P   T   D   A       40
GTG ATC ACG GAG GCG GAC CGC GTG CCG GCG TTT CCT CTC CCG CCC ACC GAT GCC      1110
 A   A   Y   E   R   E   H   V   H   N   V   Y   S   A   I   A   D   H       58
GCT GCC TAC GAG CGT GAA CAC GTG CAC AAC GTG TAC AGC GCG ATT GCC GAC CAC      1164
 F   S   S   T   R   Y   K   A   W   P   Q   V   G   A   F   L   E   G       76
TTC TCT AGC ACA CGG TAC AAG GCG TGG CCA CAG GTC GGC GCC TTC TTG GAG GGC      1218
 L   P   P   F   S   L   V   A   D   V   G   C   G   N   G   K   Y   F       94
CTA CCG CCC TTT TCC CTC GTG GCG GAT GTT GGC TGC GGA AAT GGG AAG TAC TTT      1272
 S   A   A   Q   R   L   A   L   T   A   P   S   H   P   M   T   T   S      112
TCG GCA GCA CAG CGG CTT GCC CTC ACT GCC CCG TCG CAT CCC ATG ACC ACA TCA      1326
 G   A   S   L   E   M   K   S   R   Q   Q   A   E   A   Q   P   S   P      130
GGC GCT TCT CTC GAG ATG AAG TCG AGG CAG CAA GCA GAG GCG CAG CCG TCG CCG      1380
 P   L   V   S   F   A   P   A   H   R   Y   V   L   G   L   D   Y   S      148
CCT CTT GTC TCC TTT GCA CCC GCA CAC CGC TAC GTC TTG GGC CTC GAC TAT AGT      1434
 E   E   L   L   R   S   T   Q   R   Q   L   V   D   P   N   M   H   H      166
GAG GAG CTC CTG CGC TCC ACG CAA CGT CAG CTG GTC GAC CCC AAC ATG CAT CAT      1488
 A   Q   R   R   R   R   L   S   G   K   R   A   K   N   E   A   E   A      184
GCG CAG CGG CGT CGC CGC CTT AGT GGC AAG CGT GCA AAG AAC GAG GCA GAG GCG      1542
 V   A   T   P   V   S   A   E   E   L   P   R   T   D   T   V   R   S      202
GTG GCG ACA CCT GTG TCT GCG GAG GAG CTC CCA CGA ACA GAT ACG GTG CGC AGC      1596
 D   A   L   R   C   P   L   R   S   G   V   F   D   A   A   I   S   I      220
GAC GCT CTA CGG TGC CCG TTG CGT AGC GGC GTC TTC GAC GCC GCC ATC AGT ATA      1650
 A   V   I   H   H   Y   A   S   R   E   R   R   R   L   A   V   R   E      238
GCG GTG ATT CAC CAC TAC GCG AGT CGC GAG CGG CGG AGA CTG GCG GTG CGC GAG      1704
 L   L   R   L   A   R   P   H   G   G   R   V   L   I   Y   V   W   A      256
CTC CTC CGC CTC GCT CGG CCG CAT GGT GGG CGT GTA CTT ATC TAC GTG TGG GCA      1758
 R   E   Q   R   G   H   T   K   R   L   V   D   P   E   T   G   D   G      274
CGT GAG CAG CGA GGC CAC ACA AAG CGT CTG GTC GAC CCA GAA ACC GGC GAC GGT      1812
 L   V   R   W   E   R   N   Q   K   Y   D   G   A   Q   Q   V   F   R      292
CTC GTG CGG TGG GAG CGA AAT CAG AAG TAC GAT GGG GCA CAG CAG GTG TTC CGC      1866
```

Figure 2C (cont'd)

```
 R   Y   Y   H   F   F   A   E   G   E   L   E   Q   L   C   K   D   A     310
CGC TAC TAT CAC TTT TTT GCG GAG GGA GAG CTG GAG CAG CTG TGC AAG GAC GCG   1920

 A   S   D   D   G   T   G   S   I   P   V   A   I   R   K   S   Y   Y     328
GCC AGC GAT GAT GGG ACA GGG TCG ATT CCG GTC GCA ATC AGG AAA TCT TAC TAC   1974

 D   K   E   N   W   C   V   M   L   E   R   C   *                         341
GAC AAG GAG AAT TGG TGT GTG ATG CTG GAG CGC TGT TGA  cgtcgaagtgaagggtgtg  2032

gcgactcgaacgccgcctgagatggacaacattgtgcctgtgggtttttgcatgcgcctcttagccttattc  2104

gtctacacccatctgcttggccctttcatcttgagtaataagtaggtccacctcgtcttcacaggcgcattg  2176

taaagttgcgcgcgggcattatcggggaagccgacgtgtcatcgatgtcgaggcttgcgttgacatcacccc  2248

cttccttctttgccgcgccttcgcagacggtgacggggaatggccaccgctacgagagtgaaagaaggcagc  2320

agcagagccgagaaaaaaaaaaaaaaaaaa                                            2349
```

CLONE 22 (SEQ ID No.:38 / SEQ ID No.:4) Figure 2D

```
cgagcggcgcactgggggcgggcggtggcggtgtccattccaccgccacaagcagcagcggcggtaacagcg   360

                              M   N   F   A   N   N   A   N   G   G        10
gcttcgacagtgtgcgctacaacaacttt ATG AAC TTC GCG AAC AAC GCT AAC GGG GGC     419

 C   F   G   S   L   S   A   A   A   S   A   S   A   A   A   A   A   P      28
TGC TTT GGC AGC CTC TCC GCC GCC GCG TCT GCC TCG GCG GCA GCA GCG GCG CCC    473

 T   A   V   S   Q   G   S   R   L   A   S   S   G   Q   S   N   S   H      46
ACG GCG GTG AGC CAA GGC AGC CGG CTC GCC AGC TCT GGC CAA AGC AAT AGC CAC    527

 S   G   S   A   T   L   D   W   S   A   S   P   P   S   S   G   Q   C      64
AGC GGC AGC GCA ACG CTC GAC TGG TCT GCG TCG CCG CCC TCG TCG GGT CAG TGC    581

 P   S   Q   Q   K   H   A   V   S   G   P   A   P   F   S   Y   Y   Y      82
CCT AGT CAG CAG AAG CAC GCC GTC TCT GGC CCT GCG CCG TTC TCA TAC TAC TAC    635

 Q   G   T   D   V   A   R   P   S   A   Q   V   R   H   H   T   A   A     100
CAG GGC ACC GAC GTC GCT CGC CCG TCG GCA CAA GTG CGA CAC CAC ACC GCA GCC    689

 S   A   S   A   H   F   D   I   T   N   R   V   A   A   S   V   A   A     118
TCC GCT TCC GCT CAC TTC GAC ATC ACG AAC CGC GTA GCA GCG TCC GTG GCG GCG    743

 V   S   T   S   A   D   A   G   A   E   S   H   Q   H   A   A   S   T     136
GTG TCG ACC TCG GCG GAT GCT GGT GCG GAG TCG CAC CAG CAC GCT GCA TCA ACA    797

 Q   Q   Q   Q   L   P   P   V   A   G   T   T   V   Q   L   T   S   P     154
CAG CAA CAG CAA CTG CCG CCT GTG GCT GGC ACG ACC GTG CAG CTC ACG TCA CCG    851

 S   S   S   T   T   R   G   S   G   I   N   V   N   A   Q   P   Y   Y     172
TCG TCG TCC ACC ACC CGT GGA AGC GGC ATC AAC GTC AAC GCC CAG CCG TAC TAC    905

 Y   V   S   S   R   M   R   K   Q   Q   Q   Q   Q   A   A   A   A   S     190
TAC GTT AGC AGC CGT ATG CGC AAG CAG CAG CAG CAG CAA GCG GCA GCA GCG TCG    959

 P   A   S   V   D   P   S   V   T   R   P   G   S   D   L   A   V   A     208
CCG GCT TCC GTA GAC CCA TCA GTT ACC CGC CCG GGT AGC GAC TTG GCA GTC GCT   1013
```

Figure 2D (cont'd)

```
 G   T   T   S   T   R   T   P   A   T   A   V   G   T   D   D   T   V     226
GGT ACG ACG TCG ACG AGG ACG CCA GCG ACT GCG GTA GGC ACT GAT GAC ACT GTG   1067

 A   A   V   Q   R   A   P   L   S   T   L   E   G   G   S   D   A   R     244
GCT GCC GTG CAG CGT GCG CCG TTG TCC ACC CTC GAA GGC GGC AGC GAT GCG CGC   1121

 S   P   G   S   S   F   T   S   P   A   C   V   N   S   L   A   R   F     262
TCA CCA GGC TCG TCG TTC ACG AGC CCG GCG TGT GTC AAC TCG CTG GCG CGC TTC   1175

 S   T   Y   A   R   T   T   T   D   S   V   A   G   H   A   S   Q   P     280
AGC ACG TAC GCA AGG ACG ACG ACG GAC AGT GTG GCA GGT CAT GCG TCG CAG CCG   1229

 S   G   F   R   S   G   I   E   T   V   V   S   A   M   K   M   S   G     298
AGC GGC TTC CGC AGC GGC ATC GAG ACT GTC GTG TCG GCG ATG AAG ATG TCT GGC   1283

 I   Y   G   G   S   G   G   G   G   N   N   G   N   S   T   S   R   S     316
ATT TAC GGC GGC AGC GGC GGC GGC GGC AAC AAC GGT AAC AGT ACG AGC AGG AGT   1337

 S   A   H   P   H   T   F   P   S   R   P   I   A   R   S   G   A   D     334
AGC GCG CAC CCC CAC ACC TTC CCA TCG CGG CCC ATC GCC AGG TCA GGT GCG GAC   1391

 G   G   S   G   G   E   Q   A   T   L   A   R   V   P   R   R   S   P     352
GGC GGC AGC GGC GGC GAG CAG GCG ACT TTG GCG CGC GTG CCA CGG CGG TCT CCG   1445

 H   A   D   H   Q   A   P   V   H   R   R   S   T   F   A   S   Q   H     370
CAC GCG GAT CAC CAG GCG CCG GTG CAC CGC CGC TCC ACC TTC GCG TCG CAG CAC   1499

 S   L   G   K   K   R   S   K   P   D   S   Y   K   D   Y                 385
TCA CTC GGC AAG AAG CGC TCA AAG CCT GAC AGC TAC AAG GAC TAC  tgaggtgcagt  1555

cccccgtcgcatgcgcacagagcgggttggacgatggccgcgaggcgaagagacatcgtgatcaaggcatgt  1627

gcgaaccctgtacgttggatgtgcgcgcgtgggttttgcgaagtttgcatgcccggctatcagcgcggccgt  1699

cccacatcaagcagtgcgcatctctgtctttcttcttcgttaccttcgccttcgggggcacaaggggaatca  1771

cctgcacacgcatgctcacgcacatgcagagattccagcaactaagctaacatctttctaagcaccctatct  1843

atctatctatctatatatatatatatatatatatatatgtatctatacggttcgggtatattctttttttcatgggacgatagagc
caccaaaaaaaaaaaaaaaaaaa
```

Figure 2E (cont'd)

gggccgtaggatcaggcgattcgggcgtttgccgcagacattccagcgcattgacgtatgtgtgagaaacac 5122 gtccactttcgaagtccatccggaaaggcctgctgcgctgtataacggcggcaaggggggggatcgcacgt 5194 atggaccgtttcttgcatacccgccacacattatcgccctcccctcctctatattccatttagagcgtat 5266 agcagcggataagccgtcttgtggctttatcagctactgtgactcgcgtagcgcagggggtgccgaacgcga 5338 aggtgcgacagggcccacttgagtgacggcaaagaaagggaggagggggctgaaaggatgc

CLONE 23 (SEQ ID No.: 40 / SEQ ID No.: 6) Figure 2F ggcgccggagcgccttccttgtggagtgctgaattagttcacggtaacgcggcagcgtgctgggccgaggat 1152

M T A T G P L P R D V R D 13
ccagcggacaacgcttgg ATG ACA GCT ACT GGG CCT TTA CCA CGT GAC GTC AGA GAC 1209

V A P L H R W Q T E G T S S H S E A 31
GTG GCG CCA TTG CAC CGG TGG CAA ACG GAG GGT ACC AGC TCG CAC TCT GAG GCT 1263

G G D V P A T C L F Q H P V V A L L 49
GGC GGT GAC GTA CCC GCG ACC TGC CTT TTT CAG CAT CCC GTC GTT GCT CTC CTT 1317

P S F P P L P F F L V A H R T L H K 67
CCT TCA TTT CCA CCT TTG CCT TTT TTT CTC GTG GCT CAT CGC ACA TTG CAC AAA 1371

C A L G C A P V A F T W C T V Q F T 85
TGT GCT CTG GGT TGT GCT CCT GTT GCG TTC ACT TGG TGC ACA GTG CAG TTT ACT 1425

W K R S P Q L R C F G S A N L A D I 103
TGG AAA CGC TCC CCG CAA CTG CGC TGC TTC GGA TCT GCG AAC CTT GCA GAC ATA 1479

S F G R G C D Y S A N M L R C V S R 121
TCC TTC GGT CGC GGC TGT GAT TAC TCC GCG AAT ATG CTG CGT TGT GTG TCG AGA 1533

R L W Y Q F K D L K S K V I L E K L 139
AGG CTG TGG TAT CAG TTC AAG GAC CTC AAA AGT AAG GTC ATC CTC GAA AAG CTT 1587

R N S K L Q E G V H P S D M D M E D 157
CGA AAC TCG AAA CTG CAG GAA GGT GTT CAC CCT TCT GAT ATG GAT ATG GAG GAT 1641

L A R E S G I A P P S S V N V Q D F 175
CTG GCA AGG GAA AGC GGC ATT GCG CCG CCG AGT AGT GTC AAT GTG CAG GAC TTT 1695

V H E K E A V L E M L Q E Q R L R R 193
GTG CAC GAG AAA GAG GCC GTG CTG GAG ATG CTG CAG GAA CAG CGA CTG CGC CGC 1749

I A R R E A F L E W Q A G Q R E K G 211
ATA GCC CGG CGC GAA GCG TTT CTG GAG TGG CAA GCT GGG CAG CGC GAA AAA GGC 1803

A A H R L V R Q S R K A E K Y K R R 229
GCC GCT CAC CGT CTT GTT CGC CAA TCG CGC AAA GCG GAA AAG TAC AAG CGC CGC 1857

H Y H A T S G R M L P I S L S P G Q 247
CAC TAC CAT GCC ACG AGT GGG CGA ATG CTG CCG ATA TCT CTT TCT CCG GGT CAA 1911

A P P D H R A P M S M P K A C V S S 265
GCA CCG CCA GAT CAC CGC GCA CCA ATG TCA ATG CCA AAG GCG TGC GTA TCG TCT 1965

Figure 2F (cont'd)

```
      T   E   F   L   R   G   G   P   A   E   N   R   H   A   I   H   L   S       283
     ACC GAG TTT CTA CGA GGA GGT CCG GCA GAA AAT CGG CAC GCC ATA CAC CTC TCT      2019

      L   E   K   K   *                                                           288
     TTG GAA AAG AAG TGA  gtgccccctgcagtgcgtgtgccgctctcttctgcactatgtccttgc        2085

     acaaaatgtgctgttttaaacgaagaaaaggagcgaaggtggaagggctccttctcatatctgctcgccgct     2157

     tttttgtgtgacggcagtgagagccaccagtgcttgccgcacgacaaaaaaaaaaaaaaaaaaaaa
```

CLONE 27 $\left(\dfrac{\text{SEQ ID No.: 41}}{\text{SEQ ID No.: 7}}\right)$    Figure 2G

```
                           M   V   Y   T   R   W   K   C   D   R   I   P          12
     ggtgctaacgcaacgagtcccaag ATG GTC TAC ACC CGC TGG AAG TGC GAT CGC ATC CCT    1932

      V   L   Q   L   K   L   F   T   Q   E   Y   N   M   M   A   V   V   G       30
     GTG CTG CAG CTG AAG CTG TTC ACG CAG GAG TAC AAC ATG ATG GCA GTC GTT GGT     1986

      L   L   S   M   V   F   L   F   K   H   A   S   Y   C   S   E   E   T       48
     CTG CTA TCC ATG GTG TTT CTG TTC AAG CAC GCA AGC TAC TGC TCT GAG GAG ACG     2040

      E   R   K   N   G   W   W   A   G   Y   P   Y   W   R   D   P   I   A       66
     GAG CGG AAG AAC GGC TGG TGG GCA GGC TAC CCG TAT TGG CGT GAC CCC ATT GCG     2094

      R   R   N   E   I   R   Y   K   Q   L   I   N   S   N   D   V   D   I       84
     CGT CGC AAC GAG ATT CGG TAC AAG CAA CTG ATC AAC AGC AAC GAT GTG GAC ATT     2148

      T   D   P   K   W   T   G   C   S   K   E   Q   L   E   R   L   R   A      102
     ACC GAC CCG AAG TGG ACT GGC TGT TCC AAG GAG CAG CTG GAG CGC CTG CGC GCG     2202

      I   V   *                                                                  105
     ATT GTT TGA  ggagcgcgaatgtgtggaaccgatacgtgactgcaacgggtcacctgtttgacagctgt    2270

     tctgccgtcgctttcatttttgtttctgccagccgctgctgtaagcttggtagtaacaaacagtctcatgt     2342

     agggcgggtcgcgcctacctcgttttgttctcgtccctcttcatttaggagctaagtaggaaatagtttaca    2414

     cctgtcgtgcgtagtgcaaaaagccagaaaaaaaaaaaaaaaaaaaaaaaaaaaaaaaaa  2481
```

CLONE 31 $\left(\dfrac{\text{SEQ ID No.: 42}}{\text{SEQ ID No.: 8}}\right)$    Figure 2H

```
     gtagactgccgagcgacgtgctacaacggagaaaaaagagcacacacagcaaatatacgcccacttcttttc   6120

                                              M   L   A   R   Y                    5
     tttctccgtctcatactttcttgtggctcgccctcttcgattgtaaccg ATG CTC GCT AGA TAC      6184

      L   D   P   S   V   H   P   L   R   V   G   Q   V   V   A   Y   D   Y       23
     CTC GAT CCT TCA GTT CAC CCG CTC AGA GTT GGG CAG GTG GTC GCC TAC GAC TAC    6238
```

Figure 2H (cont'd)

L H A A K T W Q W T L G T V R E I K 41
CTT CAC GCT GCG AAG ACG TGG CAG TGG ACC CTG GGT ACG GTG CGT GAG ATC AAG 6292

D Y T A V V Q Q W G L H T G D I D T 59
GAC TAC ACG GCC GTC GTG CAG CAG TGG GGC CTT CAC ACC GGA GAC ATT GAC ACG 6346

L R S I L L K E V D T E N G R M K N 77
CTG CGC TCC ATT CTC CTC AAA GAG GTC GAC ACG GAA AAT GGA CGC ATG AAG AAC 6400

Y H D M L A I A R E K L A S I R R S 95
TAT CAT GAT ATG CTG GCT ATC GCA CGA GAG AAG CTC GCA TCC ATC CGC CGT AGC 6454

N E D R V S H V R G H F D K A R E K 113
AAT GAG GAT CGT GTT TCA CAC GTT CGA GGC CAC TTT GAC AAG GCT CGT GAA AAA 6508

V E L I D E V D L R K V T A Q A A P 131
GTA GAG CTC ATT GAC GAG GTC GAT TTG CGC AAG GTC ACG GCC CAG GCC GCC CCA 6562

S P V A V A V L K A V W A V A K C D 149
TCC CCG GTT GCT GTA GCA GTG CTG AAG GCG GTG TGG GCC GTG GCC AAG TGC GAT 6616

P T A V E F Y E W A D V Q L E Y R K 167
CCC ACG GCG GTT GAG TTC TAC GAG TGG GCA GAT GTG CAA CTG GAG TAC CGG AAG 6670

P A A L D E I A K T D V L A K L Y P 185
CCA GCC GCT CTC GAT GAG ATC GCC AAG ACA GAC GTT CTC GCG AAG CTC TAT CCT 6724

S A E S L Q Q S L E Q D P K L N Y K 203
TCC GCG GAA AGC CTC CAG CAG TCC CTG GAG CAG GAC CCC AAG CTG AAC TAC AAG 6778

A A A R D S P V V A S L H A W V I T 221
GCG GCG GCG CGC GAC TCG CCG GTG GTG GCC AGC CTC CAT GCG TGG GTC ATC ACA 6832

A L A Y Q Q A Y N L L A H D K R I Q 239
GCT CTT GCC TAC CAG CAG GCG TAC AAC CTC CTG GCG CAC GAC AAG CGC ATC CAG 6886

E Q N D A I A A A I A G M K A C R A 257
GAG CAG AAC GAC GCC ATC GCA GCC GCC ATT GCT GGC ATG AAG GCC TGT CGC GCC 6940

K I A K L K D E L S S K D T A A L P 275
AAG ATC GCC AAG CTC AAG GAC GAG CTG TCT TCA AAG GAC ACG GCT GCA CTC CCT 6994

G Q V T S F T R T S V L V T I P L S 293
GGT CAG GTC ACC TCC TTC ACC AGG ACG TCA GTC CTC GTG ACC ATT CCG CTG TCT 7048

A V I S P V N V D T D V K R C V L T 311
GCC GTC ATC TCT CCC GTC AAT GTG GAC ACC GAT GTG AAG CGA TGC GTG CTG ACT 7102

K D E V E Q I P I D A K I T R Y A Q 329
AAG GAT GAG GTC GAG CAG ATC CCT ATC GAT GCC AAG ATA ACA CGA TAT GCC CAA 7156

K Q K L A I T G S H L L D Q Y A A A 347
AAA CAA AAA CTG GCT ATC ACC GGA TCT CAC CTT CTC GAT CAA TAC GCT GCC GCC 7210

T T T H I Y V T E L E D R L F F F Q 365
ACC ACT ACA CAC ATC TAC GTC ACT GAA CTG GAA GAC CGC CTC TTC TTC TTT CAG 7264

H Y M A S A L R D A Q T A A V D A H 383
CAT TAC ATG GCT TCC GCT CTA CGT GAC GCA CAG ACA GCT GCA GTA GAC GCA CAC 7318

Figure 2H (cont'd)

```
 Q   R   L   A   V   S   L   H   E   L   E   A   F   R   Q   K   R   H    401
CAG CGC CTC GCC GTC AGT CTC CAT GAG CTA GAG GCG TTC CGC CAG AAG CGC CAC  7372

 D   A   K   K   A   R   A   A   E   P   E   L   A   D   A   D   G   V    419
GAC GCC AAG AAG GCG CGC GCC GCG GAG CCG GAA CTT GCG GAT GCC GAC GGC GTG  7426

 E   P   S   S   G   P   T   S   S   R   S   P   T   G   R   A   A   P    437
GAG CCA AGC AGC GGG CCC ACC AGC AGT CGC TCT CCC ACT GGC CGC GCA GCC CCG  7480

 R   G   Q   S   A   A   P   R   G   T   A   S   Q   Q   H   K   L   L    455
CGT GGA CAG AGC GCT GCA CCG CGC GGC ACT GCA TCG CAG CAG CAC AAG CTC CTC  7534

 G   P   A   Y   Q   S   I   D   P   A   T   I   A   N   E   P   L   Y    473
GGC CCC GCC TAC CAG TCC ATC GAC CCG GCT ACC ATC GCC AAC GAG CCG CTC TAC  7588

 A   V   T   I   E   E   Y   K   A   K   D   A   A   G   E   R   A   M    491
GCC GTC ACC ATC GAA GAG TAC AAG GCC AAA GAC GCC GCA GGG GAG CGA GCC ATG  7642

 D   E   A   E   R   M   A   D   E   V   Q   R   L   A   V   E   L   E    509
GAC GAG GCG GAG CGC ATG GCG GAC GAA GTG CAG CGG CTC GCC GTG GAA CTG GAG  7696

 D   A   K   A   A   A   D   K   L   A   E   E   L   A   A   K   D   E    527
GAC GCC AAG GCG GCG GCC GAC AAG CTG GCG GAG GAG CTC GCG GCC AAG GAC GAG  7750

 E   L   A   A   H   R   Q   K   R   H   D   A   R   Q   A   R   A   S    545
GAG CTC GCC GCG CAC CGC CAG AAG CGC CAC GAT GCC CGG CAG GCG CGC GCA AGC  7804

 D   P   A   L   A   A   A   D   A   V   A   P   R   S   G   K   G   A    563
GAC CCT GCC TTG GCC GCC GCC GAC GCT GTC GCG CCG CGC AGC GGG AAG GGA GCA  7858

 A   S   P   H   V   G   A   V   Q   R   Q   A   V   D   P   A   T   V    581
GCA TCG CCG CAC GTC GGC GCA GTG CAG CGC CAG GCC GTC GAC CCT GCC ACC GTG  7912

 P   V   A   P   A   V   I   A   E   E   P   L   Y   V   A   T   A   E    599
CCC GTG GCC CCC GCC GTT ATC GCG GAG GAG CCG CTC TAC GTG GCC ACC GCG GAG  7966

 E   L   Q   H   V   R   D   F   A   D   Q   L   A   E   E   L   E   A    617
GAG CTG CAG CAT GTG CGC GAC TTC GCA GAT CAG CTC GCT GAG GAG CTA GAG GCG  8020

 F   R   Q   K   R   H   D   A   K   K   A   R   A   A   E   P   E   L    635
TTC CGC CAG AAG CGC CAC GAC GCC AAG AAG GCG CGC GCC GCG GAG CCG GAA CTT  8074

 A   D   A   D   G   V   E   P   S   S   G   P   T   S   S   R   S   P    653
GCG GAT GCC GAC GGC GTG GAG CCA AGC AGC GGG CCC ACC AGC AGT CGC TCT CCC  8128

 T   G   R   A   A   P   R   G   Q   S   A   A   P   R   G   T   A   S    671
ACT GGC CGC GCA GCC CCG CGT GGA CAG AGC GCT GCA CCG CGC GGC ACT GCA TCG  8182

 Q   Q   H   K   L   L   G   P   A   Y   Q   S   I   D   P   A   T   I    689
CAG CAG CAC AAG CTC CTC GGC CCC GCC TAC CAG TCC ATC GAC CCG GCT ACC ATC  8236

 A   N   E   P   L   Y   A   V   T   I   E   E   Y   K   A   K   D   A    707
GCC AAC GAG CCG CTC TAC GCC GTC ACC ATC GAA GAG TAC AAG GCC AAA GAC GCC  8290

 A   G   E   R   A   M   D   E   A   E   R   M   A   D   E   V   Q   R    725
GCA GGG GAG CGA GCC ATG GAC GAG GCG GAG CGC ATG GCG GAC GAA GTG CAG CGG  8344

 L   A   V   E   L   E   D   A   K   A   A   A   D   K   L   A   E   E    743
CTC GCC GTG GAA CTG GAG GAC GCC AAG GCG GCG GCC GAC AAG CTG GCG GAG GAG  8398

 L   A   A   K   D   E   E   L   A   A   H   R   Q   K   R   H   D   A    761
CTC GCG GCC AAG GAC GAG GAG CTC GCC GCG CAC CGC CAG AAG CGC CAC GAT GCC  8452
```

Figure 2H (cont'd)

R Q A R A S D P A L A A A D A V A P 779
CGG CAG GCG CGC GCA AGC GAC CCT GCC TTG GCC GCC GCC GAC GCT GTC GCG CCG 8506

R S G K G A A S P H V G A V Q R Q A 797
CGC AGC GGG AAG GGA GCA GCA TCG CCG CAC GTC GGC GCA GTG CAG CGC CAG GCC 8560

V D P A T V P V A P A V I A E E P L 815
GTC GAC CCT GCC ACC GTG CCC GTG GCC CCC GCC GTT ATC GCG GAG GAG CCG CTC 8614

Y V A T A E E L Q H V R D F A D Q L 833
TAC GTG GCC ACC GCG GAG GAG CTG CAG CAT GTG CGC GAC TTC GCA GAT CAG CTC 8668

A E E L E A F R Q K R H D A K K A R 851
GCT GAG GAG CTA GAG GCG TTC CGC CAG AAG CGC CAC GAC GCC AAG AAG GCG CGC 8722

A A E P E L A D A D G V E P S S G P 869
GCC GCG GAG CCG GAA CTT GCG GAT GCC GAC GGC GTG GAG CCA AGC AGC GGG CCC 8776

T S S R S P T G R A A P R G Q S A A 887
ACC AGC AGT CGC TCT CCC ACT GGC CGC GCA GCC CCG CGT GGA CAG AGC GCT GCA 8830

P R G T A S Q Q H K L L G P A Y Q S 905
CCG CGC GGC ACT GCA TCG CAG CAG CAC AAG CTC CTC GGC CCC GCC TAC CAG TCC 8884

I D P A T I A N E P L Y A V T I E E 923
ATC GAC CCG GCT ACC ATC GCC AAC GAG CCG CTC TAC GCC GTC ACC ATC GAA GAG 8938

Y K A K D A A G E R A M D E A E R M 941
TAC AAG GCC AAA GAC GCC GCA GGG GAG CGA GCC ATG GAC GAG GCG GAG CGC ATG 8992

A D E V Q R L A V E L E D A K A A A 959
GCG GAC GAA GTG CAG CGG CTC GCC GTG GAA CTG GAG GAC GCC AAG GCG GCG GCC 9046

D K L A E E L A A K D E E L A A H R 977
GAC AAG CTG GCG GAG GAG CTC GCG GCC AAG GAC GAG GAG CTC GCC GCG CAC CGC 9100

Q K R H D A R Q A R A S D P A L A A 995
CAG AAG CGC CAC GAT GCC CGG CAG GCG CGC GCA AGC GAC CCT GCC TTG GCC GCC 9154

A D A V A P R S G K G A A S P H V G 1013
GCC GAC GCT GTC GCG CCG CGC AGC GGG AAG GGA GCA GCA TCG CCG CAC GTC GGC 9208

A V Q R Q A V D P A T V P V A P A V 1031
GCA GTG CAG CGC CAG GCC GTC GAC CCT GCC ACC GTG CCC GTG GCC CCC GCC GTT 9262

I A E E P L Y V A T A E E L Q H V R 1049
ATC GCG GAG GAG CCG CTC TAC GTG GCC ACC GCG GAG GAG CTG CAG CAT GTG CGC 9316

D F A D Q A A H D A T A R E A E V A 1067
GAC TTC GCA GAT CAG GCT GCC CAT GAT GCA ACA GCG AGG GAA GCG GAA GTT GCT 9370

G T V E N L R N E L D D V R E M N A 1085
GGT ACC GTG GAG AAT CTG AGA AAT GAG TTG GAT GAT GTG CGC GAG ATG AAT GCT 9424

K L E D E V F A L K E Q L S D A E D 1103
AAG TTA GAA GAC GAA GTT TTT GCT TTG AAA GAG CAA CTG TCG GAC GCT GAG GAT 9478

A Y K K L A G A L V V A E D E R Q E 1121
GCA TAC AAG AAG TTA GCA GGC GCT CTG GTA GTC GCC GAA GAC GAG CGT CAA GAG 9532

L C D D L E A A L D E L E Q K K D E 1139
CTG TGT GAC GAT CTG GAG GCC GCC TTA GAC GAG CTT GAG CAG AAG AAA GAT GAA 9586

Figure 2H (cont'd)

```
 Y   D   E   L   L   G   N   L   E   E   V   Q   G   L   L   E   A   A   1157
TAC GAT GAA CTG CTC GGC AAC TTG GAG GAG GTT CAG GGT TTG CTG GAA GCT GCT  9640

 D   V   A   G   R   T   A   V   E   A   L   E   Q   R   N   R   D   M   1175
GAC GTT GCT GGG CGA ACC GCT GTG GAG GCG TTG GAG CAG CGA AAC CGA GAC ATG  9694

 A   D   L   Q   G   E   L   A   N   A   L   D   A   S   K   E   N   E   1193
GCG GAC CTG CAG GGC GAG TTG GCC AAT GCG CTG GAC GCC AGC AAA GAA AAT GAG  9748

 N   L   R   A   L   L   D   A   K   E   R   E   I   D   R   L   K   E   1211
AAT CTT CGT GCA CTG CTG GAT GCC AAG GAG AGA GAG ATC GAT AGA CTG AAA GAG  9802

 Y   N   S   F   W   T   D   T   V   G   T   G   K   Q   K   V   T   H   1229
TAC AAC AGT TTC TGG ACT GAC ACT GTC GGC ACC GGA AAG CAG AAG GTA ACA CAC  9856

 R   L   T   K   I   F   D   G   D   W   T   R   L   M   R   H   R   P   1247
AGG CTC ACA AAG ATC TTC GAT GGC GAC TGG ACT CGT TTG ATG CGT CAT AGA CCT  9910

 E   A   L   K   A   A   F   V   I   D   S   S   N   A   C   H   V   P   1265
GAG GCA CTG AAG GCA GCG TTC GTG ATT GAT TCC AGC AAC GCA TGC CAC GTG CCC  9964

 G   D   Q   I   V   Q   V   D   F   D   H   D   *                       1278
GGA GAC CAG ATT GTG CAA GTA GAT TTC GAT CAC GAT TAG  taagaacggtgtcgatggg 10022

agtttttctgctttgtaagagcccgtcatcagttttctctgcttgttttggttcgcattttcgctgagcaag 10094

acgcgctggtttgcgcctcgatcatgttggtactggtcccttgaagtgggtgagagcgcctcatcggttatt 10166

tggtttgtggagtgagtgtgctggcgttctcataccgcagagcgtgtattctgccacgtgcttatttttttc 10238

attgtattatgattcctcagtcatctgttcatggtgaacgcgcccgttgtcaccatttttttccttgcgctat 10310

ccctctttgattccatagtgatccactcttgaagtaagcgttggctcgttttgcaggacatttgtgagcttt 10382

tctcacactatcgtcttgcctgatacgtggagttacttcagtgtagtttgctgccgtgtttgtgcttttgtt 10454

cgtagactgtcttgacgatcatagttccttcatcctgttgtttgcaggtgtgtcttgtatgtctgaggacga 10526

cgcctggctcaccggttgctcagttcatcgtctgtctgtgtacgtgttcaatagtgtttctttctctcggacca

CTGAGGTGTAGACTCTCGCTTACACGCCTCAAGAAAAAAAAAAAAAAAAA 10598
```

CLONE 37 $\left(\frac{\text{SEQ ID No.: 43}}{\text{SEQ ID No.: 9}}\right)$ Figure 2I

```
                                      M   V   T   H   A   L   H   E        8
cagcattctcaccggctccgtcttggagacagaggtg ATG GTG ACG CAC GCG TTG CAT GAG      61

 S   L   F   P   R   D   A   A   S   D   A   A   G   T   A   A   T   S     26
TCA CTC TTT CCC CGT GAC GCG GCG TCC GAT GCC GCT GGC ACA GCT GCC ACC TCT   115

 L   Q   V   S   L   P   P   I   T   V   A   M   R   R   G   A   V   Q     44
CTG CAG GTG TCT CTG CCT CCC ATC ACG GTG GCA ATG CGG CGT GGC GCT GTG CAG   169

 M   R   Y   G   L   T   Y   L   R   T   F   P   A   A   L   R   D   S     62
ATG CGC TAC GGG CTC ACC TAC CTA CGC ACG TTC CCG GCG GCA TTG CGA GAC TCT   223
```

GTG CGG GTA CTG AAG ACG GCC ATG TCG TGC GAC GAC GGC GTC ACG CGC TGT CCT 277

S Y M S M T G T L V S A P L G L C C 98

TCC TAC ATG AGC ATG ACA GGG ACG CTT GTG TCG GCG CCG CTC GGA TTG TGC TGC 331

L C T S V E C A L T S D L C N A S M 116

CTC TGC ACC AGC GTG GAG TGC GCC CTC ACA AGC GAC CTG TGC AAC GCT TCG ATG 385

R A H F C F R T G A A G I T C V Q S 134

CGC GCG CAC TTT TGC TTC CGC ACC GGT GCA GCC GGA ATC ACG TGC GTA CAG AGC 439

E G I T Y H G W A V G S S S P Y Y M 152

GAG GGC ATC ACC TAC CAC GGA TGG GCC GTG GGA TCG TCG TCG CCC TAC TAC ATG 493

M H L S A S G R G I A P T T L Q L T 170

ATG CAC CTA TCC GCG AGC GGG CGA GGG ATC GCA CCG ACG ACA CTG CAG CTC ACG 547

T D A P E V Q K G A S A L Q I L R A 188

ACG GAC GCC CCT GAG GTG CAG AAG GGT GCG TCT GCT CTG CAG ATT CTT CGG GCC 601

S G V L P G E S N P T V D I S G R V 206

TCT GGT GTT TTG CCC GGA GAG TCA AAC CCC ACG GTT GAT ATT TCC GGG CGC GTT 655

L F V P S A E H S S A S R S I S T G 224

CTC TTT GTC CCC TCT GCA GAA CAC AGC AGT GCC AGC CGC AGC ATC AGC ACC GGG 709

P V R D D D P A E W L L L P A P L V 242

CCT GTG CGC GAC GAC GAC CCG GCA GAG TGG CTG TTG CTC CCG GCG CCG CTT GTC 763

S V S G N D C D K V G I S P D Y F Y 260

AGC GTC TCC GGC AAT GAT TGC GAC AAG GTC GGC ATC TCA CCA GAC TAT TTC TAC 817

S L S S T K Q C N A Q K G T C V R H 278

TCG CTC TCC AGC ACT AAG CAG TGC AAC GCG CAG AAG GGG ACG TGC GTG CGA CAC 871

Q L A D Y R A A D L E Q I A Q G V G 296

CAG CTA GCA GAC TAC CGT GCG GCG GAC CTG GAA CAG ATC GCC CAG GGC GTC GGC 925

G R Y I A A S L G T F T R Q A M R E 314

GGA CGC TAT ATC GCC GCC TCT CTG GGC ACC TTC ACG CGG CAG GCG ATG AGG GAA 979

Q E F L L D A V E R T G G A M L R W 332

CAG GAG TTC CTG CTC GAT GCG GTG GAG CGC ACG GGT GGG GCG ATG CTG CGG TGG 1033

T V N A D G L V F Q P L P V H G V L 350

ACG GTG AAT GCG GAC GGC CTC GTG TTC CAG CCG CTT CCG GTA CAC GGT GTA CTG 1087

D A I K F D S S T G I L Y V T V R N 368

GAT GCT ATC AAG TTT GAC AGC AGC ACA GGC ATC CTC TAC GTC ACG GTT CGC AAC 1141

N N T Y G G L Y Y V A V G Q C R G A 386

AAC AAC ACA TAT GGT GGC CTC TAC TAC GTT GCC GTT GGT CAG TGT CGG GGA GCA 1195

R A S N C D S D G V T H E C G R T A 404

CGC GCA TCG AAC TGC GAT AGC GAC GGC GTG ACA CAC GAG TGT GGT CGC ACG GCT 1249

L V A G A N T S S L L Q F S M V S D 422

TTG GTG GCC GGG GCT AAC ACC TCC TCG CTG TTG CAG TTC AGC ATG GTG AGC GAC 1303

L P E E V G S T A S C T V V F R D A 440

CTG CCC GAG GAG GTG GGG AGC ACC GCC TCA TGC ACC GTC GTC TTT CGC GAC GCG 1357

Figure 2I (cont'd)

```
 A   A   A   L   L   A   S   A   N   I   S   W   T   V   E   H   T   T     458
GCC GCA GCG CTG CTG GCC TCT GCA AAC ATT TCC TGG ACG GTC GAG CAC ACG ACC   1411

 T   T   P   A   P   N   A   P   K   A   E   Q   C   R   R   C   A   F     476
ACT ACG CCG GCG CCG AAT GCC CCC AAA GCG GAG CAG TGC AGA CGC TGC GCC TTT   1465

 R   D   L   R   C   L   F   S   T   V   C   E   W   Q   M   L   L   W     494
CGC GAC CTG CGG TGT CTT TTC AGC ACC GTC TGC GAG TGG CAG ATG CTC CTG TGG   1519

 T   A   V   A   V   A   V   T   W   T   P   Y   A   I   L   A   Y   W     512
ACA GCG GTG GCG GTG GCG GTG ACG TGG ACG CCG TAT GCC ATC TTG GCC TAC TGG   1573

 R   M   A   W   H   V   G   A   K   L   L   A   C   L   N   *             528
CGT ATG GCG TGG CAC GTT GGC GCC AAG CTC TTG GCG TGT CTG AAC TGA  cttcccg  1628

atacgtcgctttctctctaccctctctcccccactttcacaactcagaaacaagcgcagcgaaggccgcact  1700

cgcacacgcacgtcccttctcccccgcatacggcgagccgcaaagggtcgctgccgcagcgcctttaactt  1772

tttaatgcgtttctcctttcctcttctgtttcgtctattcactcgttcctgcaataacgcgtttctctttc  1844

tgaaacgttgtaggtttcacgtttctcgttttctttttccttgtgcacgtttgcgttttggcagtgggaaga  1916

ggggcgatggtgagggtgaggtatacgcagacgcacacgcacgcatgcatgtatatttatgtatacgtgtgg  1988

ctacatatgtgtatgtatgtatgtatgtgtgtacatgaaaaaaaaaaaaaaaaaaa
```

CLONE 38 $\left(\frac{\text{SEQ ID No.: 44}}{\text{SEQ ID No.: 10}}\right)$ Figure 2J

```
cgctgacgccaactgcgtggatcgcggacctggccgccggtctcagacgccgggctggcatcccccgaaacc  2520

gcgctgcacggcgccacgcggtgcggcgggggctcccaagcggctgcgctcccgcacgaatgtgcaggg     2589

 M   L   E   P   T   G   R   R   G   G   P   R   L   P   T   P   A   R      18
ATG CTT GAG CCC ACG GGG CGG CGG GGG GGG CCG CGC CTG CCC ACT CCC GCA CGG   2643

 V   P   V   R   V   H   W   V   A   A   V   A   G   G   W   R   W   R      36
GTG CCG GTC CGG GTG CAT TGG GTT GCC GCG GTG GCG GGT GGC TGG CGG TGG CGG   2697

 C   A   A   C   C   A   A   G   A   V   A   A   P   A   P   A   R   A      54
TGT GCT GCC TGC TGC GCC GCT GGC GCT GTG GCG GCC CCC GCC CCC GCC AGA GCC   2751

 P   A   P   T   C   V   C   H   G   G   G   R   P   G   V   V   A   G      72
CCG GCC CCC ACC TGT GTT TGC CAT GGG GGC GGC CGA CCC GGC GTT GTG GCC GGT   2805

 M   L   R   W   V   R   G   S   L   A   A   G   E   H   T   P   S   D      90
ATG CTG CGC TGG GTT CGC GGG TCG CTG GCA GCT GGG GAG CAC ACA CCG TCT GAC   2859

 A   M   V   L   N   A   M   A   W   L   R   A   P   R   S   R   G   V     108
GCA ATG GTC CTG AAC GCG ATG GCC TGG TTG CGC GCG CCT CGC TCG CGC GGC GTG   2913

 G   F   P   V   L   C   A   C   V   W   L   P   P   P   V   P   L   R     126
GGC TTC CCC GTC CTG TGT GCG TGT GTG TGG CTG CCC CCT CCC GTG CCC CTG CGA   2967

 R   A   R   G   R   F   P   V   R   W   C   V   R   V   R   G   P   L     144
AGG GCG CGT GGT CGG TTC CCT GTG CGC TGG TGC GTG CGT GTG CGC GGG CCC CTT   3021

 S   P   A   T   R   R   L   P   V   K   G   V   W   V   V   G   V   G     162
TCG CCT GCC ACG CGC CGG CTC CCT GTC AAA GGC GTA TGG GTC GTG GGT GTG GGT   3075
```

Figure 2J (cont'd)

```
 G   W   G   S   S   A   A   T   G   R   R   Q   R   L   A   C   R   G    180
GGG TGG GGC TCC TCT GCG GCC ACA GGC CGG CGG CAA CGC CTC GCC TGT CGC GGC  3129

 A   C   G   R   A   A   R   G   R   P   P   S   R   G   V   D   G   G    198
GCA TGC GGG CGG GCC GCC CGG GGA CGC CCC CCT TCT CGT GGT GTC GAC GGG GGC  3183

 G   G   C   G   Q   R   T   C   W   K   T   A   L   P   R   A   T   P    216
GGG GGA TGC GGA CAG CGG ACC TGC TGG AAA ACG GCG TTG CCT CGG GCC ACG CCC  3237

 R   G   T   G   A   V   R   T   R   C   R   A   P   L   A   W   R   I    234
CGG GGC ACG GGC GCT GTG CGC ACG CGC TGT CGG GCG CCG CTG GCA TGG CGT ATC  3291

 A   P   E   Q   S   K   E   R   S   A   E   Q   G   R   W   T   K   R    252
GCA CCC GAA CAG AGC AAG GAG AGG TCA GCA GAG CAG GGG CGG TGG ACG AAG AGG  3345

 S   R   G   Y   A   C   E   L   A   P   P   C   V   C   A   A   R   P    270
TCG CGG GGA TAC GCA TGC GAA TTA GCT CCG CCG TGC GTG TGC GCG GCG CGC CCG  3399

 A   S   P   R   C   G   R   V   C   W   R   G   A   G   A   G   S   V    288
GCG TCT CCC AGA TGT GGC CGT GTG TGC TGG CGG GGC GCC GGT GCC GGA AGC GTG  3453

 P   R   T   P   R   V   T   P   S   G   P   P   N   S   G   V   E   S    306
CCG AGA ACG CCC CGA GTG ACA CCA TCG GGC CCT CCA AAC TCC GGT GTG GAG AGC  3507

 H   R   A   V   L   W   G   A   V   A   G   G   G   E   Q   G   M   H    324
CAC CGT GCC GTG TTG TGG GGT GCC GTG GCT GGG GGG GGG GAG CAG GGC ATG CAT  3561

 A   G   C   R   V   W   G   G   P   G   L   R   L   A   G   F   L   A    342
GCC GGG TGC AGG GTC TGG GGG GGC CCT GGC CTG CGG CTG GCG GGC TTC CTC GCT  3615

 G   L   I   R   H   A   R   A   P   P   R   G   Y   S   H   G   G   R    360
GGG CTG ATC CGG CAT GCG CGT GCG CCA CCG CGT GGT TAC TCG CAC GGC GGG CGC  3669

 R   R   F   R   P   R   S   G   A   W   M   R   P   A   W   V   G   V    378
CGC CGC TTC CGC CCT CGG TCA GGA GCT TGG ATG CGG CCT GCG TGG GTC GGG GTG  3723

 C   G   P   P   G   V   C   L   A   L   I   A   W   R   V   S   E   E    396
TGC GGT CCG CCG GGT GTC TGC CTG GCG CTG ATC GCG TGG CGC GTA TCG GAA GAA  3777

 G   A   R   T   G   K   K   G   L   L   D   A   *                        409
GGG GCG AGG ACG GGC AAA AAG GGC CTG CTA GAC GCA TGA  ccccattcgactgccgacg  3835

gctcgctctggtcggccagggttttagccgcagtgcgaccgaggcaggtgagctgtggctgtgtgcttgcgt  3907

gtgtacgtactgacttgttcgcgggtggagttatatgggcacgttgctatgcagcggaagaaaaggcgaaaa  3979

gaagtgcctattattttgccatgtccgttggctcgtctctctccatgctttgcgtgtcgtcgggtgcatgtg  4051

tgtgtgtgtgcaacgacgtttttcttttgtctcttaggcgcatgccttgtttgtgtctctgccacactgactc  4123

tctggctgtggcgtcgtggagtattctaatgctgatcttgcgctggcggccttcctttttcttgtttttctcg  4195

aagaagtacccgtaaaaaaaaaaaaaaaaaaa
```

CLONE 66 (SEQ ID No.: 45 / SEQ ID No.: 11) Figure 2K

```
tttccacaccctcctttcttcgcgaatgtatatgtttatgctacggcagcttttatcggagttgcggaagca 14400
```

Figure 2K (cont'd)

```
                                                                M   P   V     3
tcctcttccatccaccgctttcggcagctgtcatccaacacgaaaagtgtttcacgtca ATG CCC GTC  14468

 I   G   Y   N   C   D   S   G   A   V   V   E   V   V   N   P   A   S     21
ATC GGC TAC AAC TGC GAT AGC GGC GCT GTG GTA GAA GTT GTA AAC CCG GCA AGT  14522

 G   A   L   G   F   A   G   K   T   V   I   P   G   G   I   V   S   A     39
GGG GCG CTT GGT TTT GCA GGA AAA ACT GTC ATC CCG GGC GGC ATT GTC TCG GCA  14576

 A   S   A   G   D   G   T   L   Y   Y   L   P   T   S   F   P   S   M     57
GCC TCC GCC GGC GAT GGT ACT CTT TAC TAC CTC CCA ACG TCG TTT CCC TCG ATG  14630

 L   H   R   R   N   L   E   S   G   A   D   E   M   V   E   S   L   A     75
CTG CAT CGG CGC AAC TTG GAG AGC GGG GCG GAT GAG ATG GTC GAG AGT TTA GCT  14684

 R   A   H   T   Q   V   F   F   H   R   N   K   V   M   C   I   S   A     93
CGC GCG CAC ACG CAG GTT TTT TTT CAC CGC AAC AAG GTC ATG TGC ATT TCC GCC  14738

 G   S   T   E   V   A   V   Y   D   P   L   C   S   V   T   E   I   I    111
GGG AGC ACC GAA GTG GCT GTT TAT GAC CCG CTC TGC AGT GTG ACT GAG ATT ATC  14792

 S   L   P   Y   R   V   V   R   A   E   P   A   D   H   G   F   V   F    129
TCT CTC CCG TAC CGT GTC GTT CGC GCC GAG CCG GCC GAC CAC GGC TTC GTC TTT  14846

 R   S   D   C   N   R   V   F   G   Y   D   F   N   K   G   L   T   E    147
CGC AGC GAC TGC AAC AGG GTG TTC GGC TAC GAT TTT AAC AAG GGC CTG ACA GAG  14900

 V   M   N   G   C   S   I   T   G   F   L   G   H   Y   K   Q   Y   A    165
GTG ATG AAC GGG TGT AGC ATA ACG GGC TTT TTG GGC CAC TAC AAG CAG TAC GCC  14954

 V   A   L   L   H   D   G   D   E   R   V   V   G   V   T   E   A   G    183
GTT GCG CTG CTT CAC GAC GGC GAC GAG CGT GTG GTG GGC GTC ACT GAG GCC GGC  15008

 S   I   V   E   L   D   A   A   L   P   C   V   P   F   T   S   L   D    201
AGC ATC GTA GAG CTA GAC GCA GCT TTG CCA TGT GTG CCG TTC ACG TCC TTG GAT  15062

 D   V   V   L   Y   T   S   E   N   E   V   V   S   L   K   G   G   S    219
GAT GTC GTT CTC TAC ACA AGT GAG AAT GAA GTG GTG TCC TTG AAG GGT GGA AGT  15116

 A   V   S   P   V   G   E   V   H   L   S   S   S   Q   P   T   D   S    237
GCG GTT TCT CCT GTC GGG GAA GTT CAC CTT TCG AGC TCG CAG CCA ACT GAT AGC  15170

 E   V   L   C   T   V   C   L   C   E   F   D   G   D   D   G   I   T    255
GAG GTC CTG TGC ACC GTT TGC TTG TGC GAG TTC GAT GGC GAC GAC GGT ATC ACC  15224

 L   D   C   G   H   Y   F   H   K   E   C   I   E   Q   W   V   G   N    273
TTG GAC TGC GGG CAT TAC TTT CAC AAA GAG TGC ATT GAG CAA TGG GTG GGC AAC  15278

 W   M   D   F   A   A   K   G   E   H   V   K   F   T   R   A   V   C    291
TGG ATG GAC TTC GCG GCG AAG GGT GAG CAC GTG AAG TTT ACC CGC GCT GTC TGC  15332

 P   G   G   C   K   H   L   V   R   H   P   L   L   A   Q   S   K   Q    309
CCT GGC GGG TGC AAG CAC TTG GTT CGC CAC CCT CTG TTG GCA CAA TCG AAG CAG  15386

 I   S   E   L   Y   T   E   V   T   A   K   K   A   E   Q   L   K   H    327
ATC AGC GAG TTG TAC ACG GAG GTG ACT GCG AAA AAG GCG GAG CAG CTG AAG CAC  15440

 F   D   A   T   K   A   Q   H   E   F   L   F   Y   L   C   G   R   C    345
TTT GAT GCG ACA AAG GCC CAG CAC GAA TTC CTT TTC TAT CTC TGC GGC AGG TGC  15494

 G   G   V   F   Y   G   G   D   Q   V   C   S   R   M   Q   G   H   E    363
GGG GGC GTG TTC TAC GGA GGC GAT CAG GTG TGC TCA CGG ATG CAG GGG CAC GAA  15548
```

Figure 2K (cont'd)

```
P   S   S   S   P   Q   E   L   V   C   D   T   C   I   G   K   D   H     381
CCG TCG TCT TCC CCG CAA GAG CTG GTC TGC GAT ACT TGC ATA GGA AAG GAC CAT 15602

R   T   C   N   T   L   M   A   V   F   K   C   R   Y   C   C   N   P     399
CGA ACA TGT AAC ACT CTG ATG GCC GTC TTC AAG TGC CGC TAC TGC TGC AAT CCC 15656

A   T   Q   R   S   F   G   T   R   F   M   C   D   R   C   I   A   R     417
GCC ACA CAG CGA TCG TTC GGT ACT CGT TTC ATG TGC GAT CGG TGC ATC GCG CGG 15710

W   D   T   A   E   P   A   L   I   P   C   P   G   A   D   S   C   P     435
TGG GAC ACC GCG GAG CCT GCG CTC ATT CCG TGC CCG GGA GCG GAC AGC TGC CCG 15764

F   H   G   N   H   P   E   P   V   C   N   I   A   A   C   L   T   C     453
TTT CAC GGA AAT CAC CCG GAG CCC GTG TGC AAC ATT GCG GCC TGT CTT ACG TGT 15818

L   D   P   A   M   V   S   H   I   F   D   R   V   A   G   V   A   D     471
CTC GAT CCG GCC ATG GTG AGC CAT ATT TTT GAT CGA GTG GCG GGC GTT GCT GAC 15872

G   A   G   G   G   T   D   *                                             479
GGT GCA GGT GGC GGC ACC GAT TAG  tctgccatgcacaggacattgtgcccctcctgtgcgagg 15935

tgttggacggtatgctggcggcattatgcaagctgcacctgccttctcttattactgtatgaatgtgcttac 16007

gctaatgagcggcttgcacgtgcactaacatgcatcatgggcgcagcaacatctcttgaacacactgtcatg 16079

tcgctttttcgccgtgtgagagtgcgtgtgatgtactcgtgctactgggacacgtcacgaggtctctgcgcg 16151

gctgttggagttggacaggacagcgcgtacaaagggagatgttctttgcgcagtcgtttgtttttggctttt 16223

ttggcagcagttgacggtcgtggtggacgcgcctttcgcgcgcgcgcggccttgtgaaacgcgatcggctct 16295

ctctctctctctcttaaaaaaaaaaaaaaaaaaaaaaaaaaaaaaaaaaaa                     16309
```

CLONE 72 (SEQ ID No.: 46 / SEQ ID No.: 12) Figure 2L

```
CGCACATGCATAAACCCACATTCGTCTTTCACTGGCTCAGGGGACTCTCACCTCTCCGTCCGCTTCCACCGAGCAGTCAAGGT
TGCTGCCGTTGCTCTTGTTGGTGTGTGTCAGTGCCGAACTCTCTAGCGCGTGTGTGCGTGCCTGTTTCATCACAGCACCGTAC
AAGACGAGCACGTCGCGCTGTCTCTCCGCGCCCTTTCCTCATTCTCTCCACACCCCCACACACGCACGCACGCGCGCGCATCC
CTCGTTAAAGCAA
 M   G   G   K   R   K   K   S   N   N   G   P   V   K   K   E   S   K      18
ATG GGC GGC AAG CGC AAG AAG TCC AAC AAC GGA CCT GTC AAG AAG GAA AGC AAG     54

 Y   K   I   P   T   R   F   D   C   P   L   C   D   A   K   A   S   I      36
TAC AAG ATC CCC ACC CGC TTT GAC TGC CCG TTG TGT GAT GCC AAG GCG TCC ATC    108

 V   V   R   M   F   R   A   T   S   D   A   T   V   Q   C   R   V   C      54
GTC GTC CGA ATG TTT CGC GCG ACA AGC GAT GCC ACG GTG CAG TGC CGC GTG TGC    162

 G   A   G   G   T   K   R   W   N   V   L   R   L   E   K   P   V   D      72
GGA GCG GGC GGG ACA AAA CGG TGG AAT GTG CTG CGC CTC GAG AAG CCA GTG GAC    216

 V   F   F   R   F   H   E   A   L   V   Q   R   D   H   A   D   L   Q      90
GTG TTT TTC CGC TTT CAC GAG GCG CTC GTT CAG CGC GAT CAC GCC GAC CTG CAG    270

 Q   V   E   M   G   R   E   A   R   L   S   V   G   A   P   N   A   V     108
CAG GTA GAG ATG GGT CGC GAG GCG AGG CTG AGC GTT GGC GCT CCC AAC GCC GTC    324
```

Figure 2L (cont'd)

```
 L   G   G   S   Q   S   S   M   G   K   E   A   Y   S   P   G   D   A     126
CTT GGT GGA AGC CAG AGC AGC ATG GGA AAG GAG GCG TAC TCT CCA GGG GAC GCA    378

 A   V   A   G   W   A   R   L   G   S   S   A   A   A   A   A   T   A     144
GCC GTG GCG GGC TGG GCT CGG CTC GGC TCC TCT GCT GCC GCC GCT GCA ACC GCG    432

 S   G   C   S   H   S   Q   H   V   K   S   L   G   E   L   Q   R   K     162
TCA GGG TGC TCG CAT TCG CAG CAC GTG AAG TCT CTA GGT GAG CTG CAG CGC AAG    486

 L   T   M   P   A   W   S   G   F   A   T   A   P   T   A   S   C   A     180
CTG ACT ATG CCA GCG TGG TCG GGT TTC GCC ACC GCG CCA ACC GCC TCG TGT GCC    540

 V   D   L   R   D   D   Y   E   G   E   A   E   G   A   A   A   H   Y     198
GTC GAC CTC CGC GAC GAC TAC GAG GGC GAG GCG GAA GGG GCA GCA GCC CAC TAC    594

 F   A   P   R   Q   E   V   H   S   A   E   D   E   D   D   E   Y   D     216
TTT GCT CCT CGT CAA GAG GTG CAC AGC GCC GAG GAT GAG GAT GAC GAG TAC GAC    648

 Q   L   F   Q   *                                                         221
CAG CTC TTT CAG TGA gagggctcgctgctgctacggttattgatgccgatgc
tgcgtttgtaaggtacagggcgccctcgtgtggtccctccttttgtttgtttggttttg
tatgcttcgcatgcttgaaaatggggaggcgatccagctgtgtttcggcgtggttgctta
ccgctgcttctcagctgctgctgttgcggtgcctcgctctgtgtgcgcgtgtgtgtacgc
tgtgatccatcagcgtgaggcagtgtaatgtcgagtggacgaaaccgggaacgtgggaga
cggtggagtgaagctgtgcgcacacattcgcgcgcggcgcctcggtgtgtatgtgcatgt
gtctgcgctactccctttgccgtccctacgacctccttctgtggtacctttatggtcgcc
gctgaacacgtcgcctttttccttcggttgtacgatgctgcgtgtatctctctctctgtc
tcgggtgtatgcgtatgtaggtgtgtgtgtgtgtgtgtgtgtgtgtgtgtgtgtgtgaat
ctgtgtggatgtgcggatgtgcatttattggctcccagtcgtgcgttggtataaaaaaaaaaaaaaaaaaaaaaaaa
```

Figure 2M (cont'd)

gtgcgccgcacatgggcagcgcctgttctttcgtttttttgtctcctggagctgcggctcaccttcatttg 4719 gatggcgcctctgccatcgctgctgtcctcacgggctatcttcaaaaaaaaaaaaaaaaaaaaaaaaaaaa 4762

Figure 3C (cont'd)

```
T   N   L   N   W   I   M   E   N   D   V   T   D   L   G   L   T   F     373
ACA AAC CTC AAC TGG ATC ATG GAG AAC GAC GTC ACA GAC CTT GGC CTG ACC TTC  1496

A   V   N   Y   D   R   F   G   S   V   E   E   A   E   L   E   P   N     391
GCC GTC AAC TAC GAT CGC TTC GGC TCG GTG GAG GAG GCG GAG TTG GAG CCG AAC  1550

G   Q   N   T   A   V   T   N   A   N   K   Q   Q   Y   V   R   L   L     409
GGC CAG AAC ACG GCC GTG ACG AAC GCG AAC AAG CAG CAG TAT GTC CGC CTC CTG  1604

C   E   F   Y   M   T   K   R   T   E   D   Q   L   L   R   F   L   K     427
TGT GAG TTT TAT ATG ACC AAG CGC ACG GAG GAT CAG CTG CTG CGC TTC CTG AAG  1658

G   F   Y   S   V   I   P   R   R   E   I   Q   C   F   T   E   K   E     445
GGC TTC TAT TCG GTG ATC CCC CGC CGC GAG ATC CAG TGC TTC ACG GAG AAG GAG  1712

L   E   L   V   I   S   G   M   P   N   I   D   V   E   D   L   R   T     463
CTG GAG CTG GTC ATC AGT GGC ATG CCC AAC ATC GAC GTC GAG GAC CTG CGC ACG  1766

H   T   V   Y   E   G   Y   S   S   T   S   P   Q   V   R   W   F   W     481
CAC ACC GTG TAC GAG GGC TAC AGC AGC ACG TCG CCG CAG GTG CGC TGG TTC TGG  1820

E   A   V   G   S   M   S   K   E   D   L   A   N   L   L   Q   F   T     499
GAG GCG GTC GGC TCC ATG AGC AAG GAG GAC CTG GCA AAC CTT CTG CAA TTT ACG  1874

T   G   S   S   K   V   P   H   G   G   F   G   H   L   E   G   S   N     517
ACC GGT TCG TCA AAG GTG CCA CAC GGC GGC TTC GGC CAT CTC GAG GGA TCG AAC  1928

G   R   S   L   P   F   T   I   S   R   W   A   V   T   K   E   D   L     535
GGC CGC TCG CTG CCC TTC ACG ATC AGC CGC TGG GCC GTA ACC AAG GAA GAC CTC  1982

L   P   Q   A   H   T   C   F   N   K   I   D   L   P   V   Y   P   S     553
CTG CCG CAG GCG CAC ACG TGC TTC AAC AAG ATC GAC CTG CCC GTC TAC CCC TCA  2036

A   A   V   L   K   E   K   L   M   L   A   I   T   Y   G   S   M   G     571
GCT GCG GTG CTC AAG GAA AAG CTG ATG CTG GCG ATC ACG TAC GGT AGC ATG GGC  2090

F   T   M   V   *                                                         576
TTC ACG ATG GTG TAG  tggtagtggtggtgtgtgtgtgtgtgcgtgcgtgtatgtggattagtaa  2156

cgtgatgcgcctgcgtggctgatgaaaaaaaaaaaaaaaaaaaa 2228
```

CLONE 20.1 (SEQ ID No.:51 / SEQ ID No.:17) Figure 3D

```
                                               M   Q   P   K   Q        5
ctacaggccgacacgcacctccttgcaccctactccatacacgcggagaag ATG CAA CCG AAG CAG  5394

K   A   A   L   G   I   N   G   T   R   T   S   G   I   A   V   R   R      23
AAG GCA GCC CTC GGC ATC AAC GGC ACC CGC ACC AGC GGC ATC GCC GTT CGC CGC  5448

E   N   V   S   A   A   L   A   V   A   N   V   V   K   S   S   L   G      41
GAG AAC GTG TCA GCC GCA TTG GCC GTG GCA AAT GTC GTT AAG TCG TCG CTG GGC  5502

P   I   G   L   D   K   M   L   V   D   D   V   G   D   V   L   V   T      59
CCC ATC GGT CTG GAC AAG ATG CTG GTG GAC GAC GTC GGT GAT GTG CTG GTG ACG  5556

N   D   G   A   T   I   L   K   S   L   D   V   E   H   P   A   A   R      77
AAC GAC GGT GCG ACG ATC CTG AAG AGT CTC GAC GTG GAG CAC CCA GCC GCG CGC  5610
```

Figure 3D (cont'd)

```
L   L   V   D   L   A   Q   L   Q   D   K   E   I   G   D   G   T   T      95
CTA CTG GTT GAT CTG GCC CAG CTC CAG GAC AAG GAG ATT GGC GAC GGA ACC ACC  5664

S   V   V   I   L   A   A   E   L   L   K   R   A   Q   E   L   V   S     113
TCT GTT GTG ATT CTT GCT GCG GAG CTG CTG AAG CGG GCC CAG GAG CTC GTG TCG  5718

Q   G   I   H   A   T   S   I   I   A   G   Y   K   L   A   M   R   E     131
CAG GGC ATC CAC GCG ACA AGC ATC ATT GCC GGC TAC AAG CTT GCC ATG CGC GAG  5772

A   L   R   Y   L   N   D   N   L   G   C   A   V   E   S   L   G   K     149
GCA CTG CGC TAC CTG AAC GAC AAC CTC GGC TGC GCC GTG GAG AGT CTC GGC AAG  5826

D   V   L   L   N   V   A   R   T   S   M   S   S   K   I   L   N   N     167
GAC GTG CTG CTG AAC GTC GCG CGC ACC TCC ATG TCG AGC AAG ATT CTG AAC AAC  5880

D   A   D   L   F   A   K   I   V   V   D   A   I   M   S   V   K   T     185
GAC GCG GAT CTT TTC GCG AAG ATC GTA GTG GAT GCT ATC ATG TCC GTC AAG ACG  5934

V   N   D   F   G   D   V   I   Y   P   R   K   A   V   S   I   L   L     203
GTG AAC GAC TTT GGT GAT GTC ATC TAC CCT CGT AAG GCG GTG TCG ATT CTG CTG  5988

Q   H   G   R   S   L   H   E   S   R   L   V   Q   G   F   A   M   N     221
CAG CAC GGC AGG AGC CTG CAC GAG TCA CGG CTG GTG CAG GGC TTC GCG ATG AAC  6042

L   S   R   A   A   Q   G   M   P   T   S   V   K   D   A   K   I   A     239
CTC TCT CGC GCC GCA CAA GGC ATG CCG ACC TCG GTG AAG GAT GCT AAG ATT GCC  6096

L   I   D   F   D   L   R   A   V   K   M   K   L   G   I   N   I   T     257
CTC ATC GAC TTC GAC TTG CGC GCT GTC AAG ATG AAG CTC GGC ATC AAC ATC ACC  6150

I   T   D   P   S   K   A   E   A   I   R   Q   R   E   L   D   I   T     275
ATC ACG GAC CCC TCC AAG GCA GAG GCG ATC CGC CAG CGT GAG CTC GAC ATC ACG  6204

K   E   R   I   Q   K   M   I   A   A   G   A   N   V   I   M   T   T     293
AAG GAG CGC ATT CAG AAG ATG ATC GCG GCC GGC GCC AAC GTC ATT ATG ACG ACG  6258

W   G   I   E   D   S   M   M   K   Y   M   V   D   N   S   V   L   G     311
TGG GGC ATC GAG GAT AGC ATG ATG AAG TAT ATG GTG GAC AAC AGC GTG CTT GGC  6312

V   R   R   V   K   K   D   D   I   R   R   I   A   K   T   T   G   A     329
GTG CGT CGT GTC AAG AAG GAC GAC ATC CGC CGC ATC GCC AAG ACT ACC GGC GCG  6366

Q   V   V   H   T   M   S   D   L   E   G   E   E   V   F   D   P   K     347
CAG GTG GTG CAC ACC ATG TCC GAC CTC GAA GGC GAG GAG GTC TTC GAC CCC AAG  6420

W   L   G   R   S   E   K   V   Y   E   E   R   I   G   D   D   D   C     365
TGG CTC GGT CGG TCG GAG AAG GTG TAC GAG GAG CGC ATT GGC GAC GAT GAC TGC  6474

I   V   I   A   G   T   S   N   A   V   C   A   T   I   V   C   R   G     383
ATC GTT ATT GCT GGC ACC TCG AAC GCC GTG TGT GCC ACC ATC GTC TGC CGC GGC  6528

A   N   Y   F   M   L   E   E   M   E   R   A   L   N   D   A   L   W     401
GCG AAC TAC TTC ATG CTA GAG GAG ATG GAG CGC GCG CTG AAC GAC GCA CTG TGG  6582

A   V   A   R   T   C   D   A   S   C   V   V   A   G   G   G   S   V     419
GCT GTG GCG CGC ACG TGC GAC GCC AGC TGC GTC GTT GCT GGC GGC GGC TCC GTG  6636

E   A   A   V   S   V   Y   L   D   N   F   A   R   T   L   S   S   R     437
GAG GCG GCG GTG TCG GTG TAC CTG GAC AAC TTT GCC CGC ACA CTC AGC TCA CGC  6690
```

Figure 3D (cont'd)

```
 E   Q   L   A   V   A   E   Y   A   E   A   L   L   V   I   P   K   V    455
GAG CAG CTG GCG GTG GCC GAG TAC GCC GAG GCA CTG CTC GTC ATT CCG AAG GTG  6744

 L   A   L   N   A   A   L   D   A   T   D   L   V   A   K   L   R   V    473
CTG GCG CTG AAT GCT GCC CTC GAC GCC ACG GAC CTC GTC GCA AAG CTT CGT GTC  6798

 E   H   T   Q   A   Q   S   S   G   Q   Q   T   E   A   R   F   T   G    491
GAG CAC ACG CAG GCA CAG AGC AGC GGC CAG CAG ACG GAG GCG CGC TTT ACC GGA  6852

 L   D   L   H   N   G   T   L   R   N   N   I   K   A   G   V   L   E    509
CTG GAT CTG CAC AAC GGC ACG CTA CGC AAC AAC ATC AAG GCG GGT GTG CTG GAG  6906

 P   K   P   S   K   I   K   S   L   Q   F   A   T   E   A   A   V   T    527
CCA AAG CCT AGC AAG ATC AAG TCC CTG CAG TTC GCG ACG GAG GCG GCT GTG ACG  6960

 V   L   R   I   D   D   C   V   R   L   N   P   D   E   E   D   Q   Q    545
GTG CTG CGT ATC GAC GAC TGC GTC CGC CTC AAC CCT GAT GAG GAG GAC CAG CAG  7014

 R   *                                                                    547
CGC TGA  ggctcgttttcccaccgattgtgagagtcggacgaggtgcagcgagcagcagcagacgccgc  7083

ataccaagacgaggcgcagaggttgagagcgcgtctacatagattgtcgcttgccaagtaagaacgaggaag  7155

tcggtccaaaggctactgtgcgcatacgcatgcctatgcgcacacgttgacgtctctctcacattatctctg  7227

tgctccttactcttgttgctttccagcgcacgtgtctgcggttctttctctctgcttgtgtgcccgtgtcgt  7299

tccgctcttgctacatcgctacgccgtctcctttttttcttggtccagttgtcggacccctcctctctctgt  7371

gttgaccttctcttcctcatcgcctgcacatatgcctctgcttcgctccggatgcgtactcgcgtgcgtgtg  7443

tgtgtgcgtgtgcgtgcgcttcgccgagacggaccctgtaataaggcagcggatgccgtgctgtttgaagga  7515

ctgagttatgtgggcggcagcgggtagaggaggtggcagaaaagagctacggcgacaaggagtggcggaagg  7587

ctgtttccaaaccgcactgcacagatgtagggagagagggagggggaacgaggggggtgagggtgaggcgtct  7659

ccgtgtgctcgtggcgtgttgtcctcgttgccgacatgtttcggcgcctactttgccgtgcctgtctcgag  7731

tgtctcccccgcccccacccgtcgcgttcgctgagcgtcgctgtctgtcggtctgtgtgtattccgttcca  7803

gcaccccaactgcttcggactgtaagaagggatgcggcgaaaaggtgcgcaaacatgcgcacctccgcacca  7875

cattataagagcacgaactctgacggcgggcgacagtgactcgtcgcaggtgttcgttcgttttacgcagat  7947

gcagattggcggggagaggtcgaggaagcgaaaaggagtgggaggcgatgtgcagctcagcgtgtcaggcgc  8019

ccacacgccgaaacacgcaaggcaaagggcaacgcgagcgcacatgtgagagaaagcggcgatcagatgtgt  8091

gtgcgtgtgtgtgcgtgtgtcttcacctacgaggacgtttattttcgttctttcctgcctcgtgtgacgat  8163

ctcgagaacggcggctggggagggacgtgaaagaggaactacaacctggcgctcgtgctcgcgcgcgcgc  8235

gcgtgtgtgtgtgtgtgctctcttttcgtttcgatgctatcgcaaatcgtcgatgcagcagcatgtagtgcg  8307

cttgaaccgcccctcctctttcccttctttggtcgtgcgggtggtctccgttggtgcgtgtgcgttaagtaa  8379

tgggcaaacagagagtgaaggagcgaaaaggcaagtgcagccacccacctttaaagcaacagcaaacaaaaa  8451

cgaataccgtgtgcgtccatgcatcccacatccacctctacccacgtgcatgtgtgtgcaagtgcctcttca  8523

ggtgactgatcggcgcgcaggtcttcgcaagcgcgcgccactgaaatcgaacgcggataaagggaaacaagg  8595

cgcagaggcgcgcacgtgcgcgggtaggcactccgacacaaaaatggagctgtgaaagcaaggaa        8660
```

Figure 3F (cont'd)

```
 Q   Y   G   L   R   C   K   R   E   I   W   R   V   N   M   T   L   S     49
CAG TAC GGT CTG CGC TGC AAG CGT GAA ATC TGG CGT GTG AAC ATG ACG CTG TCC   165

 K   M   R   R   T   A   R   L   L   L   T   L   P   E   N   H   P   R     67
AAG ATG CGC CGC ACG GCC CGT CTG CTG CTG ACG CTG CCG GAG AAC CAC CCC CGC   219

 R   L   L   E   G   S   A   I   M   R   R   C   H   E   Y   G   F   L     85
CGT CTG CTG GAG GGT TCC GCC ATC ATG CGC CGC TGC CAC GAG TAT GGC TTC CTC   273

 D   E   E   K   D   K   L   D   Y   V   L   S   L   T   V   P   D   I    103
GAC GAG GAG AAG GAC AAG CTG GAT TAC GTG CTG TCG CTG ACG GTG CCG GAC ATT   327

 L   E   R   R   L   Q   T   I   V   F   K   A   G   L   A   K   S   V    121
CTC GAG CGC CGC CTG CAG ACC ATC GTC TTC AAG GCC GGT CTC GCC AAG TCC GTG   381

 H   H   A   R   V   L   I   Q   Q   R   H   I   A   V   A   K   Q   I    139
CAC CAC GCC CGC GTC CTG ATT CAG CAG CGC CAC ATC GCC GTC GCC AAG CAG ATT   435

 V   T   I   P   S   F   I   V   R   V   S   S   E   R   H   I   A   F    157
GTG ACG ATC CCG TCC TTC ATC GTG CGC GTC AGC AGT GAG CGC CAC ATC GCC TTC   489

 A   D   A   S   P   F   G   N   G   R   A   G   R   V   K   R   V   R    175
GCC GAT GCT TCG CCG TTC GGC AAC GGC CGT GCT GGC CGC GTC AAG CGC GTG CGC   543

 A   K   A   A   K   R   H   A   G   G   G   D   D   D   E   *            191
GCG AAG GCC GCC AAG CGC CAC GCC GGC GGC GGC GAT GAC GAT GAG TAA  gatggag  598

gaagcgcgctcttgtgccgcaccggcatggggacgcgttgtgcaggctgaaggcgtttgcctctcatacgat   670

cgacgcttcgtgtacctttgggctccttgcgttgcacgtgtagagctgcccggcgccccgtcgcgtctgttt   742

tgtactcgacactgactcggcacgtatacgacgtgttgaaaacgccccgttcgtttcctttcgcttgtttgt   814

gtgtgtttgcttttttttttctatgatcctcatttcaccacccaaatccctacacaaaaaccatgcgcgcccg  886

cgcatcaccatggcaggagttttcgctgggggttttctcagcgaggacgtcatccctgtatttgtccgtacc   958

gtctcgcgtttctctcgtccgagctctcggacggcgcgaatctgttgccacgtgctactgcctatccgcccc  1030
```

CLONE 26 (SEQ ID No.: 54 / SEQ ID No.: 20) Figure 3G

```
                                     M   A   A   T   K   S   A   V   S      9
gctcacaaagcctcggttccacgcgagttgtttcga ATG GCC GCC ACC AAG TCT GCT GTG TCC  1575

 A   A   K   R   K   A   A   K   K   V   S   R   K   S   P   E   Y   T     27
GCC GCG AAG AGG AAG GCG GCG AAG AAG GTG TCG CGC AAG AGC CCC GAG TAC ACG  1629

 T   L   R   K   S   C   A   P   G   A   I   A   I   I   L   A   G   R     45
ACT CTG CGC AAG AGC TGT GCT CCC GGC GCC ATC GCG ATC ATC CTC GCC GGC CGC  1683

 F   R   G   R   R   A   V   I   L   K   Q   L   P   H   N   G   P   L     63
TTC CGC GGT CGC CGC GCC GTG ATC CTG AAG CAG CTG CCG CAC AAC GGC CCG CTG  1737

 V   V   S   G   P   M   K   Y   N   G   V   P   I   R   R   I   D   S     81
GTC GTG TCT GGC CCG ATG AAG TAC AAT GGC GTC CCC ATC CGC CGC ATC GAC TCC  1791
```

Figure 3G (cont'd)

R Y V I A T S T T V D I S S V D T A 99
CGC TAC GTG ATC GCC ACC AGC ACC ACG GTG GAC ATC TCC AGC GTT GAC ACG GCG 1845

P I T A E V F Q R P K A E K P T K S 117
CCC ATC ACC GCC GAG GTG TTC CAG CGC CCC AAG GCG GAG AAG CCG ACC AAG AGC 1899

E G D F M G D K Q K A K A E K A A K 135
GAG GGC GAC TTC ATG GGC GAC AAG CAG AAG GCT AAG GCG GAG AAG GCT GCC AAG 1953

K T S K A G K K T L V S D A R A Q L 153
AAG ACC TCC AAG GCG GGA AAG AAG ACC CTC GTC TCG GAC GCG CGC GCC CAG CTG 2007

Q K K I D A A L I A A I K K D A Q G 171
CAG AAG AAG ATC GAC GCT GCC CTC ATC GCC GCC ATC AAG AAG GAC GCT CAG GGC 2061

K E K A G Y L R S V F T V K P G D A 189
AAG GAG AAG GCC GGC TAC CTG CGC TCC GTC TTC ACG GTG AAG CCC GGT GAT GCG 2115

P H R W N W 195
CCG CAC CGC TGG AAC TGG taagcgcaggacaaccgtacgcgctctcgcagcacgtgctcgtgctg 2180 tagcctcgctacccctaaagcttctctggtgagccgcaagccgacgcgttttgcggttctcccgcaggccgt 2252 gtgcgtcttttctattttttttttttttttggtttcttcgcttcccttgtgttttgttttgtttcatccgca 2324 ac 2326

CLONE 59 (SEQ ID No. 55 / SEQ ID No. 21) Figure 3H

M V K P H L R H Y Q V V G R 14
gccaaagagaaaaca ATG GTC AAG CCG CAC TTG CGC CAC TAC CAG GTG GTC GGC CGC 1065

E S P S E K N P E P T V Y K F E V F 32
GAG TCG CCC TCG GAG AAG AAC CCT GAG CCG ACT GTG TAC AAG TTT GAG GTG TTC 1119

A P N F V V A K S R F W R M M R V K 50
GCC CCA AAC TTC GTC GTC GCC AAG AGC CGT TTC TGG CGC ATG ATG AGG GTC AAG 1173

N K V K A T H G D V L S C K V V K D 68
AAC AAG GTC AAG GCC ACG CAC GGT GAC GTG CTC TCC TGC AAG GTC GTG AAG GAT 1227

A K L V A R N Y L V D I A Y Y S Q R 86
GCG AAG CTG GTG GCG CGC AAC TAC CTG GTC GAC ATC GCG TAC TAC AGC CAG CGC 1281

C G Y T R M V K E F R D V S K T G A 104
TGC GGC TAC ACG CGC ATG GTC AAG GAG TTC CGC GAC GTC TCC AAG ACC GGC GCC 1335

V S Q A Y H D L A S R H R A R Y H N 122
GTG AGC CAG GCG TAC CAC GAC CTG GCC TCC CGC CAC CGC GCC CGC TAC CAC AAC 1389

I E V L N V K S I P D H E V K H L S 140
ATC GAG GTG CTG AAC GTG AAG AGC ATC CCG GAC CAC GAG GTG AAG CAC CTG AGC 1443

I A Q Y H A P N L S F P L L Q R R I 158
ATT GCC CAA TAC CAC GCT CCA AAC CTG TCC TTC CCG CTC CTG CAG CGC CGC ATC 1497

Figure 3H (cont'd)

```
K   A   A   R   K   D   R   A   I   F   V   K   K   N   T   K   R   A     176
AAG GCA GCC CGC AAG GAC CGT GCC ATC TTC GTC AAG AAG AAC ACG AAG CGC GCG  1551

V   V   A   *                                                             180
GTG GTG GCG TGA  ggaaggagctggtgaagcaagaacaggtggcagaggagaaagggagtgtaccagc  1618

acaaacattcgcgcacgcatatgattgcagacacatgtgtgtatgggatcgtatgcgtatgtgattgtgt  1690

gtatggaaacgcccactccctctgccctcttcccttgtctcctggctgctagtagggggtgcaggtatcgtg  1762

tgtgcgtgtttgtgtgtcggtctcgttgtcggcgcaggcacgtgcttgccaagcacgattgttacggctgtc  1834

tcgttcttcgcgggttgcgtgtgtgcgcaactgccgatgctctctcgtctttcgtttttctcgctccctccc  1906

ctggatcttgctggattgcgtcgttttgttggttcgcgatggtgatccagcggcgttgccccccccccgtcg  1978

acacacatatgcacacatgctattgctgccgggcgggggaacatcggcactggccaccggcgacaagcagtg  2050

aaggaaggggatggggaaagcgagaaaaagagaggcggcgggcaacggcagctgaaggagacggcgcgccgc  2122

tccgcttggcgtgtgttccgtgaaggttctcggactttggcgtgactttatggttcgcgtgcttcgtttctt  2194

cgcttcctctttcgtgcttgtttccgtcattttacgcgccaaaacaaatcaaaagaagcacctcaagggcc  2266

atcagcaaaacttcccctaccccgcaccggtggtgtggggtgtggattcggggcgggggtgcgtatgcgaga  2338

gacgcgcaagaacttacctttttttgttcgcagtctgcggtgcttagcctccggggcggggagacggctttg  2410

cgagccaaacacaccgccccgcctctcgcttccggtgctccttcgcctcgaaaaaaaaaaaaaaaaaaaa  2460
```

CLONE 65 (SEQ ID No.: 56 / SEQ ID No.: 22) Figure 3I

```
cttgctcatcagccaccttgcacttgctcacccactcaacgaagcacaagaggcgacgatacttatcagcga  3024

                                                   M   M   R   R          4
taagtgctgccttaaccgccatccacaaccttcagcagaaagagcagggaaat ATG ATG CGG CGC  3089

T   L   L   W   L   V   N   F   E   P   V   F   M   P   A   L   S   P     22
ACG CTG CTC TGG CTC GTG AAC TTC GAG CCC GTC TTC ATG CCA GCC CTC TCC CCG  3143

S   M   E   T   G   T   V   V   E   W   K   K   K   I   G   E   L   V     40
TCG ATG GAG ACG GGC ACG GTA GTC GAG TGG AAG AAG AAG ATC GGC GAG CTC GTG  3197

K   E   S   D   V   F   C   T   I   Q   T   D   K   A   V   V   D   Y     58
AAG GAG AGC GAT GTC TTC TGC ACC ATC CAG ACG GAC AAG GCA GTA GTG GAC TAC  3251

T   N   T   F   E   S   G   Y   L   A   K   I   Y   C   G   N   G   Q     76
ACG AAC ACC TTC GAG AGC GGC TAC CTC GCC AAG ATA TAC TGT GGG AAC GGC CAG  3305

S   A   P   V   A   K   T   I   A   V   M   V   S   D   A   A   D   V     94
TCT GCC CCC GTC GCC AAG ACG ATC GCT GTG ATG GTG AGC GAC GCC GCG GAT GTC  3359

S   K   A   D   E   Y   T   P   E   G   E   V   P   A   A   E   A   E    112
AGT AAG GCG GAC GAG TAC ACG CCT GAG GGC GAG GTG CCT GCC GCG GAG GCG GAG  3413

A   P   T   A   A   A   V   A   A   A   P   A   A   G   G   A   S   S    130
GCA CCC ACC GCT GCT GCT GTT GCC GCA GCG CCG GCC GCT GGT GGT GCC TCT TCT  3467
```

Figure 3I (cont'd)

```
K   A   P   E   G   V   T   C   E   P   V   F   M   P   A   L   S   P     148
AAG GCA CCG GAA GGC GTC ACC TGT GAG CCC GTC TTC ATG CCA GCC CTC TCC CCG  3521

S   M   E   T   G   T   V   V   E   W   K   K   K   I   G   E   L   V     166
TCG ATG GAG ACG GGC ACG GTA GTC GAG TGG AAG AAG AAG ATC GGC GAG CTC GTG  3575

K   E   S   D   V   F   C   T   I   Q   T   D   K   A   V   V   D   Y     184
AAG GAG AGC GAT GTC TTC TGC ACC ATC CAG ACG GAC AAG GCA GTA GTG GAC TAC  3629

T   N   T   F   E   S   G   Y   L   A   K   I   Y   C   G   N   G   Q     202
ACG AAC ACC TTC GAG AGC GGC TAC CTC GCC AAG ATA TAC TGT GGG AAC GGC CAG  3683

S   A   P   V   A   K   T   I   A   V   M   V   S   D   A   A   D   V     220
TCT GCC CCC GTC GCC AAG ACG ATC GCT GTG ATG GTG AGC GAC GCT GCC GAT GTG  3737

E   K   V   A   N   Y   Y   P   E   D   A   V   G   G   P   P   A   S     238
GAG AAG GTT GCC AAC TAC TAC CCC GAG GAT GCC GTT GGC GGG CCG CCG GCT TCC  3791

A   A   D   P   S   A   A   A   A   A   A   A   S   A   R   P   A   P     256
GCC GCT GAC CCT TCT GCC GCC GCT GCT GCT GCT GCG TCA GCT CGA CCG GCT CCA  3845

S   A   A   S   A   K   H   Y   G   G   S   L   D   A   A   V   A   A     274
TCC GCC GCG TCT GCC AAG CAC TAC GGT GGC TCG CTC GAT GCG GCG GTG GCG GCT  3899

S   G   P   S   V   A   R   I   A   A   G   L   E   T   S   T   L   A     292
AGT GGC CCA AGT GTG GCC CGC ATT GCT GCT GGT CTG GAG ACC AGC ACC CTT GCC  3953

G   I   A   P   S   G   K   G   G   R   F   L   K   S   D   F   S   G     310
GGC ATC GCT CCC TCT GGC AAG GGT GGG CGT TTC CTG AAA TCC GAC TTT TCT GGT  4007

Q   P   G   F   D   Y   N   D   T   T   P   A   R   A   M   Q   Q   K     328
CAA CCC GGC TTC GAC TAC AAC GAC ACC ACG CCG GCG CGA GCG ATG CAG CAG AAG  4061

A   A   P   A   A   A   A   D   E   A   S   K   T   A   A   K   S   A     346
GCG GCC CCC GCC GCT GCC GCT GAT GAG GCG AGT AAG ACG GCT GCG AAG TCT GCT  4115

A   P   A   A   V   S   G   D   I   Y   N   V   V   L   K   P   G   P     364
GCC CCG GCG GCG GTA AGC GGG GAC ATC TAC AAC GTT GTT CTC AAG CCC GGC CCT  4169

V   Y   K   S   V   S   D   T   A   L   L   K   K   L   M   H   T   M     382
GTG TAC AAG AGC GTC AGC GAC ACG GCC CTG CTG AAG AAG CTC ATG CAC ACC ATG  4223

H   V   P   K   P   K   L   K   K   A   A   E   *                         395
CAC GTT CCG AAG CCA AAG TTG AAG AAG GCC GCC GAG TAA  ggaggcggagaagtgtacc  4281

gatgcgcgcgtgtgcgcgaaacgcgtgtcttccgctcattcgccaaggggttgggggaggggatgcggatgc  4353

tgagcagaaactcttcccgtgtagtcgacgtcgtcgtgtagttcacgccgtcaatgcgggtgtggtgcaagt  4425

cagagatctctcgggaaacggatgggttggggtggggaggaggccgcagccacacaaacgggcggctacgca  4497

cttcctcacatgcacacacacacacacacacacgcacccagccactcgtcctctccttctctctcaccatct  4569

ctctgtgtctgacggtgaagcagggaaaaggcgagaggtcggtggagggcggtggggccgagcatggaggct  4641

gtgcgtgcacgatgacgaaggcaggagtgcaaagttgtggggtgcggtgtgcatgtgaaaccgactgtctgc  4713

caccctttacccgatggatgacactcgttcgtccaaccccaaggcgccttctccctgcaagaacgaggtac  4785

actcgatgtatgaaggcgggctgtcgaggcatctgacacgcaacagctgctccctacgctgacaccgtggcc  4857

atggacttgacgcacgcagatgtgccgctgtgtcttgtgcgtctccgactcgataatggccgcgttcggcag  4929
```

Figure 3J (cont'd)

```
 D   T   D   S   S   G   T   K   E   V   Q   R   T   M   L   E   L   L    311
GAC ACG GAC AGC AGC GGC ACG AAA GAG GTG CAG CGT ACG ATG CTG GAG CTG CTC  3361

 T   Q   L   D   G   F   D   S   S   N   D   V   K   V   I   M   A   T    329
ACG CAA CTG GAC GGC TTC GAT AGC AGC AAC GAC GTG AAA GTG ATC ATG GCA ACC  3415

 N   R   I   D   T   L   D   P   A   L   I   R   P   G   R   I   D   R    347
AAC CGC ATC GAC ACC CTC GAC CCG GCT CTC ATC CGC CCT GGT CGT ATC GAC CGC  3469

 K   I   E   F   P   F   P   D   E   K   T   K   R   R   I   F   E   I    365
AAG ATT GAG TTC CCC TTC CCA GAC GAG AAG ACG AAG CGC CGC ATC TTC GAA ATC  3523

 H   T   S   R   M   S   L   A   E   D   V   D   I   S   E   F   I   H    383
CAT ACA AGC CGC ATG TCA CTC GCC GAA GAC GTC GAC ATC TCC GAG TTT ATC CAC  3577

 A   K   D   E   M   S   G   A   D   V   K   A   I   C   T   E   A   G    401
GCG AAG GAT GAG ATG AGC GGC GCG GAT GTG AAG GCC ATC TGC ACA GAG GCC GGG  3631

 L   L   A   L   R   E   R   R   M   K   V   C   Q   A   D   F   I   K    419
CTG CTG GCC CTG CGT GAG CGC CGC ATG AAG GTG TGC CAA GCC GAC TTT ATC AAG  3685

 G   K   E   N   V   Q   Y   R   K   D   K   S   T   F   S   R   F   Y    437
GGC AAG GAA AAT GTG CAG TAC CGC AAG GAC AAG TCG ACG TTT TCG CGT TTT TAC  3739

 L   *                                                                    439
CTG TGA  agacccccaatcccaggaggagggagcgcgctcagccgggggggagggggacgatggaagaa  3808

agagacaccacccgacggcgtcgctggctgtttgctcgcgtgtgcatcttctctgtgtgtctgccgccttca  3880

tcctcctcgcacacacggctccccttccctcggtctcttccaccgatcctcgggtgggctcactgaaggtg  3952

cgcatgcctgtgcataggcacgagaatcagcgcgagagtgtgtgcgtgtgggagcgtttcgcccccgttttg  4024

tcttttttttctattgttgtttcggatctgtgctgcctctgatgtgtccgtgaaggtgtgctcggcatgcc  4096

ccctctttctctgtccctcactctctctctctcgctctgtgcactccgttgtatgtaccttagccttcttcg  4168

ttgtatggatgtggatgcgtgtgttttgtgggtctgccgctgttggtgccgcgtggcttgctcgtgtgcggc  4240

tccgtctttgagcacgatgatggattcgatcggcggcctggccacaaaagcaaccatcatcaccgggggtca  4312

ttaccgtatgggtgtgggtgtgtgcaacgaagcgtgtttccgctgtccggaaagctgcacacgcacgtgcac  4384

tcacatgctctcgcagcgctgatgtggaacagccgcgggagggcgcgcacgagtggccaatgcgagcacgaa  4456

tgagagaaggaacgagaagagtgcgaagatgaatagaaaaaaaaaaaaaaaaaaaaa  4528
```

Figure 4B (cont'd)

```
  I   I   Q                                                                    342
ATC ATC CAG taagccgctgtgctgtctcggacacgatgacgttggtgtgggtgcgtgtgtctgagagc       5704

gttgtgtggcggtcatggtgctgcagccctggtacgccgttgatagtgttctcatttggacgggagtgcagc      5776

ccgcctcctccacgtgacgctcaatgacccacccggtcactggcgcacaacatccatgtcgtgaaaagcaga      5848

tcgtcctctctcgctcttttttctttcgtgtttgcgtgcaccgatgggatgggccgcacctctcaacgcgag      5920

tgtgtgcgtgcgcgtgcgtctccgtgcaatcggtgcatcgattcttttcgtttctgagtaacagggataaga      5992

acaacaacAAAAAAAAAAAAAAAAAAAAAAAAAAAAAAAAAAAAAAAAA
```

CLONE 90 $\left(\dfrac{\text{SEQ ID No.: 60}}{\text{SEQ ID No.: 26}}\right)$ Figure 4C

```
  M   S   H   C   K   F   E   H   P   R   H   G   H   L   G   F   L   P     102
ATG TCT CAC TGC AAG TTC GAG CAC CCC CGC CAC GGC CAT CTC GGC TTC CTG CCG      5226

  R   K   R   S   R   Q   I   R   G   R   A   R   A   F   P   K   D   D     120
CGC AAG CGC TCG CGC CAG ATC CGC GGC CGT GCG CGC GCG TTC CCC AAG GAC GAC      5280

  A   T   Q   K   P   H   L   T   S   F   M   V   F   K   A   G   M   T     138
GCG ACG CAG AAG CCC CAC CTG ACG AGC TTC ATG GTG TTC AAG GCC GGT ATG ACG      5334

  H   I   V   R   D   V   D   R   P   G   S   K   V   N   K   K   E   V     156
CAC ATT GTG CGT GAT GTC GAT CGC CCT GGA TCG AAG GTG AAC AAG AAG GAA GTG      5388

  V   E   P   V   T   I   L   E   A   P   P   M   V   I   V   G   I   V     174
GTG GAG CCG GTG ACG ATC CTG GAG GCG CCG CCG ATG GTG ATT GTC GGC ATT GTG      5442

  G   Y   R   Q   T   P   V   G   L   K   T   I   G   T   V   W   A   H     192
GGC TAC CGC CAA ACG CCG GTT GGC CTG AAG ACG ATC GGC ACC GTG TGG GCG CAC      5496

  H   T   S   V   E   F   R   R   R   Y   Y   K   N   W   K   Q   S   A     210
CAC ACG AGC GTC GAG TTC CGC CGC CGC TAC TAC AAG AAC TGG AAG CAG TCT GCG      5550

  Q   L   A   F   S   R   Q   K   Q   F   A   N   T   K   E   G   K   V     228
CAA CTG GCC TTC TCC CGC CAG AAG CAG TTT GCG AAC ACG AAG GAG GGC AAG GTC      5604

  A   E   A   R   T   L   N   A   F   A   K   K   A   S   V   I   R   V     246
GCC GAG GCG CGC ACG CTG AAC GCG TTC GCG AAG AAG GCG TCC GTC ATC CGC GTG      5658

  I   A   H   T   Q   L   R   K   L   R   N   H   R   V   G   V   K   K     264
ATC GCG CAC ACG CAG CTG CGC AAG CTT CGC AAC CAC CGC GTG GGC GTG AAG AAG      5712

  A   H   V   Q   E   I   Q   V   N   G   G   S   V   A   A   K   I   A     282
GCG CAC GTG CAG GAG ATC CAG GTC AAC GGC GGC AGC GTT GCG GCG AAG ATC GCG      5766

  L   A   K   S   L   L   E   K   E   V   R   V   D   S   V   F   Q   Q     300
CTG GCC AAG TCC CTG CTG GAG AAG GAG GTG CGC GTC GAC TCC GTG TTC CAG CAG      5820

  S   E   A   C   D   V   C   S   V   T   K   G   H   G   T   E   G   V     318
TCC GAG GCG TGC GAC GTG TGC TCC GTC ACG AAA GGC CAC GGT ACG GAG GGC GTG      5874

  V   K   R   W   G   V   A   C   L   P   R   K   T   H   R   G   L   R     336
GTG AAG CGC TGG GGC GTT GCC TGC CTG CCA CGC AAG ACG CAC CGC GGT CTG CGC      5928
```

Figure 4C (cont'd)

```
K   V   A   C   I   G   A   W   H   P   A   R   V   M   Y   T   V   A     354
AAG GTT GCG TGC ATC GGC GCG TGG CAC CCT GCC CGC GTC ATG TAC ACT GTC GCG   5982

R   A   G   Q   H   G   Y   H   H   R   T   Q   L   N   K   K   I   Y     372
CGC GCC GGT CAG CAC GGT TAC CAC CAC CGC ACG CAG CTG AAC AAG AAG ATC TAC   6036

Q   I   G   R   S   V   A   V   E   P   N   Q   A   T   T   T   Y   D     390
CAG ATC GGC CGC TCC GTT GCT GTG GAG CCG AAC CAG GCG ACG ACG ACC TAC GAT   6090

L   T   A   K   T   I   T   P   M   G   G   F   V   G   Y   G   T   V     408
CTG ACA GCC AAG ACG ATC ACG CCC ATG GGT GGC TTC GTC GGC TAC GGT ACG GTG   6144

R   N   D   Y   V   M   L   K   G   S   V   S   G   P   R   R   R   V     426
CGC AAC GAC TAC GTG ATG CTG AAG GGC TCC GTG TCT GGC CCG CGC CGC CGT GTG   6198

M   T   L   R   R   P   M   A   P   Q   T   S   R   Q   L   K   E   K     444
ATG ACG CTG CGC CGC CCG ATG GCG CCG CAG ACG TCG CGC CAG CTG AAG GAG AAG   6252

I   V   L   K   F   I   D   T   S   S   K   I   G   H   G   R   F   Q     462
ATC GTG CTG AAG TTC ATC GAC ACG AGC TCG AAG ATC GGC CAC GGC CGC TTC CAG   6306

T   K   K   E   K   N   Q   W   F   G   P   L   K   K   D   R   I   R     480
ACG AAG AAG GAG AAG AAC CAG TGG TTC GGC CCG CTC AAG AAG GAC CGC ATC CGC   6360

R   E   E   R   L   R   K   E   R   A   A   R   A   V   E   R   K   A     498
CGC GAG GAG CGC CTG CGC AAG GAG CGC GCT GCC CGC GCC GTG GAG CGC AAG GCA   6414

K   A   A   K   K   *                                                     504
AAG GCC GCG AAG AAG TAA  gcatgccaacgcatgcacgccttttcgtgtaccccagcctctgcctg  6479

accttctcgcgtctgccagcgtgcgtcttgttccagcggtggcgttggttctcttcgtgtttcgtccgtgtc  6551

gctcgtgtgctcgttgtgcagggagtgatgcagtgtgtggaagtgggtggtggtacagatgccagaacggtc  6623

ttcttcgatagctgccctggcatccgcgcgtcccttgacgagagtgatctcgggtactagtgtgaatctgat  6695

tttctgtttttaacgtgttttcgatttcatttcactgaacgaaaagaaaacgaaagagtgaggtcggctgc  6767

ggagaagcatgtgaaccaacgtattgtccgtgctggggcagatccgcgacatcggctccttccacggcggcg  6839

ttgttagcgttcagcgagcgtatgccagaggaaccccgtttcagtttttagtggttcgctacggtgccgagc  6911

actcctcctttgctcctcgtcgttttgcgtgaagacggcaggttgtgctgagcatgtcagtggaacctctca  6983

agtttccttccactacatgtggactgtgaatctgcaggccaacattatgcgcgaagcaggcctcctagctgc  7055
```

Figure 5A (cont'd)

>CLONE71

```
 M   A   Q   C   V   R   R   L   V   L   G   D   A   R   R   C   G   G     18
ATG GCG CAG TGC GTG CGT CGG CTG GTG CTC GGC GAC GCT CGC CGC TGC GGT GGC    54

 A   A   A   V   H   E   Q   A   R   V   A   R   A   A   G   T   G   D     36
GCT GCT GCT GTG CAC GAG CAG GCT CGG GTG GCG CGT GCT GCT GGG ACG GGC GAC   108

 F   T   A   A   Q   R   T   N   T   L   A   V   L   Q   A   F   G   R     54
TTC ACT GCG GCG CAG CGG ACG AAC ACG CTG GCG GTG CTG CAG GCG TTT GGG CGT   162

 A   I   P   K   L   G   E   K   W   A   G   N   D   F   C   S   W   E     72
GCG ATC CCT AAG CTT GGG GAG AAG TGG GCG GGC AAC GAC TTC TGC TCG TGG GAG   216

 A   V   L   C   N   A   P   D   V   Y   V   S   G   I   S   P   T   Y     90
GCC GTC TTG TGC AAT GCG CCG GAC GTG TAC GTG TCG GGA ATC AGT CCG ACG TAT   270

 A   G   T   L   P   E   M   P   E   N   V   D   Y   R   H   V   V   I    108
GCC GGC ACG CTG CCG GAG ATG CCA GAG AAC GTC GAC TAC AGG CAC GTC GTG ATC   324

 R   R   L   D   F   S   E   M   G   P   G   L   S   G   T   V   P   A    126
AGG CGG CTC GAC TTT TCC GAA ATG GGG CCG GGG CTG AGC GGG ACC GTG CCC GCC   378

 S   W   H   S   M   T   S   L   E   S   L   S   I   E   K   C   E   S    144
TCA TGG CAC TCG ATG ACA TCT TTG GAG TCG TTG TCG ATT GAA AAG TGT GAA AGC   432

 I   S   G   S   V   P   P   E   W   G   S   M   T   S   L   S   V   L    162
ATC TCC GGC AGT GTG CCC CCC GAG TGG GGC TCG ATG ACA TCG CTG AGT GTT CTC   486

 N   L   R   G   T   G   I   S   G   T   L   P   P   Q   W   S   G   M    180
AAT CTG CGG GGC ACA GGC ATC TCC GGC ACG CTG CCG CCC CAG TGG AGT GGG ATG   540

 S   K   A   R   S   L   Q   L   Q   D   C   D   L   S   G   S   L   P    198
TCG AAG GCC CGG TCC CTG CAG CTG CAG GAC TGC GAC CTG TCC GGC AGT CTG CCC   594

 S   S   W   S   A   I   P   M   L   A   S   V   S   L   K   G   N   K    216
TCT TCG TGG TCT GCG ATA CCG ATG CTG GCT TCC GTC TCT CTT AAG GGC AAC AAG   648

 F   C   G   C   V   P   D   S   W   D   Q   K   A   G   L   V   V   D    234
TTC TGC GGG TGT GTG CCG GAC TCG TGG GAT CAG AAG GCT GGT CTT GTT GTG GAC   702

 I   E   D   K   H   K   G   S   D   C   L   A   A   K   D   C   A   T    252
ATC GAG GAC AAG CAC AAG GGC AGC GAC TGC TTG GCT GCT AAG GAC TGC GCA ACG   756

 T   T   T   K   P   S   A   T   T   A   T   T   P   N   L   T   N   F    270
ACC ACC ACT AAG CCC TCC GCC ACG ACA GCG ACC ACC CCG AAC CTC ACT AAC TTT   810

 P   P   T   P   R   T   T   T   E   P   L   T   T   T   S   T   E   A    288
CCC CCT ACG CCG AGG ACC ACG ACT GAG CCG CTT ACC ACA ACC AGC ACT GAG GCA   864

 P   A   E   P   T   T   T   T   E   A   P   A   E   P   T   T   T   A    306
CCG GCT GAA CCC ACA ACC ACC ACT GAG GCA CCG GCT GAA CCC ACG ACC ACT GCT   918

 T   P   T   N   T   P   T   P   A   P   E   T   E   C   E   V   D   G    324
ACC CCA ACA AAC ACG CCG ACT CCT GCA CCA GAG ACG GAG TGC GAG GTG GAT GGG   972

 C   E   V   C   E   G   D   S   A   A   R   C   A   R   C   R   E   D    342
TGT GAG GTG TGC GAG GGG GAC TCC GCT GCG AGG TGC GCG AGG TGC CGT GAG GAC  1026

 Y   F   L   T   D   E   K   T   C   L   K   H   N   D   G   G   V   A    360
TAC TTC CTG ACG GAC GAG AAG ACG TGC CTG AAG CAC AAC GAT GGC GGT GTT GCT  1080

 A   V   S   S   G   V   A   A   A   A   V   V   C   V   A   V   L   F    378
GCT GTG TCG AGC GGA GTG GCA GCA GCA GCT GTT GTG TGC GTG GCT GTG CTG TTC  1134

 S   V   G   L   A   A   *                                                385
AGC GTG GGG CTG GCG GCC TGA                                              1155
```

Figure 5B (cont'd)

```
AGC CGT AGC AAG TTC GAG GGC ATC ACG CAG CGG CTG ATC GAG CGG TCG ATT GCG   2326

 P   C   K   Q   C   M   K   D   A   G   V   E   L   K   E   I   N   D     356
CCG TGC AAG CAG TGC ATG AAG GAC GCT GGT GTG GAG CTG AAG GAG ATC AAC GAC   2380

 V   V   L   V   G   G   M   T   R   M   P   K   V   V   E   E   V   K     374
GTT GTG CTT GTT GGC GGC ATG ACG CGC ATG CCG AAG GTG GTG GAG GAG GTG AAG   2434

 K   F   F   Q   K   D   P   F   R   G   V   N   P   D   E   A   V   A     392
AAG TTC TTC CAG AAG GAC CCG TTC CGC GGC GTG AAC CCC GAC GAG GCT GTG GCG   2488

 L   G   A   A   T   L   G   G   V   L   R   G   K   A   S   D   L   I     410
CTT GGT GCC GCG ACG CTG GGC GGC GTG CTG CGG GGT AAG GCG AGT GAC TTG ATA   2542

 L   V   D   V   T   P   L   S   L   G   T   S   V   V   G   D   V   F     428
CTG GTG GAC GTG ACA CCG CTT TCG CTG GGC ACA AGT GTC GTC GGC GAC GTG TTC   2596

 T   R   M   I   P   K   N   T   T   I   P   C   M   R   S   H   I   F     446
ACG CGC ATG ATC CCG AAG AAC ACG ACG ATC CCG TGC ATG CGG AGC CAT ATC TTC   2650

 T   T   V   D   D   G   Q   T   A   I   K   F   K   V   F   Q   G   E     464
ACA ACG GTG GAC GAT GGT CAG ACA GCC ATC AAA TTC AAG GTG TTC CAG GGC GAG   2704

 R   E   I   A   S   E   N   Q   I   R   G   E   F   D   L   S   G   I     482
CGC GAA ATC GCC TCC GAA AAC CAG ATA AGG GGT GAG TTC GAT CTT AGC GGC ATC   2758

 P   P   A   P   R   G   V   P   Q   I   E   V   T   F   D   I   D   A     500
CCG CCC GCG CCG CGT GGG GTG CCG CAG ATC GAG GTG ACG TTC GAC ATC GAC GCG   2812

 N   G   I   C   H   V   T   A   K   D   K   A   T   G   K   T   Q   N     518
AAC GGC ATC TGC CAC GTG ACG GCG AAG GAC AAG GCG ACG GGC AAG ACG CAG AAC   2866

 I   T   I   T   A   N   G   G   L   S   K   E   Q   I   E   Q   M   I     536
ATC ACG ATC ACG GCG AAC GGC GGG CTG TCG AAG GAG CAG ATC GAG CAG ATG ATC   2920

 R   D   S   E   Q   H   A   E   A   D   R   V   K   R   E   L   V   E     554
CGC GAC TCG GAG CAG CAC GCG GAG GCC GAC CGC GTG AAG CGC GAG CTT GTG GAG   2974

 V   R   N   N   A   E   T   Q   L   T   T   A   E   R   Q   L   G   E     572
GTG CGC AAC AAC GCG GAG ACG CAG CTG ACA ACG GCG GAG AGG CAG CTC GGC GAG   3028

 W   K   Y   V   S   D   A   E   K   E   N   V   K   T   L   V   A   E     590
TGG AAG TAC GTG AGC GAT GCG GAG AAG GAG AAC GTG AAG ACG CTG GTG GCG GAG   3082

 L   R   K   A   M   E   N   P   N   V   A   K   D   D   L   A   A   A     608
CTG CGC AAG GCG ATG GAG AAC CCG AAC GTG GCG AAG GAT GAC CTT GCG GCT GCG   3136

 T   D   K   L   Q   K   A   V   M   E   C   G   R   T   E   Y   Q   Q     626
ACG GAC AAG CTG CAG AAG GCT GTG ATG GAG TGC GGC CGC ACA GAG TAC CAG CAG   3190

 A   A   A   A   N   S   G   Q   C   *                                     636
GCT GCC GCG GCC AAT TCT GGC CAG TGT TGA  ttttgagagcgaggcaacgatgtcgctgcga  3251

gcttggtgctcgtgtagatgcgggccttctttgttgttggggaaaaggacatggcgatagtgcacagccctg  3323

tttcttgtgcatgctggtatcactgacgaagtgctcgtcatgaagaggggtagacttcttcgtgtttcgggt  3395

gttgtgtcggcgcggatgcctgtggcatcgagtcctgtgtcttctttcgcgctaggcaccgccttacggtcg  3467

gctgacggccaactgaatgggatgcacctcacgtctaaaattatgaaaggctcaactggctcaccgtcaggt
```

CLONE 42 (SEQ ID No.: 63 / SEQ ID No.: 29) Figure 5C

Figure 5C (cont'd)

```
  1 matsraalca vavvcvvlav acaparaiyv gtpaaalfee fkrtyqrayg tlteeqqrla
 61 nfernlelmr ehqarnphar fgitkffdls eaefaaryln gaayfaaakq hagqhyrkar
121 adlsavpdav dwrekgavtp vknqgaggsc wafsavgnie sqwavaghkl vrlseqqlvs
181 cdhvdngcgg glmlqafewv lrpmngtvft eksypyvsgn gdvpecsnss elapgaridg
241 yvsmesserv maawlakngp lsiavdassf msyhsgvlts cigeqlnhgv llvgynmtge
301 vpywviknsw gedwgekgyv rvtmgvnacl ltgypvsvhv sqsptpgpnt tttthapkrv
361 tvkqitctdy fcrkgckttv iptkeclpng aggsfqmecg dhqvlkltyt smnctgeaky
421 tvtregkcgi swsgssksic qyv
```

CLONE42 Figure 5C (cont'd)

M A T S R A A L C A V A V V C V V L 18
ATG GCG ACG TCG AGG GCC GCT CTC TGC GCT GTT GCG GTT GTG TGC GTG GTG CTT 54

A V A C A P A R A I Y V G T P A A A 36
GCG GTT GCC TGC GCG CCC GCG CGC GCG ATA TAC GTG GGC ACG CCG GCT GCT GCG 108

L F E E F K R T Y Q R A Y G T L T E 54
CTG TTC GAG GAG TTC AAG CGG ACG TAC CAG CGC GCG TAC GGG ACG CTG ACC GAG 162

E Q Q R L A N F E R N L E L M R E H 72
GAG CAG CAG CGG CTG GCG AAC TTC GAG CGC AAC CTG GAG CTG ATG CGC GAG CAT 216

Q A R N P H A R F G I T K F F D L S 90
CAG GCG AGG AAC CCA CAC GCG AGG TTC GGG ATC ACG AAG TTC TTT GAC CTG TCG 270

E A E F A A R Y L N G A A Y F A A A 108
GAG GCG GAG TTC GCC GCG CGC TAC CTG AAC GGC GCC GCG TAC TTC GCA GCG GCG 324

K Q H A G Q H Y R K A R A D L S A V 126
AAG CAG CAC GCC GGC CAG CAC TAC CGC AAG GCG CGC GCG GAC CTG TCG GCG GTG 378

P D A V D W R E K G A V T P V K N Q 144
CCT GAT GCG GTG GAC TGG CGC GAG AAG GGC GCC GTG ACG CCG GTG AAG AAT CAG 432

G A C G S C W A F S A V G N I E S Q 162
GGT GCG TGC GGG TCG TGC TGG GCG TTC TCG GCG GTC GGC AAC ATC GAG TCG CAG 486

W A V A G H K L V R L S E Q Q L V S 180
TGG GCC GTT GCC GGC CAC AAG CTG GTG AGG CTG TCG GAG CAG CAG CTG GTG AGC 540

C D H V D N G C G G G L M L Q A F E 198
TGC GAT CAC GTG GAC AAT GGT TGC GGC GGC GGG CTG ATG TTG CAG GCA TTC GAG 594

W V L R N M N G T V F T E K S Y P Y 216
TGG GTG CTG CGA AAC ATG AAC GGG ACC GTG TTC ACG GAG AAG AGC TAC CCC TAC 648

V S G N G D V P E C S N S S E L A P 234
GTC TCC GGC AAC GGT GAT GTG CCC GAG TGC TCG AAC AGC AGT GAA CTC GCT CCC 702

G A R I D G Y V S M E S S E R V M A 252
GGT GCG CGA ATC GAC GGG TAC GTG TCG ATG GAA AGC AGC GAA AGA GTT ATG GCT 756

A W L A K N G P I S I A V D A S S F 270
GCG TGG CTT GCG AAG AAT GGC CCC ATC TCG ATT GCG GTC GAC GCC AGC TCC TTT 810

M S Y H S G V L T S C I G E Q L N H 288
ATG TCT TAC CAT AGC GGC GTC CTG ACC AGC TGC ATT GGT GAG CAG CTG AAC CAT 864

G V L L V G Y N M T G E V P Y W V I 306
GGC GTG CTG CTC GTT GGG TAC AAC ATG ACT GGT GAG GTT CCG TAC TGG GTG ATC 918

K N S W G E D W G E K G Y V R V T M 324
AAG AAC TCG TGG GGT GAG GAC TGG GGC GAG AAG GGC TAC GTG CGC GTG ACC ATG 972

G V N A C L L T G Y P V S V H V S Q 342
GGG GTG AAC GCG TGC CTG CTC ACT GGG TAC CCC GTG TCC GTG CAT GTG TCG CAG 1026

S P T P G P N T T T T T H A P K R V 360
AGC CCC ACC CCT GGC CCA AAC ACG ACC ACC ACG ACG CAC GCT CCT AAA CGG GTG 1080

T V K Q I T C T D Y F C R K G C K T 378
ACG GTG AAG CAG ATC ACC TGC ACG GAT TAT TTC TGC CGA AAG GGG TGC AAG ACG 1134

T V I P T K E C L P N G A G G S F Q 396
ACG GTG ATC CCC ACG AAA GAG TGC CTG CCG AAC GGG GCA GGC GGC TCT TTT CAG 1188

```
 M   E   C   G   D   H   Q   V   L   K   L   T   Y   T   S   M   N   C     414
ATG GAG TGC GGT GAC CAT CAG GTG TTG AAG CTC ACC TAC ACC TCC ATG AAT TGC   1242

 T   G   E   A   K   Y   T   V   T   R   E   G   K   C   G   I   S   W     432
ACT GGT GAG GCC AAG TAT ACG GTG ACA AGG GAG GGT AAG TGC GGG ATA TCG TGG   1296

 S   G   S   S   K   S   I   C   Q   Y   V   *                             444
TCC GGC TCG AGC AAG AGC ATT TGC CAG TAC GTG TAG                           1332
```

```
 D   K   E   N   W   C   V   M   L   E   R   C   *                          341
GAC AAG GAG AAT TGG TGT GTG ATG CTG GAG CGC TGT TGA  cgtcgaagtgaagggtgtg  2032

gcgactcgaacgccgcctgagatggacaacattgtgcctgtgggttttgcatgcgcctcttagccttattc  2104

gtctacacccatctgcttggccctttcatcttgagtaataagtaggtccacctcgtcttcacaggcgcattg  2176

taaagttgcgcgcgggcattatcggggaagccgacgtgtcatcgatgtcgaggcttgcgttgacatcacccc  2248

cttccttctttgccgcgccttcgcagacggtgacggggaatggccaccgctacgagagtgaaagaaggcagc  2320

agcagagccgagaaaaaaaaaaaaaaaa                                              2349
```

CLONE 21 (SEQ ID No.: 65 / SEQ ID No.: 31) Figure 5E

```
naagaattttncaccagatcagtttctgtactttattgaagacctttgaaccaacgctactaaccaaagcac    72

acacgtctactactttttcttccttccacgttttctgtttgccctccgattctcgctcaaggngcgtacatc   144

                                                     M   A   T   T         4
accctctcctttcacgcgctcgactttcctttcacccccctccccgtgtaaacc ATG GCC ACC ACG   210

 Y   E   E   F   S   A   K   L   D   R   L   D   E   E   F   N   R   K     22
TAC GAG GAG TTC TCG GCG AAG CTG GAC CGC CTG GAT GAG GAG TTC AAC AGG AAG   264

 M   Q   E   Q   N   A   K   F   F   A   D   K   P   D   E   S   T   L     40
ATG CAG GAA CAG AAC GCC AAG TTC TTT GCG GAC AAG CCG GAT GAG TCG ACG CTG   318

 S   P   E   M   K   E   H   Y   E   K   F   E   R   M   I   K   E   H     58
TCG CCC GAG ATG AAG GAG CAC TAC GAG AAG TTC GAG CGC ATG ATC AAG GAG CAC   372

 T   E   K   F   N   K   K   M   H   E   H   S   E   H   F   K   Q   K     76
ACA GAG AAG TTC AAC AAG AAG ATG CAC GAG CAC TCG GAG CAC TTC AAG CAG AAG   426

 F   A   E   L   L   E   Q   Q   K   A   A   Q   Y   P   S   K             92
TTC GCC GAG CTG CTC GAG CAG CAG AAG GCT GCG CAG TAC CCG TCC AAG  taagaca  481
```

CLONE 57 (SEQ ID No.: 66 / SEQ ID No.: 32) Figure 5F

```
                                  M   P   A   D   K   S   Y   A   L        9
gtcaccccggttagagtgaaagcatcagcccatc ATG CCC GCT GAC AAG AGC TAC GCG CTG   1357

 K   Q   V   Q   T   F   G   K   K   K   T   A   I   A   V   A   T   V     27
```

```
                AAG CAG GTG CAG ACC TTC GGC AAG AAG AAG ACG GCA ATC GCC GTG GCC ACG GTC   1411
   T   K   A   A   Q   C   N   I   K   V   N   G   V   P   L   Q   Q   I    45
  ACC AAG GCT GCC CAG TGC AAC ATC AAG GTG AAC GGT GTG CCG CTG CAG CAG ATC   1465
   L   P   D   T   L   R   A   K   I   M   E   A   I   T   V   V   G   S    63
  CTG CCC GAT ACG CTG CGC GCG AAG ATC ATG GAG GCC ATC ACC GTG GTG GGA TCC   1519
   K   Y   Y   S   R   L   R   I   D   V   A   V   H   G   G   G   Q   V    81
  AAG TAC TAC TCG CGG CTG CGC ATC GAT GTG GCG GTG CAC GGT GGC GGC CAG GTG   1573
   S   Q   A   Y   A   A   R   Q   A   I   A   K   G   L   I   A   F   F    99
  TCG CAG GCG TAC GCC GCG CGC CAG GCG ATC GCG AAG GGC CTC ATT GCG TTC TTT   1627
   Q   K   Y   H   N   E   V   E   K   A   A   L   K   D   K   F   L   A   117
  CAG AAG TAC CAC AAC GAG GTG GAG AAG GCC GCG CTG AAG GAC AAG TTC CTG GCG   1681
   Y   D   K   F   L   L   I   A   D   P   R   R   C   E   P   K   K   W   135
  TAC GAC AAG TTC CTG CTC ATC GCC GAT CCC CGC CGC TGC GAG CCG AAG AAG TGG   1735
   G   R   H   S   A   R   T   R   F   T   K   S   Y   R                   149
  GGT CGC CAC TCT GCC CGC ACA CGC TTC ACC AAG TCC TAC CGG taagctcatgtacgt   1792
ctggggtttgcatgcgcgtgcgcatgtgcatgcgtctggctgcttgctcgtgtgcggctgatccgtcgatgc   1864
tgcacggacagggcacaacgcattgccactgtatgggacacacatgcgcacgcacatgcacctcgcacgctg   1936
cttaggatgtggagagatcgtgcatggcagtcatcgcggctgggttttttgtatgcgtctgtgcgcgagcgcg   2008
tgcgtgtgccagcggatccgtgtcttgttagccgtgaccagcatgcatcgctccgcatccctctccgcaca   2080
gacggtccactgggtgccaccgcagaccgtcagtcagtcggttacgtacgggctcttcgtaattttccttt   2152
ccctgacattattttgttccgcacataagcacatcacacagcctacacacacacacacctacacgcatgatg   2224
tacgtgtgtgtgtgtgcgacggaggcgtgcgctggcctaggcgtcagtgacttcgtgcagcatgcgccat    2296
```

CLONE 74 $\left(\dfrac{\text{SEQ ID No.: 67}}{\text{SEQ ID No.: 33}}\right)$  Figure 5G

```
gcgccgcacccctcctctgcaccacctccgccgcactctcctctctctcctctctgtcctctccctcggtct  2160
 ctcctcccaccaccggcacacgccgcccccgcttgcctgcccgccgcgcgcagataaccagctcgctatcta  2232
                                       M   G   K   D   K   V   H   M   N   L   V   V   12
  acatcacgctctccgctattcacc ATG GGC AAG GAT AAG GTG CAC ATG AAC CTT GTG GTC  2292
   V   G   H   V   D   A   G   K   S   T   A   T   G   H   L   I   Y   K    30
  GTC GGC CAT GTC GAC GCC GGC AAG TCC ACC GCC ACT GGC CAC TTG ATC TAC AAG   2346
   C   G   G   I   D   K   R   T   I   E   K   F   E   K   E   A   A   E    48
  TGC GGT GGC ATC GAC AAG CGC ACG ATC GAG AAG TTC GAG AAG GAG GCC GCC GAG   2400
   I   G   K   A   S   F   K   Y   A   W   V   L   D   K   L   K   A   E    66
  ATC GGC AAG GCG TCC TTC AAG TAC GCG TGG GTG CTC GAC AAG CTG AAG GCG GAG   2454
   R   E   R   G   I   T   I   D   I   A   L   W   K   F   E   S   P   K    84
  CGC GAG CGC GGC ATC ACG ATC GAC ATT GCG CTG TGG AAG TTC GAG TCG CCC AAG   2508
   S   V   F   T   I   I   D   A   P   G   H   R   D   F   I   K   N   M   102
  TCC GTG TTC ACG ATC ATC GAT GCG CCC GGC CAC CGC GAC TTC ATC AAG AAC ATG   2562
```

Figure 5G (cont'd)

I T G T S Q A D A A I L M I D S T H 120
ATC ACG GGC ACG TCG CAG GCG GAC GCC GCC ATT CTG ATG ATC GAC TCG ACG CAT 2616

G G F E A G I S K D G Q T R E H A L 138
GGC GGC TTC GAG GCT GGC ATC TCG AAG GAC GGC CAG ACC CGC GAG CAC GCG CTG 2670

L A F T L G V K Q M V V C C N K M D 156
CTT GCC TTC ACT CTT GGC GTG AAG CAG ATG GTG GTG TGC TGC AAC AAG ATG GAC 2724

D K T V T Y A Q S R Y D E I S K E V 174
GAC AAG ACG GTG ACG TAC GCG CAG TCA CGC TAC GAT GAG ATC AGC AAG GAG GTG 2778

G A Y L K R V G Y N P E K V R F I P 192
GGC GCG TAC CTG AAG CGC GTG GGC TAC AAC CCG GAG AAG GTG CGC TTC ATC CCG 2832

I S G W Q G D N M I E K S D N M P W 210
ATC TCG GGC TGG CAG GGC GAC AAC ATG ATC GAG AAG TCG GAC AAC ATG CCG TGG 2886

Y K G P T L L D A L G M L E P P V R 228
TAC AAG GGT CCC ACG CTG CTG GAC GCG CTC GGC ATG CTG GAG CCG CCG GTG CGC 2940

P V D K P L R L P L Q D V Y K I G G 246
CCG GTG GAC AAG CCG CTG CGC CTG CCC CTG CAG GAC GTG TAC AAG ATC GGC GGT 2994

I G T V P V G R V E T G I M K P G D 264
ATC GGG ACG GTG CCC GTG GGC CGC GTG GAG ACC GGC ATC ATG AAG CCG GGC GAC 3048

V V T F A P A N V T T E V K S I E M 282
GTG GTG ACG TTC GCG CCC GCC AAC GTG ACG ACT GAG GTG AAG TCG ATC GAG ATG 3102

H H E Q L A E A Q P G D N V G F N V 300
CAC CAC GAG CAG CTG GCG GAG GCG CAG CCC GGC GAC AAC GTC GGC TTC AAC GTG 3156

K N V S V K D I R R G N V C G N S K 318
AAG AAC GTG TCG GTG AAG GAC ATC CGC CGT GGT AAC GTG TGC GGC AAC TCG AAG 3210

N D P P K E A A D F T A Q V I V L N 336
AAC GAC CCG CCG AAG GAG GCG GCC GAC TTC ACG GCG CAG GTG ATC GTG CTG AAC 3264

H P G Q I S N G Y A P V L D C H T S 354
CAC CCC GGC CAG ATC AGC AAC GGC TAT GCG CCG GTG CTG GAC TGC CAC ACG AGC 3318

H I A C R F A E I E S K I D R R S G 372
CAC ATT GCG TGC CGC TTC GCG GAA ATC GAG TCC AAG ATC GAC CGC CGC TCC GGC 3372

K E L E K N P K A I K S G D A A I V 390
AAG GAG CTG GAG AAG AAC CCC AAG GCG ATC AAG TCT GGC GAT GCC GCG ATC GTG 3426

K M V P Q K P M C V E V F N D Y A P 408
AAG ATG GTG CCG CAG AAG CCG ATG TGC GTG GAG GTG TTC AAC GAC TAC GCG CCG 3480

L G R F A V R D M R Q T V A V G I I 426
CTG GGC CGC TTT GCC GTG CGC GAC ATG CGC CAG ACG GTG GCC GTG GGC ATC ATC 3534

K G V N K K E G S G G K V T K A A A 444
AAG GGC GTG AAC AAG AAG GAG GGC AGC GGC GGT AAG GTG ACC AAG GCG GCC GCG 3588

K A S K K * 450
AAG GCT TCG AAG AAG TAA gcgtgcggtgctccgccgcccgcgccccctccctccaccccctttctt 3653 ttcgcttgtatccctcccccacgcgtcccgcggggcctctcctcttttcccccaaacccacgcacgcccacg 3725 cccacgccccctctctctctctttcgatatatatgcgtgtgcgcttcagcgttatataactcctgttgtta 3797

Figure 5G (cont'd)

```
tgtgcacttaggtgtggagaggctttagctagtggcctacgctgcggtagaggtctcggtgtcgagtgctgt  3869
gtttgtggg                                                                 3878
```

CLONE 13 (SEQ ID No.: 34 / SEQ ID No.: 68)

Figure 5H

```
ttccttttcgttttgcaaagaaaa ATG CAG CGC TCA TTC CTT GTT TTT GTT CTG TGC GCC  276
                          M   Q   R   S   F   L   V   F   V   L   C   A    12

CTT CTC TTC TGC GTC GCG TCC GCA GAG GTG CAG GTG GCC ACT AAG GAC AAC TTT  330
 L   L   F   C   V   A   S   A   E   V   Q   V   A   T   K   D   N   F    30
```

Figure 5H (cont'd)

```
GAC AAG GTC GTA ATC GGG GAT CTC ACG TTG GTC AAG TTT TAT GCT CCG TGG TGC   384
 D   K   V   V   I   G   D   L   T   L   V   K   F   Y   A   P   W   C     48

GGC CAC TGC AAG ACA CTC GCC CCG GAG TTT GTA AAG GCC GCT GAC ATG CTG GCC   438
 G   H   C   K   T   L   A   P   E   F   V   K   A   A   D   M   L   A     66

GGC ATC GCG ACC CTT GCA GAG GTC GAT TGC ACC AAA GAA GAG AGC CTT GCT GAG   492
 G   I   A   T   L   A   E   V   D   C   T   K   E   E   S   L   A   E     84

AAG TAC GAA ATC AAG GGG TTC CCC ACG CTG TAC ATC TTC CGT AAC GGT GAG AAA   546
 K   Y   E   I   K   G   F   P   T   L   Y   I   F   R   N   G   E   K    102

GTG AAG ATC TAC GAT GGT CCC CGC ACT GCC GCC GGC ATC GCG TCG TAC ATG AAG   600
 V   K   I   Y   D   G   P   R   T   A   A   G   I   A   S   Y   M   K    120

GCG CAT GTC GGT CCA TCG ATG AAG GCC ATC TCA ACG GCT GAA GAG CTG GAG GAG   654
 A   H   V   G   P   S   M   K   A   I   S   T   A   E   E   L   E   E    138

CTC AAG AAG GAG ACT TTC CCG GTG TGC GTG GTG AAG ACA GCG AGC ACC GAC TCG   708
 L   K   K   E   T   F   P   V   C   V   V   K   T   A   S   T   D   S    156

GAG ATG GCG TCG ATG ATA ACC AAG GTG GCG GAC TCT CTC CGC TCG CAG ATG AAC   762
 E   M   A   S   M   I   T   K   V   A   D   S   L   R   S   Q   M   N    174

TTT GTG CTC GTG ACG GAT GCG GCC ATC TCT CCG AAT GAT GCC ATG GAG TCG GTT   816
 F   V   L   V   T   D   A   A   I   S   P   N   D   A   M   E   S   V    192

ACG GTG TAT CGC AAG AAT GCG GAG CGC GAG GCG TAC ACC GGC GCT ACA CCA ATG   870
 T   V   Y   R   K   N   A   E   R   E   A   Y   T   G   A   T   P   M    210

ACG GCA GAG TCG GTG AAG AGC TTT CTC ACG AGT GCT GTG TTG GAC TAC TTT GGC   924
 T   A   E   S   V   K   S   F   L   T   S   A   V   L   D   Y   F   G    228

GAG CTC GGC CAG GAG AGC TTT CAG AAG TAC ATG GAA GCG AAC AAG GAT AAA CCT   978
 E   L   G   Q   E   S   F   Q   K   Y   M   E   A   N   K   D   K   P    246

CTT GGG TGG GTG TTC ATC GAC AAG AAC ACG GAT TCT GCG TTG AAG GGG TCA CTT  1032
 L   G   W   V   F   I   D   K   N   T   D   S   A   L   K   G   S   L    264

GTG GCG GTG GCG GAG AAG TAC CGC TCG CAG GTG TTG CTA ACC TAC ATT GAC GGC  1086
 V   A   V   A   E   K   Y   R   S   Q   V   L   L   T   Y   I   D   G    282

GAT CAG TAC CGC CCC GTC TCG CGC CAG CTG GGC ATT CCT GAG GAT GCG AAG TTC  1140
 D   Q   Y   R   P   V   S   R   Q   L   G   I   P   E   D   A   K   F    300

CCG GCG TTT GTG GTC GAT TTC GAG CGC CGC CAT CAC GTG ATG GGG ACG GAC ACC  1194
 P   A   F   V   V   D   F   E   R   R   H   H   V   M   G   T   D   T    318

CCA GTC ACC TCC GAG TCT GTC GCT GCG TTT GTG GAG AAG TAT GTC AAG GGC GAG  1248
 P   V   T   S   E   S   V   A   A   F   V   E   K   Y   V   K   G   E    336

ACG AAG CAG ACC GTG ATG TCC GAC GCG ATT CCC GCT AAG GAG ACG GTG AAC GGC  1302
 T   K   Q   T   V   M   S   D   A   I   P   A   K   E   T   V   N   G    354

CTC ACA ACG GTG GTG GGT CAG ACT TTT GCG AAG TAC ACG GAC GGC ACA CAA AAC  1356
 L   T   T   V   V   G   Q   T   F   A   K   Y   T   D   G   T   Q   N    372

GTG ATG CTG CTC TTC TAC GCG CCG TGG TGC GGA CAC TGC AAG AAG CTG CAC CCC  1410
 V   M   L   L   F   Y   A   P   W   C   G   H   C   K   K   L   H   P    390

GTC TAC GAT AAA GTA GCC AAG AGC TTC GAG TCT GAG AAT GTG ATC ATT GCG AAG  1464
 V   Y   D   K   V   A   K   S   F   E   S   E   N   V   I   I   A   K    408

ATG GAT GCC ACG ACG AAC GAC TTT GAC CGC GAG AAG TTT GAG GTG TCT GGA TTT  1518
```

```
M   D   A   T   T   N   D   F   D   R   E   K   F   E   V   S   G   F    426

CCA ACG ATT TAC TTC ATC CCA GCC GGC AAG CCG CCA ATC GTG TAC GAG GGT GGC  1572
 P   T   I   Y   F   I   P   A   G   K   P   P   I   V   Y   E   G   G    444

CGC ACC GCA GAC GAA ATC CAG GTG TTT GTG AAG TCT CAC CTG ACC GCC TCC GCC  1626
 R   T   A   D   E   I   Q   V   F   V   K   S   H   L   T   A   S   A    462

GCT CCA TCT GGC GGC CCT TCC GGC AAC AGC GAA GAG GAA GAT TTG TAG  gactgca 1681
 A   P   S   G   G   P   S   G   N   S   E   E   E   D   L   *            478

agggatgtggcgtttataggctgccctgccttcccttgctgtttctatgacggattaggcttttttttgtta 1753

tatgtggggtggtcaagagagtgccagggctccttctttatatccttgcgctttcttttattttgcttcctt 1825

gtgttgacgtctatgcatgcgtgctgtcgacgactctttgtcaacctgcgtcctatctagtagcatcgatgt 1897

gaaaagaagagtagagggaggtaacgatgcgtgcgctggctgccgttttcatgggcgcaatttcgagaagga 1969

aaatcggaaaatggacaggatagcgaaattagcgcaacgacaaggtcgtgcgtctttctctatcggtcatta 2041

aatttctgggctttgtaacaatgaaagaagtcacacaaaaaaaaaaaaaaaaa                    2094
```

POLYPEPTIDES OF *LEISHMANIA MAJOR* AND POLYNUCLEOTIDES ENCODING SAME AND VACCINAL, THERAPEUTICAL AND DIAGNOSTIC APPLICATIONS THEREOF

FIELD OF THE INVENTION

The present invention relates to new proteins of *Leishmania major* and to therapeutical and diagnostic applications thereof. More particularly, the present invention relates to excreted/secreted polypeptides and polynucleotides encoding same, compositions comprising the same, and methods of diagnosis, vaccination and treatment of Leishmaniasis.

BRIEF DESCRIPTION OF THE PRIOR ART

The leishmaniases are a heterogeneous group of diseases that affect millions of people in tropical and subtropical areas of the world [Desjeux, 1996]. Depending on *Leishmania* species involved and the immunological status of the human host, the disease ranges from asymptomatic infections to self-limiting cutaneous lesion(s) or fatal visceral forms. During their life cycle, parasites alternate between two stages: flagellated promastigotes in the midgut of the insect vector and amastigotes in the host macrophage [Alexander, 1992; Handman, 1999]. At this later stage, *Leishmania* parasites are sequestered and resist in the phagolysosome, originated from the fusion of phagosomes with lysosomes [Handman, 1999; Duclos and Desjardins, 2000; Sacks, 2001; Amer and Swanson, 2002; Cunningham, 2002].

Over the past decades, several molecules playing a key role either in the biology of the parasite or as target for antibody or cellular responses have been identified. Previous observations indicate that excreted molecules from intracellular pathogens such as *Mycobacterium tuberculosis* and *Toxoplasma gondii* contain antigens that are highly immunogenic and protective in vaccine models [Prigione, 2000; Mustafa, 2002; Daryani, 2003; Pym, 2003; Shams, 2004]. Similarly, *Leishmania* promastigote culture filtrate proteins also elicit strong immunity and protection in *L. major* BALB/c infection [Webb, 1998; Mendez, 2002]. However, there is no data on the secreted/excreted molecules from the amastigote stage of the parasite, the invading form that disseminate in the mammalian host. Due to their location, antigens secreted/excreted by *Leishmania* amastigotes are of high importance, partly due to their capacity to generate peptides that can be loaded onto CMH class I or II molecules and may serve as an interesting target for cellular immune responses. On the contrary, molecules released into the *Leishmania* phagosome may also subvert the presentation machinery associated with endoplasmic reticulum-mediated phagocytosis, which may represent an immune evasion strategy to avoid cellular immune response.

In an effort to attempt to identify new secreted/excreted molecules of *Leishmania major* parasite, we used culture supernatants of stationary phase promastigotes cultivated during 8 hours in serum-free medium, at pH and temperature that mimic the phagosome conditions, to immunize mice. Immune sera were then used to screen a cDNA expression library of *L. major*. A total of 34 different clones were isolated and sequenced. 21 percent of molecules exhibit significant sequence homology to a group of secreted proteins. The others are not described and constitute new sequences. Some of these proteins are logical candidates for analysis as potential vaccine components or drug targets.

There is therefore a need in the art for new HIV treatments or vaccines that elicit a broad, long-lasting and neutralizing immune response. There is also a need to provide for new diagnostic and immunomonitoring methods with regards to HIV infections.

SUMMARY

The present invention satisfies at least one of the above-mentioned needs.

More specifically, an object of the invention concerns an isolated polynucleotide comprising a sequence encoding an excreted/secreted polypeptide of *Leishmania major*, said sequence comprising a nucleotide sequence substantially identical to a sequence selected from the group consisting of SEQ ID NOS 1 to 34 and functional fragments thereof.

Other objects of the invention concern an isolated or purified excreted/secreted polypeptide of *Leishmania major*, said polypeptide comprising an amino acid sequence substantially identical to a sequence selected from the group consisting of SEQ ID NOS: 35 to 68 and functional derivatives thereof.

Still another object of the invention is to provide an immunogenic composition generating an immune response against a leishmaniasis, comprising a polynucleotide of the invention or a polypeptide of the invention, and an acceptable carrier.

Yet another object of the invention concerns a vaccine composition generating a protecting response against a leishmaniasis, comprising a polynucleotide of the invention or a polypeptide of the invention, and an acceptable carrier.

Yet another object of the invention concerns an antibody obtainable by the immunization of an animal with a polypeptide of the invention.

Yet another object of the invention concerns an expression or a cloning vector containing a polynucleotide of the invention.

Yet another object of the invention concerns a method for preventing and/or treating a patient against an infection with a *Leishmania major* strain, the method comprising the step of administering to the patient a therapeutically effective amount of a composition of the invention or of an antibody of the invention Yet another object of the invention concerns a method for identifying an excreted/secreted polypeptide of a *Leishmania major* strain, comprising in vitro cultivating *Leishmania* promastigotes under pH and temperature conditions naturally found in a host cell infected by a *Leishmania major* strain.

Yet another object of the invention concerns an in vitro diagnostic method for the detection of the presence or absence of antibodies indicative of a *Leishmania major* strain, which bind to a polypeptide of the invention to form an immune complex, comprising the steps of a) contacting said polypeptide with a biological sample for a time and under conditions sufficient to form an immune complex; and b) detecting the presence or absence of the immune complex formed in a).

A further object of the invention concerns a diagnostic kit for the detection of the presence or absence of antibodies indicative of a *Leishmania major* strain, comprising:

a polypeptide of the invention;

a reagent to detect polypeptide-antibody immune complex;

optionally a biological reference sample lacking antibodies that immunologically bind with said peptide; and optionally a comparison sample comprising antibodies which can specifically bind to said peptide;

wherein said polypeptide, reagent, biological reference sample, and comparison sample are present in an amount sufficient to perform said detection.

A further object of the invention concerns an in vitro diagnostic method for the detection of the presence or absence of polypeptides indicative of a *Leishmania major* strain, which bind to an antibody of the invention to form an immune complex, comprising the steps of:

a) contacting said antibody with a biological sample for a time and under conditions sufficient to form an immune complex; and b) detecting the presence or absence of the immune complex formed in a).

A further object of the invention concerns a diagnostic kit for the detection of the presence or absence of polypeptides indicative of a *Leishmania major* strain, comprising:

an antibody of the invention;

a reagent to detect polypeptide-antibody immune complex;

optionally a biological reference sample lacking polypeptides that immunologically bind with said antibody; and optionally a comparison sample comprising polypeptides which can specifically bind to said antibody;

wherein said antibody, reagent, biological reference sample, and comparison sample are present in an amount sufficient to perform said detection.

A further object of the invention concerns a genetically modified *Leishmania* strain comprising at least one gene having a sequence comprising a nucleotide sequence substantially identical to a sequence selected from the group consisting of SEQ ID NOS 1 to 34, and wherein said at least one gene is underexpressed compared to a corresponding gene of a wild-type strain of *Leishmania.*

A further object of the invention concerns a genetically modified *Leishmania* strain comprising at least one gene having a sequence comprising a nucleotide sequence substantially identical to a sequence selected from the group consisting of SEQ ID NOS 1 to 34, and wherein said at least one gene is inactivated.

A further object of the invention concerns a method for detecting the presence or absence of lymphocytic stimulation in a subject suspected of Leishmaniasis, comprising the steps of:

a) obtaining a sample containing T Lymphocytes from said subject;

b) contacting the T lymphocytes with a polypeptide of the invention; and c) detecting the presence or absence of a proliferative response of said T lymphocyte to the polypeptide.

A further object of the invention concerns a method for detecting the presence or absence of lymphocytic stimulation in a subject suspected of Leishmaniasis, comprising the steps of:

a) obtaining a sample containing T Lymphocytes from said subject;

b) contacting the T lymphocytes with a polypeptide of the invention; and c) detecting the presence or absence of cytokines indicative of lymphocytic stimulation.

BRIEF DESCRIPTION OF THE FIGURES

FIG. 2A depicts the amino acid sequence (SEQ ID NO: 35) and the nucleotide sequence (SEQ ID NO: 1) for clone 9.1.

FIG. 2B depicts the amino acid sequence (SEQ ID NO: 36) and the nucleotide sequence (SEQ ID NO: 2) for clone 15.

FIG. 2C depicts the amino acid sequence (SEQ ID NO: 37) and the nucleotide sequence (SEQ ID NO: 3) for clone 20.2.

FIG. 2D depicts the amino acid sequence (SEQ ID NO: 38) and the nucleotide sequence (SEQ ID NO: 4) for clone 22.

FIG. 2E depicts the amino acid sequence (SEQ ID NO: 39) and the nucleotide sequence (SEQ ID NO: 5) for clone 22.S.

FIG. 2F depicts the amino acid sequence (SEQ ID NO: 40) and the nucleotide sequence (SEQ ID NO: 6) for clone 23.

FIG. 2G depicts the amino acid sequence (SEQ ID NO: 41) and the nucleotide sequence (SEQ ID NO: 7) for clone 27.

FIG. 2H depicts the amino acid sequence (SEQ ID NO: 42) and the nucleotide sequence (SEQ ID NO: 8) for clone 31.

FIG. 2I depicts the amino acid sequence (SEQ ID NO: 43) and the nucleotide sequence (SEQ ID NO: 9) for clone 37.

FIG. 2J depicts the amino acid sequence (SEQ ID NO: 44) and the nucleotide sequence (SEQ ID NO: 10) for clone 38.

FIG. 2K depicts the amino acid sequence (SEQ ID NO: 45) and the nucleotide sequence (SEQ ID NO: 11) for clone 66.

FIG. 2L depicts the amino acid sequence (SEQ ID NO: 46) and the nucleotide sequence (SEQ ID NO: 12) for clone 72.

FIG. 2M depicts the amino acid sequence (SEQ ID NO: 47) and the nucleotide sequence (SEQ ID NO: 13) for clone 78.

FIG. 3A depicts the amino acid sequence (SEQ ID NO: 48) and the nucleotide sequence (SEQ ID NO: 14) for clone 9.2.

FIG. 3B depicts the amino acid sequence (SEQ ID NO: 49) and the nucleotide sequence (SEQ ID NO: 15) for clone 11.

FIG. 3C depicts the amino acid sequence (SEQ ID NO: 50) and the nucleotide sequence (SEQ ID NO: 16) for clone 12.

FIG. 3D depicts the amino acid sequence (SEQ ID NO: 51) and the nucleotide sequence (SEQ ID NO: 17) for clone 20.1.

FIG. 3E depicts the amino acid sequence (SEQ ID NO: 52) and the nucleotide sequence (SEQ ID NO: 18) for clone 20.3.

FIG. 3F depicts the amino acid sequence (SEQ ID NO: 53) and the nucleotide sequence (SEQ ID NO: 19) for clone 22.1.

FIG. 3G depicts the amino acid sequence (SEQ ID NO: 54) and the nucleotide sequence (SEQ ID NO: 20) for clone 26.

FIG. 3H depicts the amino acid sequence (SEQ ID NO: 55) and the nucleotide sequence (SEQ ID NO: 21) for clone 59.

FIG. 3I depicts the amino acid sequence (SEQ ID NO: 56) and the nucleotide sequence (SEQ ID NO: 22) for clone 65.

FIG. 3J depicts the amino acid sequence (SEQ ID NO: 57) and the nucleotide sequence (SEQ ID NO: 23) for clone 77.

FIG. 4A depicts the amino acid sequence (SEQ ID NO: 58) and the nucleotide sequence (SEQ ID NO: 24) for clone 39.

FIG. 4B depicts the amino acid sequence (SEQ ID NO: 59) and the nucleotide sequence (SEQ ID NO: 25) for clone 68.

FIG. 4C depicts the amino acid sequence (SEQ ID NO: 60) and the nucleotide sequence (SEQ ID NO: 26) for clone 90.

FIG. 5A depicts the amino acid sequence (SEQ ID NO: 61) and the nucleotide sequence (SEQ ID NO: 27) for clone 71.

FIG. 5B depicts the amino acid sequence (SEQ ID NO: 62) and the nucleotide sequence (SEQ ID NO: 28) for clone 32.

FIG. 5C depicts the amino acid sequence (SEQ ID NO: 63) and the nucleotide sequence (SEQ ID NO: 29) for clone 42.

FIG. 5D depicts the amino acid sequence (SEQ ID NO: 64) and the nucleotide sequence (SEQ ID NO: 30) for clone 8.2.

FIG. 5E depicts the amino acid sequence (SEQ ID NO: 65) and the nucleotide sequence (SEQ ID NO: 31) for clone 21.

FIG. 5F depicts the amino acid sequence (SEQ ID NO: 66) and the nucleotide sequence (SEQ ID NO: 32) for clone 57.

FIG. 5G depicts the amino acid sequence (SEQ ID NO: 67) and the nucleotide sequence (SEQ ID NO: 33) for clone 74.

FIG. 5H depicts the amino acid sequence (SEQ ID NO: 68) and the nucleotide sequence (SEQ ID NO: 34) for clone 13.

DETAILED DESCRIPTION OF THE INVENTION

Figure 1:
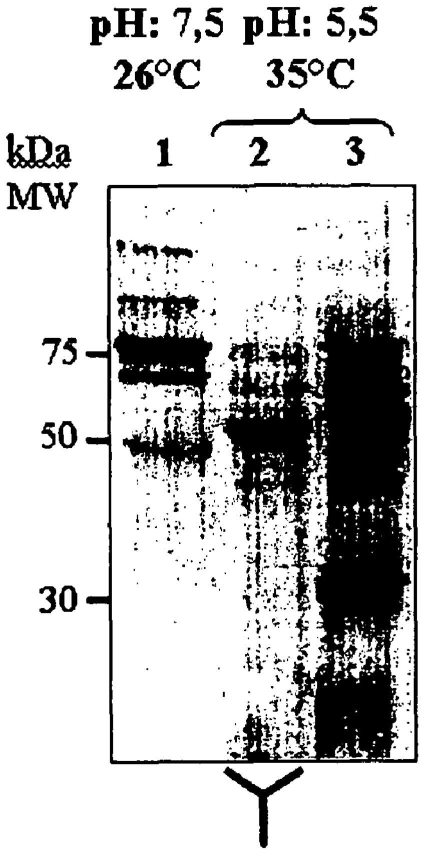
FIG. 1 shows a SDS-PAGE illustrating excreted/secreted proteins of *Leishmania major* under different culture conditions.

The present invention is directed to excreted/secreted polypeptides of *Leishmania major* and polynucleotide encoding same and their use in the preparation of compositions and vaccines. More specifically, the present invention is concerned with compositions, vaccines and methods for providing an immune response and/or a protective immunity to mammals against a *Leishmania major* strain as well as methods for the diagnosis of a Leishmaniasis. The term "leishmaniasis" means an infection caused by any of the flagellate protozoans of the genus *Leishmania*, such as *Leishmania major.*

As used herein, the term "excreted/secreted polypeptide" of a *Leishmania major* strain refers to a polypeptide which is first synthetized into the parasite and then released into the extracellular medium by a secretion or excretion mechanism.

As used herein, the term "immune response" refers to the T cell response or the increased serum levels of antibodies to an antigen, or presence of neutralizing antibodies to an antigen, such as a *Leishmania major* protein. The term "immune response" is to be understood as including a humoral response and a cellular response.

The term "protection" or "protective immunity" refers herein to the ability of the serum antibodies and/or cellular response induced during immunization to protect (partially or totally) against Leishmaniasis caused by an infectious agent, such as *Leishmania major*. Thus, a mammal immunized by the compositions or vaccines of the invention will experience limited growth and spread of an infectious *Leishmania major.*

As used herein, the term "mammal" refers to any mammal that is susceptible to be infected by a *Leishmania major* strain. Among the mammals which are known to be potentially infected by *Leishmania major*, there are particularly humans.

1. Polynucleotides and Polypeptides

In a first embodiment, the present invention concerns an isolated polynucleotide comprising a sequence encoding an excreted/secreted polypeptide of *Leishmania major*, said sequence comprising a nucleotide sequence substantially identical to a sequence selected from the group consisting of SEQ ID NOS 1 to 34 and functional fragments thereof.

As used herein, the term "functional fragment" refers to a polypeptide which possesses biological function or activity that is identified through a defined functional assay and which is associated with a particular biologic, morphologic, or phenotypic alteration in a cell or cell mechanism.

By the term "substantially identical", it is meant that the polynucleotide of the invention has a nucleic acid sequence which is at least 65% identical, more particularly 80% identical and even more particularly 95% identical to any one of SEQ ID NO: 1 to 34.

Preferably, the polynucleotide of the invention comprises a nucleotide sequence substantially identical to a sequence selected from the group consisting of SEQ ID NOS 1 to 13 (FIG. 2; Table 1: Group 1) and functional fragments thereof, or from the group consisting of SEQ ID NOS 14 to 23 (FIG. 3; Table 1: Group 2) and functional fragments thereof, or from the group consisting of SEQ ID NOS 24 to 26 (FIG. 4; Table 1: Group 3) and functional fragments thereof, or from the group consisting of SEQ ID NOS 27 to 34 (FIG. 5; Table 1: Group 4) and functional fragments thereof.

As used herein, the terms "Isolated or Purified" means altered "by the hand of man" from its natural state, i.e., if it occurs in nature, it has been changed or removed from its original environment, or both. For example, a polynucleotide or a protein/peptide naturally present in a living organism is neither "isolated" nor purified, the same polynucleotide separated from the coexisting materials of its natural state, obtained by cloning, amplification and/or chemical synthesis is "isolated" as the term is employed herein. Moreover, a polynucleotide or a protein/peptide that is introduced into an organism by transformation, genetic manipulation or by any other recombinant method is "isolated" even if it is still present in said organism.

Amino acid or nucleotide sequence "identity" and "similarity" are determined from an optimal global alignment between the two sequences being compared. An optimal global alignment is achieved using, for example, the Needleman-Wunsch algorithm (Needleman and Wunsch, 1970, J. Mol. Biol. 48:443-453). "Identity" means that an amino acid or nucleotide at a particular position in a first polypeptide or polynucleotide is identical to a corresponding amino acid or nucleotide in a second polypeptide or polynucleotide that is in an optimal global alignment with the first polypeptide or polynucleotide. In contrast to identity, "similarity" encompasses amino acids that are conservative substitutions. A "conservative" substitution is any substitution that has a positive score in the blosum62 substitution matrix (Hentikoff and Hentikoff, 1992, Proc. Natl. Acad. Sci. USA 89: 10915-10919). By the statement "sequence A is n % similar to sequence B" is meant that n % of the positions of an optimal global alignment between sequences A and B consists of identical residues or nucleotides and conservative substitutions. By the statement "sequence A is n % identical to sequence B" is meant that n % of the positions of an optimal global alignment between sequences A and B consists of identical residues or nucleotides.

As used herein, the term "polynucleotide(s)" generally refers to any polyribonucleotide or poly-deoxyribonucleotide, which may be unmodified RNA or DNA or modified RNA or DNA. This definition includes, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. "Polynucleotide(s)" embraces short polynucleotides or fragments often referred to as oligonucleotide(s). The term "polynucleotide(s)" as it is employed herein thus embraces such chemically, enzymatically or metabolically modified forms of polynucleotides, as well as the chemical forms of DNA and RNA characteristic of viruses and cells, including, for example, simple and complex cells which exhibits the same biological function as the polypeptide encoded by SEQ ID NO.1 to 34. The term "polynucleotide(s)" also embraces short nucleotides or fragments, often referred to as "oligonucleotides", that due to mutagenesis are not 100% identical but nevertheless code for the same amino acid sequence.

In another embodiment, the present invention concerns an isolated or purified excreted/secreted polypeptide of *Leishmania major* comprising an amino acid sequence substantially identical to a sequence selected from the group consisting of SEQ ID NOS: 35 to 68 and functional derivatives thereof. By the term "substantially identical", it is meant that the polypeptide of the present invention preferably has an amino sequence having at least 80% homology, or even preferably 85% homology to part or all of SEQ ID NO: 35 to 68.

Yet, more preferably, the polypeptide comprises an amino acid sequence substantially the same or having 100% identity with SEQ ID NO: 35 to 68.

According to a preferred embodiment, the polypeptide of the present invention comprises an amino acid sequence substantially identical to a sequence selected from the group consisting of SEQ ID NOS: 35 to 47 (Annex A; Table 1: Group 1) and functional derivatives thereof, or from the group consisting of SEQ ID NOS: 48 to 57 (Annex B; Table 1: Group 2) and functional derivatives thereof, or from the group consisting of SEQ ID NOS: 58 to 60 (Annex C; Table 1: Group3) and functional derivatives thereof, or from the group consisting of SEQ ID NOS: 61 to 68 (Annex D; Table 1: Group 4) and functional derivatives thereof.

A "functional derivative", as is generally understood and used herein, refers to a protein/peptide sequence that possesses a functional biological activity that is substantially similar to the biological activity of the whole protein/peptide sequence. A functional derivative of a protein/peptide may or may not contain post-translational modifications such as covalently linked carbohydrate, if such modification is not necessary for the performance of a specific function. The term "functional derivative" is intended to the "fragments", "segments", "variants", "analogs" or "chemical derivatives" of a protein/peptide.

As used herein, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene-encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation, selenoylation, sulfation and transfer-RNA mediated addition of amino acids to proteins, such as arginylation, and ubiquitination. See, for instance: PROTEINS—STRUCTURE AND MOLECULAR PROPERTIES, 2nd Ed., T. E. Creighton, W.H. Freeman and Company, New York (1993); Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York (1983); Seifter et al., Meth. Enzymol. 182:626-646 (1990); and Rattan et al., Protein Synthesis: Posttranslational Modifications and Aging, Ann. N.Y. Acad. Sci. 663: 48-62 (1992). Polypeptides may be branched or cyclic, with or without branching. Cyclic, branched and branched circular polypeptides may result from post-translational natural processes and may be made by entirely synthetic methods, as well.

2. Vectors and Cells

In a third embodiment, the invention is also directed to a host, such as a genetically modified cell, comprising any of the polynucleotide sequence according to the invention and more preferably, a host capable of expressing the polypeptide encoded by this polynucleotide.

Transformed or transfected cells preferably contemplated by the present invention contain a polynucleotide having a sequence comprising a nucleotide sequence substantially identical to a sequence selected from the group consisting of SEQ ID NOS 1 to 13 and functional fragments thereof. Examples of such cells are those consisting of an *Escherichia coli* bacterium selected from the group consisting of *Escherichia coli* bacteria filed at the CNCM. under accession numbers I-3394, I-3393, I-3395, I-3396, I-3377, I-3371, I-3376, I-3373, I-3379, I-3397, I-3384, I-3383 and I-3382 on Feb. 24, 2005.

Other transformed or transfected cells preferably contemplated by the present invention contain a polynucleotide having a sequence comprising a nucleotide sequence substantially identical to a sequence selected from the group consisting of SEQ ID NOS 14 to 23 and functional fragments thereof. Examples of such cells are those consisting of an *Escherichia coli* bacterium selected from the group consisting of *Escherichia coli* bacteria filed at the CNCM. under accession numbers I-3386, I-3378, I-3385, I-3381, I-3372, I-3392, I-3380, I-3367, I-3370, and I-3366 on Feb. 24, 2005.

Other transformed or transfected cells preferably contemplated by the present invention contain a polynucleotide having a sequence comprising a nucleotide sequence substantially identical to a sequence selected from the group consisting of SEQ ID NOS 24 to 26 and functional fragments thereof. Examples of such cells are those consisting of an *Escherichia coli* bacterium selected from the group consisting of *Escherichia coli* bacteria filed at the CNCM. under accession numbers I-3365, I-3369 and I-3368 on Feb. 24, 2005.

Other transformed or transfected cells preferably contemplated by the present invention contain a polynucleotide having a sequence comprising a nucleotide sequence substantially identical to a sequence selected from the group consisting of SEQ ID NOS 27 to 34 and functional fragments thereof. Examples of such cells are those consisting of an *Escherichia coli* bacterium selected from the group consisting of *Escherichia coli* bacteria filed at the CNCM. under accession numbers I-3364, I-3387, I-3391, I-3389, I-3390, I-3388, I-3374, and I-3375 on Feb. 24, 2005.

In another embodiment, the invention is further directed to cloning or expression vector comprising a polynucleotide sequence as defined above, and more particularly directed to a cloning or expression vector which is capable of directing expression of the polypeptide encoded by the polynucleotide sequence in a vector-containing cell.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector.

A number of vectors suitable for stable transfection of cells and bacteria are available to the public (e.g. plasmids, adenoviruses, baculoviruses, yeast baculoviruses, plant viruses, adeno-associated viruses, retroviruses, Herpes Simplex Viruses, Alphaviruses, Lentiviruses), as are methods for constructing such cell lines. It will be understood that the present invention encompasses any type of vector comprising any of the polynucleotide molecule of the invention.

In another embodiment, the invention is concerned with genetically modified *Leishmania* strains. A first preferred genetically modified *Leishmania* strain comprises at least one gene having a sequence comprising a nucleotide sequence substantially identical to a sequence selected from the group consisting of SEQ ID NOS 1 to 34, and wherein said at least one gene is inactivated, preferably by knock-out. A second preferred genetically modified *Leishmania* strain contemplated by the present invention comprises at least one gene having a sequence comprising a nucleotide sequence substantially identical to a sequence selected from the group consisting of SEQ ID NOS 1 to 34, and wherein said at least one gene is underexpressed compared to a corresponding gene of a wild-type strain of *Leishmania*. Methods by which such strains are genetically modified are known to one skilled in the art and will not be further discussed.

3. Antibodies

In another embodiment, the invention features purified antibodies that specifically bind to the isolated or purified polypeptide as defined above or fragments thereof. The antibodies of the invention may be prepared by a variety of methods using the polypeptides described above. For example, the polypeptide, or antigenic fragments thereof, may be administered to an animal in order to induce the production of polyclonal antibodies. Alternatively, antibodies used as described herein may be monoclonal antibodies, which are prepared using hybridoma technology (see, e.g., Hammerling et al., In Monoclonal Antibodies and T-Cell Hybridomas, Elsevier, N.Y., 1981).

As mentioned above, the present invention is preferably directed to antibodies that specifically bind to *Leishmanina major* excreted/secreted polypeptides, or fragments thereof as defined above. In particular, the invention features "neutralizing" antibodies. By "neutralizing" antibodies is meant antibodies that interfere with any of the biological activities of any of the *Leishmanina major* excreted/secreted polypeptides. Any standard assay known to one skilled in the art may be used to assess potentially neutralizing antibodies. Once produced, monoclonal and polyclonal antibodies are preferably tested for specific *Leishmanina major* excreted/secreted polypeptides recognition by Western blot, immunoprecipitation analysis or any other suitable method.

With respect to antibodies of the invention, the term "specifically binds to" refers to antibodies that bind with a relatively high affinity to one or more epitopes of a protein of interest, but which do not substantially recognize and bind molecules other than the one(s) of interest. As used herein, the term "relatively high affinity" means a binding affinity between the antibody and the protein of interest of at least $10^6$ $M^{-1}$, and preferably of at least about $10^7$ $M^{-1}$ and even more preferably $10^8$ $M^{-1}$ to $10^{10}$ $M^{-1}$. Determination of such affinity is preferably conducted under standard competitive binding immunoassay conditions which is common knowledge to one skilled in the art. As used herein, "antibody" and "antibodies" include all of the possibilities mentioned hereinafter: antibodies or fragments thereof obtained by purification, proteolytic treatment or by genetic engineering, artificial constructs comprising antibodies or fragments thereof and artificial constructs designed to mimic the binding of antibodies or fragments thereof. Such antibodies are discussed in Colcher et al. (*Q J Nucl Med* 1998; 42: 225-241). They include complete antibodies, $F(ab')_2$ fragments, Fab fragments, Fv fragments, scFv fragments, other fragments, CDR peptides and mimetics. These can easily be obtained and prepared by those skilled in the art. For example, enzyme digestion can be used to obtain $F(ab')_2$ and Fab fragments by subjecting an IgG molecule to pepsin or papain cleavage respectively. Recombinant antibodies are also covered by the present invention.

Preferably, the antibody of the invention is a human or animal immunoglobulin such as IgG1, IgG2, IgG3, IgG4, IgM, IgA, IgE or IgD carrying rat or mouse variable regions (chimeric) or CDRs (humanized or "animalized"). Furthermore, the antibody of the invention may also be conjugated to any suitable carrier known to one skilled in the art in order to provide, for instance, a specific delivery and prolonged retention of the antibody, either in a targeted local area or for a systemic application.

The term "humanized antibody" refers to an antibody derived from a non-human antibody, typically murine, that retains or substantially retains the antigen-binding properties of the parent antibody but which is less immunogenic in humans. This may be achieved by various methods including (a) grafting only the non-human CDRs onto human framework and constant regions with or without retention of critical framework residues, or (b) transplanting the entire non-human variable domains, but "cloaking" them with a human-like section by replacement of surface residues. Such methods are well known to one skilled in the art.

As mentioned above, the antibody of the invention is immunologically specific to the polypeptide of the present invention and immunological derivatives thereof. As used herein, the term "immunological derivative" refers to a polypeptide that possesses an immunological activity that is substantially similar to the immunological activity of the whole polypeptide, and such immunological activity refers to the capacity of stimulating the production of antibodies immunologically specific to the *Leishmanina major* excreted/secreted polypeptides or derivative thereof. The term "immunological derivative" therefore encompass "fragments", "segments", "variants", or "analogs" of a polypeptide.

4. Compositions and Vaccines

The polypeptides of the present invention, the polynucleotides coding the same, and antibodies produced according to the invention, may be used in many ways for the diagnosis, the treatment or the prevention of Leishmaniasis.

In another embodiment, the present invention relates to an immunogenic composition generating an immune response against a leishmaniasis, comprising a polynucleotide as defined above or a polypeptide as defined above, and an acceptable carrier. According to a related aspect, the present invention relates to a vaccine composition generating a protecting response against a leishmaniasis, comprising a polynucleotide as defined above or a polypeptide as defined above, and an acceptable carrier. As used herein, the term "treating" refers to a process by which the symptoms of Leishmaniasis are alleviated or completely eliminated. As used herein, the term "preventing" refers to a process by which a Leishmaniasis is obstructed or delayed. The composition of the vaccine of the invention comprises a polynucleotide and/or a polypeptide as defined above and an acceptable carrier.

As used herein, the expression "an acceptable carrier" means a vehicle for containing the polynucleotide and/or a polypeptide that can be injected into a mammalian host without adverse effects. Suitable carriers known in the art include, but are not limited to, gold particles, sterile water, saline, glucose, dextrose, or buffered solutions. Carriers may include auxiliary agents including, but not limited to, diluents, stabilizers (i. e., sugars and amino acids), preservatives, wetting agents, emulsifying agents, pH buffering agents, viscosity enhancing additives, colors and the like.

Further agents can be added to the composition and vaccine of the invention. For instance, the composition of the invention may also comprise agents such as drugs, immunostimulants (such as α-interferon, β-interferon, γ-interferon, granulocyte macrophage colony stimulator factor (GM-CSF), macrophage colony stimulator factor (M-CSF), interleukin 2 (IL2), interleukin 12 (IL12), and CpG oligonucleotides), antioxidants, surfactants, flavoring agents, volatile oils, buffering agents, dispersants, propellants, and preservatives. For preparing such compositions, methods well known in the art may be used.

The amount of polynucleotide and/or a polypeptide present in the compositions of the present invention is preferably a therapeutically effective amount. A therapeutically effective amount of polynucleotide and/or a polypeptide is that amount necessary to allow the same to perform their immunological role without causing, overly negative effects in the host to which the composition is administered. The exact amount of polynucleotide and/or a polypeptide to be used and the composition/vaccine to be administered will vary according to factors such as the type of condition being treated, the mode of administration, as well as the other ingredients in the composition.

5. Method for Identifying a Polypeptide of the Invention

In another object, the present invention provides a method for identifying an excreted/secreted polypeptide of a *Leishmania major* strain. The method comprises in vitro cultivating *Leishmania* promastigotes under pH and temperature conditions naturally found in a host cell infected by a *Leishmania major* strain. Preferably, the pH is about 5.5 and the temperature is about 35° C. By "about", it is meant that the value of said pH or temperature can vary within a certain range depending on the margin of error of the method used to evaluate such pH or temperature.

In a related aspect, the excreted/secreted polypeptides identified by the method as defined above finds a particular use as drug target for identifying a molecule capable of preventing a Leishmaniasis.

6. Methods of Use

In another embodiment, the present invention relates to a method for preventing and/or treating a patient against an infection with a *Leishmania major* strain, the method comprising the step of administering to the patient a therapeutically effective amount of a immunogenic and/or a vaccine composition as defined above and/or an antibody as defined above.

The vaccine, antibody and immunogenic composition of the invention may be given to a patient through various routes of administration. For instance, the composition may be administered in the form of sterile injectable preparations, such as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents. They may be given parenterally, for example intravenously, intramuscularly or sub-cutaneously by injection, by infusion or per os. The vaccine and the composition of the invention may also be formulated as creams, ointments, lotions, gels, drops, suppositories, sprays, liquids or powders for topical administration. They may also be administered into the airways of a subject by way of a pressurized aerosol dispenser, a nasal sprayer, a nebulizer, a metered dose inhaler, a dry powder inhaler, or a capsule. Suitable dosages will vary, depending upon factors such as the amount of each of the components in the composition, the desired effect (short or long term), the route of administration, the age and the weight of the mammal to be treated. Any other methods well known in the art may be used for administering the vaccine, antibody and the composition of the invention.

The present invention is also directed to an in vitro diagnostic method for the detection of the presence or absence of antibodies indicative of a *Leishmania major* strain, which bind to a polypeptide as defined above to form an immune complex, comprising the steps of a) contacting said polypeptide with a biological sample for a time and under conditions sufficient to form an immune complex; and b) detecting the presence or absence of the immune complex formed in a).

In a further embodiment, a diagnostic kit for the detection of the presence or absence of antibodies indicative of of a *Leishmania major* strain is provided. Accordingly, the kit comprises:

a polypeptide as defined above;

a reagent to detect polypeptide-antibody immune complex;

optionally a biological reference sample lacking antibodies that immunologically bind with the polypeptide; and optionally a comparison sample comprising antibodies which can specifically bind to the polypeptide;

wherein the polypeptide, reagent, biological reference sample, and comparison sample are present in an amount sufficient to perform the detection.

The present invention also proposes an in vitro diagnostic method for the detection of the presence or absence of polypeptides indicative a *Leishmania major* strain, which bind to the antibody of the present invention to form an immune complex, comprising the steps of:

a) contacting the antibody of the invention with a biological sample for a time and under conditions sufficient to form an immune complex; and b) detecting the presence or absence of the immune complex formed in a).

In a further embodiment, a diagnostic kit for the detection of the presence or absence of polypeptides indicative of *Leishmania major* strain is provided. Accordingly, the kit comprises:

an antibody as defined above;

a reagent to detect polypeptide-antibody immune complex;

optionally a biological reference sample lacking polypeptides that immunologically bind with the antibody; and optionally a comparison sample comprising polypeptides which can specifically bind to the antibody;

wherein said antibody, reagent, biological reference sample, and comparison sample are present in an amount sufficient to perform the detection.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

A further object of the invention concerns a method for detecting the presence or absence of lymphocytic stimulation in a subject suspected of Leishmaniasis, comprising the steps of:

a) obtaining a sample containing T Lymphocytes from said subject;

b) contacting the T lymphocytes with a polypeptide of the invention; and c) detecting the presence or absence of a proliferative response of said T lymphocyte to the polypeptide.

A further object of the invention concerns a method for detecting the presence or absence of lymphocytic stimulation in a subject suspected of Leishmaniasis, comprising the steps of:

a) obtaining a sample containing T Lymphocytes from said subject;

b) contacting the T lymphocytes with a polypeptide of the invention; and c) detecting the presence or absence of cytokines indicative of lymphocytic stimulation.

The present invention will be more readily understood by referring to the following example. This example is illustrative of the wide range of applicability of the present invention and is not intended to limit its scope. Modifications and variations can be made therein without departing from the spirit and scope of the invention. Although any method and material similar or equivalent to those described herein can be used in the practice for testing of the present invention, the preferred methods and materials are described.

| | Clone/Protein homologue | Designation | Signal Peptide/Cons domains | Extracellular localization | Function | Virulence factor | Immunogenicity |
|---|---|---|---|---|---|---|---|
| GR1 | Clone 9.1/hypothetical protein | CAC24683.1 | -/4TMs | | | | |
| | Clone 15/Fibrion 1 [*Drosophila melanogaster*] | | +/5TMs/Serine and alanine rich domains | | | | |
| | Clone 20.2/Similar to methyltransferase like [*Neurospora crassa*] | CAD01117.1 | - | | | | |
| | Clone22/possible cyclin 2-related protein | CAB88217.1 | + | | | | |
| | Clone 22s/seven transmembrane helix receptor [*Homo sapieus*] | ? | -/4TMs | | | | |
| | Clone23/hypothetical protein [*Leishmania major*] | | -/2TMs | | | | |
| | Clone 27/ hypothetical protein Chr3_0870 [*Leishmania major*] | NP_859520.1 | + | | | | |
| | Clone 31/repetitive protein antigen 3 [*Trypanosoma cruzi*] | D60110/2$^{c}$-09 | -2TMs/ER retention signal | | | | |

-continued

| | | | | | |
|---|---|---|---|---|---|
| | Clone 37 | | +/2TMs | + | |
| | Clone 38/putative PHA synthase [*Streptomyces anrerofaciens*] | Q8GFF3/9$^{e}$-06 | +/TM | | |
| | Clone 66/Similar zinc finger (C3HC4-type RING finger) [*Arabidopsis thaliana*] | NP_178507 | -/RING domain | | |
| | Clone 72/hypothetical protein [*Trypanosoma brucei*] | CAB95438.1 | -/Putative zinc binding domain (DUF701) | | |
| | Clone 78 | | -/TM | | |
| GR2 | Clone 9.2/ Ribosomal protein S18[*Ixodes ricinus*] | AAQ21388.1 | | | Structural constituent of ribosome |
| GR2 | Clone 11/Ribosomal protein L27 [*Leishmania major*] | AAO45619.1 | | | Structural constituent of ribosome |
| GR2 | Clone 12/Ubiquitin protein ligase [*Magnaporthe grisea*] | EAA51657.1 | -/HECT domains | | Proteins degradation |
| GR2 | Clone 20.1/Chaperonin subunit alpha [*Trypanasoma brucei*] | AAL56959.1 | | | |
| GR2 | Clone 20.3/Ribosomal protein L31 [*Cyanophora paradoxo*] | CAB45375.1 | | | Structural constituent of ribosome |
| GR2 | Clone 22.1/ Ribosomal protein S9 [*Trypanosoma brucei*] | S12674 | | | Structural constituent of ribosome |
| GR2 | Clone 26/ Ribosomal protein L6 [*Leishmania braziliensis*] | AAD26571.1 | | | Structural constituent of ribosome |
| GR2 | Clone 59/ Ribosomal protein RpL18A [*Drosophila melanogasier*] | AAR09828.1 | | | Structural constituent of ribosome |
| GR2 | Clone 65/ dihydrolipoamide acetyltransferase [*Dictyostelium discoideum*] | AAA16511.1 | /lipoyl attachment domain | | |
| GR2 | Clone 77/ Probable proteasome regulatory ATPase subunit 2 | CAD19436.1 | | | |

-continued

| | | | | | | | |
|---|---|---|---|---|---|---|---|
| GR3 | Clone 39/ Cytochrome C [*Crithidia fasciculata*] | P00078 | | | | | |
| | Clone 68/ Ribosomal protein L7a-Like protein [*Trypanosoma cruzi*] | AAG53670.1 | | | Structural constituent of ribosome | | Vaccine candidate/ Serodiognosis |
| | Clone 90/ Ribosomal protein L3 [*Trypanoplasma borrell*] | AAF62506.1 | | | Structural constituent of ribosome | | |
| GR4/a | Clone 71/promastigote surface antigen-2 precursor [*Leishmania major*] | A41710 | + | ++ | ? | ++ | Vaccine candidate *Leishmania* |
| GR4/b | Clone 32/ Heat shock 70-related protein 1 precursor [*Leishmania major*] | CAA45498.2 | + | + | Induced by the temperature and displayed chaperone activity | ++ | Serodiagnosis/ Vaccine candidate |
| | Clone 42/ Cathepsin-L-protease [*Leishmania major*] | AAB48120.1 | + | + | Endopeptidase + carboxypeptidase activities | ++ | Vaccine candidate |
| GR4/c | Clone 8.2/Spermidine synthase 1 [*Leishmania major*] | CAC44919.1 | - | | | + | |
| | Clone 21/ KMP-11 [*Leishmania major*] | | - | | ? | + | Vaccine candidate *Leishmania* |
| | Clone 57/ Ribosomal protein S16 [*Leishmania entriettil*] | Q86L12 | | | Structural constituent of ribosome | | |
| | Clone 74/ factor 1-alpha [*Leishmania donovani*] | AAL08019.1 | -/3 GTP binding domains | | Transalational factor | | |
| GR4/d | Clone 13/ LmPDI | AAN75008 | + | + | Catalyses disulfide bond formation, isomerisation, and reduction within the ER, and it displays chaperone activity | ++ | ? |

TABLE 2

| I number CNCM (Paris France) | SEQ ID Number | Name of the inserted plasmid. |
|---|---|---|
| I-3394 | ID 1 | pMOS-9.1 |
| I-3393 | ID 2 | pBK-15 |
| I-3395 | ID 3 | pMOS-20.2 |
| I-3396 | ID 4 | pBK-22 |
| I-3377 | ID 5 | pBK-22s |

TABLE 2-continued

| I number CNCM (Paris France) | SEQ ID Number | Name of the inserted plasmid. |
|---|---|---|
| I-3371 | ID 6 | pBK-23 |
| I-3376 | ID 7 | pBK-27 |
| I-3373 | ID 8 | pBK-31 |
| I-3379 | ID 9 | pBK-37 |
| I-3397 | ID 10 | pBK-38 |

TABLE 2-continued

| I number CNCM (Paris France) | SEQ ID Number | Name of the inserted plasmid. |
|---|---|---|
| I-3384 | ID 11 | pBK-66 |
| I-3383 | ID 12 | pBK-72 |
| I-3382 | ID 13 | pBK-78 |

TABLE 3

| I number CNCM (Paris France) | SEQ ID Number | Name of the inserted plasmid. |
|---|---|---|
| I-3386 | ID 14 | pMOS-9.2 |
| I-3378 | ID 15 | pBK-11 |
| I-3385 | ID 16 | pBK-12 |
| I-3381 | ID 17 | pBK-20.1 |
| I-3372 | ID 18 | pBK-20.3 |
| I-3392 | ID 19 | pMOS-22.1 |
| I-3380 | ID 20 | pBK-26 |
| I-3367 | ID 21 | pBK-59 |
| I-3370 | ID 22 | pBK-65 |
| I-3366 | ID 23 | pBK-77 |

TABLE 4

| I number CNCM (Paris France) | SEQ ID Number | Name of the inserted plasmid. |
|---|---|---|
| I-3365 | ID 24 | pBK-39 |
| I-3369 | ID 25 | pBK-68 |
| I-3368 | ID 26 | pBK-90 |

TABLE 5

| I number CNCM (Paris France) | SEQ ID Number | Name of the inserted plasmid. |
|---|---|---|
| I-3364 | ID 27 | pBK-71 |
| I-3387 | ID 28 | pBK-32 |
| I-3391 | ID 29 | pBK-42 |
| I-3389 | ID 30 | pMOS-8.2 |
| I-3390 | ID 31 | pBK-21 |
| I-3388 | ID 32 | pBK-57 |
| I-3374 | ID 33 | pBK-74 |
| I-3375 | ID 34 | pBK-13 |

Description of Characterizing Features for the Deposited Biological Material pBK15: *E. coli* XL1-Blue bacteria are transformed by the pBK-CMV plasmid (Amersham) containing the DNA sequence coding for protein 15 of *Leishmania major*. Gene 15 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pMOS-20.2: *E. coli* XL1-Blue bacteria are transformed by the pMOS-Blue plasmid (Amersham) containing the DNA sequence coding for protein 20.2 of *Leishmania major*. Gene 20.2 has been cloned at the EcoR V restriction site. The recombinant (transformed) bacteria are resistant to tetracycline and ampicillin. The genes which give resistance to ampicillin and to tetracycline are carried by the recombinant pMOS-Blue plasmid and XL1-Blue bacteria, respectively.

pBK22: *E. coli* XL1-Blue bacteria are transformed by the pBK-CMV plasmid (Amersham) containing the DNA sequence coding for protein 22 of *Leishmania major*. Gene 22 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-22s: *E. coli* XL1-Blue bacteria are transformed by the pBK-CMV plasmid (Amersham) containing the DNA sequence coding for protein 22s of *Leishmania major*. Gene 22s has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-23: *E. coli* XL1-Blue bacteria are transformed by the pBK-CMV plasmid (Amersham) containing the DNA sequence coding for protein 23 of *Leishmania major*. Gene 23 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-27: *E. coli* XL1-Blue bacteria are transformed by the pBK-CMV plasmid (Amersham) containing the DNA sequence coding for protein 27 of *Leishmania major*. Gene 27 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-31: *E. coli* XL1-Blue bacteria are transformed by the pBK-CMV plasmid (Amersham) containing the DNA sequence coding for protein 31 of *Leishmania major*. Gene 31 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-37: *E. coli* XL1-Blue bacteria are transformed by the pBK-CMV plasmid (Amersham) containing the DNA sequence coding for protein 37 of *Leishmania major*. Gene 37 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-38: *E. coli* XL1-Blue bacteria are transformed by the pBK-CMV plasmid (Amersham) containing the DNA sequence coding for protein 38 of *Leishmania major*. Gene 38 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-66: *E. coli* XL1-Blue bacteria are transformed by the pBK-CMV plasmid (Amersham) containing the DNA sequence coding for protein 66 of *Leishmania major*. Gene 66 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-72: *E. coli* XL1-Blue bacteria are transformed by the pBK-CMV plasmid (Amersham) containing the DNA sequence coding for protein 72 of *Leishmania major*. Gene 72 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-78: *E. coli* XL1-Blue bacteria are transformed by the pBK-CMV plasmid (Amersham) containing the DNA sequence coding for protein 78 of *Leishmania major*. Gene 78 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pMOS-9.2: *E. coli* XL1-Blue bacteria are transformed by the pMOS-Blue plasmid (Amersham) containing the DNA sequence coding for protein 9.2 of *Leishmania major*. Gene 9.2 has been cloned at the EcoR V restriction site. The recombinant (transformed) bacteria are resistant to tetracycline and ampicillin. The genes which give resistance to ampicillin and to tetracycline are carried by the recombinant pMOS-Blue plasmid and XL1-Blue bacteria, respectively.

pBK-11: *E. coli* XL1-Blue bacteria are transformed by the pBK-CMV plasmid (Amersham) containing the DNA sequence coding for protein 11 of *Leishmania major*. Gene 11 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-12: *E. coli* XL1-Blue bacteria are transformed by the pBK-CMV plasmid (Amersham) containing the DNA sequence coding for protein 12 of *Leishmania major*. Gene 12 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-20.1: *E coli* XL1-Blue bacteria are transformed by the pBK-CMV plasmid (Amersham) containing the DNA sequence coding for protein 20.1 of *Leishmania major*. Gene 20.1 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-20.3: *E coli* XL1-Blue bacteria are transformed by the pBK-CMV plasmid (Amersham) containing the DNA sequence coding for protein 20.3 of *Leishmania major*. Gene 20.3 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-22.1: *E. coli* XL1-Blue bacteria are transformed by the pBK-CMV plasmid (Amersham) containing the DNA sequence coding for protein 22.1 of *Leishmania major*. Gene 22.1 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-26: *E. coli* XL1-Blue bacteria are transformed by the pBK-CMV plasmid (Amersham) containing the DNA sequence coding for protein 26 of *Leishmania major*. Gene 26 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-59: *E. coli* XL1-Blue bacteria are transformed by the pBK-CMV plasmid (Amersham) containing the DNA sequence coding for protein 59 of *Leishmania major*. Gene 59 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-65: *E. coli* XL1-Blue bacteria are transformed by the pBK-CMV plasmid (Amersham) containing the DNA sequence coding for protein 65 of *Leishmania major*. Gene 65 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-77: *E. coli* XL 1-Blue bacteria are transformed by the pBK-CMV plasmid (Amersham) containing the DNA sequence coding for protein 77 of *Leishmania major*. Gene 77 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-39: *E. coli* XL1-Blue bacteria are transformed by the pBK-CMV plasmid (Amersham) containing the DNA sequence coding for protein 39 of *Leishmania major*. Gene 39 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-68: *E. coli* XL1-Blue bacteria are transformed by the pBK-CMV plasmid (Amersham) containing the DNA sequence coding for protein 68 of *Leishmania major*. Gene 68 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-90: *E. coli* XL1-Blue bacteria are transformed by the pBK-CMV plasmid (Amersham) containing the DNA sequence coding for protein 90 of *Leishmania major*. Gene 90 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-71: *E. coli* XL1-Blue bacteria are transformed by the pBK-CMV plasmid (Amersham) containing the DNA sequence coding for protein 71 of *Leishmania major*. Gene 71 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-42: *E. coli* XL1-Blue bacteria are transformed by the pBK-CMV plasmid (Amersham) containing the DNA sequence coding for protein 42 of *Leishmania major*. Gene 42 has been cloned at the Xhol and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-32: *E. coli* XL1-Blue bacteria are transformed by the pBK-CMV plasmid (Amersham) containing the DNA sequence coding for protein 32 of *Leishmania major*. Gene 32 has been cloned at the XhoI and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pMOS-8.2: *E. coli* XL1-Blue bacteria are transformed by the pMOS-Blue plasmid (Amersham) containing the DNA sequence coding for protein 8.2 of *Leishmania major*. Gene 8.2 has been cloned at the EcoR V restriction site. The recombinant (transformed) bacteria are resistant to tetracycline and ampicillin. The genes which give resistance to ampicillin and to tetracycline are carried by the recombinant pMOS-Blue plasmid and XL1-Blue bacteria, respectively.

pBK-21: *E. coli* XL1-Blue bacteria are transformed by the pBK-CMV plasmid (Amersham) containing the DNA sequence coding for protein 21 of *Leishmania major*. Gene 21 has been cloned at the XhoI and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-57: *E. coli* XL1-Blue bacteria are transformed by the pBK-CMV plasmid (Amersham) containing the DNA sequence coding for protein 57 of *Leishmania major*. Gene 57 has been cloned at the XhoI and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-74: *E. coli* XL1-Blue bacteria are transformed by the pBK-CMV plasmid (Amersham) containing the DNA sequence coding for protein 74 of *Leishmania major*. Gene 74 has been cloned at the XhoI and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

pBK-13: *E. coli* XL1-Blue bacteria are transformed by the pBK-CMV plasmid (Amersham) containing the DNA sequence coding for protein 13 of *Leishmania major*. Gene 13 has been cloned at the XhoI and EcoR I restriction sites. The recombinant (transformed) bacteria are resistant to tetracycline and kanamycin. The genes which give resistance to kanamycin and to tetracycline are carried by the recombinant pBK-CMV plasmid and XL1-Blue bacteria, respectively.

The above biological material is submitted to the following conditions.

1—Culture Conditions

Culture Medium

The recombinant bacteria are grown either on a liquid culture medium, or on a solid culture medium.

The liquid culture medium is Luria-Broth (LB), and comprises: 1% (w/v) Bactotryptone; 0.5% (w/v) yeast extract and 1% (w/v) NaCl. The pH of medium is set to 7. This medium is appropriate for the multiplication of the pMOS-Blue plasmids or the pBK-CMV plasmids containing the genes repectively described above.

The solid culture medium is Luria-Broth-Agar (LB-Agar), and comprises 1% (w/v) bactotryptone; 0.5% (w/v) yeast extract; 1% (w/v) NaCl and 1.5% (w/v) agar. This medium is essentially appropriate for growing recombinant bacteria, which have been frozen at −80° C. These two media are sterilized at 120° C. for 20 minutes, immediately after having being prepared.

Inoculation Conditions

The recombinant bacteria, which have been frozen at −80° C., are placed on a dish containing LB-Agar solid culture medium, supplemented with 15 microgrammes/mL of tetracycline, and 50 microgrammes/mL of ampicillin (for the cells containing recombinant pMOS-Blue plasmids or 15 microgrammes/mL of tetracycline, and 50 microgrammes/mL of kanamycin) (for the cells containing recombinant pBK-CMV plasmids) for 18 hours at 37° C. A colony is then isolated, and placed for incubation in 5 mL of LB, supplemented with the same antibiotics. The culture is conducted for 18 hours at 37° C.

Incubation (Temperature, Atmosphere, Stirring, Illumination)

The culture is made at a temperature 37° C. under stirring at 200 revolutions/min (SANYO Orbital incubator). The culture is made at ambient temperature, and under natural light.

Conditions for Storage

The recombinant bacteria can be stored by freezing at −80° C. in a LB medium, supplemented with 10% glycerol. The cell concentration can be of about $10^9$ cfu/mL.

2—Activities to be Checked to Confirm the Viability of the Microorganism

The XL1-Blue bacteria, which have been frozen at −80° C. and which contain the recombinant pMOS-Blue plasmid or the recombinant pBK-CMV plasmid, are placed on a LB-Agar medium, supplemented with 15 microgrammes/mL of tetracycline, and of 50 microgrammes/mL of ampicillin, or 15 microgrammes/mL of tetracycline (for the cells containing the pMOS-Blue plasmids), and of 50 microgrammes/mL of kanamycin (for the cells containing the pBK-CMV plasmids), for 18 h at 37° C. The viability of the frozen bacteria is checked by the presence or absence of bacterial colonies.

3—Additional Information

Origin of the Microorganism

The non-recombinant *E. coli* XL1-Blue bacteria have been bought from Stratagen (La Jolla, Calif., USA). The recombinant bacteria containing the plasmid of interest have been made in our laboratory, i.e., the Laboratoire d'Immunologie et de Vaccinologie Moléculaire (LIVGM) of the Pasteur Institute of Tunis (Tunisia).

EXAMPLE

Identification of Excreted/Secreted Proteins by *Leishmania major* Parasite

Materials and Methods

Parasites Culture.

A High virulent isolate of *L. major* (zymodeme MON25; MHOM/TN/94/GLC94), obtained from human ZCL lesion was used in this study [Kébaier, 2001]. Parasites were cultivated on NNN medium at 26° C. and were then progressively adapted to RPMI 1640 medium (Sigma, St. Louis, Mo.) containing 2 mmol/ml L-glutamine, 100 U/ml penicillin, 100 μg/ml streptomycin, and 10% heat-inactivated foetal calf serum (complete medium). Promastigotes collected at the logarithmic-growth phase culture were adjusted to $10^6$ parasites/ml in a constant volume and further incubated at 26° C. The stationary phase was reached after 6 days with parasite concentration of $8\times10^7$ parasites/ml. Stationary phase promastigotes were used for proteins labeling and preparation of excreted/secreted proteins of *L. major*.

Preparation of *L. major* Excreted-Secreted Protein (LMES).

Confluent parasites from six culture flasks of *L. major* stationary phase promastigotes were incubated overnight in RPMI 1640 complete medium pH 7.6 at 35° C. under 5% $CO_2$ atmosphere. To eliminate any contaminant protein of foetal calf serum, parasites were washed six times with RPMI 1640 media. Parasites were then resuspended at $2\times10^7$ parasites/ml in RPMI minimum media pH 5.5 and incubated for 6 hours at 35° C. under 5% $CO_2$ atmosphere. The viability of the parasites after 6 hours of incubation was assessed by the Trypan blue exclusion test of cell viability [Berredo-Pinho, 2001] and found to be over 97%. Following this incubation, the supernatant containing secreted/excreted proteins (LMES) was collected by centrifugation at 4000×g for 20 min at 4° C. then lyophilized using a speed-vaccum concentrator (Savant, Holbrook, N.Y.). Before use, proteins were reconstituted with distilled water. The amounts of proteins in LMES were determined by the Lowry assay.

Generation of Rabbit Anti-LMES Sera.

One rabbit was immunized by intramuscular (IM) route with 250 μg of the LMES emulsified in incomplete Freund's adjuvant (Sigma, Steinheim, Germany). The rabbit received one additional IM injection with the same amount of protein emulsified in incomplete Freund's adjuvant by the intramuscular route 15 days after the first injection. One month later, a final injection with 250 μg of the LMES without adjuvant was administered by intradermal injections in eight different sites. The rabbit was bled starting 10 days after the final injection. The rabbit immune sera raised against excreted-secreted proteins were tested then used for the immunoscreening of *L. major* cDNA library and immunoprecipitation experiments.

Proteins Labeling and Separation.

Labeling experiments were performed in MEM-based methionine free media (Gibco BRL, Paisley, Scotland) titrated to pH 5.5 with 20 mM succinic acid [2]. Promatigotes ($1\times10^8$ cells) from *L. major* stationary phase were preincubated for one hour at different temperature and pH conditions (35° C., pH 5.5 and 26° C., pH 7.6) in complete medium. Parasites were then labeled by further incubation for another 6 hours in the same medium containing 20 μCi/ml of [$^{35}$S] methionine (specific activity, >1,000 Ci/mmol; Amersham, UK). Following labeling, the supernatant containing excreted/secreted proteins was collected by centrifugation at 4,000×g for 20 min at 4° C. and treated with a mixture of protease inhibitors (containing pepstatin, leupeptin and PMSF, Boehringer, Mannheim, Germany). The radiolabled proteins released in the supernatants were concentrated to 1/10 of the initial volume by centrifugation with nominal 10.000-molecular-weight-cutoff Centricon YM-10 tubes (Millipore, Bedford, Mass.) as described by the manufacturer. Ten μl of radiolabled concentrated supernatants were resuspended in 1×SDS sample buffer, heated at 95° C. for 10 min and analyzed by SDS-PAGE. The gel was dried, exposed to X-OMAT™ films (Eastman Kodak Co, Rochester, N.Y.) and developed by immersion in X-ray film processing (AGFA-Gevaert, Mortsel, Belgium).

Immunoprecipitation of Labeled Proteins.

The [$^{35}$S] methionine radiolabeled excreted-secreted proteins were immunoprecipitated by rabbit antiserum raised against LMES. Prior to immunoprecipitation, concentrated *L. major* supernatants were incubated in NP-40 buffer (50 mM Tris-Hcl [pH 7.5], 150 mM NaCl, 0.5% [v/v] Nonidet P-40) in the presence of a mixture of protease inhibitors (Boehringer, Mannheim, Germany). Insoluble fraction was removed from the supernatant by centrifugation at 12,000×g for 20 min at 4° C. The supernatant fraction was incubated overnight at 4° C. with 20 μl of antiserum to LMES. Immune complexes were adsorbed on protein A-Sepharose CL4B beads (Pharmacia, Uppsala, Sweden) by incubation at 4° C. with constant rocking for two hours. Sepharose CL4B beads were recovered by centrifugation, washed three times in NP-40 buffer, and separated by SDS-PAGE followed by autoradiography.

Immunoscreening of cDNA Library of *L. major* Promastigote.

An oligo (dT)-primed cDNA library from *L. major* promastigote poly(A)+RNA was constructed in ZAP II Phage expression vector according to the instructions of the manufacturer (Stratagene, La Jolla, Calif.). The resultant library was estimated to contain 1.48 $10^8$ plaque forming units per ml [4]. A lawn of XL1-MRF' host cells infected with about $1\times10^4$ PFU of the phage stock was prepared on a 82-mm plates and incubated for 8 h at 37° C. The lawn was then overlaid with a Hybond™-C nitrocellulose membrane disc (Amersham-Life science, UK) presoaked in 10 mM isopropyl-β-thiogalactopyranoside (IPTG) for induction of protein expression by further incubation at 37° C. for overnight. The plate and membrane were indexed and oriented for matching corresponding plate and membrane position. Approximately $5\times10^5$ plaques were screened. After transfer, membranes were then washed five times in TBS-T (20 mM Tris-Hcl [pH 7.5], 150 mM NaCl, 0.05% [v/v] Tween 20) and blocked in 5% (w/v) nonfat dried milk-TBS-T at room temperature for 1 hour. Membranes from the expression library were incubated with antiserum to LMES diluted to 1:500 in blocking solution for 2 h with rocking at room temperature and with pre-immune serum to 1:500 as control followed by three washes in TBS-T. A secondary antibody of peroxidase-conjugated goat anti-rabbit IgG (Amersham-Pharmacia, UK) diluted to 1:2, 000 in TBS-T was added to the membranes and allowed to incubate for 1 h at room temperature. After a final wash, colorimetric detection was performed using diaminobenzidine tetrahydrochloride (Sigma, St. Louis, Mo.) in 50 mM Tris-Hcl [pH 7.6] containing 0.03% hydrogen peroxide (Sigma, St. Louis, Mo.). The reaction was stopped by washing two times in distilled $H_2O$. Positive plaques were cored out, and recombinant phage was eluted in 500 μl of SM buffer (50 mM Tris-HCl [pH 7.5] 100 mM NaCl, 10 mM $MgSO_4$) containing 2% chloroform (Stratagene manual). These were replated at about 50 to 200 PFU on 82-mm plates for secondary and tertiary screenings using the same anti-LMES sera. Positive recombinant phage clones from tertiary screenings were subjected to pBK-CMV phagemid vector excision from the ZAP Express vector using the ExAssist helper phage according to the manufacturer protocol. The recombinant plasmids DNA were purified with an anion-exchange silica-gel membrane (Qiagen GmbH, Germany) as recommended by the manufacturer.

Sequence Analysis of CDNA Inserts, Databases and Software.

The recombinant plasmids were DNA sequenced using the forward T3 (5'-aattaaccctcactaaaggg-3' (SEQ ID NO: 69)) and the backward T7(5-'gtaatacgactcactatagggc-3' (SEQ ID NO: 70)) vectors primers (Stratagene manual) by the dideoxy chain terminator method using fluorescent BigDye™ terminators in ABI PRISM 377-A Stretch DNA sequencer (Perkin-Elmer). The nucleotide sequence of the isolated cDNA clones were compared with known nucleic acid sequences (Blast and *L. major* OmniBlast) and amino acid sequences were deduced (Blast, Scanprosite and PSORT II) in various databases (NCBI, EBI, Sanger Institute and SMART). The presence and location of signal peptide cleavage sites in the amino acid sequences of the translated cDNAs were predicted using SignalP server (http://www.cbs.dtu.dk/services/SignalP/).

Preparation of *E. coli* Crude Extracts and Western Blot Analysis.

Overnight cultures of XL1 -Blue MRF' harbouring the recombinant plasmide pBK-CMV were diluted to 1:100 in fresh Lauria Broth (Amersham-Pharmacia, UK) containing 50 μg of Kanamycin per ml and grown with vigorous shaking to an optical density at 600 nm ($OD_{600}$) of 0.6. Isopropyl-β-thiogalactopyranoside (IPTG) was added to the culture to a final concentration of 1 mM, and the induced culture was grown for an additional 4 hours. Crude cell extracts were prepared by washing cells with TE (10 mM Tris-Hcl [pH 7.5], 1 mM EDTA), resuspending them in 1×SDS sample buffer, and heating them at 95° C. for 10 min. Protein was separated by sodium dodecyl sulfate-18% polyacrylamide gel electrophoresis (SDS-PAGE) and transferred onto nitrocellulose membranes (Amersham-Pharmacia, UK) by Western blotting using the Bio-Rad TransBlotter (according to the manufacturer's protocol). After transfer, membranes were blocked for 1 hour in TBS-T buffer containing 3% (w/v) nonfat dried milk (blocking solution) at room temperature for 1 hour. Incubation with antiserum to LMES diluted to 1:500 in blocking solution and with pre-immune serum diluted to 1:500 as control was carried out with rocking for 1 h at room temperature. The nitrocellulose membranes were then washed three times with TBS-T before incubation with goat anti-rabbit IgG secondary antibody conjugated to peroxidase (1:1000 in 3% nonfat dried milk-TBS-T) for another 1 h at room temperature. The nitrocellulose membranes were again washed three times in TBS-T, and revealed using DAB-$H_2O_2$ substrate as described previously.

Results and Discussion

Characterization of *leishmania major* Excreted-secreted Antigens.

In order to identify proteins that *Leishmania* parasites possibly release into the phagolysosomal vacuole of host macrophages, stationary phase promastigotes were exposed to conditions that partially mimic the macrophages vacuole environment. Therefore, promastigotes from *L. major* isolates GLC94 were first cultured in complete medium at pH7.5 and at 26° C. until stationary phase was reached. Parasites were in vivo labeled by $^{35}$S methionine incubation at pH5.5 and at 35° C. Control cultures were maintained at pH 7.5 and at 26° C. A short incubation period of only 6 hours was used to avoid excessive cell death and proteins release from dead parasites. Radiolabeled proteins released in the culture media were concentrated using centricon YM-10 Centrifugal Filter and analyzed by SDS-PAGE (FIG. 1 lanes 1 and 3). As expected, several proteins were detected in both culture conditions. Interestingly, the pattern of these proteins were different. At pH 7.5 and at 26° C., few proteins were observed with 3 major proteins migrating at a molecular weight of 70 kDa, 66 kDa and 50 kDa (FIG. 1, lane 1). In contrast, at pH5.5 and 35° C., several proteins were detected ranging from 15 kDa to 70 kDa MW (FIG. 1, lane 2). Interestingly, two proteins with a molecular weight of approximatively 50 kDa and 30 kDa appear to be highly induced by these culture conditions.

In order to characterize the observed proteins, the rabbit polyclonal antiserum raised against excreted-secreted products of *L. major* parasites (anti-LMES) was used to immunoprecipitate them. As shown in the FIG. 1, at pH5.5 and 35° C., anti-LMES reacts essentially with a 50 kDa protein.

To identify *Leishmania* excreted antigens, anti-LMES was used to isolate clones from a cDNA expression library from *L. major* promastigotes. From a screen of approximately 5×10$^5$ plaques, 52 immunoreactive clones were isolated and sequenced. The analysis of the isolated sequences reveal that some of them were identical and therefore a total of 34 clones were different. The sequence search for homology of the isolated clones with known sequences carried out using many bioinformatic programs; Blast from NCBI and EBI (http://www.ncbi.nlm.nih.gov, http://www.ebi.ac.uk) and *L. major* OmniBlast form the Sanger Institute (http://www.sanger.ac.uk) Server programs for both nucleotide and peptide revealed that 62% of cDNA clones displayed significant homologies with known genes of proteins from *Leishmania* and other species (table 1). Potential open reading frames (ORFs) were identified using traduction multiple (http://www.infobiogen.fr/) and proteins sequence analysis were carried out using Blast from NCBI and EBI, SMART (http://smart-.embl-heidelberg.de), Scanprosite (http://au.expasy.org), PSORT II (http://psort.nibb.ac.ip) and SignalP server (http://www.cbs.dtu.dk/services/SignalP).

LmPDI

PDI is a member of the thioredoxin superfamily which is composed of several redox proteins playing a key role in disulfide bond formation, isomerisation, and reduction within the ER, and it displays chaperone activity [Ferrari, 1999; Wilkinson, 2004]. These molecules are essential for assisting unfolded or incorrectly folded proteins to attain their native state [Ferrari, 1999; Wilkinson, 2004]. Different cellular localizations were attributed to the Protein Disulfide Isomerase (PDI) family. First, in the lumen of the endoplasmic reticulum via its ER retention signal KDEL, second, in the plasma membrane and finally, released in the extracellular space [Turano, 2002; Geldof, 2003]. The *Leishmania major* protein disulfide isomerase (LmPDI) has been recently described as a putative virulence protein of the parasite [Ben Achour, 2002]. In fact, the LmPDI gene is predominantly expressed, at both mRNA and protein levels, in highly virulent isolates than in lower virulent isolates. In addition, specific PDI inhibitors ablated the enzymatic activity of the recombinant protein LmPDI and profoundly affected parasite growth in vitro and in vivo. However, the mechanism by which excreted/secreted LmPDI may affect parasite virulence is presently unknown.

PSA-2

The promastigote Surface Antigen-2 (PSA-2) complex proteins are protozoan specific proteins. The exact function of the PSA-2 protein is not known but its localization, expression and immnogenicity were fully characterized in *Leishmania. Leishmania* PSA-2 is a family of glycosylinositol phospholipid-anchored polypeptides. Interestingly, several studies have described PSA-2 proteins as excreted/secreted proteins [Symons, 1994; Webb, 1998]. In addition, the genes of PSA-2 family are differentially expressed during the parasite life cycle [Handman, 1995; Jimenez-Ruiz, 1998]. Some of them are more expressed in the promastigotes stationary phase and may be involved in the metacyclogenesis. Other members of this family are essentially expressed by *Leishmania* amastigotes suggesting that they may exert their function during the intracellular stage of the parasite. The immunogenicity of the PSA-2 complex proteins was well studied in human and in the mouse model of experimental leishmaniasis, it was demonstrated that the PSA-2 protein induces a Th1 type of response in both patients with self-resolved CL and in infected mice [Handman, 1995; Kemp, 1998]. In addition, the PSA-2 protein induces a significant protection of mice against a parasite challenge using virulent *Leishmania* [Handman, 1995].

HSP-70

The heat shock proteins 70 are highly conserved among different species (Archaea, eubacteria and eukaryotes) and are highly represented under conditions of cellular stress. The HSP-70 display chaperone activity and are therefore involved in protein folding and transport [Bassan, 1998]. Interestingly, recent studies showed that these proteins specifically inhibit the cellular apoptosis [Garrido, 2003]. Interestingly, the HSP-70 was described as an excreted/secreted protein [Pockley, 1998; 1999; Rea, 2001].

In *Leishmania*, the hsp 70 gene was well characterized and as reported for hsp70 genes from different species, its expression increased, in vitro and in vivo, in response to a heat and/or oxidant stress [Garlpati, 1999]. This response may be involved in parasite survival and proliferation into mammalian host cells. It has also been described that the *trypanosmatidae*Hsp70 proteins displayed high immunostimulatory properties. Recently, Planelles et al, (2001) showed that the DNA immunization of mice with *Trypanosoma cruzi* KMP11 -HSP70 fused genes elicited both an immunoglobulin G2a long-lasting humoral immune response against KMP11 protein and activation of CD8+ cytotoxic T lymphocytes specific to KMP-11. Moreover, protection against the parasite challenge was observed in mice immunized with the chimeric gene [Planelles, 2001]. In *Leishmania*, the nuclease P4 fused with the Hsp70 (P4/Hsp70) was proposed as a vaccine candidate [Campbell, 2003]. It was demonstrated that the P4/Hsp70 induced a Th1 cytokine profile in BALB/c mice immunized by a DNA vaccine containing P4/Hsp70 fused genes. In addition, the DNA vaccine encoding P4/HSP70 induced significant protection against *L. major* challenge. It was reported by Rico et al (2002) that *Leishmania* heat shock proteins Hsp70 and Hsp83, are potent mitogens for murine splenocytes. In vitro incubation of spleen cells with the *Leishmania* Hsps leads to the expansion of B220-bearing populations, suggesting a direct effect of these proteins on B lymphocytes. an indication that the MBP-Hsp70 and MBP-Hsp83 recombinant proteins behave as T cell-independent mitogens of B cells. Furthermore, both proteins were able to induce proliferation on B cell populations purified from BALB/c spleen [Rico, 2002].

Cathepsin L-like Protease

The cathespin L proteins are members of the papain superfamily and are expressed by several species. In *Faciola Hepatica* parasite the cathepsin L protease was well studied and it was demonstrated that this protein is excreted/secreted and involved in the virulence of the parasite [Collins, 2004]. Recently, it was shown that it may constitute a good vaccine candidate [Dalton, 2003; Harmsen,2004]. In *Leishmania*, the cysteine proteinases have been also described as virulence factors [Motram, 1996; Matlashewki, 2001]. The gene of the cathepsin L-like proteinase is stage regulated with high expression in amastigotes, lower expression in metacyclics and very low in procyclics [Souza, 1994]. These results suggest that this enzyme may play an important role in intracellular survival of the parasite.

KMP-11

The Kinetoplast Membrane Protein-11 (KMP-11) is a surface glycoprotein of Kinetoplastidae parasites. In *Leishmania*, KMP-11 is tightly associated with lipophosphoglycan (LPG) and contributes to its stability. KMP-11 is expressed in both promastigotes and amastigotes stages at the surface of the parasite [Tolson, 1994; Jardim, 1995]. Mukhopadhyay et al. (1998), have been shown that the KMP-11 protein may be involved in *Leishmania* virulence [Mukhopadhyay, 1998]. In addition to its role in the pathogenicity of the parasite, KMP-11 was proposed by different authors as a good vaccine candidate. In fact, it was described to elicit potent lymphoproliferative and antibody responses in leishmaniasis patients or experimentally infected mice [Jensen, 1998; Requena, 2000; Delgado, 2004]. Interestingly, a strong protective effect was observed in mice vaccinated with Langerhans cells pulsed with different *Leishmania* antigens, KMP-11, LACK, PSA-2 and gp63 after a virulent challenge with *L. major* [Berberich, 2003].

Spermidine Synthase

The spermidine synthase protein is involved in the polyamine biosynthetic pathway [Kaiser, 2003]. The spermidine synthase catalyzes the synthesis of spermidine by transfering a propylamine group from decarboxylated S-adenosylmethionine to putrescine. The spermidine synthase is well conserved among several species [Kaiser, 2003]. In protozoa including *Leishmania*, spermidine may play a crucial role in cell proliferation, cell differentiation, and biosynthesis of macromolecules [Kaiser, 2003]. Targeting polyamines of protozoa by chemotherapy may constitute a new way for the identification of new anti-leishmanial drugs [Kaiser, 2003]. In fact recent studies have shown that specific inhibitors of spermidine synthase decrease parasite proliferation [Kaiser, 2003].

Cytochrome C

Cytochromes c can be defined as electron-transfer proteins having one or several haem c groups, bound to the protein by one or, more commonly two, thioesther bonds involving sulphydryl groups of cysteine residues. Cyt c possesses a wide range of properties and function in a large number of different redox processes [Namslauer, 2004]. This protein is released in the extracellular culture medium in the early steps of cell apoptotisis [Saelens, 2004]. A recent study showed that the induced *Leishmania* apoptosis is accompanied with cytochrome c release from the mitochondria [Akarid, 2004]. Interestingly, cytochrome c of *Mycobacterium tuberculosis* induces IFN-gamma secretion and proliferation of human PBMC from purified protein derivative-(PPD)-positive individuals [Moran, 1999]. Thus it was proposed as a good vaccine candidate.

Ribosomal Proteins and Proteins Associated With the Proteasome

Two kinds of ribosomal proteins family have been detected in the culture medium: those associated with the large subunit of the ribosome (L) and those associated with the small subunit (S). All these proteins are well conserved among eukaryotic and prokaryotic species. It was reported that different ribosomal proteins are released in the culture medium of different pathogens including *Leishmania* [Ouaissi, 2004]. Moreover, the ribosomal protein L7/L12 of *Brucella abortus* was proposed as a good vaccine candidate. In fact, it confers a protection in the mouse model after a virulent challenge [Kurar, 1997; Pontes, 2003]. In *Leishmania*, Probst et al, (2001) using parasite-specific T cell lines derived from an immune donor showed that the ribosomal protein S4 induces high lymphoproliferative responses associated with a secretion of significant amounts of IFN-g [Probst, 2001]. Sequence analysis the *Leishmania* ribosomal proteins did not reveal any signal peptide and thus it is not clear by which mechanism they might be secreted. Two proteins with significant homologies with proteins associated with the proteasome were also released in the culture medium. These proteins may be involved in intracellular proteolytic processes of the parasite. Like ribosomal proteins, these proteins lack signal peptide and therefore mechanisms by which these proteins are exported outside the parasite remain to be determined.

*Leishmania* Proteins That did not Display any Homologies With Known Proteins

Thirteen proteins detected in the culture medium did not correspond to proteins described in sequences libraries. However a majority of these proteins displayed very specific conserved functional domains and almost all contain a signal peptide. Additional studies are in progress to characterize these proteins.

The following *E. coli* strain was deposited at the Collection Nationale de Cultures de Microorganismes ("C.N.C.M."), Institut Pasteur, 28, rue du Docteur Roux, 75724 Paris Cedex 15, France as follows:

| Accession No. | Deposit Date |
|---|---|
| I-3394 | Feb. 24, 2005. |

REFERENCES

Akarid K, Arnoult D, Micic-Polianski J, Sif J, Estaquier J, Ameisen J C, *Leishmania major*-mediated prevention of programmed cell death induction in infected macrophages is associated with the repression of mitochondrial release of cytochrome c. J Leukoc Biol. 2004 July; 76(1):95-103.

Bassan M, Zamostiano R, Giladi E et al. The identification of secreted heat shock 60-like protein from rat glial cells and a human neuroblastoma cell line. *Neurosci Lett* 1998; 250: 37-40.

Berberich C, Ramirez-Pineda J R, Hambrecht C, Alber G, Skeiky Y A, Moll H, Dendritic cell (DC)-based protection against an intracellular pathogen is dependent upon DC-derived IL-12 and can be induced by molecularly defined antigens. J Immunol. 2003 Mar 15; 170(6):3171-9.

Berredo-Pinho M, Peres-Sampaio C E, Chrispim P P, Belmont-Firpo R, Lemos A P, Martiny A, Vannier-Santos M A, Mever-Fernandes J R, A Mg-dependent ecto-ATPase in *Leishmania* amazonensis and its possible role in adenosine acquisition and virulence. Arch Biochem Biophys. 2001 Jul 1; 391(1):16-24.

Campbell K, Diao H, Ji J, Soong L, DNA immunization with the gene encoding P4 nuclease of *Leishmania* amazonensis protects mice against cutaneous Leishmaniasis. Infect Immun. 2003 November; 71(11):6270-8.

Collins P R, Stack C M, O'Neill S M, Doyle S, Ryan T, Brennan G P, Mousley A, Stewart M, Maule A G, Dalton J P, Donnelly S, Cathepsin L1, the major protease involved in liver fluke (Fasciola hepatica) virulence: propetide cleavage sites and autoactivation of the zymogen secreted from gastrodermal cells. J Biol Chem. 2004; 279(17):17038-46.

Dalton J P, Neill S O, Stack C, Collins P, Walshe A, Sekiya M, Doyle S, Mulcahy G, Hoyle D, Khaznadji E, Moire N, Brennan G, Mousley A, Kreshchenko N, Maule A G, Donnelly S M, Fasciola hepatica cathepsin L-like proteases: biology, function, and potential in the development of first generation liver fluke vaccines. Int J Parasitol. 2003 Sep 30; 33(11):1173-81. Review.

Darvani A, Hosseini A Z, Dalimi A, Immune responses against excreted/secreted antigens of Toxoplasma gondii tachyzoites in the murine model. Vet Parasitol. 2003 Apr 18; 113(2):123-34.

Delgado G, Parra-Lopez C A, Vargas L E, Hova R. Estupinan M, Guzman F, Torres A, Alonso C, Velez I D, Spinel C, Patarrovo M E, Characterizing cellular immune response to kinetoplastid membrane protein-11 (KMP-11) during *Leishmania* (Viannia) panamensis infection using dendritic cells (DCs) as antigen presenting cells (APCs). Parasite Immunol. 2003; 25(4): 199-209.

Garlapati S, Dahan E, Shapira M, Effect of acidic pH on heat shock gene expression in *Leishmania*. Mol Biochem Parasitol. 1999 May 15; 100(1):95-101.

Garrido C, Schmitt E, Cande C, Vahsen N, Parcellier A, Kroemer G, HSP27 and HSP70: potentially oncogenic apoptosis inhibitors. Cell Cycle. 2003 November-December; 2(6):579-84.

Geldhof P, Vercauteren I, Knox D, Demaere V, Van Zeveren A, Berx G, Vercruvsse J, Claerebout E, Protein disulphide isomerase of Ostertagia ostertagi: an excretory-secretory product of L4 and adult worms? Int J Parasitol. 2003 February; 33(2):129-36.

Handman E. Osborn A H, Symons F, van Driel R, Cappai R, The *Leishmania* promastigote surface antigen 2 complex is differentially expressed during the parasite life cycle. Mol Biochem Parasitol. 1995 November; 74(2):189-200.

Handman E, Symons F M, Baldwin T M, Curtis J M, Scheerlinck J P, Protective vaccination with promastigote surface antigen 2 from *Leishmania major* is mediated by a TH1 type of immune response. Infect Immun. 1995 November; 63(11):4261-7.

Harmsen M M, Cornelissen J B, Buiis H E, Boersma W J, Jeurissen S H, van Milligen F J, Identification of a novel Fasciola hepatica cathepsin L protease containing protective epitopes within the propeptide. Int J Parasitol. 2004 May; 34(6):675-82.

Jensen A T, Gasim S, Ismail A, Gaafar A, Kurtzhals J A, Kemp M, El Hassan A M, Kharazmi A, Theander T G, Humoral and cellular immune responses to synthetic peptides of the *Leishmania* donovani kinetoplastid membrane protein-11. Scand J Immunol. 1998 July; 48(1):103-9.

Jimenez-Ruiz A, Boceta C, Bonay P, Requena J M, Alonso C, Cloning, sequencing, and expression of the PSA genes from *Leishmania* infantum. Eur J Biochem. 1998 Jan 15; 251(1-2):389-97.

Kaiser A E, Gottwald A M, Wiersch C S, Maier W A, Seitz H M, Spermidine metabolism in parasitic protozoa—a comparison to the situation in prokaryotes, viruses, plants and fungi. Folia Parasitol (Praha). 2003 March; 50(1):3-18.

Kemp M, Handman E, Kemp K, Ismail A, Mustafa M D, Kordofani A Y, Bendtzen K, Kharazmi A, Theander T G, The *Leishmania* promastigote surface antigen-2 (PSA-2) is specifically recognised by Th1 cells in humans with naturally acquired immunity to *L. major.*

Kurar E, Splitter G A, Nucleic acid vaccination of Brucella abortus ribosomal L7/L12 gene elicits immune response. Vaccine. 1997 December; 15(17-18):1851-7.

Matlashewski G, *Leishmania* infection and virulence. Med Microbiol Immunol (Berl). 2001 November; 190(1-2):37-42.

Mendez S, Belkaid Y, Seder R A, Sacks D, Optimization of DNA vaccination against cutaneous leishmaniasis. Vaccine. 2002 Nov 1; 20(31-32):3702-8.

Moran A J, Doran J L, Wu J, Treit J D, Ekpo P, Kerr V J, Roberts A D, Orme I M, Galant S, Ress S R, Nano F E, Identification of novel immunogenic *Mycobacterium tuberculosis* peptides that stimulate mononuclear cells from immune donors.

Mottram J C, Souza A E, Hutchison J E, Carter R, Frame M J, Coombs G H, Evidence from disruption of the lmcpb gene array of *Leishmania* mexicana that cysteine proteinases are virulence factors.

Mukhopadhyav S, Sen P, Maiumder H K, Roy S, Reduced expression of lipophosphoglycan (LPG) and kinetoplastid membrane protein (KMP)-11 in *Leishmania* donovani promastigotes in axenic culture. J Parasitol. 1998 June; 84(3): 644-7.

Mustafa A S, Development of new vaccines and diagnostic reagents against tuberculosis. Mol Immunol. 2002 September; 39(1-2):113-9.

Namslauer A, Brzezinski P, Structural elements involved in electron-coupled proton transfer in cytochrome c oxidase. FEBS Lett. 2004 Jun 1; 567(1):103-10.

Saelens X, Festiens N, Vande Walle L, van Gurp M, van Loo G, Vandenabeele P, Toxic proteins released from mitochondria in cell death. Oncogene. 2004 Apr 12; 23(16):2861-74.

Ouaissi A, Ouaissi M, Tavares J, Cordeiro-Da-Silva A, Host Cell Phenotypic Variability Induced by Trypanosomatid-Parasite-Released Immunomodulatory Factors: Physiopathological Implications. J Biomed Biotechnol. 2004; 2004 (3):167-174.

Pockley A G, Shepherd J, Corton J M, Detection of heat shock protein 70 (Hsp70) and anti-Hsp70 antibodies in the serum of normal individuals. *Immunol Invest* 1998; 27: 367-77.

Pockley A G, Bulmer J, Hanks B M, Wright B H, Identification of human heat shock protein 60 (Hsp60) and anti-Hsp60 antibodies in the peripheral circulation of normal individuals. *Cell Stress Chaperones* 1999; 4: 29-35

Pontes D S, Dorella F A, Ribeiro L A, Mivoshi A, Le Loir Y, Gruss A, Oliveira S C, Langella P, Azevedo V, Induction of partial protection in mice after oral administration of Lactococcus lactis producing Brucella abortus L7/L12 antigen. J Drug Target. 2003; 11(8-10):489-93.

Planelles L, Thomas M C, Alonso C, Lopez M C, DNA immunization with Trypanosoma cruzi HSP70 fused to the KMP11 protein elicits a cytotoxic and humoral immune response against the antigen and leads to protection. Infect Immun. 2001 October; 69(10):6558-63.

Prigione I, Facchetti P, Lecordier L, Deslee D, Chiesa S, Cesbron-Delauw M F, Pistoia V, Tcell clones raised from chronically infected healthy humans by stimulation with Toxoplasma gondii excretory-secretory antigens cross-react with live tachyzoites: characterization of the fine antigenic specificity of the clones and implications for vaccine development. J Immunol. 2000 Apr 1; 164(7):3741-8.

Probst P, Stromberg E, Ghalib H W, Mozel M, Badaro R, Reed S G, Webb J R, Identification and characterization of T cell-stimulating antigens from *Leishmania* by CD4 T cell expression cloning. J Immunol. 2001 Jan 1; 166(1):498-505.

Pym A S, Brodin P, Mailessi L, Brosch R, Demangel C, Williams A, Griffiths K E, Marchal G, Leclerc C, Cole S T, Recombinant BCG exporting ESAT-6 confers enhanced protection against tuberculosis. Nat Med. 2003 May; 9(5):533-9.

Ramirez J R, Gilchrist K, Robledo S, Sepulveda J C, Moll H, Soldati D, Berberich C, Attenuated Toxoplasma gondii ts-4 mutants engineered to express the *Leishmania* antigen KMP-11 elicit a specific immune response in BALB/c mice. Vaccine. 2001 Nov 12; 20(3-4):455-61.

Rea I M, McNerlan S, Pockley A G, Serum heat shock protein and anti-heat shock protein antibody levels in aging. *Exp Gerontol* 2001; 36: 341-52

Requena J M, Soto M, Doria M D, Alonso C, Immune and clinical parameters associated with *Leishmania infantum* infection in the golden hamster model. Vet Immunol Immunopathol. 2000 Oct 31; 76(3-4):269-81.

Rico A I, Girones N, Fresno M, Alonso C, Requena J M, The heat shock proteins, Hsp70 and Hsp83, of *Leishmania infantum* are mitogens for mouse B cells. Cell Stress Chaperones. 2002 October; 7(4):339-46.

Shams H, Klucar P, Weis S E, Lalvani A, Moonan P K, Safi H, Wizel B, Ewer K, Nepom G T, Lewinsohn D M, Andersen P, Barnes P F, Characterization of a *Mycobacterium tuberculosis* peptide that is recognized by human CD4+ and CD8+ T cells in the context of multiple HLA alleles. J Immunol. 2004 Aug 1; 173(3):1966-77.

Souza A E, Bates P A, Coombs G H, Mottram J C, Null mutants for the lmcpa cysteine proteinase gene in *Leishmania mexicana*. Mol Biochem Parasitol. 1994 February; 63(2): 213-20.

Symons F M, Murray P J, Ji H, Simpson R J, Osborn A H, Cappai R, Handman E, Characterization of a polymorphic family of integral membrane proteins in promastigotes of different *Leishmania* species. Mol Biochem Parasitol. 1994 September; 67(1):103-13.

Turano C, Coppari S, Altieri F, Ferraro A, Proteins of the PDI family: unpredicted non-ER locations and functions. J Cell Physiol. 2002 November; 193(2):154-63.

Webb J R, CamDos-Neto A, Ovendale P J, Martin T I, Stromberg E J, Badaro R, Reed S G, Human and murine immune responses to a novel *Leishmania major* recombinant protein encoded by members of a multicopy gene family. Infect Immun. 1998 July; 66(7):3279-89.

Wilkinson B, Gilbert H F, Protein disulfide isomerase. Biochim Biophys Acta. 2004 Jun 1; 1699(1-2):35-44.

The invention claimed is:

1. An isolated polynucleotide consisting of a sequence encoding an excreted/secreted polypeptide of *Leishmania major*, said sequence having SEQ ID NO:1 or said sequence having at least 95% identity to SEQ ID NO:1.

2. An immunogenic composition comprising a polynucleotide as defined in claim 1 and an acceptable carrier.

3. An expression or a cloning vector containing a polynucleotide of claim 1.

4. A method for inducing an immune response in a patient infected with a *Leishmania major* strain, the method comprising administering to the patient a therapeutically effective amount of a composition as defined in claim 2.

5. A transformed or transfected cell that contains a vector as defined in claim 3.

6. A transformed or transfected cell that contains a polynucleotide of claim 1.

7. The cell of claim 6, consisting of an *Escherichia coli* bacterium deposited at the C.N.C.M. under accession number I-3994.

8. A genetically modified, transformed, *Leishmania major* strain comprising at least one gene having a sequence comprising SEQ ID NO:1 wherein said at least one gene is inactivated.

9. The genetically modified *Leishmania major* strain of claim 8, wherein the gene is inactivated by knock-out.

10. A genetically modified, transformed, *Leishmania major* strain comprising at least one gene having a sequence comprising SEQ ID NO:1 wherein said at least one gene is expressed.

* * * * *

SEQUENCE LISTING

```
<160> NUMBER OF SEQ ID NOS: 70

<210> SEQ ID NO 1
<211> LENGTH: 1734
<212> TYPE: DNA
<213> ORGANISM: Leishmania major
<220> FEATURE:
<221> NAME/KEY: CDS
<222> LOCATION: (1)..(1731)

<400> SEQUENCE: 1
```

-continued

```
atg gat aga gaa gga agc tac tcg tcc cac agc aca cgt tgt gcc agc       48
Met Asp Arg Glu Gly Ser Tyr Ser Ser His Ser Thr Arg Cys Ala Ser
1               5                   10                  15

ggc agc gtg ggc aat caa cga tgg agt gcc agc aac aga agc tcc ggc       96
Gly Ser Val Gly Asn Gln Arg Trp Ser Ala Ser Asn Arg Ser Ser Gly
            20                  25                  30

act gcc gtc ggc gcc act ggc gag gat ttc aac tct ctc atc gtg gcg      144
Thr Ala Val Gly Ala Thr Gly Glu Asp Phe Asn Ser Leu Ile Val Ala
        35                  40                  45

ttt tac acc cgt gtg tac ccc tcc gcg gat gtc ttc gct gac gac gcc      192
Phe Tyr Thr Arg Val Tyr Pro Ser Ala Asp Val Phe Ala Asp Asp Ala
    50                  55                  60

gcg gag ttt gac ctg gag gac atc agc gag gct gtc acg gag ctt gcc      240
Ala Glu Phe Asp Leu Glu Asp Ile Ser Glu Ala Val Thr Glu Leu Ala
65                  70                  75                  80

aat gaa gtg tca gcg ctg caa gaa gaa acg cac gta ctt ggc tcc cac      288
Asn Glu Val Ser Ala Leu Gln Glu Glu Thr His Val Leu Gly Ser His
                85                  90                  95

gtg cag aca ctg cag cag cgg cgt cca ggt ggt ggc gcc acc gtg agt      336
Val Gln Thr Leu Gln Gln Arg Arg Pro Gly Gly Gly Ala Thr Val Ser
            100                 105                 110

atc ccc aat atc tcc gaa tcc gcc ggc att cag ctc gat gcg gcc gac      384
Ile Pro Asn Ile Ser Glu Ser Ala Gly Ile Gln Leu Asp Ala Ala Asp
        115                 120                 125

aat agc ggc tca ggt gcg ctc tcg cca gta gat acc acc gtt ttt ctt      432
Asn Ser Gly Ser Gly Ala Leu Ser Pro Val Asp Thr Thr Val Phe Leu
    130                 135                 140

ctc ggc ggc gac tat gag ctt tcc atg ggc acc tcg cgc aca tct ggc      480
Leu Gly Gly Asp Tyr Glu Leu Ser Met Gly Thr Ser Arg Thr Ser Gly
145                 150                 155                 160

ggc ggc gcg gcc gat aca gtc ggc agc acg agc gga acc ggt cgg cgc      528
Gly Gly Ala Ala Asp Thr Val Gly Ser Thr Ser Gly Thr Gly Arg Arg
                165                 170                 175

ggc cgc agc ttc cgt cgc cgc tcg ctc gct gac gta gat gcc ttc atg      576
Gly Arg Ser Phe Arg Arg Arg Ser Leu Ala Asp Val Asp Ala Phe Met
            180                 185                 190

cgg gta gac gac aag gcc gtg ttg ctg cgg cag gaa acg gct cgg ctg      624
Arg Val Asp Asp Lys Ala Val Leu Leu Arg Gln Glu Thr Ala Arg Leu
        195                 200                 205

cgc aca cag gaa gaa aag gcc gct aag gag gcg gag ggc gtg cac gag      672
Arg Thr Gln Glu Glu Lys Ala Ala Lys Glu Ala Glu Gly Val His Glu
    210                 215                 220

atg ctc gtc gcc acc gtc gag gag gcc att cga cgt cgg cag gag ctc      720
Met Leu Val Ala Thr Val Glu Glu Ala Ile Arg Arg Arg Gln Glu Leu
225                 230                 235                 240

cgc ctt gag atg ctg cag ttc gaa cga gag gtg ctg agg aac ggg ggc      768
Arg Leu Glu Met Leu Gln Phe Glu Arg Glu Val Leu Arg Asn Gly Gly
                245                 250                 255

gca gag gac gac acg gcg gag gtt tcc gcg cac cgg cgc aac cct tta      816
Ala Glu Asp Asp Thr Ala Glu Val Ser Ala His Arg Arg Asn Pro Leu
            260                 265                 270

ggg gac gcg aag aag ctg acg gtc tca tcc gcg gct gtc gcg aca acc      864
Gly Asp Ala Lys Lys Leu Thr Val Ser Ser Ala Ala Val Ala Thr Thr
        275                 280                 285

gca gac gag ctg ctg cgc tac cta gag cgc cgg cac agc act cag gtg      912
Ala Asp Glu Leu Leu Arg Tyr Leu Glu Arg Arg His Ser Thr Gln Val
    290                 295                 300

agc tat ctc gac aag ctg gag gtg caa tgc cag gcg gca gag cag gat      960
Ser Tyr Leu Asp Lys Leu Glu Val Gln Cys Gln Ala Ala Glu Gln Asp
```

-continued

```
305                 310                 315                 320

atc gca cga gca cag cag ctg gtg cgg cag cgt cgc gcc gcc ggt gag     1008
Ile Ala Arg Ala Gln Gln Leu Val Arg Gln Arg Arg Ala Ala Gly Glu
                325                 330                 335

gca ttc caa gcc gtt gac atg gag cag ctg cgc atc gag cac aag cag     1056
Ala Phe Gln Ala Val Asp Met Glu Gln Leu Arg Ile Glu His Lys Gln
            340                 345                 350

ttt agc gag cgc atg gag gcc aag aac aaa gag ctg gcg gag cta aag     1104
Phe Ser Glu Arg Met Glu Ala Lys Asn Lys Glu Leu Ala Glu Leu Lys
        355                 360                 365

ggc acg tcg acg cgc acg gtg cag cag ctg aac cac ctc atg ggc caa     1152
Gly Thr Ser Thr Arg Thr Val Gln Gln Leu Asn His Leu Met Gly Gln
    370                 375                 380

ctc aac gag ctg gcg agc gaa cag act cgg ctg aag cgc gag gcg aag     1200
Leu Asn Glu Leu Ala Ser Glu Gln Thr Arg Leu Lys Arg Glu Ala Lys
385                 390                 395                 400

agc cgc tca gaa tac ttg tcg cgc tgc ggg aaa gag atc gcg acg gcg     1248
Ser Arg Ser Glu Tyr Leu Ser Arg Cys Gly Lys Glu Ile Ala Thr Ala
                405                 410                 415

acg gcg gag gct gtg cag gcg gag tcg aag cac atg aca ctc aag gca     1296
Thr Ala Glu Ala Val Gln Ala Glu Ser Lys His Met Thr Leu Lys Ala
            420                 425                 430

cag cag gag gcc gtc aag gtg ccc aag att gag gag tac atg gcg cag     1344
Gln Gln Glu Ala Val Lys Val Pro Lys Ile Glu Glu Tyr Met Ala Gln
        435                 440                 445

aag gca gag gag gtg gag ctc cag aag gca gtg aag aac ttg gag cgc     1392
Lys Ala Glu Glu Val Glu Leu Gln Lys Ala Val Lys Asn Leu Glu Arg
    450                 455                 460

aag gtg cag atc gcc gaa ggc cag gct gcg gtg gtg cga cag cag tcg     1440
Lys Val Gln Ile Ala Glu Gly Gln Ala Ala Val Val Arg Gln Gln Ser
465                 470                 475                 480

cgt cgg ttg cag gcg cag cgc gca tct gcc ata aaa tac gca aat gag     1488
Arg Arg Leu Gln Ala Gln Arg Ala Ser Ala Ile Lys Tyr Ala Asn Glu
                485                 490                 495

aag cac ctg agt cgc aat tcc acc acg tcg agg gcc aca gcc tca gca     1536
Lys His Leu Ser Arg Asn Ser Thr Thr Ser Arg Ala Thr Ala Ser Ala
            500                 505                 510

gga gcg aca gca tct tcg cgg cct gca gct gga agt gca cgt ggc ctg     1584
Gly Ala Thr Ala Ser Ser Arg Pro Ala Ala Gly Ser Ala Arg Gly Leu
        515                 520                 525

ttg atg cag cgc cgg caa cag cgg gaa cag gaa caa cag ccg cca tcg     1632
Leu Met Gln Arg Arg Gln Gln Arg Glu Gln Glu Gln Gln Pro Pro Ser
    530                 535                 540

ctg cca gaa gcg agc acc gtc gag caa gac ggt agc gct gca gca cca     1680
Leu Pro Glu Ala Ser Thr Val Glu Gln Asp Gly Ser Ala Ala Ala Pro
545                 550                 555                 560

gcg gcg gac cag cca gca gca gcg gcg aca acg gcg acg gtc tca tcc     1728
Ala Ala Asp Gln Pro Ala Ala Ala Ala Thr Thr Ala Thr Val Ser Ser
                565                 570                 575

atg taa                                                             1734
Met


<210> SEQ ID NO 2
<211> LENGTH: 2825
<212> TYPE: DNA
<213> ORGANISM: Leishmania major
<220> FEATURE:
<221> NAME/KEY: CDS
<222> LOCATION: (12)..(2516)

<400> SEQUENCE: 2
```

-continued

```
gttaaacgct t atg ctg ttt gtc ttg cag tgc act gca cac aca cac acg      50
             Met Leu Phe Val Leu Gln Cys Thr Ala His Thr His Thr
             1               5                   10

cac aca cac aca tgc agg cct cag cat ctc gtt gct cct ctc gcc tcc       98
His Thr His Thr Cys Arg Pro Gln His Leu Val Ala Pro Leu Ala Ser
    15                  20                  25

cta tgt cgc tca ctc gtc gtt gtc tct gca tcc ctc tct cct ttt cac      146
Leu Cys Arg Ser Leu Val Val Val Ser Ala Ser Leu Ser Pro Phe His
30                  35                  40                  45

cgt ccg tcg ctg cgg gtt ggg cac acg gtg caa tgc cag gca cgc tcg      194
Arg Pro Ser Leu Arg Val Gly His Thr Val Gln Cys Gln Ala Arg Ser
                50                  55                  60

cac gtg tcc cct ctc ccc aca cac ttg ctc ttc tct tct ttg gcc ctc      242
His Val Ser Pro Leu Pro Thr His Leu Leu Phe Ser Ser Leu Ala Leu
            65                  70                  75

gcc gca tgc gca cac gca cgg cgc gcg tgt agg gga gca ttc tca tac      290
Ala Ala Cys Ala His Ala Arg Arg Ala Cys Arg Gly Ala Phe Ser Tyr
        80                  85                  90

ctc aca gcc acc acc att acc att acc gtt acc act acc ttt acc acc      338
Leu Thr Ala Thr Thr Ile Thr Ile Thr Val Thr Thr Thr Phe Thr Thr
    95                  100                 105

ttc ttc ctc ttc tcc gtt gtg ctc cac ccc cgc ttc aac ggc gac aga      386
Phe Phe Leu Phe Ser Val Val Leu His Pro Arg Phe Asn Gly Asp Arg
110                 115                 120                 125

gca gcg aag gcg aag acg gga aag aag atg tgg cgg cgc agc tgt tgc      434
Ala Ala Lys Ala Lys Thr Gly Lys Lys Met Trp Arg Arg Ser Cys Cys
                130                 135                 140

gta ttg gcc ccg agc atc ccg cga agc gtc tgg gac ccg gcg cac tac      482
Val Leu Ala Pro Ser Ile Pro Arg Ser Val Trp Asp Pro Ala His Tyr
            145                 150                 155

aac gag aac tgg gtg gac agc tac agc acc agc att gcc gac cgc cga      530
Asn Glu Asn Trp Val Asp Ser Tyr Ser Thr Ser Ile Ala Asp Arg Arg
        160                 165                 170

cac tgg cca gcg aag aag tgg tcc atc ggc ctc gaa ccc cgc acc cct      578
His Trp Pro Ala Lys Lys Trp Ser Ile Gly Leu Glu Pro Arg Thr Pro
    175                 180                 185

cgt gat tgg ctg cgc ttc tct tac cga aac ctt gcc tac gcc tac aac      626
Arg Asp Trp Leu Arg Phe Ser Tyr Arg Asn Leu Ala Tyr Ala Tyr Asn
190                 195                 200                 205

ggc gcg ctg cgt gcc tgc gcg acg ttt ccg gag atg ctc gtc tac tac      674
Gly Ala Leu Arg Ala Cys Ala Thr Phe Pro Glu Met Leu Val Tyr Tyr
                210                 215                 220

aag gag atg aag cag cgc ggg gtc aag gtg gac gtg gac acg ctg aac      722
Lys Glu Met Lys Gln Arg Gly Val Lys Val Asp Val Asp Thr Leu Asn
            225                 230                 235

gcg ctg ctc tcg cgc gcg gca cgg tac gag cac atc cag gtc gat gat      770
Ala Leu Leu Ser Arg Ala Ala Arg Tyr Glu His Ile Gln Val Asp Asp
        240                 245                 250

gtg ttt ctt ctc ttc gac gaa ctc acc gcc ctg ggt gcc cgt ccg gat      818
Val Phe Leu Leu Phe Asp Glu Leu Thr Ala Leu Gly Ala Arg Pro Asp
    255                 260                 265

atc gcg tcc gtg gag acg ctg cac aca gta ctc gag cac gcc gcg cat      866
Ile Ala Ser Val Glu Thr Leu His Thr Val Leu Glu His Ala Ala His
270                 275                 280                 285

cag ccg ccg gag tgg cgt gag acg cgc cgt cgt cag ctg gtg gaa ctg      914
Gln Pro Pro Glu Trp Arg Glu Thr Arg Arg Arg Gln Leu Val Glu Leu
                290                 295                 300

tac cag tac ctt gcg ttg gag gag atc gag cgc ctc gcc ccg cat cgc      962
Tyr Gln Tyr Leu Ala Leu Glu Glu Ile Glu Arg Leu Ala Pro His Arg
```

-continued

```
            305                 310                 315

gtc gat gca ttg ttg tct gcg cag atc gcg cgt ctg cga gga aac ctc      1010
Val Asp Ala Leu Leu Ser Ala Gln Ile Ala Arg Leu Arg Gly Asn Leu
        320                 325                 330

aag caa ctc aac gcg agc ctc agc cca tcc gtg tac cgg cgc tac ttt      1058
Lys Gln Leu Asn Ala Ser Leu Ser Pro Ser Val Tyr Arg Arg Tyr Phe
    335                 340                 345

gcg gct atc gac ctc ggt gag aca ctg atc cag gaa gtc cac aac ttt      1106
Ala Ala Ile Asp Leu Gly Glu Thr Leu Ile Gln Glu Val His Asn Phe
350                 355                 360                 365

ttg tgg gag tac gtc ggc gcc gat cac gct gcg atg gat gtg ccg tcg      1154
Leu Trp Glu Tyr Val Gly Ala Asp His Ala Ala Met Asp Val Pro Ser
                370                 375                 380

ctg cag ctt cgc atc ccc ttc gtg gcc tcc gtg atg aag cgg ccg ctg      1202
Leu Gln Leu Arg Ile Pro Phe Val Ala Ser Val Met Lys Arg Pro Leu
            385                 390                 395

gcg acg gca gac cct gcc aag gtg aag gcg acc gac ttt gag gac acg      1250
Ala Thr Ala Asp Pro Ala Lys Val Lys Ala Thr Asp Phe Glu Asp Thr
        400                 405                 410

gac gtg tgt agc gtg cta ctt gcg gcg gtg gag cgc tgc gtc gac gga      1298
Asp Val Cys Ser Val Leu Leu Ala Ala Val Glu Arg Cys Val Asp Gly
    415                 420                 425

aac ttc cac gac agg cgg cct gtg tct gag cgg cgc atg tat ctc gcc      1346
Asn Phe His Asp Arg Arg Pro Val Ser Glu Arg Arg Met Tyr Leu Ala
430                 435                 440                 445

ttg ctg acc atg ctc acc tcc agt ggc gtc ctg tat aca gcc gat ctc      1394
Leu Leu Thr Met Leu Thr Ser Ser Gly Val Leu Tyr Thr Ala Asp Leu
                450                 455                 460

atg gcg cag atg atg gat gtt gtg aag tac tcg cgc gac gat cgc gga      1442
Met Ala Gln Met Met Asp Val Val Lys Tyr Ser Arg Asp Asp Arg Gly
            465                 470                 475

cgt gac cgc gat gcg cag cgg ctg ctg cgg tac gcc ctg cgc ggg tcc      1490
Arg Asp Arg Asp Ala Gln Arg Leu Leu Arg Tyr Ala Leu Arg Gly Ser
        480                 485                 490

tcg gca gcc aac gac gcc gct tac cgc gag ctg tgg cga gct gtg gcg      1538
Ser Ala Ala Asn Asp Ala Ala Tyr Arg Glu Leu Trp Arg Ala Val Ala
    495                 500                 505

cct ccc gtg gat gcg cgc gtg gtg gga cgg tac ctg gca agc agg gac      1586
Pro Pro Val Asp Ala Arg Val Val Gly Arg Tyr Leu Ala Ser Arg Asp
510                 515                 520                 525

ccg tgg tca ccg gtg cat atc tgc tat gac cgc agt ttt caa ttt cga      1634
Pro Trp Ser Pro Val His Ile Cys Tyr Asp Arg Ser Phe Gln Phe Arg
                530                 535                 540

gcg ttc ccg gcg ctg cag caa atc acc cag agc caa tgc agc agc agc      1682
Ala Phe Pro Ala Leu Gln Gln Ile Thr Gln Ser Gln Cys Ser Ser Ser
            545                 550                 555

agc agc agc agc agc agc agc agc acc gac gcc gca gca gta gcg gcg      1730
Ser Ser Ser Ser Ser Ser Ser Ser Thr Asp Ala Ala Ala Val Ala Ala
        560                 565                 570

tcg acg gct gcc ggg gca gga agc tcc tct act gcg gcg gcg gcc gcc      1778
Ser Thr Ala Ala Gly Ala Gly Ser Ser Ser Thr Ala Ala Ala Ala Ala
    575                 580                 585

gag ccg gac gaa gcg tta gaa ggc gtg agc gcc ggc cct ccc ccc ggc      1826
Glu Pro Asp Glu Ala Leu Glu Gly Val Ser Ala Gly Pro Pro Pro Gly
590                 595                 600                 605

act gtt gcc gcc aag acg gcg gag gcg ctg cag cag cgc tgg gac gat      1874
Thr Val Ala Ala Lys Thr Ala Glu Ala Leu Gln Gln Arg Trp Asp Asp
                610                 615                 620

gta cgc cga ttg atc gac atc aca ggc gtt ctc aag ccg ggc gcg ggt      1922
```

-continued

```
Val Arg Arg Leu Ile Asp Ile Thr Gly Val Leu Lys Pro Gly Ala Gly
            625                 630                 635

ctg aca agt gca aga acc ggc tcc gcc gcg cca aca cag gag gcg gcg     1970
Leu Thr Ser Ala Arg Thr Gly Ser Ala Ala Pro Thr Gln Glu Ala Ala
        640                 645                 650

cag cag gcg atg gag gtc ttc acc ggc gcg gcg gcg ttc ctg cgc ggg     2018
Gln Gln Ala Met Glu Val Phe Thr Gly Ala Ala Ala Phe Leu Arg Gly
    655                 660                 665

gtg gcc acg ggc tgc cgc tac ggt gag ttg gcg gac gcg cta gca att     2066
Val Ala Thr Gly Cys Arg Tyr Gly Glu Leu Ala Asp Ala Leu Ala Ile
670                 675                 680                 685

caa gca gta gga gat ggg caa cag cag cac cac cac gcg cca cgt gcg     2114
Gln Ala Val Gly Asp Gly Gln Gln Gln His His His Ala Pro Arg Ala
                690                 695                 700

acg ccg ctc gga ggc gca gca gcc aca gca ggc gcc gcg cgc agc agc     2162
Thr Pro Leu Gly Gly Ala Ala Ala Thr Ala Gly Ala Ala Arg Ser Ser
            705                 710                 715

agc ggc aat gtg aac aca gag ctg tac gcc ggc ggc ctc gac ttt gat     2210
Ser Gly Asn Val Asn Thr Glu Leu Tyr Ala Gly Gly Leu Asp Phe Asp
        720                 725                 730

gtc tgg cag cga ctc atg cag tgc gtg cag cag ctg cgt cag gac atg     2258
Val Trp Gln Arg Leu Met Gln Cys Val Gln Gln Leu Arg Gln Asp Met
    735                 740                 745

gag cag ttc atg gct cag cag tac gag gcg cat ggt ctg cag gtg gag     2306
Glu Gln Phe Met Ala Gln Gln Tyr Glu Ala His Gly Leu Gln Val Glu
750                 755                 760                 765

ccg gag ttc gag tgc tgg gag gct atg ctc gtg gtg ctg cgc tgc atc     2354
Pro Glu Phe Glu Cys Trp Glu Ala Met Leu Val Val Leu Arg Cys Ile
                770                 775                 780

ttg gac ttc tgc ctg gtg cac acg cag cag tac ggc cgt acg gct ggt     2402
Leu Asp Phe Cys Leu Val His Thr Gln Gln Tyr Gly Arg Thr Ala Gly
            785                 790                 795

ggt ggc atg gcg gag aat ctg ttc ctg gag tcg gcg cag ctg cgc gcg     2450
Gly Gly Met Ala Glu Asn Leu Phe Leu Glu Ser Ala Gln Leu Arg Ala
        800                 805                 810

cag ttg gtg gag gaa agt cgc acc cgc ttc aat ggc cgc atg cgc atc     2498
Gln Leu Val Glu Glu Ser Arg Thr Arg Phe Asn Gly Arg Met Arg Ile
    815                 820                 825

ttg tgg ctg caa gag gtt taggctgtcg gtctgtaaaa ccactgctgc            2546
Leu Trp Leu Gln Glu Val
830                 835

tgtgctgaca atattgggcc cattcacgtg cttgccaggg ctaccagcag cgcgcgcgca   2606

ctccaccgcc attcttcggc tccgtttttt gtgtgtctgt ccgtctgtgt gtgtgtgtgt   2666

ttgtgttgat aatgtgcgct gacaatgatg atcttgagtg tgcttaatct ctctctctct   2726

ctgtacgtgt gtgtgtgcgc gcgcacgcgc agggcacatc tccgccgccc ttgcggaatc   2786

cttcaccgtg ctgcacgaca aaaaaaaaaa aaaaaaaaa                          2825


<210> SEQ ID NO 3
<211> LENGTH: 1485
<212> TYPE: DNA
<213> ORGANISM: Leishmania major
<220> FEATURE:
<221> NAME/KEY: CDS
<222> LOCATION: (127)..(1146)

<400> SEQUENCE: 3

ttccgttgct ctgacacccc cgcaaaactg ctgcgccagt gaagtgcgtc gtgccgcttc     60

atccatcttc gcctttggca cgcgtacttg cattgcttac caaaggtaca cgtacacagg    120
```

-continued

```
cgagag atg tca gct aac tgc gcg ggt ccc gca tca aca ccc gac gcg       168
       Met Ser Ala Asn Cys Ala Gly Pro Ala Ser Thr Pro Asp Ala
       1               5                   10

aag aag gcc cga gtg gaa gcc gat gtg atc acg gag gcg gac cgc gtg      216
Lys Lys Ala Arg Val Glu Ala Asp Val Ile Thr Glu Ala Asp Arg Val
15                  20                  25                  30

ccg gcg ttt cct ctc ccg ccc acc gat gcc gct gcc tac gag cgt gaa      264
Pro Ala Phe Pro Leu Pro Pro Thr Asp Ala Ala Ala Tyr Glu Arg Glu
                35                  40                  45

cac gtg cac aac gtg tac agc gcg att gcc gac cac ttc tct agc aca      312
His Val His Asn Val Tyr Ser Ala Ile Ala Asp His Phe Ser Ser Thr
            50                  55                  60

cgg tac aag gcg tgg cca cag gtc ggc gcc ttc ttg gag ggc cta ccg      360
Arg Tyr Lys Ala Trp Pro Gln Val Gly Ala Phe Leu Glu Gly Leu Pro
        65                  70                  75

ccc ttt tcc ctc gtg gcg gat gtt ggc tgc gga aat ggg aag tac ttt      408
Pro Phe Ser Leu Val Ala Asp Val Gly Cys Gly Asn Gly Lys Tyr Phe
    80                  85                  90

tcg gca gca cag cgg ctt gcc ctc act gcc ccg tcg cat ccc atg acc      456
Ser Ala Ala Gln Arg Leu Ala Leu Thr Ala Pro Ser His Pro Met Thr
95                  100                 105                 110

aca tca ggc gct tct ctc gag atg aag tcg agg cag caa gca gag gcg      504
Thr Ser Gly Ala Ser Leu Glu Met Lys Ser Arg Gln Gln Ala Glu Ala
                115                 120                 125

cag ccg tcg ccg cct ctt gtc tcc ttt gca ccc gca cac cgc tac gtc      552
Gln Pro Ser Pro Pro Leu Val Ser Phe Ala Pro Ala His Arg Tyr Val
            130                 135                 140

ttg ggc ctc gac tat agt gag gag ctc ctg cgc tcc acg caa cgt cag      600
Leu Gly Leu Asp Tyr Ser Glu Glu Leu Leu Arg Ser Thr Gln Arg Gln
        145                 150                 155

ctg gtc gac ccc aac atg cat cat gcg cag cgg cgt cgc cgc ctt agt      648
Leu Val Asp Pro Asn Met His His Ala Gln Arg Arg Arg Arg Leu Ser
    160                 165                 170

ggc aag cgt gca aag aac gag gca gag gcg gtg gcg aca cct gtg tct      696
Gly Lys Arg Ala Lys Asn Glu Ala Glu Ala Val Ala Thr Pro Val Ser
175                 180                 185                 190

gcg gag gag ctc cca cga aca gat acg gtg cgc agc gac gct cta cgg      744
Ala Glu Glu Leu Pro Arg Thr Asp Thr Val Arg Ser Asp Ala Leu Arg
                195                 200                 205

tgc ccg ttg cgt agc ggc gtc ttc gac gcc gcc atc agt ata gcg gtg      792
Cys Pro Leu Arg Ser Gly Val Phe Asp Ala Ala Ile Ser Ile Ala Val
            210                 215                 220

att cac cac tac gcg agt cgc gag cgg cgg aga ctg gcg gtg cgc gag      840
Ile His His Tyr Ala Ser Arg Glu Arg Arg Arg Leu Ala Val Arg Glu
        225                 230                 235

ctc ctc cgc ctc gct cgg ccg cat ggt ggg cgt gta ctt atc tac gtg      888
Leu Leu Arg Leu Ala Arg Pro His Gly Gly Arg Val Leu Ile Tyr Val
    240                 245                 250

tgg gca cgt gag cag cga ggc cac aca aag cgt ctg gtc gac cca gaa      936
Trp Ala Arg Glu Gln Arg Gly His Thr Lys Arg Leu Val Asp Pro Glu
255                 260                 265                 270

acc ggc gac ggt ctc gtg cgg tgg gag cga aat cag aag tac gat ggg      984
Thr Gly Asp Gly Leu Val Arg Trp Glu Arg Asn Gln Lys Tyr Asp Gly
                275                 280                 285

gca cag cag gtg ttc cgc cgc tac tat cac ttt ttt gcg gag gga gag     1032
Ala Gln Gln Val Phe Arg Arg Tyr Tyr His Phe Phe Ala Glu Gly Glu
            290                 295                 300

ctg gag cag ctg tgc aag gac gcg gcc agc gat gat ggg aca ggg tcg     1080
Leu Glu Gln Leu Cys Lys Asp Ala Ala Ser Asp Asp Gly Thr Gly Ser
```

-continued 305 310 315 att ccg gtc gca atc agg aaa tct tac tac gac aag gag aat tgg tgt 1128
Ile Pro Val Ala Ile Arg Lys Ser Tyr Tyr Asp Lys Glu Asn Trp Cys
320 325 330 gtg atg ctg gag cgc tgt tgacgtcgaa gtgaagggtg tggcgactcg 1176
Val Met Leu Glu Arg Cys
335 340 aacgccgcct gagatggaca acattgtgcc tgtgggtttt tgcatgcgcc tcttagcctt 1236 attcgtctac acccatctgc ttggcccttt catcttgagt aataagtagg tccacctcgt 1296 cttcacaggc gcattgtaaa gttgcgcgcg ggcattatcg gggaagccga cgtgtcatcg 1356 atgtcgaggc ttgcgttgac atcacccccct tccttctttg ccgcgccttc gcagacggtg 1416 acggggaatg gccaccgcta cgagagtgaa agaaggcagc agcagagccg agaaaaaaaa 1476 aaaaaaaaa 1485

<210> SEQ ID NO 4
<211> LENGTH: 1662
<212> TYPE: DNA
<213> ORGANISM: Leishmania major
<220> FEATURE:
<221> NAME/KEY: CDS
<222> LOCATION: (102)..(1256)

<400> SEQUENCE: 4
cgagcggcgc actgggggcg ggcggtggcg gtgtccattc caccgccaca agcagcagcg 60
gcggtaacag cggcttcgac agtgtgcgct acaacaactt t atg aac ttc gcg aac 116
Met Asn Phe Ala Asn
1 5 aac gct aac ggg ggc tgc ttt ggc agc ctc tcc gcc gcc gcg tct gcc 164
Asn Ala Asn Gly Gly Cys Phe Gly Ser Leu Ser Ala Ala Ala Ser Ala
10 15 20 tcg gcg gca gca gcg gcg ccc acg gcg gtg agc caa ggc agc cgg ctc 212
Ser Ala Ala Ala Ala Ala Pro Thr Ala Val Ser Gln Gly Ser Arg Leu
25 30 35 gcc agc tct ggc caa agc aat agc cac agc ggc agc gca acg ctc gac 260
Ala Ser Ser Gly Gln Ser Asn Ser His Ser Gly Ser Ala Thr Leu Asp
40 45 50 tgg tct gcg tcg ccg ccc tcg tcg ggt cag tgc cct agt cag cag aag 308
Trp Ser Ala Ser Pro Pro Ser Ser Gly Gln Cys Pro Ser Gln Gln Lys
55 60 65 cac gcc gtc tct ggc cct gcg ccg ttc tca tac tac tac cag ggc acc 356
His Ala Val Ser Gly Pro Ala Pro Phe Ser Tyr Tyr Tyr Gln Gly Thr
70 75 80 85 gac gtc gct cgc ccg tcg gca caa gtg cga cac cac acc gca gcc tcc 404
Asp Val Ala Arg Pro Ser Ala Gln Val Arg His His Thr Ala Ala Ser
90 95 100 gct tcc gct cac ttc gac atc acg aac cgc gta gca gcg tcc gtg gcg 452
Ala Ser Ala His Phe Asp Ile Thr Asn Arg Val Ala Ala Ser Val Ala
105 110 115 gcg gtg tcg acc tcg gcg gat gct ggt gcg gag tcg cac cag cac gct 500
Ala Val Ser Thr Ser Ala Asp Ala Gly Ala Glu Ser His Gln His Ala
120 125 130 gca tca aca cag caa cag caa ctg ccg cct gtg gct ggc acg acc gtg 548
Ala Ser Thr Gln Gln Gln Gln Leu Pro Pro Val Ala Gly Thr Thr Val
135 140 145 cag ctc acg tca ccg tcg tcg tcc acc acc cgt gga agc ggc atc aac 596
Gln Leu Thr Ser Pro Ser Ser Ser Thr Thr Arg Gly Ser Gly Ile Asn
150 155 160 165

-continued

```
gtc aac gcc cag ccg tac tac tac gtt agc agc cgt atg cgc aag cag      644
Val Asn Ala Gln Pro Tyr Tyr Tyr Val Ser Ser Arg Met Arg Lys Gln
                170                 175                 180

cag cag cag caa gcg gca gca gcg tcg ccg gct tcc gta gac cca tca      692
Gln Gln Gln Gln Ala Ala Ala Ala Ser Pro Ala Ser Val Asp Pro Ser
            185                 190                 195

gtt acc cgc ccg ggt agc gac ttg gca gtc gct ggt acg acg tcg acg      740
Val Thr Arg Pro Gly Ser Asp Leu Ala Val Ala Gly Thr Thr Ser Thr
        200                 205                 210

agg acg cca gcg act gcg gta ggc act gat gac act gtg gct gcc gtg      788
Arg Thr Pro Ala Thr Ala Val Gly Thr Asp Asp Thr Val Ala Ala Val
    215                 220                 225

cag cgt gcg ccg ttg tcc acc ctc gaa ggc ggc agc gat gcg cgc tca      836
Gln Arg Ala Pro Leu Ser Thr Leu Glu Gly Gly Ser Asp Ala Arg Ser
230                 235                 240                 245

cca ggc tcg tcg ttc acg agc ccg gcg tgt gtc aac tcg ctg gcg cgc      884
Pro Gly Ser Ser Phe Thr Ser Pro Ala Cys Val Asn Ser Leu Ala Arg
                250                 255                 260

ttc agc acg tac gca agg acg acg acg gac agt gtg gca ggt cat gcg      932
Phe Ser Thr Tyr Ala Arg Thr Thr Thr Asp Ser Val Ala Gly His Ala
            265                 270                 275

tcg cag ccg agc ggc ttc cgc agc ggc atc gag act gtc gtg tcg gcg      980
Ser Gln Pro Ser Gly Phe Arg Ser Gly Ile Glu Thr Val Val Ser Ala
        280                 285                 290

atg aag atg tct ggc att tac ggc ggc agc ggc ggc ggc ggc aac aac     1028
Met Lys Met Ser Gly Ile Tyr Gly Gly Ser Gly Gly Gly Gly Asn Asn
    295                 300                 305

ggt aac agt acg agc agg agt agc gcg cac ccc cac acc ttc cca tcg     1076
Gly Asn Ser Thr Ser Arg Ser Ser Ala His Pro His Thr Phe Pro Ser
310                 315                 320                 325

cgg ccc atc gcc agg tca ggt gcg gac ggc ggc agc ggc ggc gag cag     1124
Arg Pro Ile Ala Arg Ser Gly Ala Asp Gly Gly Ser Gly Gly Glu Gln
                330                 335                 340

gcg act ttg gcg cgc gtg cca cgg cgg tct ccg cac gcg gat cac cag     1172
Ala Thr Leu Ala Arg Val Pro Arg Arg Ser Pro His Ala Asp His Gln
            345                 350                 355

gcg ccg gtg cac cgc cgc tcc acc ttc gcg tcg cag cac tca ctc ggc     1220
Ala Pro Val His Arg Arg Ser Thr Phe Ala Ser Gln His Ser Leu Gly
        360                 365                 370

aag aag cgc tca aag cct gac agc tac aag gac tac tgaggtgcag          1266
Lys Lys Arg Ser Lys Pro Asp Ser Tyr Lys Asp Tyr
    375                 380                 385

tcccccgtcg catgcgcaca gagcgggttg gacgatggcc gcgaggcgaa gagacatcgt   1326

gatcaaggca tgtgcgaacc ctgtacgttg gatgtgcgcg cgtgggtttt gcgaagtttg   1386

catgcccggc tatcagcgcg gccgtcccac atcaagcagt gcgcatctct gtctttcttc   1446

ttcgttacct tcgccttcgg gggcacaagg ggaatcacct gcacacgcat gctcacgcac   1506

atgcagagat tccagcaact aagctaacat ctttctaagc accctatcta tctatctatc   1566

tatatatata tatatatata tatatgtatc tatacggttc gggtatattc ttttttcatg   1626

ggacgataga gccaccaaaa aaaaaaaaaa aaaaaa                             1662
```

<210> SEQ ID NO 5
<211> LENGTH: 1872
<212> TYPE: DNA
<213> ORGANISM: Leishmania major
<220> FEATURE:
<221> NAME/KEY: CDS
<222> LOCATION: (214)..(816)

-continued

<400> SEQUENCE: 5
tgtgttcttc tcgtatgtgt gtgtgtgtgt cggtgtgtgt ctttcccgtt tctagagcat 60
gtttactttg atggtgaagc gtgcacacac gcgcacgcag aaaggcgcgc gaacgcactg 120
cacttttcct ttccgtttcc tttcatcagt tttccgcctt cgatcttttt ttttttttgt 180
ttggtccacc cccatgttca cggatgctgt gcg atg tat cac tcc cgt acg gag 234
Met Tyr His Ser Arg Thr Glu
1 5 act gta tcg aga cga gac gaa caa cgc cac cac cgc att cgg cag aga 282
Thr Val Ser Arg Arg Asp Glu Gln Arg His His Arg Ile Arg Gln Arg
10 15 20 aca gca acc tat tgt atg tgc gtg tgt cgg cgt gcc tgc ctt gtc ttc 330
Thr Ala Thr Tyr Cys Met Cys Val Cys Arg Arg Ala Cys Leu Val Phe
25 30 35 gat acc ccc act ttt ttt ttc gtt tcc gtt tac tct cat tcc gtc act 378
Asp Thr Pro Thr Phe Phe Phe Val Ser Val Tyr Ser His Ser Val Thr
40 45 50 55 tgc ttg cgt gtt ctt ctc gta tgt gtg tgt gtg tgt gtg tct gtg tct 426
Cys Leu Arg Val Leu Leu Val Cys Val Cys Val Cys Val Ser Val Ser
60 65 70 ctc tgc caa ccc ctt ccc cct ctt ttt tat tgt ata ttc ttc aca cac 474
Leu Cys Gln Pro Leu Pro Pro Leu Phe Tyr Cys Ile Phe Phe Thr His
75 80 85 aca cac aca cac aca gag agg aaa cag ttg gcc cgc ttc agc tcg tgc 522
Thr His Thr His Thr Glu Arg Lys Gln Leu Ala Arg Phe Ser Ser Cys
90 95 100 aac gtg gcg cgg tct ctg gcg act tgt tcc ctc ctc ctt ttt tgt tgc 570
Asn Val Ala Arg Ser Leu Ala Thr Cys Ser Leu Leu Leu Phe Cys Cys
105 110 115 ttt cgc gta gga tgc ttg cgt gtg tgt gtg tgt gcc aca acg gaa tcc 618
Phe Arg Val Gly Cys Leu Arg Val Cys Val Cys Ala Thr Thr Glu Ser
120 125 130 135 att tac atg cac aca ata gtg tcg ttt act gtt ctc gtt ttt atg tct 666
Ile Tyr Met His Thr Ile Val Ser Phe Thr Val Leu Val Phe Met Ser
140 145 150 cta aaa cct gac ggc ggg aag ggg gta cac aca cct ctc ggt gca tgg 714
Leu Lys Pro Asp Gly Gly Lys Gly Val His Thr Pro Leu Gly Ala Trp
155 160 165 cat cgc agg gtc tca cgt aca cac ccg ccc tgc caa tgc cag aac cgc 762
His Arg Arg Val Ser Arg Thr His Pro Pro Cys Gln Cys Gln Asn Arg
170 175 180 ctg tgg cgg tgg cag gct caa gtg cct ggc atg tgc gga ggg gtc aca 810
Leu Trp Arg Trp Gln Ala Gln Val Pro Gly Met Cys Gly Gly Val Thr
185 190 195 gcg atg taacgccgct ggtatgccgg cggtcatgcg ctggacggcg tggcatcggg 866
Ala Met
200 gcgacctgcg acggtgcaca cgtttgcaca tccacatgat gggcacagcg ccgaccgagc 926 tcgagcgtat cccgcccggc ccctgactgc ctgctggtgt gaagcctgcg tgccacaccg 986 agggggatgc accaggtggc ggccggcgtg atgggggcgg ctgcgaggcg acacgcggag 1046 cggtggtgcg tagcgtgtga ggcagaggcc gtgctctcag ctgactggga cggcacacag 1106 ctgcaacgcg tgtgcgaacg acatgcttcg caccaggcga cggggcctgt ggcagacagg 1166 cgggtggtgg tggtggtgca gagtggcgct tgactcctgt tgcgtggcag agctggcgcg 1226 ctgcagaaaa caacaatgtt cttgactgtt tcaggaatcc gaacggatgt gggaagcggc 1286 gttctgaggc tgcgtgccgc acaggagtgt ctttgaggca gactactgat ttgccaaact 1346

-continued

```
acggaaagga caacgcggcg cgcttcgtgt caggaaagag ggaggccccg acggcggcga   1406

tggtgaaaga cgcgccgttg tctggccgag aagtttttg tgaaggtatc gaggctcgcg   1466

cagctggcgg gccgaatggg ttacgacgcc agaggtgctg atgtcggctg gaacgcgggc   1526

cgtaggatca ggcgattcgg gcgtttgccg cagacattcc agcgcattga cgtatgtgtg   1586

agaaacacgt ccactttcga agtccatccg gaaaggcctg ctgcgctgta taacggcggc   1646

aaggggggg gatcgcacgt atggaccgtt ttcttgcata cccgccacac attatcgccc   1706

tccccctcct ctatattcca tttagagcgt atagcagcgg ataagccgtc ttgtggcttt   1766

atcagctact gtgactcgcg tagcgcaggg ggtgccgaac gcgaaggtgc gacagggccc   1826

acttgagtga cggcaaagaa agggaggagg ggggctgaaa ggatgc                   1872


<210> SEQ ID NO 6
<211> LENGTH: 1143
<212> TYPE: DNA
<213> ORGANISM: Leishmania major
<220> FEATURE:
<221> NAME/KEY: CDS
<222> LOCATION: (91)..(951)

<400> SEQUENCE: 6

ggcgccggag cgccttcctt gtggagtgct gaattagttc acggtaacgc ggcagcgtgc     60

tgggccgagg atccagcgga caacgcttgg atg aca gct act ggg cct tta cca     114
                                 Met Thr Ala Thr Gly Pro Leu Pro
                                 1               5

cgt gac gtc aga gac gtg gcg cca ttg cac cgg tgg caa acg gag ggt      162
Arg Asp Val Arg Asp Val Ala Pro Leu His Arg Trp Gln Thr Glu Gly
    10                  15                  20

acc agc tcg cac tct gag gct ggc ggt gac gta ccc gcg acc tgc ctt      210
Thr Ser Ser His Ser Glu Ala Gly Gly Asp Val Pro Ala Thr Cys Leu
25                  30                  35                  40

ttt cag cat ccc gtc gtt gct ctc ctt cct tca ttt cca cct ttg cct      258
Phe Gln His Pro Val Val Ala Leu Leu Pro Ser Phe Pro Pro Leu Pro
                45                  50                  55

ttt ttt ctc gtg gct cat cgc aca ttg cac aaa tgt gct ctg ggt tgt      306
Phe Phe Leu Val Ala His Arg Thr Leu His Lys Cys Ala Leu Gly Cys
            60                  65                  70

gct cct gtt gcg ttc act tgg tgc aca gtg cag ttt act tgg aaa cgc      354
Ala Pro Val Ala Phe Thr Trp Cys Thr Val Gln Phe Thr Trp Lys Arg
        75                  80                  85

tcc ccg caa ctg cgc tgc ttc gga tct gcg aac ctt gca gac ata tcc      402
Ser Pro Gln Leu Arg Cys Phe Gly Ser Ala Asn Leu Ala Asp Ile Ser
    90                  95                  100

ttc ggt cgc ggc tgt gat tac tcc gcg aat atg ctg cgt tgt gtg tcg      450
Phe Gly Arg Gly Cys Asp Tyr Ser Ala Asn Met Leu Arg Cys Val Ser
105                 110                 115                 120

aga agg ctg tgg tat cag ttc aag gac ctc aaa agt aag gtc atc ctc      498
Arg Arg Leu Trp Tyr Gln Phe Lys Asp Leu Lys Ser Lys Val Ile Leu
                125                 130                 135

gaa aag ctt cga aac tcg aaa ctg cag gaa ggt gtt cac cct tct gat      546
Glu Lys Leu Arg Asn Ser Lys Leu Gln Glu Gly Val His Pro Ser Asp
            140                 145                 150

atg gat atg gag gat ctg gca agg gaa agc ggc att gcg ccg ccg agt      594
Met Asp Met Glu Asp Leu Ala Arg Glu Ser Gly Ile Ala Pro Pro Ser
        155                 160                 165

agt gtc aat gtg cag gac ttt gtg cac gag aaa gag gcc gtg ctg gag      642
Ser Val Asn Val Gln Asp Phe Val His Glu Lys Glu Ala Val Leu Glu
    170                 175                 180
```

-continued

```
atg ctg cag gaa cag cga ctg cgc cgc ata gcc cgg cgc gaa gcg ttt      690
Met Leu Gln Glu Gln Arg Leu Arg Arg Ile Ala Arg Arg Glu Ala Phe
185                 190                 195                 200

ctg gag tgg caa gct ggg cag cgc gaa aaa ggc gcc gct cac cgt ctt      738
Leu Glu Trp Gln Ala Gly Gln Arg Glu Lys Gly Ala Ala His Arg Leu
                205                 210                 215

gtt cgc caa tcg cgc aaa gcg gaa aag tac aag cgc cgc cac tac cat      786
Val Arg Gln Ser Arg Lys Ala Glu Lys Tyr Lys Arg Arg His Tyr His
            220                 225                 230

gcc acg agt ggg cga atg ctg ccg ata tct ctt tct ccg ggt caa gca      834
Ala Thr Ser Gly Arg Met Leu Pro Ile Ser Leu Ser Pro Gly Gln Ala
        235                 240                 245

ccg cca gat cac cgc gca cca atg tca atg cca aag gcg tgc gta tcg      882
Pro Pro Asp His Arg Ala Pro Met Ser Met Pro Lys Ala Cys Val Ser
    250                 255                 260

tct acc gag ttt cta cga gga ggt ccg gca gaa aat cgg cac gcc ata      930
Ser Thr Glu Phe Leu Arg Gly Gly Pro Ala Glu Asn Arg His Ala Ile
265                 270                 275                 280

cac ctc tct ttg gaa aag aag tgagtgcccc cctgcagtgc gtgtgccgct         981
His Leu Ser Leu Glu Lys Lys
                285

ctcttttctg cactatgtcc ttgcacaaaa tgtgctgttt taaacgaaga aaaggagcga   1041

aggtggaagg gctccttctc atatctgctc gccgcttttt ttgtgtgacg gcagtgagag   1101

ccaccagtgc ttgccgcacg acaaaaaaaa aaaaaaaaaa aa                      1143


<210> SEQ ID NO 7
<211> LENGTH: 603
<212> TYPE: DNA
<213> ORGANISM: Leishmania major
<220> FEATURE:
<221> NAME/KEY: CDS
<222> LOCATION: (25)..(336)

<400> SEQUENCE: 7

ggtgctaacg caacgagtcc caag atg gtc tac acc cgc tgg aag tgc gat        51
                           Met Val Tyr Thr Arg Trp Lys Cys Asp
                           1               5

cgc atc cct gtg ctg cag ctg aag ctg ttc acg cag gag tac aac atg       99
Arg Ile Pro Val Leu Gln Leu Lys Leu Phe Thr Gln Glu Tyr Asn Met
10                  15                  20                  25

atg gca gtc gtt ggt ctg cta tcc atg gtg ttt ctg ttc aag cac gca      147
Met Ala Val Val Gly Leu Leu Ser Met Val Phe Leu Phe Lys His Ala
                30                  35                  40

agc tac tgc tct gag gag acg gag cgg aag aac ggc tgg tgg gca ggc      195
Ser Tyr Cys Ser Glu Glu Thr Glu Arg Lys Asn Gly Trp Trp Ala Gly
            45                  50                  55

tac ccg tat tgg cgt gac ccc att gcg cgt cgc aac gag att cgg tac      243
Tyr Pro Tyr Trp Arg Asp Pro Ile Ala Arg Arg Asn Glu Ile Arg Tyr
        60                  65                  70

aag caa ctg atc aac agc aac gat gtg gac att acc gac ccg aag tgg      291
Lys Gln Leu Ile Asn Ser Asn Asp Val Asp Ile Thr Asp Pro Lys Trp
    75                  80                  85

act ggc tgt tcc aag gag cag ctg gag cgc ctg cgc gcg att gtt          336
Thr Gly Cys Ser Lys Glu Gln Leu Glu Arg Leu Arg Ala Ile Val
90                  95                  100

tgaggagcgc gaatgtgtgg aaccgatacg tgactgcaac gggtcacctg tttgacagct    396

gttctgccgt cgctttcatt tttgttttct gccagccgct gctgtaagct tggtagtaac    456

aaacagtctc atgtagggcg ggtcgcgcct acctcgtttt gttctcgtcc ctcttcattt    516
```

-continued

```
aggagctaag taggaaatag tttacacctg tcgtgcgtag tgcaaaaagc cagaaaaaaa    576

aaaaaaaaaa aaaaaaaaaa aaaaaaa                                        603


<210> SEQ ID NO 8
<211> LENGTH: 4602
<212> TYPE: DNA
<213> ORGANISM: Leishmania major
<220> FEATURE:
<221> NAME/KEY: CDS
<222> LOCATION: (122)..(3952)

<400> SEQUENCE: 8

gtagactgcc gagcgacgtg ctacaacgga gaaaaaagag cacacacagc aaatatacgc     60

ccacttcttt tctttctccg tctcatactt tcttgtggct cgccctcttc gattgtaacc    120

g atg ctc gct aga tac ctc gat cct tca gtt cac ccg ctc aga gtt ggg    169
  Met Leu Ala Arg Tyr Leu Asp Pro Ser Val His Pro Leu Arg Val Gly
  1               5                   10                  15

cag gtg gtc gcc tac gac tac ctt cac gct gcg aag acg tgg cag tgg      217
Gln Val Val Ala Tyr Asp Tyr Leu His Ala Ala Lys Thr Trp Gln Trp
            20                  25                  30

acc ctg ggt acg gtg cgt gag atc aag gac tac acg gcc gtc gtg cag      265
Thr Leu Gly Thr Val Arg Glu Ile Lys Asp Tyr Thr Ala Val Val Gln
        35                  40                  45

cag tgg ggc ctt cac acc gga gac att gac acg ctg cgc tcc att ctc      313
Gln Trp Gly Leu His Thr Gly Asp Ile Asp Thr Leu Arg Ser Ile Leu
    50                  55                  60

ctc aaa gag gtc gac acg gaa aat gga cgc atg aag aac tat cat gat      361
Leu Lys Glu Val Asp Thr Glu Asn Gly Arg Met Lys Asn Tyr His Asp
65                  70                  75                  80

atg ctg gct atc gca cga gag aag ctc gca tcc atc cgc cgt agc aat      409
Met Leu Ala Ile Ala Arg Glu Lys Leu Ala Ser Ile Arg Arg Ser Asn
                85                  90                  95

gag gat cgt gtt tca cac gtt cga ggc cac ttt gac aag gct cgt gaa      457
Glu Asp Arg Val Ser His Val Arg Gly His Phe Asp Lys Ala Arg Glu
            100                 105                 110

aaa gta gag ctc att gac gag gtc gat ttg cgc aag gtc acg gcc cag      505
Lys Val Glu Leu Ile Asp Glu Val Asp Leu Arg Lys Val Thr Ala Gln
        115                 120                 125

gcc gcc cca tcc ccg gtt gct gta gca gtg ctg aag gcg gtg tgg gcc      553
Ala Ala Pro Ser Pro Val Ala Val Ala Val Leu Lys Ala Val Trp Ala
    130                 135                 140

gtg gcc aag tgc gat ccc acg gcg gtt gag ttc tac gag tgg gca gat      601
Val Ala Lys Cys Asp Pro Thr Ala Val Glu Phe Tyr Glu Trp Ala Asp
145                 150                 155                 160

gtg caa ctg gag tac cgg aag cca gcc gct ctc gat gag atc gcc aag      649
Val Gln Leu Glu Tyr Arg Lys Pro Ala Ala Leu Asp Glu Ile Ala Lys
                165                 170                 175

aca gac gtt ctc gcg aag ctc tat cct tcc gcg gaa agc ctc cag cag      697
Thr Asp Val Leu Ala Lys Leu Tyr Pro Ser Ala Glu Ser Leu Gln Gln
            180                 185                 190

tcc ctg gag cag gac ccc aag ctg aac tac aag gcg gcg gcg cgc gac      745
Ser Leu Glu Gln Asp Pro Lys Leu Asn Tyr Lys Ala Ala Ala Arg Asp
        195                 200                 205

tcg ccg gtg gtg gcc agc ctc cat gcg tgg gtc atc aca gct ctt gcc      793
Ser Pro Val Val Ala Ser Leu His Ala Trp Val Ile Thr Ala Leu Ala
    210                 215                 220

tac cag cag gcg tac aac ctc ctg gcg cac gac aag cgc atc cag gag      841
Tyr Gln Gln Ala Tyr Asn Leu Leu Ala His Asp Lys Arg Ile Gln Glu
225                 230                 235                 240
```

-continued

```
cag aac gac gcc atc gca gcc gcc att gct ggc atg aag gcc tgt cgc      889
Gln Asn Asp Ala Ile Ala Ala Ala Ile Ala Gly Met Lys Ala Cys Arg
                245                 250                 255

gcc aag atc gcc aag ctc aag gac gag ctg tct tca aag gac acg gct      937
Ala Lys Ile Ala Lys Leu Lys Asp Glu Leu Ser Ser Lys Asp Thr Ala
            260                 265                 270

gca ctc cct ggt cag gtc acc tcc ttc acc agg acg tca gtc ctc gtg      985
Ala Leu Pro Gly Gln Val Thr Ser Phe Thr Arg Thr Ser Val Leu Val
        275                 280                 285

acc att ccg ctg tct gcc gtc atc tct ccc gtc aat gtg gac acc gat     1033
Thr Ile Pro Leu Ser Ala Val Ile Ser Pro Val Asn Val Asp Thr Asp
    290                 295                 300

gtg aag cga tgc gtg ctg act aag gat gag gtc gag cag atc cct atc     1081
Val Lys Arg Cys Val Leu Thr Lys Asp Glu Val Glu Gln Ile Pro Ile
305                 310                 315                 320

gat gcc aag ata aca cga tat gcc caa aaa caa aaa ctg gct atc acc     1129
Asp Ala Lys Ile Thr Arg Tyr Ala Gln Lys Gln Lys Leu Ala Ile Thr
                325                 330                 335

gga tct cac ctt ctc gat caa tac gct gcc gcc acc act aca cac atc     1177
Gly Ser His Leu Leu Asp Gln Tyr Ala Ala Ala Thr Thr Thr His Ile
            340                 345                 350

tac gtc act gaa ctg gaa gac cgc ctc ttc ttc ttt cag cat tac atg     1225
Tyr Val Thr Glu Leu Glu Asp Arg Leu Phe Phe Phe Gln His Tyr Met
        355                 360                 365

gct tcc gct cta cgt gac gca cag aca gct gca gta gac gca cac cag     1273
Ala Ser Ala Leu Arg Asp Ala Gln Thr Ala Ala Val Asp Ala His Gln
    370                 375                 380

cgc ctc gcc gtc agt ctc cat gag cta gag gcg ttc cgc cag aag cgc     1321
Arg Leu Ala Val Ser Leu His Glu Leu Glu Ala Phe Arg Gln Lys Arg
385                 390                 395                 400

cac gac gcc aag aag gcg cgc gcc gcg gag ccg gaa ctt gcg gat gcc     1369
His Asp Ala Lys Lys Ala Arg Ala Ala Glu Pro Glu Leu Ala Asp Ala
                405                 410                 415

gac ggc gtg gag cca agc agc ggg ccc acc agc agt cgc tct ccc act     1417
Asp Gly Val Glu Pro Ser Ser Gly Pro Thr Ser Ser Arg Ser Pro Thr
            420                 425                 430

ggc cgc gca gcc ccg cgt gga cag agc gct gca ccg cgc ggc act gca     1465
Gly Arg Ala Ala Pro Arg Gly Gln Ser Ala Ala Pro Arg Gly Thr Ala
        435                 440                 445

tcg cag cag cac aag ctc ctc ggc ccc gcc tac cag tcc atc gac ccg     1513
Ser Gln Gln His Lys Leu Leu Gly Pro Ala Tyr Gln Ser Ile Asp Pro
    450                 455                 460

gct acc atc gcc aac gag ccg ctc tac gcc gtc acc atc gaa gag tac     1561
Ala Thr Ile Ala Asn Glu Pro Leu Tyr Ala Val Thr Ile Glu Glu Tyr
465                 470                 475                 480

aag gcc aaa gac gcc gca ggg gag cga gcc atg gac gag gcg gag cgc     1609
Lys Ala Lys Asp Ala Ala Gly Glu Arg Ala Met Asp Glu Ala Glu Arg
                485                 490                 495

atg gcg gac gaa gtg cag cgg ctc gcc gtg gaa ctg gag gac gcc aag     1657
Met Ala Asp Glu Val Gln Arg Leu Ala Val Glu Leu Glu Asp Ala Lys
            500                 505                 510

gcg gcg gcc gac aag ctg gcg gag gag ctc gcg gcc aag gac gag gag     1705
Ala Ala Ala Asp Lys Leu Ala Glu Glu Leu Ala Ala Lys Asp Glu Glu
        515                 520                 525

ctc gcc gcg cac cgc cag aag cgc cac gat gcc cgg cag gcg cgc gca     1753
Leu Ala Ala His Arg Gln Lys Arg His Asp Ala Arg Gln Ala Arg Ala
    530                 535                 540

agc gac cct gcc ttg gcc gcc gcc gac gct gtc gcg ccg cgc agc ggg     1801
Ser Asp Pro Ala Leu Ala Ala Ala Asp Ala Val Ala Pro Arg Ser Gly
```

-continued

```
545                 550                 555                 560

aag gga gca gca tcg ccg cac gtc ggc gca gtg cag cgc cag gcc gtc      1849
Lys Gly Ala Ala Ser Pro His Val Gly Ala Val Gln Arg Gln Ala Val
                565                 570                 575

gac cct gcc acc gtg ccc gtg gcc ccc gcc gtt atc gcg gag gag ccg      1897
Asp Pro Ala Thr Val Pro Val Ala Pro Ala Val Ile Ala Glu Glu Pro
            580                 585                 590

ctc tac gtg gcc acc gcg gag gag ctg cag cat gtg cgc gac ttc gca      1945
Leu Tyr Val Ala Thr Ala Glu Glu Leu Gln His Val Arg Asp Phe Ala
        595                 600                 605

gat cag ctc gct gag gag cta gag gcg ttc cgc cag aag cgc cac gac      1993
Asp Gln Leu Ala Glu Glu Leu Glu Ala Phe Arg Gln Lys Arg His Asp
    610                 615                 620

gcc aag aag gcg cgc gcc gcg gag ccg gaa ctt gcg gat gcc gac ggc      2041
Ala Lys Lys Ala Arg Ala Ala Glu Pro Glu Leu Ala Asp Ala Asp Gly
625                 630                 635                 640

gtg gag cca agc agc ggg ccc acc agc agt cgc tct ccc act ggc cgc      2089
Val Glu Pro Ser Ser Gly Pro Thr Ser Ser Arg Ser Pro Thr Gly Arg
                645                 650                 655

gca gcc ccg cgt gga cag agc gct gca ccg cgc ggc act gca tcg cag      2137
Ala Ala Pro Arg Gly Gln Ser Ala Ala Pro Arg Gly Thr Ala Ser Gln
            660                 665                 670

cag cac aag ctc ctc ggc ccc gcc tac cag tcc atc gac ccg gct acc      2185
Gln His Lys Leu Leu Gly Pro Ala Tyr Gln Ser Ile Asp Pro Ala Thr
        675                 680                 685

atc gcc aac gag ccg ctc tac gcc gtc acc atc gaa gag tac aag gcc      2233
Ile Ala Asn Glu Pro Leu Tyr Ala Val Thr Ile Glu Glu Tyr Lys Ala
    690                 695                 700

aaa gac gcc gca ggg gag cga gcc atg gac gag gcg gag cgc atg gcg      2281
Lys Asp Ala Ala Gly Glu Arg Ala Met Asp Glu Ala Glu Arg Met Ala
705                 710                 715                 720

gac gaa gtg cag cgg ctc gcc gtg gaa ctg gag gac gcc aag gcg gcg      2329
Asp Glu Val Gln Arg Leu Ala Val Glu Leu Glu Asp Ala Lys Ala Ala
                725                 730                 735

gcc gac aag ctg gcg gag gag ctc gcg gcc aag gac gag gag ctc gcc      2377
Ala Asp Lys Leu Ala Glu Glu Leu Ala Ala Lys Asp Glu Glu Leu Ala
            740                 745                 750

gcg cac cgc cag aag cgc cac gat gcc cgg cag gcg cgc gca agc gac      2425
Ala His Arg Gln Lys Arg His Asp Ala Arg Gln Ala Arg Ala Ser Asp
        755                 760                 765

cct gcc ttg gcc gcc gcc gac gct gtc gcg ccg cgc agc ggg aag gga      2473
Pro Ala Leu Ala Ala Ala Asp Ala Val Ala Pro Arg Ser Gly Lys Gly
    770                 775                 780

gca gca tcg ccg cac gtc ggc gca gtg cag cgc cag gcc gtc gac cct      2521
Ala Ala Ser Pro His Val Gly Ala Val Gln Arg Gln Ala Val Asp Pro
785                 790                 795                 800

gcc acc gtg ccc gtg gcc ccc gcc gtt atc gcg gag gag ccg ctc tac      2569
Ala Thr Val Pro Val Ala Pro Ala Val Ile Ala Glu Glu Pro Leu Tyr
                805                 810                 815

gtg gcc acc gcg gag gag ctg cag cat gtg cgc gac ttc gca gat cag      2617
Val Ala Thr Ala Glu Glu Leu Gln His Val Arg Asp Phe Ala Asp Gln
            820                 825                 830

ctc gct gag gag cta gag gcg ttc cgc cag aag cgc cac gac gcc aag      2665
Leu Ala Glu Glu Leu Glu Ala Phe Arg Gln Lys Arg His Asp Ala Lys
        835                 840                 845

aag gcg cgc gcc gcg gag ccg gaa ctt gcg gat gcc gac ggc gtg gag      2713
Lys Ala Arg Ala Ala Glu Pro Glu Leu Ala Asp Ala Asp Gly Val Glu
    850                 855                 860

cca agc agc ggg ccc acc agc agt cgc tct ccc act ggc cgc gca gcc      2761
```

-continued

```
Pro Ser Ser Gly Pro Thr Ser Ser Arg Ser Pro Thr Gly Arg Ala Ala
865                 870                 875                 880

ccg cgt gga cag agc gct gca ccg cgc ggc act gca tcg cag cag cac      2809
Pro Arg Gly Gln Ser Ala Ala Pro Arg Gly Thr Ala Ser Gln Gln His
                885                 890                 895

aag ctc ctc ggc ccc gcc tac cag tcc atc gac ccg gct acc atc gcc      2857
Lys Leu Leu Gly Pro Ala Tyr Gln Ser Ile Asp Pro Ala Thr Ile Ala
            900                 905                 910

aac gag ccg ctc tac gcc gtc acc atc gaa gag tac aag gcc aaa gac      2905
Asn Glu Pro Leu Tyr Ala Val Thr Ile Glu Glu Tyr Lys Ala Lys Asp
        915                 920                 925

gcc gca ggg gag cga gcc atg gac gag gcg gag cgc atg gcg gac gaa      2953
Ala Ala Gly Glu Arg Ala Met Asp Glu Ala Glu Arg Met Ala Asp Glu
    930                 935                 940

gtg cag cgg ctc gcc gtg gaa ctg gag gac gcc aag gcg gcg gcc gac      3001
Val Gln Arg Leu Ala Val Glu Leu Glu Asp Ala Lys Ala Ala Ala Asp
945                 950                 955                 960

aag ctg gcg gag gag ctc gcg gcc aag gac gag gag ctc gcc gcg cac      3049
Lys Leu Ala Glu Glu Leu Ala Ala Lys Asp Glu Glu Leu Ala Ala His
                965                 970                 975

cgc cag aag cgc cac gat gcc cgg cag gcg cgc gca agc gac cct gcc      3097
Arg Gln Lys Arg His Asp Ala Arg Gln Ala Arg Ala Ser Asp Pro Ala
            980                 985                 990

ttg gcc gcc gcc gac gct gtc gcg  ccg cgc agc ggg aag  gga gca gca    3145
Leu Ala Ala Ala Asp Ala Val Ala  Pro Arg Ser Gly Lys  Gly Ala Ala
        995                 1000                 1005

tcg ccg  cac gtc ggc gca gtg  cag cgc cag gcc gtc  gac cct gcc      3190
Ser Pro  His Val Gly Ala Val  Gln Arg Gln Ala Val  Asp Pro Ala
    1010                 1015                 1020

acc gtg  ccc gtg gcc ccc gcc  gtt atc gcg gag gag  ccg ctc tac      3235
Thr Val  Pro Val Ala Pro Ala  Val Ile Ala Glu Glu  Pro Leu Tyr
    1025                 1030                 1035

gtg gcc  acc gcg gag gag ctg  cag cat gtg cgc gac  ttc gca gat      3280
Val Ala  Thr Ala Glu Glu Leu  Gln His Val Arg Asp  Phe Ala Asp
    1040                 1045                 1050

cag gct  gcc cat gat gca aca  gcg agg gaa gcg gaa  gtt gct ggt      3325
Gln Ala  Ala His Asp Ala Thr  Ala Arg Glu Ala Glu  Val Ala Gly
    1055                 1060                 1065

acc gtg  gag aat ctg aga aat  gag ttg gat gat gtg  cgc gag atg      3370
Thr Val  Glu Asn Leu Arg Asn  Glu Leu Asp Asp Val  Arg Glu Met
    1070                 1075                 1080

aat gct  aag tta gaa gac gaa  gtt ttt gct ttg aaa  gag caa ctg      3415
Asn Ala  Lys Leu Glu Asp Glu  Val Phe Ala Leu Lys  Glu Gln Leu
    1085                 1090                 1095

tcg gac  gct gag gat gca tac  aag aag tta gca ggc  gct ctg gta      3460
Ser Asp  Ala Glu Asp Ala Tyr  Lys Lys Leu Ala Gly  Ala Leu Val
    1100                 1105                 1110

gtc gcc  gaa gac gag cgt caa  gag ctg tgt gac gat  ctg gag gcc      3505
Val Ala  Glu Asp Glu Arg Gln  Glu Leu Cys Asp Asp  Leu Glu Ala
    1115                 1120                 1125

gcc tta  gac gag ctt gag cag  aag aaa gat gaa tac  gat gaa ctg      3550
Ala Leu  Asp Glu Leu Glu Gln  Lys Lys Asp Glu Tyr  Asp Glu Leu
    1130                 1135                 1140

ctc ggc  aac ttg gag gag gtt  cag ggt ttg ctg gaa  gct gct gac      3595
Leu Gly  Asn Leu Glu Glu Val  Gln Gly Leu Leu Glu  Ala Ala Asp
    1145                 1150                 1155

gtt gct  ggg cga acc gct gtg  gag gcg ttg gag cag  cga aac cga      3640
Val Ala  Gly Arg Thr Ala Val  Glu Ala Leu Glu Gln  Arg Asn Arg
    1160                 1165                 1170
```

-continued gac atg gcg gac ctg cag ggc gag ttg gcc aat gcg ctg gac gcc 3685
Asp Met Ala Asp Leu Gln Gly Glu Leu Ala Asn Ala Leu Asp Ala
1175 1180 1185 agc aaa gaa aat gag aat ctt cgt gca ctg ctg gat gcc aag gag 3730
Ser Lys Glu Asn Glu Asn Leu Arg Ala Leu Leu Asp Ala Lys Glu
1190 1195 1200 aga gag atc gat aga ctg aaa gag tac aac agt ttc tgg act gac 3775
Arg Glu Ile Asp Arg Leu Lys Glu Tyr Asn Ser Phe Trp Thr Asp
1205 1210 1215 act gtc ggc acc gga aag cag aag gta aca cac agg ctc aca aag 3820
Thr Val Gly Thr Gly Lys Gln Lys Val Thr His Arg Leu Thr Lys
1220 1225 1230 atc ttc gat ggc gac tgg act cgt ttg atg cgt cat aga cct gag 3865
Ile Phe Asp Gly Asp Trp Thr Arg Leu Met Arg His Arg Pro Glu
1235 1240 1245 gca ctg aag gca gcg ttc gtg att gat tcc agc aac gca tgc cac 3910
Ala Leu Lys Ala Ala Phe Val Ile Asp Ser Ser Asn Ala Cys His
1250 1255 1260 gtg ccc gga gac cag att gtg caa gta gat ttc gat cac gat 3952
Val Pro Gly Asp Gln Ile Val Gln Val Asp Phe Asp His Asp
1265 1270 1275 tagtaagaac ggtgtcgatg ggagtttttc tgctttgtaa gagcccgtca tcagttttct 4012 ctgcttgttt tggttcgcat tttcgctgag caagacgcgc tggtttgcgc ctcgatcatg 4072 ttggtactgg tcccttgaag tgggtgagag cgcctcatcg gttatttggt ttgtggagtg 4132 agtgtgctgg cgttctcata ccgcagagcg tgtattctgc cacgtgctta ttttttttcat 4192 tgtattatga ttcctcagtc atctgttcat ggtgaacgcg cccgttgtca ccattttttc 4252 cttgcgctat ccctctttga ttccatagtg atccactctt gaagtaagcg ttggctcgtt 4312 ttgcaggaca tttgtgagct tttctcacac tatcgtcttg cctgatacgt ggagttactt 4372 cagtgtagtt tgctgccgtg tttgtgcttt tgttcgtaga ctgtcttgac gatcatagtt 4432 ccttcatcct gttgtttgca ggtgtgtctt gtatgtctga ggacgacgcc tggctcaccg 4492 gttgctcagt tcatcgtctg tctgtgtacg tgttcaatag tgtttctttc tctcggacca 4552 ctgaggtgta gactctcgct tacacgcctc aagaaaaaaa aaaaaaaaaa 4602

<210> SEQ ID NO 9
<211> LENGTH: 2046
<212> TYPE: DNA
<213> ORGANISM: Leishmania major
<220> FEATURE:
<221> NAME/KEY: CDS
<222> LOCATION: (38)..(1618)

<400> SEQUENCE: 9
cagcattctc accggctccg tcttggagac agaggtg atg gtg acg cac gcg ttg 55
Met Val Thr His Ala Leu
1 5 cat gag tca ctc ttt ccc cgt gac gcg gcg tcc gat gcc gct ggc aca 103
His Glu Ser Leu Phe Pro Arg Asp Ala Ala Ser Asp Ala Ala Gly Thr
10 15 20 gct gcc acc tct ctg cag gtg tct ctg cct ccc atc acg gtg gca atg 151
Ala Ala Thr Ser Leu Gln Val Ser Leu Pro Pro Ile Thr Val Ala Met
25 30 35 cgg cgt ggc gct gtg cag atg cgc tac ggg ctc acc tac cta cgc acg 199
Arg Arg Gly Ala Val Gln Met Arg Tyr Gly Leu Thr Tyr Leu Arg Thr
40 45 50 ttc ccg gcg gca ttg cga gac tct gtg cgg gta ctg aag acg gcc atg 247
Phe Pro Ala Ala Leu Arg Asp Ser Val Arg Val Leu Lys Thr Ala Met -continued

```
55                  60                  65                  70

tcg tgc gac gac ggc gtc acg cgc tgt cct tcc tac atg agc atg aca      295
Ser Cys Asp Asp Gly Val Thr Arg Cys Pro Ser Tyr Met Ser Met Thr
                75                  80                  85

ggg acg ctt gtg tcg gcg ccg ctc gga ttg tgc tgc ctc tgc acc agc      343
Gly Thr Leu Val Ser Ala Pro Leu Gly Leu Cys Cys Leu Cys Thr Ser
            90                  95                  100

gtg gag tgc gcc ctc aca agc gac ctg tgc aac gct tcg atg cgc gcg      391
Val Glu Cys Ala Leu Thr Ser Asp Leu Cys Asn Ala Ser Met Arg Ala
        105                 110                 115

cac ttt tgc ttc cgc acc ggt gca gcc gga atc acg tgc gta cag agc      439
His Phe Cys Phe Arg Thr Gly Ala Ala Gly Ile Thr Cys Val Gln Ser
    120                 125                 130

gag ggc atc acc tac cac gga tgg gcc gtg gga tcg tcg tcg ccc tac      487
Glu Gly Ile Thr Tyr His Gly Trp Ala Val Gly Ser Ser Ser Pro Tyr
135                 140                 145                 150

tac atg atg cac cta tcc gcg agc ggg cga ggg atc gca ccg acg aca      535
Tyr Met Met His Leu Ser Ala Ser Gly Arg Gly Ile Ala Pro Thr Thr
                155                 160                 165

ctg cag ctc acg acg gac gcc cct gag gtg cag aag ggt gcg tct gct      583
Leu Gln Leu Thr Thr Asp Ala Pro Glu Val Gln Lys Gly Ala Ser Ala
            170                 175                 180

ctg cag att ctt cgg gcc tct ggt gtt ttg ccc gga gag tca aac ccc      631
Leu Gln Ile Leu Arg Ala Ser Gly Val Leu Pro Gly Glu Ser Asn Pro
        185                 190                 195

acg gtt gat att tcc ggg cgc gtt ctc ttt gtc ccc tct gca gaa cac      679
Thr Val Asp Ile Ser Gly Arg Val Leu Phe Val Pro Ser Ala Glu His
    200                 205                 210

agc agt gcc agc cgc agc atc agc acc ggg cct gtg cgc gac gac gac      727
Ser Ser Ala Ser Arg Ser Ile Ser Thr Gly Pro Val Arg Asp Asp Asp
215                 220                 225                 230

ccg gca gag tgg ctg ttg ctc ccg gcg ccg ctt gtc agc gtc tcc ggc      775
Pro Ala Glu Trp Leu Leu Leu Pro Ala Pro Leu Val Ser Val Ser Gly
                235                 240                 245

aat gat tgc gac aag gtc ggc atc tca cca gac tat ttc tac tcg ctc      823
Asn Asp Cys Asp Lys Val Gly Ile Ser Pro Asp Tyr Phe Tyr Ser Leu
            250                 255                 260

tcc agc act aag cag tgc aac gcg cag aag ggg acg tgc gtg cga cac      871
Ser Ser Thr Lys Gln Cys Asn Ala Gln Lys Gly Thr Cys Val Arg His
        265                 270                 275

cag cta gca gac tac cgt gcg gcg gac ctg gaa cag atc gcc cag ggc      919
Gln Leu Ala Asp Tyr Arg Ala Ala Asp Leu Glu Gln Ile Ala Gln Gly
    280                 285                 290

gtc ggc gga cgc tat atc gcc gcc tct ctg ggc acc ttc acg cgg cag      967
Val Gly Gly Arg Tyr Ile Ala Ala Ser Leu Gly Thr Phe Thr Arg Gln
295                 300                 305                 310

gcg atg agg gaa cag gag ttc ctg ctc gat gcg gtg gag cgc acg ggt     1015
Ala Met Arg Glu Gln Glu Phe Leu Leu Asp Ala Val Glu Arg Thr Gly
                315                 320                 325

ggg gcg atg ctg cgg tgg acg gtg aat gcg gac ggc ctc gtg ttc cag     1063
Gly Ala Met Leu Arg Trp Thr Val Asn Ala Asp Gly Leu Val Phe Gln
            330                 335                 340

ccg ctt ccg gta cac ggt gta ctg gat gct atc aag ttt gac agc agc     1111
Pro Leu Pro Val His Gly Val Leu Asp Ala Ile Lys Phe Asp Ser Ser
        345                 350                 355

aca ggc atc ctc tac gtc acg gtt cgc aac aac aac aca tat ggt ggc     1159
Thr Gly Ile Leu Tyr Val Thr Val Arg Asn Asn Asn Thr Tyr Gly Gly
    360                 365                 370

ctc tac tac gtt gcc gtt ggt cag tgt cgg gga gca cgc gca tcg aac     1207
```

-continued

```
Leu Tyr Tyr Val Ala Val Gly Gln Cys Arg Gly Ala Arg Ala Ser Asn
375                 380                 385                 390

tgc gat agc gac ggc gtg aca cac gag tgt ggt cgc acg gct ttg gtg      1255
Cys Asp Ser Asp Gly Val Thr His Glu Cys Gly Arg Thr Ala Leu Val
                395                 400                 405

gcc ggg gct aac acc tcc tcg ctg ttg cag ttc agc atg gtg agc gac      1303
Ala Gly Ala Asn Thr Ser Ser Leu Leu Gln Phe Ser Met Val Ser Asp
            410                 415                 420

ctg ccc gag gag gtg ggg agc acc gcc tca tgc acc gtc gtc ttt cgc      1351
Leu Pro Glu Glu Val Gly Ser Thr Ala Ser Cys Thr Val Val Phe Arg
        425                 430                 435

gac gcg gcc gca gcg ctg ctg gcc tct gca aac att tcc tgg acg gtc      1399
Asp Ala Ala Ala Ala Leu Leu Ala Ser Ala Asn Ile Ser Trp Thr Val
    440                 445                 450

gag cac acg acc act acg ccg gcg ccg aat gcc ccc aaa gcg gag cag      1447
Glu His Thr Thr Thr Thr Pro Ala Pro Asn Ala Pro Lys Ala Glu Gln
455                 460                 465                 470

tgc aga cgc tgc gcc ttt cgc gac ctg cgg tgt ctt ttc agc acc gtc      1495
Cys Arg Arg Cys Ala Phe Arg Asp Leu Arg Cys Leu Phe Ser Thr Val
                475                 480                 485

tgc gag tgg cag atg ctc ctg tgg aca gcg gtg gcg gtg gcg gtg acg      1543
Cys Glu Trp Gln Met Leu Leu Trp Thr Ala Val Ala Val Ala Val Thr
            490                 495                 500

tgg acg ccg tat gcc atc ttg gcc tac tgg cgt atg gcg tgg cac gtt      1591
Trp Thr Pro Tyr Ala Ile Leu Ala Tyr Trp Arg Met Ala Trp His Val
        505                 510                 515

ggc gcc aag ctc ttg gcg tgt ctg aac tgacttcccg atacgtcgct           1638
Gly Ala Lys Leu Leu Ala Cys Leu Asn
    520                 525

ttctctctac cctctctccc ccactttcac aactcagaaa caagcgcagc gaaggccgca   1698

ctcgcacacg cacgtccctt ctccccccgc atacggcgag ccgcaaaggg tcgctgccgc   1758

agcgccttta actttttaat gcgtttctcc tttcctcttc tgtttcgtct attcactcgt   1818

tcctgcaata acgcgtttct cttttctgaa acgttgtagg tttcacgttt ctcgttttct   1878

ttttccttgt gcacgtttgc gttttggcag tgggaagagg ggcgatggtg agggtgaggt   1938

atacgcagac gcacacgcac gcatgcatgt atatttatgt atacgtgtgg ctacatatgt   1998

gtatgtatgt atgtatgtgt gtacatgaaa aaaaaaaaaa aaaaaaaa                 2046


<210> SEQ ID NO 10
<211> LENGTH: 1779
<212> TYPE: DNA
<213> ORGANISM: Leishmania major
<220> FEATURE:
<221> NAME/KEY: CDS
<222> LOCATION: (142)..(1365)

<400> SEQUENCE: 10

cgctgacgcc aactgcgtgg atcgcggacc tggccgccgg tctcagacgc cgggctggca     60

tcccccgaaa ccgcgctgca cggcgccacg cggtgcggcg ggggctccca agcggctgcg    120

ctcccgcacg aatgtgcagg g atg ctt gag ccc acg ggg cgg cgg ggg ggg      171
                        Met Leu Glu Pro Thr Gly Arg Arg Gly Gly
                        1               5                   10

ccg cgc ctg ccc act ccc gca cgg gtg ccg gtc cgg gtg cat tgg gtt      219
Pro Arg Leu Pro Thr Pro Ala Arg Val Pro Val Arg Val His Trp Val
                15                  20                  25

gcc gcg gtg gcg ggt ggc tgg cgg tgg cgg tgt gct gcc tgc tgc gcc      267
Ala Ala Val Ala Gly Gly Trp Arg Trp Arg Cys Ala Ala Cys Cys Ala
            30                  35                  40
```

-continued

```
gct ggc gct gtg gcg gcc ccc gcc ccc gcc aga gcc ccg gcc ccc acc      315
Ala Gly Ala Val Ala Ala Pro Ala Pro Ala Arg Ala Pro Ala Pro Thr
        45                  50                  55

tgt gtt tgc cat ggg ggc ggc cga ccc ggc gtt gtg gcc ggt atg ctg      363
Cys Val Cys His Gly Gly Gly Arg Pro Gly Val Val Ala Gly Met Leu
    60                  65                  70

cgc tgg gtt cgc ggg tcg ctg gca gct ggg gag cac aca ccg tct gac      411
Arg Trp Val Arg Gly Ser Leu Ala Ala Gly Glu His Thr Pro Ser Asp
75                  80                  85                  90

gca atg gtc ctg aac gcg atg gcc tgg ttg cgc gcg cct cgc tcg cgc      459
Ala Met Val Leu Asn Ala Met Ala Trp Leu Arg Ala Pro Arg Ser Arg
                95                  100                 105

ggc gtg ggc ttc ccc gtc ctg tgt gcg tgt gtg tgg ctg ccc cct ccc      507
Gly Val Gly Phe Pro Val Leu Cys Ala Cys Val Trp Leu Pro Pro Pro
            110                 115                 120

gtg ccc ctg cga agg gcg cgt ggt cgg ttc cct gtg cgc tgg tgc gtg      555
Val Pro Leu Arg Arg Ala Arg Gly Arg Phe Pro Val Arg Trp Cys Val
        125                 130                 135

cgt gtg cgc ggg ccc ctt tcg cct gcc acg cgc cgg ctc cct gtc aaa      603
Arg Val Arg Gly Pro Leu Ser Pro Ala Thr Arg Arg Leu Pro Val Lys
    140                 145                 150

ggc gta tgg gtc gtg ggt gtg ggt ggg tgg ggc tcc tct gcg gcc aca      651
Gly Val Trp Val Val Gly Val Gly Gly Trp Gly Ser Ser Ala Ala Thr
155                 160                 165                 170

ggc cgg cgg caa cgc ctc gcc tgt cgc ggc gca tgc ggg cgg gcc gcc      699
Gly Arg Arg Gln Arg Leu Ala Cys Arg Gly Ala Cys Gly Arg Ala Ala
                175                 180                 185

cgg gga cgc ccc cct tct cgt ggt gtc gac ggg ggc ggg gga tgc gga      747
Arg Gly Arg Pro Pro Ser Arg Gly Val Asp Gly Gly Gly Gly Cys Gly
            190                 195                 200

cag cgg acc tgc tgg aaa acg gcg ttg cct cgg gcc acg ccc cgg ggc      795
Gln Arg Thr Cys Trp Lys Thr Ala Leu Pro Arg Ala Thr Pro Arg Gly
        205                 210                 215

acg ggc gct gtg cgc acg cgc tgt cgg gcg ccg ctg gca tgg cgt atc      843
Thr Gly Ala Val Arg Thr Arg Cys Arg Ala Pro Leu Ala Trp Arg Ile
    220                 225                 230

gca ccc gaa cag agc aag gag agg tca gca gag cag ggg cgg tgg acg      891
Ala Pro Glu Gln Ser Lys Glu Arg Ser Ala Glu Gln Gly Arg Trp Thr
235                 240                 245                 250

aag agg tcg cgg gga tac gca tgc gaa tta gct ccg ccg tgc gtg tgc      939
Lys Arg Ser Arg Gly Tyr Ala Cys Glu Leu Ala Pro Pro Cys Val Cys
                255                 260                 265

gcg gcg cgc ccg gcg tct ccc aga tgt ggc cgt gtg tgc tgg cgg ggc      987
Ala Ala Arg Pro Ala Ser Pro Arg Cys Gly Arg Val Cys Trp Arg Gly
            270                 275                 280

gcc ggt gcc gga agc gtg ccg aga acg ccc cga gtg aca cca tcg ggc     1035
Ala Gly Ala Gly Ser Val Pro Arg Thr Pro Arg Val Thr Pro Ser Gly
        285                 290                 295

cct cca aac tcc ggt gtg gag agc cac cgt gcc gtg ttg tgg ggt gcc     1083
Pro Pro Asn Ser Gly Val Glu Ser His Arg Ala Val Leu Trp Gly Ala
    300                 305                 310

gtg gct ggg ggg ggg gag cag ggc atg cat gcc ggg tgc agg gtc tgg     1131
Val Ala Gly Gly Gly Glu Gln Gly Met His Ala Gly Cys Arg Val Trp
315                 320                 325                 330

ggg ggc cct ggc ctg cgg ctg gcg ggc ttc ctc gct ggg ctg atc cgg     1179
Gly Gly Pro Gly Leu Arg Leu Ala Gly Phe Leu Ala Gly Leu Ile Arg
                335                 340                 345

cat gcg cgt gcg cca ccg cgt ggt tac tcg cac ggc ggg cgc cgc cgc     1227
His Ala Arg Ala Pro Pro Arg Gly Tyr Ser His Gly Gly Arg Arg Arg
```

-continued

```
            350                 355                 360

ttc cgc cct cgg tca gga gct tgg atg cgg cct gcg tgg gtc ggg gtg      1275
Phe Arg Pro Arg Ser Gly Ala Trp Met Arg Pro Ala Trp Val Gly Val
        365                 370                 375

tgc ggt ccg ccg ggt gtc tgc ctg gcg ctg atc gcg tgg cgc gta tcg      1323
Cys Gly Pro Pro Gly Val Cys Leu Ala Leu Ile Ala Trp Arg Val Ser
    380                 385                 390

gaa gaa ggg gcg agg acg ggc aaa aag ggc ctg cta gac gca              1365
Glu Glu Gly Ala Arg Thr Gly Lys Lys Gly Leu Leu Asp Ala
395                 400                 405

tgaccccatt cgactgccga cggctcgctc tggtcggcca gggttttagc cgcagtgcga   1425

ccgaggcagg tgagctgtgg ctgtgtgctt gcgtgtgtac gtactgactt gttcgcgggt   1485

ggagttatat gggcacgttg ctatgcagcg gaagaaaagg cgaaaagaag tgcctattat   1545

tttgccatgt ccgttggctc gtctctctcc atgctttgcg tgtcgtcggg tgcatgtgtg   1605

tgtgtgtgca acgacgtttt cttttgtctc ttaggcgcat gccttgtttg tgtctctgcc   1665

acactgactc tctggctgtg gcgtcgtgga gtattctaat gctgatcttg cgctggcggc   1725

cttccttttt cttgttttct cgaagaagta cccgtaaaaa aaaaaaaaaa aaaa         1779


<210> SEQ ID NO 11
<211> LENGTH: 2025
<212> TYPE: DNA
<213> ORGANISM: Leishmania major
<220> FEATURE:
<221> NAME/KEY: CDS
<222> LOCATION: (132)..(1565)

<400> SEQUENCE: 11

tttccacacc ctcctttctt cgcgaatgta tatgtttatg ctacggcagc ttttatcgga     60

gttgcggaag catcctcttc catccaccgc tttcggcagc tgtcatccaa cacgaaaagt    120

gtttcacgtc a atg ccc gtc atc ggc tac aac tgc gat agc ggc gct gtg     170
             Met Pro Val Ile Gly Tyr Asn Cys Asp Ser Gly Ala Val
             1               5                   10

gta gaa gtt gta aac ccg gca agt ggg gcg ctt ggt ttt gca gga aaa      218
Val Glu Val Val Asn Pro Ala Ser Gly Ala Leu Gly Phe Ala Gly Lys
    15                  20                  25

act gtc atc ccg ggc ggc att gtc tcg gca gcc tcc gcc ggc gat ggt      266
Thr Val Ile Pro Gly Gly Ile Val Ser Ala Ala Ser Ala Gly Asp Gly
30                  35                  40                  45

act ctt tac tac ctc cca acg tcg ttt ccc tcg atg ctg cat cgg cgc      314
Thr Leu Tyr Tyr Leu Pro Thr Ser Phe Pro Ser Met Leu His Arg Arg
                50                  55                  60

aac ttg gag agc ggg gcg gat gag atg gtc gag agt tta gct cgc gcg      362
Asn Leu Glu Ser Gly Ala Asp Glu Met Val Glu Ser Leu Ala Arg Ala
            65                  70                  75

cac acg cag gtt ttt ttt cac cgc aac aag gtc atg tgc att tcc gcc      410
His Thr Gln Val Phe Phe His Arg Asn Lys Val Met Cys Ile Ser Ala
        80                  85                  90

ggg agc acc gaa gtg gct gtt tat gac ccg ctc tgc agt gtg act gag      458
Gly Ser Thr Glu Val Ala Val Tyr Asp Pro Leu Cys Ser Val Thr Glu
    95                  100                 105

att atc tct ctc ccg tac cgt gtc gtt cgc gcc gag ccg gcc gac cac      506
Ile Ile Ser Leu Pro Tyr Arg Val Val Arg Ala Glu Pro Ala Asp His
110                 115                 120                 125

ggc ttc gtc ttt cgc agc gac tgc aac agg gtg ttc ggc tac gat ttt      554
Gly Phe Val Phe Arg Ser Asp Cys Asn Arg Val Phe Gly Tyr Asp Phe
                130                 135                 140
```

-continued

```
aac aag ggc ctg aca gag gtg atg aac ggg tgt agc ata acg ggc ttt        602
Asn Lys Gly Leu Thr Glu Val Met Asn Gly Cys Ser Ile Thr Gly Phe
            145                 150                 155

ttg ggc cac tac aag cag tac gcc gtt gcg ctg ctt cac gac ggc gac        650
Leu Gly His Tyr Lys Gln Tyr Ala Val Ala Leu Leu His Asp Gly Asp
        160                 165                 170

gag cgt gtg gtg ggc gtc act gag gcc ggc agc atc gta gag cta gac        698
Glu Arg Val Val Gly Val Thr Glu Ala Gly Ser Ile Val Glu Leu Asp
    175                 180                 185

gca gct ttg cca tgt gtg ccg ttc acg tcc ttg gat gat gtc gtt ctc        746
Ala Ala Leu Pro Cys Val Pro Phe Thr Ser Leu Asp Asp Val Val Leu
190                 195                 200                 205

tac aca agt gag aat gaa gtg gtg tcc ttg aag ggt gga agt gcg gtt        794
Tyr Thr Ser Glu Asn Glu Val Val Ser Leu Lys Gly Gly Ser Ala Val
                210                 215                 220

tct cct gtc ggg gaa gtt cac ctt tcg agc tcg cag cca act gat agc        842
Ser Pro Val Gly Glu Val His Leu Ser Ser Ser Gln Pro Thr Asp Ser
            225                 230                 235

gag gtc ctg tgc acc gtt tgc ttg tgc gag ttc gat ggc gac gac ggt        890
Glu Val Leu Cys Thr Val Cys Leu Cys Glu Phe Asp Gly Asp Asp Gly
        240                 245                 250

atc acc ttg gac tgc ggg cat tac ttt cac aaa gag tgc att gag caa        938
Ile Thr Leu Asp Cys Gly His Tyr Phe His Lys Glu Cys Ile Glu Gln
    255                 260                 265

tgg gtg ggc aac tgg atg gac ttc gcg gcg aag ggt gag cac gtg aag        986
Trp Val Gly Asn Trp Met Asp Phe Ala Ala Lys Gly Glu His Val Lys
270                 275                 280                 285

ttt acc cgc gct gtc tgc cct ggc ggg tgc aag cac ttg gtt cgc cac       1034
Phe Thr Arg Ala Val Cys Pro Gly Gly Cys Lys His Leu Val Arg His
                290                 295                 300

cct ctg ttg gca caa tcg aag cag atc agc gag ttg tac acg gag gtg       1082
Pro Leu Leu Ala Gln Ser Lys Gln Ile Ser Glu Leu Tyr Thr Glu Val
            305                 310                 315

act gcg aaa aag gcg gag cag ctg aag cac ttt gat gcg aca aag gcc       1130
Thr Ala Lys Lys Ala Glu Gln Leu Lys His Phe Asp Ala Thr Lys Ala
        320                 325                 330

cag cac gaa ttc ctt ttc tat ctc tgc ggc agg tgc ggg ggc gtg ttc       1178
Gln His Glu Phe Leu Phe Tyr Leu Cys Gly Arg Cys Gly Gly Val Phe
    335                 340                 345

tac gga ggc gat cag gtg tgc tca cgg atg cag ggg cac gaa ccg tcg       1226
Tyr Gly Gly Asp Gln Val Cys Ser Arg Met Gln Gly His Glu Pro Ser
350                 355                 360                 365

tct tcc ccg caa gag ctg gtc tgc gat act tgc ata gga aag gac cat       1274
Ser Ser Pro Gln Glu Leu Val Cys Asp Thr Cys Ile Gly Lys Asp His
                370                 375                 380

cga aca tgt aac act ctg atg gcc gtc ttc aag tgc cgc tac tgc tgc       1322
Arg Thr Cys Asn Thr Leu Met Ala Val Phe Lys Cys Arg Tyr Cys Cys
            385                 390                 395

aat ccc gcc aca cag cga tcg ttc ggt act cgt ttc atg tgc gat cgg       1370
Asn Pro Ala Thr Gln Arg Ser Phe Gly Thr Arg Phe Met Cys Asp Arg
        400                 405                 410

tgc atc gcg cgg tgg gac acc gcg gag cct gcg ctc att ccg tgc ccg       1418
Cys Ile Ala Arg Trp Asp Thr Ala Glu Pro Ala Leu Ile Pro Cys Pro
    415                 420                 425

gga gcg gac agc tgc ccg ttt cac gga aat cac ccg gag ccc gtg tgc       1466
Gly Ala Asp Ser Cys Pro Phe His Gly Asn His Pro Glu Pro Val Cys
430                 435                 440                 445

aac att gcg gcc tgt ctt acg tgt ctc gat ccg gcc atg gtg agc cat       1514
Asn Ile Ala Ala Cys Leu Thr Cys Leu Asp Pro Ala Met Val Ser His
                450                 455                 460
```

-continued

```
att ttt gat cga gtg gcg ggc gtt gct gac ggt gca ggt ggc ggc acc      1562
Ile Phe Asp Arg Val Ala Gly Val Ala Asp Gly Ala Gly Gly Gly Thr
            465                 470                 475

gat tagtctgcca tgcacaggac attgtgcccc tcctgtgcga ggtgttggac          1615
Asp

ggtatgctgg cggcattatg caagctgcac ctgccttctc ttattactgt atgaatgtgc   1675

ttacgctaat gagcggcttg cacgtgcact aacatgcatc atgggcgcag caacatctct   1735

tgaacacact gtcatgtcgc tttttcgccg tgtgagagtg cgtgtgatgt actcgtgcta   1795

ctgggacacg tcacgaggtc tctgcgcggc tgttggagtt ggacaggaca gcgcgtacaa   1855

agggagatgt tctttgcgca gtcgtttgtt tttggctttt ttggcagcag ttgacggtcg   1915

tggtggacgc gcctttcgcg cgcgcgcggc cttgtgaaac gcgatcggct ctctctctct   1975

ctctctctta aaaaaaaaaa aaaaaaaaaa aaaaaaaaaa aaaaaaaaaa              2025


<210> SEQ ID NO 12
<211> LENGTH: 1522
<212> TYPE: DNA
<213> ORGANISM: Leishmania major
<220> FEATURE:
<221> NAME/KEY: CDS
<222> LOCATION: (263)..(922)

<400> SEQUENCE: 12

cgcacatgca taaacccaca ttcgtctttc actggctcag gggactctca cctctccgtc     60

cgcttccacc gagcagtcaa ggttgctgcc gttgctcttg ttggtgtgtg tcagtgccga    120

actctctagc gcgtgtgtgc gtgcctgttt catcacagca ccgtacaaga cgagcacgtc    180

gcgctgtctc tccgcgccct ttcctcattc tctccacacc cccacacacg cacgcacgcg    240

cgcgcatccc tcgttaaagc aa atg ggc ggc aag cgc aag aag tcc aac aac     292
                         Met Gly Gly Lys Arg Lys Lys Ser Asn Asn
                         1               5                   10

gga cct gtc aag aag gaa agc aag tac aag atc ccc acc cgc ttt gac      340
Gly Pro Val Lys Lys Glu Ser Lys Tyr Lys Ile Pro Thr Arg Phe Asp
                15                  20                  25

tgc ccg ttg tgt gat gcc aag gcg tcc atc gtc gtc cga atg ttt cgc      388
Cys Pro Leu Cys Asp Ala Lys Ala Ser Ile Val Val Arg Met Phe Arg
            30                  35                  40

gcg aca agc gat gcc acg gtg cag tgc cgc gtg tgc gga gcg ggc ggg      436
Ala Thr Ser Asp Ala Thr Val Gln Cys Arg Val Cys Gly Ala Gly Gly
        45                  50                  55

aca aaa cgg tgg aat gtg ctg cgc ctc gag aag cca gtg gac gtg ttt      484
Thr Lys Arg Trp Asn Val Leu Arg Leu Glu Lys Pro Val Asp Val Phe
    60                  65                  70

ttc cgc ttt cac gag gcg ctc gtt cag cgc gat cac gcc gac ctg cag      532
Phe Arg Phe His Glu Ala Leu Val Gln Arg Asp His Ala Asp Leu Gln
75                  80                  85                  90

cag gta gag atg ggt cgc gag gcg agg ctg agc gtt ggc gct ccc aac      580
Gln Val Glu Met Gly Arg Glu Ala Arg Leu Ser Val Gly Ala Pro Asn
                95                  100                 105

gcc gtc ctt ggt gga agc cag agc agc atg gga aag gag gcg tac tct      628
Ala Val Leu Gly Gly Ser Gln Ser Ser Met Gly Lys Glu Ala Tyr Ser
            110                 115                 120

cca ggg gac gca gcc gtg gcg ggc tgg gct cgg ctc ggc tcc tct gct      676
Pro Gly Asp Ala Ala Val Ala Gly Trp Ala Arg Leu Gly Ser Ser Ala
        125                 130                 135

gcc gcc gct gca acc gcg tca ggg tgc tcg cat tcg cag cac gtg aag      724
Ala Ala Ala Ala Thr Ala Ser Gly Cys Ser His Ser Gln His Val Lys
```

-continued

```
    140                 145                 150

tct cta ggt gag ctg cag cgc aag ctg act atg cca gcg tgg tcg ggt       772
Ser Leu Gly Glu Leu Gln Arg Lys Leu Thr Met Pro Ala Trp Ser Gly
155                 160                 165                 170

ttc gcc acc gcg cca acc gcc tcg tgt gcc gtc gac ctc cgc gac gac       820
Phe Ala Thr Ala Pro Thr Ala Ser Cys Ala Val Asp Leu Arg Asp Asp
                175                 180                 185

tac gag ggc gag gcg gaa ggg gca gca gcc cac tac ttt gct cct cgt       868
Tyr Glu Gly Glu Ala Glu Gly Ala Ala Ala His Tyr Phe Ala Pro Arg
            190                 195                 200

caa gag gtg cac agc gcc gag gat gag gat gac gag tac gac cag ctc       916
Gln Glu Val His Ser Ala Glu Asp Glu Asp Asp Glu Tyr Asp Gln Leu
        205                 210                 215

ttt cag tgagagggct cgctgctgct acggttattg atgccgatgc tgcgtttgta       972
Phe Gln
    220

aggtacaggg cgccctcgtg tggtccctcc ttttgtttgt ttggtttttg tatgcttcgc   1032

atgcttgaaa atggggaggc gatccagctg tgtttcggcg tggttgctta ccgctgcttc   1092

tcagctgctg ctgttgcggt gcctcgctct gtgtgcgcgt gtgtgtacgc tgtgatccat   1152

cagcgtgagg cagtgtaatg tcgagtggac gaaaccggga acgtgggaga cggtggagtg   1212

aagctgtgcg cacacattcg cgcgcggcgc ctcggtgtgt atgtgcatgt gtctgcgcta   1272

ctccctttgc cgtccctacg acctccttct gtggtacctt tatggtcgcc gctgaacacg   1332

tcgccttttt ccttcggttg tacgatgctg cgtgtatctc tctctctgtc tcgggtgtat   1392

gcgtatgtag gtgtgtgtgt gtgtgtgtgt gtgtgtgtgt gtgtgtgaat ctgtgtggat   1452

gtgcggatgt gcatttattg gctcccagtc gtgcgttggt ataaaaaaaa aaaaaaaaaa   1512

aaaaaaaaaa                                                          1522


<210> SEQ ID NO 13
<211> LENGTH: 1623
<212> TYPE: DNA
<213> ORGANISM: Leishmania major
<220> FEATURE:
<221> NAME/KEY: CDS
<222> LOCATION: (59)..(580)

<400> SEQUENCE: 13

cgttgctgct ggtcacccgg tggagtgctc gccactccta cgcgggagta gtacgtga       58

atg tgc att ggc cac aca cgg aca cac aca cac aca cgc gca cgt ctc      106
Met Cys Ile Gly His Thr Arg Thr His Thr His Thr Arg Ala Arg Leu
1               5                   10                  15

tgg gta tct gct atc atg gct tct ctt cag ttt tct gct ttt ctg ctc      154
Trp Val Ser Ala Ile Met Ala Ser Leu Gln Phe Ser Ala Phe Leu Leu
            20                  25                  30

ctc ccc cct ttc ttc ttc cac cgc gca ccg tgt cgt gcc tct aca acg      202
Leu Pro Pro Phe Phe Phe His Arg Ala Pro Cys Arg Ala Ser Thr Thr
        35                  40                  45

ctt act gtc ttt cac aca agt aca caa ctg ctt cgt tat cct atc acg      250
Leu Thr Val Phe His Thr Ser Thr Gln Leu Leu Arg Tyr Pro Ile Thr
    50                  55                  60

tgc aaa aca cga gtg cga aca gca cac aac acg cgg ttt atg gag gtg      298
Cys Lys Thr Arg Val Arg Thr Ala His Asn Thr Arg Phe Met Glu Val
65                  70                  75                  80

ttt ggc atg cta gta cag tca tgc aca tcc ata cca gcg cat gta cgc      346
Phe Gly Met Leu Val Gln Ser Cys Thr Ser Ile Pro Ala His Val Arg
                85                  90                  95
```

-continued

```
cag cac tgc agg ggt gtg cag ctg ccg tgg atc cca cca gta gtg agc      394
Gln His Cys Arg Gly Val Gln Leu Pro Trp Ile Pro Pro Val Val Ser
            100                 105                 110

gtg ttg acc cat agc gta gaa gac ggg agc agc agc aaa gac gag aag      442
Val Leu Thr His Ser Val Glu Asp Gly Ser Ser Ser Lys Asp Glu Lys
        115                 120                 125

aga ctt aaa gca gaa gag ccg cat ggc aca cat gct gtg atg agg gcg      490
Arg Leu Lys Ala Glu Glu Pro His Gly Thr His Ala Val Met Arg Ala
    130                 135                 140

tgc cgc gaa gac cga atg ctg cag act aac tct ctt gct ctt ctt cct      538
Cys Arg Glu Asp Arg Met Leu Gln Thr Asn Ser Leu Ala Leu Leu Pro
145                 150                 155                 160

cgg cca gcg agt gag tgt gca tca gcc ccc ctc gga agt aat              580
Arg Pro Ala Ser Glu Cys Ala Ser Ala Pro Leu Gly Ser Asn
                165                 170

taacacacat atacgcgcaa gctcatcagt accgcatccc attggtccga ctccgctgca    640

tccctctcgc acgcgatagg atgtatgccg gacaagcgta ttccgtatgc ggctgtggtc    700

ttgatggcgc agagggggcc ccgcttccgc tgagttacga tgtgccggcc cggaaaagca    760

gctatgcatg ggtttctcgt gcatggccaa gcctcgcgcg gcctcatgtc tgcggaggtc    820

aagaaaggtt acaccggctg ccgatcatac ctcatgagcg ccgaagattt gggaaagggc    880

ggacgcctta cgcacagtga gattctcatt gcgaatgaag caatcatcaa gcaaaggagg    940

gagggggtgc aggtgtcgga ggagtacgtc cgtcgcctcg agggccaggc ccgcagcacc   1000

tgccttgaat cggttctcag cagatcggtg gaagccgccc gcgcccgctg ccgggagacg   1060

aagcggatgc ggacatgggt ctcgtggagc actcaaacct tgtccaaatc gtcagaacca   1120

gcacgtgttg cccaggcatc gtacacgatg cagaccctcg tcgtcgtctc ggcgatctac   1180

ggcgtcgcat tcaatgagcg cggcatgacg ccagcagaga accgcgacac cgcgctgacc   1240

ttgaagaggg ccttcgactg cctcctcaac tccggcgtgg ccctcgcacg tgctcactct   1300

ctgcagtgcc cactcccggg acgagcggac gatgggcccc gtggccctga tgtgtttaac   1360

cgcgagcaag agcaggagac gagggcgcga caggaagaga gcacgcgccc gcagaacggc   1420

tggaaatcag ggtgccgctt cgggcacgcg atggaggcac ggccctgccg accgtgtagg   1480

tgcgccgcac atgggcagcg cctgttcttt cgttttttttt gtctcctgga gctgcggctc   1540

accttcattt ggatggcgcc tctgccatcg ctgctgtcct cacgggctat cttcaaaaaa   1600

aaaaaaaaaa aaaaaaaaaa aaa                                            1623


<210> SEQ ID NO 14
<211> LENGTH: 1317
<212> TYPE: DNA
<213> ORGANISM: Leishmania major
<220> FEATURE:
<221> NAME/KEY: CDS
<222> LOCATION: (17)..(475)

<400> SEQUENCE: 14

cgcagagtat ccaagg atg tct ctg acg ctt atc cct gac cac ttc cag cac     52
                  Met Ser Leu Thr Leu Ile Pro Asp His Phe Gln His
                  1               5                   10

att gtg cgt ctg ctc aac acg aat gtg gag ggc aag cgc aag gtg ccg      100
Ile Val Arg Leu Leu Asn Thr Asn Val Glu Gly Lys Arg Lys Val Pro
        15                  20                  25

ttc gcg ctg cgc atg gtg aag ggc gtt ggt atc cgc ttt gcc tac ctg      148
Phe Ala Leu Arg Met Val Lys Gly Val Gly Ile Arg Phe Ala Tyr Leu
    30                  35                  40
```

-continued

```
gtg tgc aag aag gcc ggg att gac gtg gag cgc cgc gcg ggc act ctg      196
Val Cys Lys Lys Ala Gly Ile Asp Val Glu Arg Arg Ala Gly Thr Leu
45                  50                  55                  60

acc gcg gag gag ctg gag aag atc gcc gag atc atc gcc gac ccc gcg      244
Thr Ala Glu Glu Leu Glu Lys Ile Ala Glu Ile Ile Ala Asp Pro Ala
                65                  70                  75

aag ttc aag atc ccg gac tgg ttc ctg aac cgt cag cgc gac ccc aag      292
Lys Phe Lys Ile Pro Asp Trp Phe Leu Asn Arg Gln Arg Asp Pro Lys
            80                  85                  90

acc ggc aag acg gag cac ctg tcc agc tcg atg gtg gac acc cgc ctg      340
Thr Gly Lys Thr Glu His Leu Ser Ser Ser Met Val Asp Thr Arg Leu
        95                  100                 105

cgc gac gac ctt gag cgc ctg aag aag atg cgc gcg cac cgt ggc gtg      388
Arg Asp Asp Leu Glu Arg Leu Lys Lys Met Arg Ala His Arg Gly Val
    110                 115                 120

cgt cac gcc tac ggc ctc cgc gtg cgc ggc cag cac acg tgc acg agt      436
Arg His Ala Tyr Gly Leu Arg Val Arg Gly Gln His Thr Cys Thr Ser
125                 130                 135                 140

ggc cgc cac ggc aag acg gtc ggc gtc tcc cgc ggc aag taaattcagt       485
Gly Arg His Gly Lys Thr Val Gly Val Ser Arg Gly Lys
                145                 150

atggcgtagc gcatgcggct cctcctctgc tccttatctg gtgccggatc accgcccatg    545

aggccgcctg ctccacgttg cgtttctcag cgttaacggc ggctgcgacg ggaagcagct    605

ctgcgctgat ttttcggttc atggaggcag agctggggat ggagtggctg cactgaggtt    665

tgggttactc tgtggagtct acagtgcatc tttggttacg ttttttgtgt tgtttttaat    725

tttgcgtttt cttttcttcg accaccgcaa caagacattg aatacgtaaa agcaatccat    785

attcgtgcgc gtgcacgcag aggattccct gcccagcaaa ccctctgctt gcagagacgt    845

ctgccaagtt tgttgctgct cctgtgtgga tgccgtggta tctttgcacc ctctcgtcct    905

cttccgactc ttgcgcccct cctctgttgt ctcctgtgtt gctcggcgga ttattgccct    965

cacattgcgc ggtaataaaa atccgctggc aagtcgcatg cgctgccgga agagagagcg   1025

aggggttagc aatgtcagaa gcagaaatgg gaggactacc aagtagatac tcacgcggcg   1085

ccgcttttgg gtgacacgtc ggaacgctta tgcgttcaga agaacctttg tgttctgctc   1145

cgtgcagcgc acccagcaca acaagcttct tccaccggct gccatctcta cccacgtact   1205

ttcatggcga cggatgtctt caatttttca tgccaactcg tgcttctttc tgttcctcct   1265

ctgacgtttt ccttttcacc gcaaaaaaaa aaaaaaaaaa aaaaaaaaaa aa           1317


<210> SEQ ID NO 15
<211> LENGTH: 1496
<212> TYPE: DNA
<213> ORGANISM: Leishmania major
<220> FEATURE:
<221> NAME/KEY: CDS
<222> LOCATION: (79)..(480)

<400> SEQUENCE: 15

cttcgcgctt gctttgcgtg gtaccccttt gattctccct cttcagcatt ttgccttgta     60

cttccacttc cgcacgag atg acg aag ttc ctg aag ccc ggt aag gtg gtc      111
                    Met Thr Lys Phe Leu Lys Pro Gly Lys Val Val
                    1               5                   10

atc gtg acg gct ggc cgc tac gcc ggc cac aag gcg gtg atc gtg cag      159
Ile Val Thr Ala Gly Arg Tyr Ala Gly His Lys Ala Val Ile Val Gln
            15                  20                  25

aac tct gac gtc gtg acg aag gag cgc ccg tac ggc cgc gca ctg ctt      207
Asn Ser Asp Val Val Thr Lys Glu Arg Pro Tyr Gly Arg Ala Leu Leu
```

-continued

```
        30                  35                  40

gct ggc atc aag aag tac ccg aag aag gtc gtg cgc ggg atg agc aag      255
Ala Gly Ile Lys Lys Tyr Pro Lys Lys Val Val Arg Gly Met Ser Lys
    45                  50                  55

cag aca atc gcg cgc cgc tcg cag gtg ggc gtg ttc ctg cgc gtt gtg      303
Gln Thr Ile Ala Arg Arg Ser Gln Val Gly Val Phe Leu Arg Val Val
60                  65                  70                  75

aac cac aag cac ttc ctg ccc acc cgc tac aac gtg gac atg tcg aag      351
Asn His Lys His Phe Leu Pro Thr Arg Tyr Asn Val Asp Met Ser Lys
                80                  85                  90

gag ctg cgc ggc aag atc aat gtg tct gac gcg tcg aag cgc tcg cgc      399
Glu Leu Arg Gly Lys Ile Asn Val Ser Asp Ala Ser Lys Arg Ser Arg
            95                  100                 105

tcg aag agg ctg gtg agg cac gtg ttc cag gcg cgc tac aac gcc ggc      447
Ser Lys Arg Leu Val Arg His Val Phe Gln Ala Arg Tyr Asn Ala Gly
        110                 115                 120

agc agc atg tgg ttc ttc cag cgc ctg cgc ttc taagcagcgg agacacggag    500
Ser Ser Met Trp Phe Phe Gln Arg Leu Arg Phe
    125                 130

caggctgaga agggctcctt gggcaggcgc ggcggacggc tgatctggag gctcgagagt    560

gccgaagagg ggcacggccg ccttctttgt cccttccgac taatctgtgc aaagccgcta    620

acgtccccg cctccgggtg ttcgaatggg cgctctcgtg gacgcccgac ttcctcttgg     680

gcgtgccctc ccgctcggct cgtcgtacac gtgtccgcat ccgcctgttt catcgatgtg    740

ttctgttgct ctcttttgcg ctcagcgtga tatgcgcctg cgtgcgtctc tcccgctctt    800

ggcgtgcttg agcggctgct ctcgcgccgt agcgccaggc agcgtcggga gattcggcga    860

agaaatacac acccagacgt gcgtgaggtg aaaaacaaaa cagaaggcag gagaggcggt    920

tgccagcgcg ccgtgacatg cgcgtattat gtgcgattgg ggcgtggtgt ggtggcggcg    980

ggggatactg tgcggcagac ggtcttttcg cgagatgcct gcgcgtggaa ttccgagtgc   1040

agcgaccggc gacggagaag gatagaggaa gaggaaagcg agtcagcgca cgcgctcttt   1100

caggaggggg gaggagtgag ggatgacagc tcgagaaacg aaggacgagt gggagaggcg   1160

cctacgtgat gagctgcgaa agcgtggcat ttgtggtgca cctccagagc agtggggctg   1220

gccttcgtca tcaagagggt tcctagagct gctcacatgt atcttttctc ctcgctctct   1280

gcgtcttggc gaagcgccgc gttaccttct ctctctctct ccctctctgt gtgtgtgtat   1340

gtgcgttcac agactccttt ctttgtccca cttcgacgtt gccgttcaag caggtgcgtg   1400

cgtgccggtg cgcctacacg catgcgcgtc tctctctctt tccttttcgt ttcgttgttt   1460

cttcttttcg agcttcaaaa aaaaaaaaaa aaaaaa                             1496


<210> SEQ ID NO 16
<211> LENGTH: 1841
<212> TYPE: DNA
<213> ORGANISM: Leishmania major
<220> FEATURE:
<221> NAME/KEY: CDS
<222> LOCATION: (18)..(1742)

<400> SEQUENCE: 16

tcgacaccga cactgtc atg gcg ctt ctt gtc aag ctc gat atc aag aac        50
                   Met Ala Leu Leu Val Lys Leu Asp Ile Lys Asn
                   1               5                   10

agc gaa ggc gac gcc atc cag ctg ctc ttc gag ccc tac gtg gcc acc       98
Ser Glu Gly Asp Ala Ile Gln Leu Leu Phe Glu Pro Tyr Val Ala Thr
            15                  20                  25
```

-continued

```
atg cgc tcc gag cca cgc gcc ttc acc atg ctg tgg cgg gca agc cag       146
Met Arg Ser Glu Pro Arg Ala Phe Thr Met Leu Trp Arg Ala Ser Gln
        30                  35                  40

gcg tac ctt ctc gac gtg tcg acg ctg ctg gag cac gtg gca ccg aaa       194
Ala Tyr Leu Leu Asp Val Ser Thr Leu Leu Glu His Val Ala Pro Lys
    45                  50                  55

gag gtc ctt ccg ctt ccc tcg tgc gtc tca tcc atc ctc caa act ttc       242
Glu Val Leu Pro Leu Pro Ser Cys Val Ser Ser Ile Leu Gln Thr Phe
60                  65                  70                  75

tgc aag tac cac ctg agc gag tca cgg ctg ctc ggc gcc tct tcc agc       290
Cys Lys Tyr His Leu Ser Glu Ser Arg Leu Leu Gly Ala Ser Ser Ser
                80                  85                  90

gca cgc acc ctg acg gac agt cgc agc agc tta gct gga gag acg gag       338
Ala Arg Thr Leu Thr Asp Ser Arg Ser Ser Leu Ala Gly Glu Thr Glu
            95                  100                 105

cac ttc ctg cac gcc tcg acg aag ccg tcg tcc gtg tcg gac cgc gcg       386
His Phe Leu His Ala Ser Thr Lys Pro Ser Ser Val Ser Asp Arg Ala
        110                 115                 120

gtg cgc gag ttg gca gag cga ccg gat gct gcg cag tgg atg acg gcc       434
Val Arg Glu Leu Ala Glu Arg Pro Asp Ala Ala Gln Trp Met Thr Ala
    125                 130                 135

gcc ggc acg cgg ctg tcc gaa gaa ggg cta aag agc tcc gag gag ctg       482
Ala Gly Thr Arg Leu Ser Glu Glu Gly Leu Lys Ser Ser Glu Glu Leu
140                 145                 150                 155

cag cac cgt cgg ctg ccg cgt gtg gtg cgg atg gtg cta gag gag aac       530
Gln His Arg Arg Leu Pro Arg Val Val Arg Met Val Leu Glu Glu Asn
                160                 165                 170

cgc acg acg ctg aac acg ctc ctg cac tgg gat ggc aat ctc ttg aag       578
Arg Thr Thr Leu Asn Thr Leu Leu His Trp Asp Gly Asn Leu Leu Lys
            175                 180                 185

gac agc ttt gcc ttt ctc aag tac gag ccg aac ttg atc gac ttc aac       626
Asp Ser Phe Ala Phe Leu Lys Tyr Glu Pro Asn Leu Ile Asp Phe Asn
        190                 195                 200

ttc aag ctg acg gac ttc cgg cgg cgg ctg ggc tcg cgg cgt ggg ccg       674
Phe Lys Leu Thr Asp Phe Arg Arg Arg Leu Gly Ser Arg Arg Gly Pro
    205                 210                 215

aac att ctg ctg cgc gtg aac cgc cag act tgc ctg ctc gat agc ttc       722
Asn Ile Leu Leu Arg Val Asn Arg Gln Thr Cys Leu Leu Asp Ser Phe
220                 225                 230                 235

aag gag ctg cag aag gtt aag tcc ttt ggc ggc cag ttg cac atc cgc       770
Lys Glu Leu Gln Lys Val Lys Ser Phe Gly Gly Gln Leu His Ile Arg
                240                 245                 250

ttc cat ggc gag gaa ggt gcc gac gcc ggc ggc ctg acg cgg gag tgg       818
Phe His Gly Glu Glu Gly Ala Asp Ala Gly Gly Leu Thr Arg Glu Trp
            255                 260                 265

ctg cag ctc ctc tcc gag gcc att gtg gac gag agg tac gcg ctc ttc       866
Leu Gln Leu Leu Ser Glu Ala Ile Val Asp Glu Arg Tyr Ala Leu Phe
        270                 275                 280

atc cac tcg cag gat agc att tcc ttc cag ccg aac ccg ttc tcc agc       914
Ile His Ser Gln Asp Ser Ile Ser Phe Gln Pro Asn Pro Phe Ser Ser
    285                 290                 295

gtc aac ccg aac cac ctc gag tac ttt cag ttt gcg ggc gtc gtg aca       962
Val Asn Pro Asn His Leu Glu Tyr Phe Gln Phe Ala Gly Val Val Thr
300                 305                 310                 315

ggg ctg gcg atc gcg cac aac gtc ccc att gat atc cac ttc acg cgt      1010
Gly Leu Ala Ile Ala His Asn Val Pro Ile Asp Ile His Phe Thr Arg
                320                 325                 330

gcg ttc tac cgg cac atc att ggc cac cgc cct gtc ttc gcc gac ctg      1058
Ala Phe Tyr Arg His Ile Ile Gly His Arg Pro Val Phe Ala Asp Leu
            335                 340                 345
```

```
cag agc ttc gac cca gag ctg tac aca aac ctc aac tgg atc atg gag      1106
Gln Ser Phe Asp Pro Glu Leu Tyr Thr Asn Leu Asn Trp Ile Met Glu
        350                 355                 360

aac gac gtc aca gac ctt ggc ctg acc ttc gcc gtc aac tac gat cgc      1154
Asn Asp Val Thr Asp Leu Gly Leu Thr Phe Ala Val Asn Tyr Asp Arg
    365                 370                 375

ttc ggc tcg gtg gag gag gcg gag ttg gag ccg aac ggc cag aac acg      1202
Phe Gly Ser Val Glu Glu Ala Glu Leu Glu Pro Asn Gly Gln Asn Thr
380                 385                 390                 395

gcc gtg acg aac gcg aac aag cag cag tat gtc cgc ctc ctg tgt gag      1250
Ala Val Thr Asn Ala Asn Lys Gln Gln Tyr Val Arg Leu Leu Cys Glu
                400                 405                 410

ttt tat atg acc aag cgc acg gag gat cag ctg ctg cgc ttc ctg aag      1298
Phe Tyr Met Thr Lys Arg Thr Glu Asp Gln Leu Leu Arg Phe Leu Lys
            415                 420                 425

ggc ttc tat tcg gtg atc ccc cgc cgc gag atc cag tgc ttc acg gag      1346
Gly Phe Tyr Ser Val Ile Pro Arg Arg Glu Ile Gln Cys Phe Thr Glu
        430                 435                 440

aag gag ctg gag ctg gtc atc agt ggc atg ccc aac atc gac gtc gag      1394
Lys Glu Leu Glu Leu Val Ile Ser Gly Met Pro Asn Ile Asp Val Glu
    445                 450                 455

gac ctg cgc acg cac acc gtg tac gag ggc tac agc agc acg tcg ccg      1442
Asp Leu Arg Thr His Thr Val Tyr Glu Gly Tyr Ser Ser Thr Ser Pro
460                 465                 470                 475

cag gtg cgc tgg ttc tgg gag gcg gtc ggc tcc atg agc aag gag gac      1490
Gln Val Arg Trp Phe Trp Glu Ala Val Gly Ser Met Ser Lys Glu Asp
                480                 485                 490

ctg gca aac ctt ctg caa ttt acg acc ggt tcg tca aag gtg cca cac      1538
Leu Ala Asn Leu Leu Gln Phe Thr Thr Gly Ser Ser Lys Val Pro His
            495                 500                 505

ggc ggc ttc ggc cat ctc gag gga tcg aac ggc cgc tcg ctg ccc ttc      1586
Gly Gly Phe Gly His Leu Glu Gly Ser Asn Gly Arg Ser Leu Pro Phe
        510                 515                 520

acg atc agc cgc tgg gcc gta acc aag gaa gac ctc ctg ccg cag gcg      1634
Thr Ile Ser Arg Trp Ala Val Thr Lys Glu Asp Leu Leu Pro Gln Ala
    525                 530                 535

cac acg tgc ttc aac aag atc gac ctg ccc gtc tac ccc tca gct gcg      1682
His Thr Cys Phe Asn Lys Ile Asp Leu Pro Val Tyr Pro Ser Ala Ala
540                 545                 550                 555

gtg ctc aag gaa aag ctg atg ctg gcg atc acg tac ggt agc atg ggc      1730
Val Leu Lys Glu Lys Leu Met Leu Ala Ile Thr Tyr Gly Ser Met Gly
                560                 565                 570

ttc acg atg gtg tagtggtagt ggtggtgtgt gtgtgtgtgt gcgtgcgtgt          1782
Phe Thr Met Val
            575

atgtggatta gtaacgtgat gcgcctgcgt ggctgatgaa aaaaaaaaaa aaaaaaaaa    1841


<210> SEQ ID NO 17
<211> LENGTH: 3332
<212> TYPE: DNA
<213> ORGANISM: Leishmania major
<220> FEATURE:
<221> NAME/KEY: CDS
<222> LOCATION: (52)..(1689)

<400> SEQUENCE: 17

ctacaggccg acacgcacct ccttgcaccc tactccatac acgcggagaa g atg caa       57
                                                          Met Gln
                                                          1

ccg aag cag aag gca gcc ctc ggc atc aac ggc acc cgc acc agc ggc      105
```

-continued

```
Pro Lys Gln Lys Ala Ala Leu Gly Ile Asn Gly Thr Arg Thr Ser Gly
        5                   10                  15

atc gcc gtt cgc cgc gag aac gtg tca gcc gca ttg gcc gtg gca aat      153
Ile Ala Val Arg Arg Glu Asn Val Ser Ala Ala Leu Ala Val Ala Asn
    20                  25                  30

gtc gtt aag tcg tcg ctg ggc ccc atc ggt ctg gac aag atg ctg gtg      201
Val Val Lys Ser Ser Leu Gly Pro Ile Gly Leu Asp Lys Met Leu Val
35                  40                  45                  50

gac gac gtc ggt gat gtg ctg gtg acg aac gac ggt gcg acg atc ctg      249
Asp Asp Val Gly Asp Val Leu Val Thr Asn Asp Gly Ala Thr Ile Leu
                55                  60                  65

aag agt ctc gac gtg gag cac cca gcc gcg cgc cta ctg gtt gat ctg      297
Lys Ser Leu Asp Val Glu His Pro Ala Ala Arg Leu Leu Val Asp Leu
            70                  75                  80

gcc cag ctc cag gac aag gag att ggc gac gga acc acc tct gtt gtg      345
Ala Gln Leu Gln Asp Lys Glu Ile Gly Asp Gly Thr Thr Ser Val Val
        85                  90                  95

att ctt gct gcg gag ctg ctg aag cgg gcc cag gag ctc gtg tcg cag      393
Ile Leu Ala Ala Glu Leu Leu Lys Arg Ala Gln Glu Leu Val Ser Gln
    100                 105                 110

ggc atc cac gcg aca agc atc att gcc ggc tac aag ctt gcc atg cgc      441
Gly Ile His Ala Thr Ser Ile Ile Ala Gly Tyr Lys Leu Ala Met Arg
115                 120                 125                 130

gag gca ctg cgc tac ctg aac gac aac ctc ggc tgc gcc gtg gag agt      489
Glu Ala Leu Arg Tyr Leu Asn Asp Asn Leu Gly Cys Ala Val Glu Ser
                135                 140                 145

ctc ggc aag gac gtg ctg ctg aac gtc gcg cgc acc tcc atg tcg agc      537
Leu Gly Lys Asp Val Leu Leu Asn Val Ala Arg Thr Ser Met Ser Ser
            150                 155                 160

aag att ctg aac aac gac gcg gat ctt ttc gcg aag atc gta gtg gat      585
Lys Ile Leu Asn Asn Asp Ala Asp Leu Phe Ala Lys Ile Val Val Asp
        165                 170                 175

gct atc atg tcc gtc aag acg gtg aac gac ttt ggt gat gtc atc tac      633
Ala Ile Met Ser Val Lys Thr Val Asn Asp Phe Gly Asp Val Ile Tyr
    180                 185                 190

cct cgt aag gcg gtg tcg att ctg ctg cag cac ggc agg agc ctg cac      681
Pro Arg Lys Ala Val Ser Ile Leu Leu Gln His Gly Arg Ser Leu His
195                 200                 205                 210

gag tca cgg ctg gtg cag ggc ttc gcg atg aac ctc tct cgc gcc gca      729
Glu Ser Arg Leu Val Gln Gly Phe Ala Met Asn Leu Ser Arg Ala Ala
                215                 220                 225

caa ggc atg ccg acc tcg gtg aag gat gct aag att gcc ctc atc gac      777
Gln Gly Met Pro Thr Ser Val Lys Asp Ala Lys Ile Ala Leu Ile Asp
            230                 235                 240

ttc gac ttg cgc gct gtc aag atg aag ctc ggc atc aac atc acc atc      825
Phe Asp Leu Arg Ala Val Lys Met Lys Leu Gly Ile Asn Ile Thr Ile
        245                 250                 255

acg gac ccc tcc aag gca gag gcg atc cgc cag cgt gag ctc gac atc      873
Thr Asp Pro Ser Lys Ala Glu Ala Ile Arg Gln Arg Glu Leu Asp Ile
    260                 265                 270

acg aag gag cgc att cag aag atg atc gcg gcc ggc gcc aac gtc att      921
Thr Lys Glu Arg Ile Gln Lys Met Ile Ala Ala Gly Ala Asn Val Ile
275                 280                 285                 290

atg acg acg tgg ggc atc gag gat agc atg atg aag tat atg gtg gac      969
Met Thr Thr Trp Gly Ile Glu Asp Ser Met Met Lys Tyr Met Val Asp
                295                 300                 305

aac agc gtg ctt ggc gtg cgt cgt gtc aag aag gac gac atc cgc cgc     1017
Asn Ser Val Leu Gly Val Arg Arg Val Lys Lys Asp Asp Ile Arg Arg
            310                 315                 320
```

-continued

```
atc gcc aag act acc ggc gcg cag gtg gtg cac acc atg tcc gac ctc     1065
Ile Ala Lys Thr Thr Gly Ala Gln Val Val His Thr Met Ser Asp Leu
        325                 330                 335

gaa ggc gag gag gtc ttc gac ccc aag tgg ctc ggt cgg tcg gag aag     1113
Glu Gly Glu Glu Val Phe Asp Pro Lys Trp Leu Gly Arg Ser Glu Lys
    340                 345                 350

gtg tac gag gag cgc att ggc gac gat gac tgc atc gtt att gct ggc     1161
Val Tyr Glu Glu Arg Ile Gly Asp Asp Asp Cys Ile Val Ile Ala Gly
355                 360                 365                 370

acc tcg aac gcc gtg tgt gcc acc atc gtc tgc cgc ggc gcg aac tac     1209
Thr Ser Asn Ala Val Cys Ala Thr Ile Val Cys Arg Gly Ala Asn Tyr
                375                 380                 385

ttc atg cta gag gag atg gag cgc gcg ctg aac gac gca ctg tgg gct     1257
Phe Met Leu Glu Glu Met Glu Arg Ala Leu Asn Asp Ala Leu Trp Ala
            390                 395                 400

gtg gcg cgc acg tgc gac gcc agc tgc gtc gtt gct ggc ggc ggc tcc     1305
Val Ala Arg Thr Cys Asp Ala Ser Cys Val Val Ala Gly Gly Gly Ser
        405                 410                 415

gtg gag gcg gcg gtg tcg gtg tac ctg gac aac ttt gcc cgc aca ctc     1353
Val Glu Ala Ala Val Ser Val Tyr Leu Asp Asn Phe Ala Arg Thr Leu
    420                 425                 430

agc tca cgc gag cag ctg gcg gtg gcc gag tac gcc gag gca ctg ctc     1401
Ser Ser Arg Glu Gln Leu Ala Val Ala Glu Tyr Ala Glu Ala Leu Leu
435                 440                 445                 450

gtc att ccg aag gtg ctg gcg ctg aat gct gcc ctc gac gcc acg gac     1449
Val Ile Pro Lys Val Leu Ala Leu Asn Ala Ala Leu Asp Ala Thr Asp
                455                 460                 465

ctc gtc gca aag ctt cgt gtc gag cac acg cag gca cag agc agc ggc     1497
Leu Val Ala Lys Leu Arg Val Glu His Thr Gln Ala Gln Ser Ser Gly
            470                 475                 480

cag cag acg gag gcg cgc ttt acc gga ctg gat ctg cac aac ggc acg     1545
Gln Gln Thr Glu Ala Arg Phe Thr Gly Leu Asp Leu His Asn Gly Thr
        485                 490                 495

cta cgc aac aac atc aag gcg ggt gtg ctg gag cca aag cct agc aag     1593
Leu Arg Asn Asn Ile Lys Ala Gly Val Leu Glu Pro Lys Pro Ser Lys
    500                 505                 510

atc aag tcc ctg cag ttc gcg acg gag gcg gct gtg acg gtg ctg cgt     1641
Ile Lys Ser Leu Gln Phe Ala Thr Glu Ala Ala Val Thr Val Leu Arg
515                 520                 525                 530

atc gac gac tgc gtc cgc ctc aac cct gat gag gag gac cag cag cgc     1689
Ile Asp Asp Cys Val Arg Leu Asn Pro Asp Glu Glu Asp Gln Gln Arg
                535                 540                 545

tgaggctcgt ttttcccacc gattgtgaga gtcggacgag gtgcagcgag cagcagcaga   1749

cgccgcatac caagacgagg cgcagaggtt gagagcgcgt ctacatagat tgtcgcttgc   1809

caagtaagaa cgaggaagtc ggtccaaagg ctactgtgcg catacgcatg cctatgcgca   1869

cacgttgacg tctctctcac attatctctg tgctccttac tcttgttgct ttccagcgca   1929

cgtgtctgcg gttctttctc tctgcttgtg tgcccgtgtc gttccgctct tgctacatcg   1989

ctacgccgtc tcctttttttt cttggtccag ttgtcggacc cctcctctct ctgtgttgac   2049

cttctcttcc tcatcgcctg cacatatgcc tctgcttcgc tccggatgcg tactcgcgtg   2109

cgtgtgtgtg tgcgtgtgcg tgcgcttcgc cgagacggac cctgtaataa ggcagcggat   2169

gccgtgctgt ttgaaggact gagttatgtg ggcggcagcg ggtagaggag gtggcagaaa   2229

agagctacgg cgacaaggag tggcggaagg ctgtttccaa accgcactgc acagatgtag   2289

ggagagaggg agggggaacg agggggtgag ggtgaggcgt ctccgtgtgc tcgtggcgtg   2349

ttgtcctcgt tgccgacatg ttttcggcgc ctactttgcc gtgcctgtct cgagtgtctc   2409
```

-continued cccccgcccc cacccgtcgc gttcgctgag cgtcgctgtc tgtcggtctg tgtgtattcc 2469 gttccagcac cccaactgct tcggactgta agaagggatg cggcgaaaag gtgcgcaaac 2529 atgcgcacct ccgcaccaca ttataagagc acgaactctg acggcgggcg acagtgactc 2589 gtcgcaggtg ttcgttcgtt ttacgcagat gcagattggc ggggagaggt cgaggaagcg 2649 aaaaggagtg ggaggcgatg tgcagctcag cgtgtcaggc gcccacacgc cgaaacacgc 2709 aaggcaaagg gcaacgcgag cgcacatgtg agagaaagcg gcgatcagat gtgtgtgcgt 2769 gtgtgtgcgt gtgtcttcac ctacgaggac gtttattttt cgttctttcc tgcctcgtgt 2829 gacgatctcg agaacggcgg ctggggaggg acgtgaaaga ggaactacaa cctggcgctc 2889 gtgctcgcgc gcgcgcgcgc gtgtgtgtgt gtgtgctctc ttttcgtttc gatgctatcg 2949 caaatcgtcg atgcagcagc atgtagtgcg cttgaaccgc ccctcctctt tcccttcttt 3009 ggtcgtgcgg gtggtctccg ttggtgcgtg tgcgttaagt aatgggcaaa cagagagtga 3069 aggagcgaaa aggcaagtgc agccacccac ctttaaagca acagcaaaca aaaacgaata 3129 ccgtgtgcgt ccatgcatcc cacatccacc tctacccacg tgcatgtgtg tgcaagtgcc 3189 tcttcaggtg actgatcggc gcgcaggtct tcgcaagcgc gcgccactga aatcgaacgc 3249 ggataaaggg aaacaaggcg cagaggcgcg cacgtgcgcg ggtaggcact ccgacacaaa 3309 aatggagctg tgaaagcaag gaa 3332

<210> SEQ ID NO 18
<211> LENGTH: 826
<212> TYPE: DNA
<213> ORGANISM: Leishmania major
<220> FEATURE:
<221> NAME/KEY: CDS
<222> LOCATION: (51)..(482)

<400> SEQUENCE: 18
agagccgcaa gaaccgcgat gacaagcgct ggaagcgcgt gcttgcgaac atg gac 56
Met Asp
1 gag gag aag cgc aag aag ttc cac ggc gtc ggc aac acg gcg aag aac 104
Glu Glu Lys Arg Lys Lys Phe His Gly Val Gly Asn Thr Ala Lys Asn
5 10 15 tcg cgc gtg cgc ggt gcg acc cgc gcg tcc ctg ctc aag cgc act ggc 152
Ser Arg Val Arg Gly Ala Thr Arg Ala Ser Leu Leu Lys Arg Thr Gly
20 25 30 cgc aag ccc gac gct gtg agc atg gag gcg acg atc cac ctg tcg aag 200
Arg Lys Pro Asp Ala Val Ser Met Glu Ala Thr Ile His Leu Ser Lys
35 40 45 50 ctg ctg aag aag aag acc ttc tcg aag cgc gct ccg ctg gcg atc aag 248
Leu Leu Lys Lys Lys Thr Phe Ser Lys Arg Ala Pro Leu Ala Ile Lys
55 60 65 cgc atc aag gcg ttt gtg ggc cgt ctg atg aag acg aag gac aac cgc 296
Arg Ile Lys Ala Phe Val Gly Arg Leu Met Lys Thr Lys Asp Asn Arg
70 75 80 att gac gcg tcg ctg aac acg tac atc tgg cac aag ggc gtg aag ggc 344
Ile Asp Ala Ser Leu Asn Thr Tyr Ile Trp His Lys Gly Val Lys Gly
85 90 95 gtc cct ggc cgc gtg cgt gtg ctg atc cag cgc aag tcg gag acg acg 392
Val Pro Gly Arg Val Arg Val Leu Ile Gln Arg Lys Ser Glu Thr Thr
100 105 110 gag ggc aac aag cac aag cac ttc tac acg gtc atc tcc aac gtg ccg 440
Glu Gly Asn Lys His Lys His Phe Tyr Thr Val Ile Ser Asn Val Pro
115 120 125 130

-continued

```
gtt gcg tcc ttc aag ggc ctg acc acg aag acg gtg gag cag             482
Val Ala Ser Phe Lys Gly Leu Thr Thr Lys Thr Val Glu Gln
                135                 140

taatcgtgcg cgtctgtcct cagcgtctcg gcgttatgcg tgtgttcggt ttcgttttga    542

atccgtttct ctttctctct tttctgtcgt tttacgcttg ttttgtttgg gtttcagcga    602

ggatgtgctc tacaggggtg acacccctgc ggtgtgtgtg tgtgtgtgta cgcttatgcg    662

aggcgtgcac cttgttcagt gagcgtctct tacgatgtgt cctcccattt gcccatgccg    722

cacagagaga cacgcctaca cgggtccctc atgaagcttc tgtaggcaca acgtgcgctg    782

ttattatgct cttcccttcc ctaaaaaaaa aaaaaaaaaa aaaa                    826


<210> SEQ ID NO 19
<211> LENGTH: 1030
<212> TYPE: DNA
<213> ORGANISM: Leishmania major
<220> FEATURE:
<221> NAME/KEY: CDS
<222> LOCATION: (19)..(588)

<400> SEQUENCE: 19

gtccgataag attcgaac atg cgc aac tac aac aac ttc aac cgc gtg tgg      51
                    Met Arg Asn Tyr Asn Asn Phe Asn Arg Val Trp
                    1               5                   10

aag gcg ccg cgc cgt ccg ttt gag aag gag cgc ctc gac cgc gag atg      99
Lys Ala Pro Arg Arg Pro Phe Glu Lys Glu Arg Leu Asp Arg Glu Met
            15                  20                  25

aag ctc tgt ggt cag tac ggt ctg cgc tgc aag cgt gaa atc tgg cgt     147
Lys Leu Cys Gly Gln Tyr Gly Leu Arg Cys Lys Arg Glu Ile Trp Arg
        30                  35                  40

gtg aac atg acg ctg tcc aag atg cgc cgc acg gcc cgt ctg ctg ctg     195
Val Asn Met Thr Leu Ser Lys Met Arg Arg Thr Ala Arg Leu Leu Leu
    45                  50                  55

acg ctg ccg gag aac cac ccc cgc cgt ctg ctg gag ggt tcc gcc atc     243
Thr Leu Pro Glu Asn His Pro Arg Arg Leu Leu Glu Gly Ser Ala Ile
60                  65                  70                  75

atg cgc cgc tgc cac gag tat ggc ttc ctc gac gag gag aag gac aag     291
Met Arg Arg Cys His Glu Tyr Gly Phe Leu Asp Glu Glu Lys Asp Lys
                80                  85                  90

ctg gat tac gtg ctg tcg ctg acg gtg ccg gac att ctc gag cgc cgc     339
Leu Asp Tyr Val Leu Ser Leu Thr Val Pro Asp Ile Leu Glu Arg Arg
            95                  100                 105

ctg cag acc atc gtc ttc aag gcc ggt ctc gcc aag tcc gtg cac cac     387
Leu Gln Thr Ile Val Phe Lys Ala Gly Leu Ala Lys Ser Val His His
        110                 115                 120

gcc cgc gtc ctg att cag cag cgc cac atc gcc gtc gcc aag cag att     435
Ala Arg Val Leu Ile Gln Gln Arg His Ile Ala Val Ala Lys Gln Ile
    125                 130                 135

gtg acg atc ccg tcc ttc atc gtg cgc gtc agc agt gag cgc cac atc     483
Val Thr Ile Pro Ser Phe Ile Val Arg Val Ser Ser Glu Arg His Ile
140                 145                 150                 155

gcc ttc gcc gat gct tcg ccg ttc ggc aac ggc cgt gct ggc cgc gtc     531
Ala Phe Ala Asp Ala Ser Pro Phe Gly Asn Gly Arg Ala Gly Arg Val
                160                 165                 170

aag cgc gtg cgc gcg aag gcc gcc aag cgc cac gcc ggc ggc ggc gat     579
Lys Arg Val Arg Ala Lys Ala Ala Lys Arg His Ala Gly Gly Gly Asp
            175                 180                 185

gac gat gag taagatggag gaagcgcgct cttgtgccgc accggcatgg             628
Asp Asp Glu
        190
```

-continued

```
ggacgcgttg tgcaggctga aggcgtttgc ctctcatacg atcgacgctt cgtgtacctt    688

tgggctcctt gcgttgcacg tgtagagctg cccggcgccc cgtcgcgtct gttttgtact    748

cgacactgac tcggcacgta tacgacgtgt tgaaaacgcc ccgttcgttt cctttcgctt    808

gtttgtgtgt gtttgctttt tttttctatg atcctcattt caccacccaa atccctacac    868

aaaaaccatg cgcgcccgcg catcaccatg gcaggagttt tcgctggggg ttttctcagc    928

gaggacgtca tccctgtatt tgtccgtacc gtctcgcgtt tctctcgtcc gagctctcgg    988

acggcgcgaa tctgttgcca cgtgctactg cctatccgcc cc                      1030


<210> SEQ ID NO 20
<211> LENGTH: 814
<212> TYPE: DNA
<213> ORGANISM: Leishmania major
<220> FEATURE:
<221> NAME/KEY: CDS
<222> LOCATION: (37)..(621)

<400> SEQUENCE: 20

gctcacaaag cctcggttcc acgcgagttg tttcga atg gcc gcc acc aag tct       54
                                        Met Ala Ala Thr Lys Ser
                                        1               5

gct gtg tcc gcc gcg aag agg aag gcg gcg aag aag gtg tcg cgc aag      102
Ala Val Ser Ala Ala Lys Arg Lys Ala Ala Lys Lys Val Ser Arg Lys
            10                  15                  20

agc ccc gag tac acg act ctg cgc aag agc tgt gct ccc ggc gcc atc      150
Ser Pro Glu Tyr Thr Thr Leu Arg Lys Ser Cys Ala Pro Gly Ala Ile
        25                  30                  35

gcg atc atc ctc gcc ggc cgc ttc cgc ggt cgc cgc gcc gtg atc ctg      198
Ala Ile Ile Leu Ala Gly Arg Phe Arg Gly Arg Arg Ala Val Ile Leu
    40                  45                  50

aag cag ctg ccg cac aac ggc ccg ctg gtc gtg tct ggc ccg atg aag      246
Lys Gln Leu Pro His Asn Gly Pro Leu Val Val Ser Gly Pro Met Lys
55                  60                  65                  70

tac aat ggc gtc ccc atc cgc cgc atc gac tcc cgc tac gtg atc gcc      294
Tyr Asn Gly Val Pro Ile Arg Arg Ile Asp Ser Arg Tyr Val Ile Ala
                75                  80                  85

acc agc acc acg gtg gac atc tcc agc gtt gac acg gcg ccc atc acc      342
Thr Ser Thr Thr Val Asp Ile Ser Ser Val Asp Thr Ala Pro Ile Thr
            90                  95                  100

gcc gag gtg ttc cag cgc ccc aag gcg gag aag ccg acc aag agc gag      390
Ala Glu Val Phe Gln Arg Pro Lys Ala Glu Lys Pro Thr Lys Ser Glu
        105                 110                 115

ggc gac ttc atg ggc gac aag cag aag gct aag gcg gag aag gct gcc      438
Gly Asp Phe Met Gly Asp Lys Gln Lys Ala Lys Ala Glu Lys Ala Ala
    120                 125                 130

aag aag acc tcc aag gcg gga aag aag acc ctc gtc tcg gac gcg cgc      486
Lys Lys Thr Ser Lys Ala Gly Lys Lys Thr Leu Val Ser Asp Ala Arg
135                 140                 145                 150

gcc cag ctg cag aag aag atc gac gct gcc ctc atc gcc gcc atc aag      534
Ala Gln Leu Gln Lys Lys Ile Asp Ala Ala Leu Ile Ala Ala Ile Lys
                155                 160                 165

aag gac gct cag ggc aag gag aag gcc ggc tac ctg cgc tcc gtc ttc      582
Lys Asp Ala Gln Gly Lys Glu Lys Ala Gly Tyr Leu Arg Ser Val Phe
            170                 175                 180

acg gtg aag ccc ggt gat gcg ccg cac cgc tgg aac tgg taagcgcagg       631
Thr Val Lys Pro Gly Asp Ala Pro His Arg Trp Asn Trp
        185                 190                 195

acaaccgtac gcgctctcgc agcacgtgct cgtgctgtag cctcgctacc cctaaagctt    691
```

-continued

```
ctctggtgag ccgcaagccg acgcgttttg cggttctccc gcaggccgtg tgcgtctttt    751

ctattttttt tttttttttg gtttcttcgc ttcccttgtg ttttgttttg tttcatccgc    811

aac                                                                  814


<210> SEQ ID NO 21
<211> LENGTH: 1474
<212> TYPE: DNA
<213> ORGANISM: Leishmania major
<220> FEATURE:
<221> NAME/KEY: CDS
<222> LOCATION: (16)..(552)

<400> SEQUENCE: 21

gccaaagaga aaaca atg gtc aag ccg cac ttg cgc cac tac cag gtg gtc      51
                 Met Val Lys Pro His Leu Arg His Tyr Gln Val Val
                 1               5                   10

ggc cgc gag tcg ccc tcg gag aag aac cct gag ccg act gtg tac aag       99
Gly Arg Glu Ser Pro Ser Glu Lys Asn Pro Glu Pro Thr Val Tyr Lys
        15                  20                  25

ttt gag gtg ttc gcc cca aac ttc gtc gtc gcc aag agc cgt ttc tgg      147
Phe Glu Val Phe Ala Pro Asn Phe Val Val Ala Lys Ser Arg Phe Trp
    30                  35                  40

cgc atg atg agg gtc aag aac aag gtc aag gcc acg cac ggt gac gtg      195
Arg Met Met Arg Val Lys Asn Lys Val Lys Ala Thr His Gly Asp Val
45                  50                  55                  60

ctc tcc tgc aag gtc gtg aag gat gcg aag ctg gtg gcg cgc aac tac      243
Leu Ser Cys Lys Val Val Lys Asp Ala Lys Leu Val Ala Arg Asn Tyr
                65                  70                  75

ctg gtc gac atc gcg tac tac agc cag cgc tgc ggc tac acg cgc atg      291
Leu Val Asp Ile Ala Tyr Tyr Ser Gln Arg Cys Gly Tyr Thr Arg Met
            80                  85                  90

gtc aag gag ttc cgc gac gtc tcc aag acc ggc gcc gtg agc cag gcg      339
Val Lys Glu Phe Arg Asp Val Ser Lys Thr Gly Ala Val Ser Gln Ala
        95                  100                 105

tac cac gac ctg gcc tcc cgc cac cgc gcc cgc tac cac aac atc gag      387
Tyr His Asp Leu Ala Ser Arg His Arg Ala Arg Tyr His Asn Ile Glu
    110                 115                 120

gtg ctg aac gtg aag agc atc ccg gac cac gag gtg aag cac ctg agc      435
Val Leu Asn Val Lys Ser Ile Pro Asp His Glu Val Lys His Leu Ser
125                 130                 135                 140

att gcc caa tac cac gct cca aac ctg tcc ttc ccg ctc ctg cag cgc      483
Ile Ala Gln Tyr His Ala Pro Asn Leu Ser Phe Pro Leu Leu Gln Arg
                145                 150                 155

cgc atc aag gca gcc cgc aag gac cgt gcc atc ttc gtc aag aag aac      531
Arg Ile Lys Ala Ala Arg Lys Asp Arg Ala Ile Phe Val Lys Lys Asn
            160                 165                 170

acg aag cgc gcg gtg gtg gcg tgaggaagga gctggtgaag caagaacagg         582
Thr Lys Arg Ala Val Val Ala
        175

tggcagagga gaaagggagt gtaccagcac aaacattcgc gcacgcatat gattgcagac    642

acatgtgtgt gtatgggatc gtatgcgtat gtgattgtgt gtatggaaac gcccactccc    702

tctgccctct tcccttgtct cctggctgct agtagggggt gcaggtatcg tgtgtgcgtg    762

tttgtgtgtc ggtctcgttg tcggcgcagg cacgtgcttg ccaagcacga ttgttacggc    822

tgtctcgttc ttcgcgggtt gcgtgtgtgc gcaactgccg atgctctctc gtctttcgtt    882

tttctcgctc cctcccctgg atcttgctgg attgcgtcgt tttgttggtt cgcgatggtg    942

atccagcggc gttgcccccc ccccgtcgac acacatatgc acacatgcta ttgctgccgg   1002
```

-continued

```
gcgggggaac atcggcactg gccaccggcg acaagcagtg aaggaagggg atggggaaag   1062

cgagaaaaag agaggcggcg ggcaacggca gctgaaggag acggcgcgcc gctccgcttg   1122

gcgtgtgttc cgtgaaggtt ctcggacttt ggcgtgactt tatggttcgc gtgcttcgtt   1182

tcttcgcttc ctcttttcgt gcttgtttcc gtcattttac gcgccaaaac aaatcaaaag   1242

aagcacctca agggccatca gcaaaacttc ccctaccccg caccggtggt gtggggtgtg   1302

gattcggggc gggggtgcgt atgcgagaga cgcgcaagaa cttacctttt tttgttcgca   1362

gtctgcggtg cttagcctcc ggggcgggga gacggctttg cgagccaaac acaccgcccc   1422

gcctctcgct tccggtgctc cttcgcctcg aaaaaaaaaa aaaaaaaaaa aa           1474


<210> SEQ ID NO 22
<211> LENGTH: 1977
<212> TYPE: DNA
<213> ORGANISM: Leishmania major
<220> FEATURE:
<221> NAME/KEY: CDS
<222> LOCATION: (126)..(1307)

<400> SEQUENCE: 22

cttgctcatc agccaccttg cacttgctca cccactcaac gaagcacaag aggcgacgat     60

acttatcagc gataagtgct gccttaaccg ccatccacaa ccttcagcag aaagagcagg    120

gaaat atg atg cgg cgc acg ctg ctc tgg ctc gtg aac ttc gag ccc gtc    170
      Met Met Arg Arg Thr Leu Leu Trp Leu Val Asn Phe Glu Pro Val
      1               5                   10                  15

ttc atg cca gcc ctc tcc ccg tcg atg gag acg ggc acg gta gtc gag      218
Phe Met Pro Ala Leu Ser Pro Ser Met Glu Thr Gly Thr Val Val Glu
                20                  25                  30

tgg aag aag aag atc ggc gag ctc gtg aag gag agc gat gtc ttc tgc      266
Trp Lys Lys Lys Ile Gly Glu Leu Val Lys Glu Ser Asp Val Phe Cys
            35                  40                  45

acc atc cag acg gac aag gca gta gtg gac tac acg aac acc ttc gag      314
Thr Ile Gln Thr Asp Lys Ala Val Val Asp Tyr Thr Asn Thr Phe Glu
        50                  55                  60

agc ggc tac ctc gcc aag ata tac tgt ggg aac ggc cag tct gcc ccc      362
Ser Gly Tyr Leu Ala Lys Ile Tyr Cys Gly Asn Gly Gln Ser Ala Pro
    65                  70                  75

gtc gcc aag acg atc gct gtg atg gtg agc gac gcc gcg gat gtc agt      410
Val Ala Lys Thr Ile Ala Val Met Val Ser Asp Ala Ala Asp Val Ser
80                  85                  90                  95

aag gcg gac gag tac acg cct gag ggc gag gtg cct gcc gcg gag gcg      458
Lys Ala Asp Glu Tyr Thr Pro Glu Gly Glu Val Pro Ala Ala Glu Ala
                100                 105                 110

gag gca ccc acc gct gct gct gtt gcc gca gcg ccg gcc gct ggt ggt      506
Glu Ala Pro Thr Ala Ala Ala Val Ala Ala Ala Pro Ala Ala Gly Gly
            115                 120                 125

gcc tct tct aag gca ccg gaa ggc gtc acc tgt gag ccc gtc ttc atg      554
Ala Ser Ser Lys Ala Pro Glu Gly Val Thr Cys Glu Pro Val Phe Met
        130                 135                 140

cca gcc ctc tcc ccg tcg atg gag acg ggc acg gta gtc gag tgg aag      602
Pro Ala Leu Ser Pro Ser Met Glu Thr Gly Thr Val Val Glu Trp Lys
    145                 150                 155

aag aag atc ggc gag ctc gtg aag gag agc gat gtc ttc tgc acc atc      650
Lys Lys Ile Gly Glu Leu Val Lys Glu Ser Asp Val Phe Cys Thr Ile
160                 165                 170                 175

cag acg gac aag gca gta gtg gac tac acg aac acc ttc gag agc ggc      698
Gln Thr Asp Lys Ala Val Val Asp Tyr Thr Asn Thr Phe Glu Ser Gly
                180                 185                 190
```

-continued

```
tac ctc gcc aag ata tac tgt ggg aac ggc cag tct gcc ccc gtc gcc      746
Tyr Leu Ala Lys Ile Tyr Cys Gly Asn Gly Gln Ser Ala Pro Val Ala
            195                 200                 205

aag acg atc gct gtg atg gtg agc gac gct gcc gat gtg gag aag gtt      794
Lys Thr Ile Ala Val Met Val Ser Asp Ala Ala Asp Val Glu Lys Val
        210                 215                 220

gcc aac tac tac ccc gag gat gcc gtt ggc ggg ccg ccg gct tcc gcc      842
Ala Asn Tyr Tyr Pro Glu Asp Ala Val Gly Gly Pro Pro Ala Ser Ala
    225                 230                 235

gct gac cct tct gcc gcc gct gct gct gct gcg tca gct cga ccg gct      890
Ala Asp Pro Ser Ala Ala Ala Ala Ala Ala Ala Ser Ala Arg Pro Ala
240                 245                 250                 255

cca tcc gcc gcg tct gcc aag cac tac ggt ggc tcg ctc gat gcg gcg      938
Pro Ser Ala Ala Ser Ala Lys His Tyr Gly Gly Ser Leu Asp Ala Ala
                260                 265                 270

gtg gcg gct agt ggc cca agt gtg gcc cgc att gct gct ggt ctg gag      986
Val Ala Ala Ser Gly Pro Ser Val Ala Arg Ile Ala Ala Gly Leu Glu
            275                 280                 285

acc agc acc ctt gcc ggc atc gct ccc tct ggc aag ggt ggg cgt ttc     1034
Thr Ser Thr Leu Ala Gly Ile Ala Pro Ser Gly Lys Gly Gly Arg Phe
        290                 295                 300

ctg aaa tcc gac ttt tct ggt caa ccc ggc ttc gac tac aac gac acc     1082
Leu Lys Ser Asp Phe Ser Gly Gln Pro Gly Phe Asp Tyr Asn Asp Thr
    305                 310                 315

acg ccg gcg cga gcg atg cag cag aag gcg gcc ccc gcc gct gcc gct     1130
Thr Pro Ala Arg Ala Met Gln Gln Lys Ala Ala Pro Ala Ala Ala Ala
320                 325                 330                 335

gat gag gcg agt aag acg gct gcg aag tct gct gcc ccg gcg gcg gta     1178
Asp Glu Ala Ser Lys Thr Ala Ala Lys Ser Ala Ala Pro Ala Ala Val
                340                 345                 350

agc ggg gac atc tac aac gtt gtt ctc aag ccc ggc cct gtg tac aag     1226
Ser Gly Asp Ile Tyr Asn Val Val Leu Lys Pro Gly Pro Val Tyr Lys
            355                 360                 365

agc gtc agc gac acg gcc ctg ctg aag aag ctc atg cac acc atg cac     1274
Ser Val Ser Asp Thr Ala Leu Leu Lys Lys Leu Met His Thr Met His
        370                 375                 380

gtt ccg aag cca aag ttg aag aag gcc gcc gag taaggaggcg gagaagtgta   1327
Val Pro Lys Pro Lys Leu Lys Lys Ala Ala Glu
    385                 390

ccgatgcgcg cgtgtgcgcg aaacgcgtgt cttccgctca ttcgccaagg ggttgggga    1387

ggggatgcgg atgctgagca gaaactcttc ccgtgtagtc gacgtcgtcg tgtagttcac   1447

gccgtcaatg cgggtgtggt gcaagtcaga gatctctcgg gaaacggatg ggttggggtg   1507

gggaggaggc cgcagccaca caaacgggcg gctacgcact tcctcacatg cacacacaca   1567

cacacacaca cgcacccagc cactcgtcct ctccttctct ctcaccatct ctctgtgtct   1627

gacggtgaag cagggaaaag gcgagaggtc ggtggagggc ggtggggccg agcatggagg   1687

ctgtgcgtgc acgatgacga aggcaggagt gcaaagttgt ggggtgcggt gtgcatgtga   1747

aaccgactgt ctgccaccct tttacccgat ggatgacact cgttcgtcca accccaaggc   1807

gccttctccc tgcaagaacg aggtacactc gatgtatgaa ggcgggctgt cgaggcatct   1867

gacacgcaac agctgctccc tacgctgaca ccgtggccat ggacttgacg cacgcagatg   1927

tgccgctgtg tcttgtgcgt ctccgactcg ataatggccg cgttcggcag              1977
```

<210> SEQ ID NO 23
<211> LENGTH: 2282
<212> TYPE: DNA

-continued

<213> ORGANISM: Leishmania major
<220> FEATURE:
<221> NAME/KEY: CDS
<222> LOCATION: (197)..(1510)

<400> SEQUENCE: 23
gctacgccgc atctacatgc agatacacag aggcgtcgag gcacacagac acacacacac 60
acacacacat atatatatac atatataggc gctgctctcc tctccgtacc acaccccatc 120
cccagtgcac gcacacacgc acacgcacgc acacgccatc tcacatcagg acgcgtttct 180
gaccagggag ggaacc atg ggg cag aac atg cca aag ccg ccg ggt gcc ggc 232
Met Gly Gln Asn Met Pro Lys Pro Pro Gly Ala Gly
1 5 10 aaa cca gag aag tgg gaa cct cct gtg gcg ccg gag atc ggc aag cgc 280
Lys Pro Glu Lys Trp Glu Pro Pro Val Ala Pro Glu Ile Gly Lys Arg
15 20 25 aag aag aag cgc ggc ccc gac gcg gcc acg cgc att ccg aag gtc tat 328
Lys Lys Lys Arg Gly Pro Asp Ala Ala Thr Arg Ile Pro Lys Val Tyr
30 35 40 ccg aac cgc gcc tgc ctc ctc cga aag tac cgc ctt gag cgc tgc aag 376
Pro Asn Arg Ala Cys Leu Leu Arg Lys Tyr Arg Leu Glu Arg Cys Lys
45 50 55 60 gac tac ctc ctg cta gag gaa gag ttc ctg cgc aca atc aac gcc cag 424
Asp Tyr Leu Leu Leu Glu Glu Glu Phe Leu Arg Thr Ile Asn Ala Gln
65 70 75 cgc gac gcg cag tcg aac ctg gag gag ggt gcg atg ggc cac tac gag 472
Arg Asp Ala Gln Ser Asn Leu Glu Glu Gly Ala Met Gly His Tyr Glu
80 85 90 gcg gag ctg aag cgc gtc gag gac att cgt ggc acc ccg ctg gag gtg 520
Ala Glu Leu Lys Arg Val Glu Asp Ile Arg Gly Thr Pro Leu Glu Val
95 100 105 gcg acg ctc gag gag gca gtg gac gac tcg cac gcg atc gtc tcc atc 568
Ala Thr Leu Glu Glu Ala Val Asp Asp Ser His Ala Ile Val Ser Ile
110 115 120 tct ggc acc gag tac tac gtg ccc ctc atg tcg ttc gta gac aag gag 616
Ser Gly Thr Glu Tyr Tyr Val Pro Leu Met Ser Phe Val Asp Lys Glu
125 130 135 140 cag tta gag ctg ggg tgc agc gtg ctg ctg cat gac cgg cag cac agc 664
Gln Leu Glu Leu Gly Cys Ser Val Leu Leu His Asp Arg Gln His Ser
145 150 155 atc gtt ggc gtg ctt aag gac gac gtc gac ccg ctg gtg agt gtc atg 712
Ile Val Gly Val Leu Lys Asp Asp Val Asp Pro Leu Val Ser Val Met
160 165 170 aag gtt gac aag gcg ccg gag gac acg tac gcg gac att ggt ggc ctg 760
Lys Val Asp Lys Ala Pro Glu Asp Thr Tyr Ala Asp Ile Gly Gly Leu
175 180 185 gag cag cag atc cag gag atc aag gag gcg gtc gag ttt cca ctc tcc 808
Glu Gln Gln Ile Gln Glu Ile Lys Glu Ala Val Glu Phe Pro Leu Ser
190 195 200 cac cca gag ctg tac gac gag ata ggc atc aag cca ccg aag ggt gtc 856
His Pro Glu Leu Tyr Asp Glu Ile Gly Ile Lys Pro Pro Lys Gly Val
205 210 215 220 att ctc tac ggt gtc ccc ggc acc ggc aag acg ctg ctg gcc aaa gcc 904
Ile Leu Tyr Gly Val Pro Gly Thr Gly Lys Thr Leu Leu Ala Lys Ala
225 230 235 gtc gcg aac cgc acc agc gcc acg ttc ctg cgg gtg gtg gga tcg gag 952
Val Ala Asn Arg Thr Ser Ala Thr Phe Leu Arg Val Val Gly Ser Glu
240 245 250 ctg att cag aag tac tcc ggc gag ggc ccc aag ctc gtg cgt gag ctc 1000
Leu Ile Gln Lys Tyr Ser Gly Glu Gly Pro Lys Leu Val Arg Glu Leu -continued

```
        255                 260                 265

ttc cgg gtt gcg gag gag cac tcg cca gcg atc gtg ttc att gat gaa     1048
Phe Arg Val Ala Glu Glu His Ser Pro Ala Ile Val Phe Ile Asp Glu
    270                 275                 280

atc gac gcc atc ggc acg aag cgc tac gac acg gac agc agc ggc acg     1096
Ile Asp Ala Ile Gly Thr Lys Arg Tyr Asp Thr Asp Ser Ser Gly Thr
285                 290                 295                 300

aaa gag gtg cag cgt acg atg ctg gag ctg ctc acg caa ctg gac ggc     1144
Lys Glu Val Gln Arg Thr Met Leu Glu Leu Leu Thr Gln Leu Asp Gly
                305                 310                 315

ttc gat agc agc aac gac gtg aaa gtg atc atg gca acc aac cgc atc     1192
Phe Asp Ser Ser Asn Asp Val Lys Val Ile Met Ala Thr Asn Arg Ile
            320                 325                 330

gac acc ctc gac ccg gct ctc atc cgc cct ggt cgt atc gac cgc aag     1240
Asp Thr Leu Asp Pro Ala Leu Ile Arg Pro Gly Arg Ile Asp Arg Lys
        335                 340                 345

att gag ttc ccc ttc cca gac gag aag acg aag cgc cgc atc ttc gaa     1288
Ile Glu Phe Pro Phe Pro Asp Glu Lys Thr Lys Arg Arg Ile Phe Glu
    350                 355                 360

atc cat aca agc cgc atg tca ctc gcc gaa gac gtc gac atc tcc gag     1336
Ile His Thr Ser Arg Met Ser Leu Ala Glu Asp Val Asp Ile Ser Glu
365                 370                 375                 380

ttt atc cac gcg aag gat gag atg agc ggc gcg gat gtg aag gcc atc     1384
Phe Ile His Ala Lys Asp Glu Met Ser Gly Ala Asp Val Lys Ala Ile
                385                 390                 395

tgc aca gag gcc ggg ctg ctg gcc ctg cgt gag cgc cgc atg aag gtg     1432
Cys Thr Glu Ala Gly Leu Leu Ala Leu Arg Glu Arg Arg Met Lys Val
            400                 405                 410

tgc caa gcc gac ttt atc aag ggc aag gaa aat gtg cag tac cgc aag     1480
Cys Gln Ala Asp Phe Ile Lys Gly Lys Glu Asn Val Gln Tyr Arg Lys
        415                 420                 425

gac aag tcg acg ttt tcg cgt ttt tac ctg tgaagacccc caatcccagg       1530
Asp Lys Ser Thr Phe Ser Arg Phe Tyr Leu
    430                 435

aggagggagc gcgctcagcc ggggggggagg ggggacgatg gaagaaagag acaccacccg   1590

acggcgtcgc tggctgtttg ctcgcgtgtg catcttctct gtgtgtctgc cgccttcatc   1650

ctcctcgcac acacggctcc cccttccctc ggtctcttcc accgatcctc gggtgggctc   1710

actgaaggtg cgcatgcctg tgcataggca cgagaatcag cgcgagagtg tgtgcgtgtg   1770

ggagcgtttc gcccccgttt tgtctttttt tttctattgt tgtttcggat ctgtgctgcc   1830

tctgatgtgt ccgtgaaggt gtgctcggca tgccccctct ttctctgtcc ctcactctct   1890

ctctctcgct ctgtgcactc cgttgtatgt accttagcct tcttcgttgt atggatgtgg   1950

atgcgtgtgt tttgtgggtc tgccgctgtt ggtgccgcgt ggcttgctcg tgtgcggctc   2010

cgtctttgag cacgatgatg gattcgatcg gcggcctggc cacaaaagca accatcatca   2070

ccgggggtca ttaccgtatg ggtgtgggtg tgtgcaacga agcgtgtttc cgctgtccgg   2130

aaagctgcac acgcacgtgc actcacatgc tctcgcagcg ctgatgtgga acagccgcgg   2190

gagggcgcgc acgagtggcc aatgcgagca cgaatgagag aaggaacgag aagagtgcga   2250

agatgaatag aaaaaaaaaa aaaaaaaaaa aa                                 2282
```

```
<210> SEQ ID NO 24
<211> LENGTH: 1120
<212> TYPE: DNA
<213> ORGANISM: Leishmania major
<220> FEATURE:
<221> NAME/KEY: CDS
```

-continued

<222> LOCATION: (37)..(375)

<400> SEQUENCE: 24

```
cacacaaacc ttacacacgc atacaccgca ctcatc atg ccg ccg aag gct cgt       54
                                        Met Pro Pro Lys Ala Arg
                                        1               5

gcc cct ctg ccg cct ggt gac gtg gag cgc ggc gag aag ctg ttc aag      102
Ala Pro Leu Pro Pro Gly Asp Val Glu Arg Gly Glu Lys Leu Phe Lys
            10                  15                  20

ggc cgc gct gct cag tgc cac acc gcg acc aag ggc ggc tcg aac ggt      150
Gly Arg Ala Ala Gln Cys His Thr Ala Thr Lys Gly Gly Ser Asn Gly
        25                  30                  35

gtg ggc ccg aac ctg ttc ggc atc gtc aac cgt ccc tcc ggc aag gtc      198
Val Gly Pro Asn Leu Phe Gly Ile Val Asn Arg Pro Ser Gly Lys Val
    40                  45                  50

gag ggc ttc acg tac agc aag gcg aac gcc gag tca ggc gta atc tgg      246
Glu Gly Phe Thr Tyr Ser Lys Ala Asn Ala Glu Ser Gly Val Ile Trp
55                  60                  65                  70

acg ccg gaa gtg ctg gac gtg tac ctg gag aac ccg aag aag ttt atg      294
Thr Pro Glu Val Leu Asp Val Tyr Leu Glu Asn Pro Lys Lys Phe Met
                75                  80                  85

cct ggc acg aag atg tcg ttt gcc ggc atc aag aag ccg caa gag cgc      342
Pro Gly Thr Lys Met Ser Phe Ala Gly Ile Lys Lys Pro Gln Glu Arg
            90                  95                  100

gct gac gtg atc gcg tac ctc gag act ctc aag taagacgagg acaccgtcgt    395
Ala Asp Val Ile Ala Tyr Leu Glu Thr Leu Lys
        105                 110

gcacagtgtc gctgtgtgac ccaccttccg ctgggtttgt gtcttaacgc ctacagacac    455

gggcacaggc acgcctgtat cactcgcgcc ggtccgtgaa cggggcacta actacaatcg    515

aagaggctgt ccctacttaa cgaagaacgt tgccctggtg acgggcagcg gggggagaga    575

acgacacgag agaagcggag agtgaggaat gaggcacggg tgggggtgga agacgttgtc    635

gggtcgcggc taatgcgctg ccgaaaggcc gtgaatgggg gtgggggctc ggtggcacaa    695

cgagaggagg aggagcagga gcaacgatga ttgggtccgg taggcgtgag ttttggcagg    755

ggtgtacggc acgtgtgctg tcattactgc aacagcagtg tcggcacttc cccgtgtcca    815

tgtccgcatt cgcttcgctc tgtgcctcgc cttgcacccc ttcctccttt cctataacgt    875

ggcccgtgct ctgccctccc gtcggctctt ccccctatcc gtgccagccc tccgccctcc    935

ctccacaccc acgcagtacg gctgtactgt ttagactcag tacttcaccg tcgccgagcc    995

accaccacca ccaccaccca caacaaaaaa ataggtggag aagtcgtaaa gcgcccacac   1055

gaacgggccg tgcgcacacg cagatgacga acgcggaaaa tgtaacaaaa aaaaaaaaaa   1115

aaaaa                                                               1120
```

<210> SEQ ID NO 25
<211> LENGTH: 1505
<212> TYPE: DNA
<213> ORGANISM: Leishmania major
<220> FEATURE:
<221> NAME/KEY: CDS
<222> LOCATION: (84)..(1109)

<400> SEQUENCE: 25

```
cattggttct ctctgcctac ctcgccgttg cctcttccca ttttcgtccc ttttattggc     60

ttctttccta ttacttcata tac atg tat atg tat cta tac aca cac aca cac    113
                          Met Tyr Met Tyr Leu Tyr Thr His Thr His
                          1               5                   10
```

-continued

```
acc atc gct tgg cgc gtg tgt gtg tct gtg cgt tgc gtg atg ggc tgc      161
Thr Ile Ala Trp Arg Val Cys Val Ser Val Arg Cys Val Met Gly Cys
                15                  20                  25

ttt gtg ctt gcc ttc cac ccc ctt gca cct tcg cct tca ccg cca tca      209
Phe Val Leu Ala Phe His Pro Leu Ala Pro Ser Pro Ser Pro Pro Ser
            30                  35                  40

cca acg acg cca tgg cgt cct ttg tac gac gtg cac cgt tcc cgc aca      257
Pro Thr Thr Pro Trp Arg Pro Leu Tyr Asp Val His Arg Ser Arg Thr
        45                  50                  55

ccc aca cgc cga aac acg cat tat cca cgt cca cac gca cag gac gtt      305
Pro Thr Arg Arg Asn Thr His Tyr Pro Arg Pro His Ala Gln Asp Val
    60                  65                  70

tgc atc tgc agc atg ccc ggc aag gaa gtg aag aag gtg acg cag ccc      353
Cys Ile Cys Ser Met Pro Gly Lys Glu Val Lys Lys Val Thr Gln Pro
75                  80                  85                  90

gcg aag gcc gcg tct ccg tac aag aag ccc gcc gtt gcg tcg cat ttc      401
Ala Lys Ala Ala Ser Pro Tyr Lys Lys Pro Ala Val Ala Ser His Phe
                95                  100                 105

gcg gcc cgc ccg aag aac ttc ggt att ggc cag gat gtg ccg tac gcg      449
Ala Ala Arg Pro Lys Asn Phe Gly Ile Gly Gln Asp Val Pro Tyr Ala
            110                 115                 120

cgt gac ctg tcc cgc ttc atg cgg tgg ccg acg ttc gtg acg atg cag      497
Arg Asp Leu Ser Arg Phe Met Arg Trp Pro Thr Phe Val Thr Met Gln
        125                 130                 135

cgc aag aag cgc gtg ctg cag cgc cgc ctg aag gtg ccg ccg gcg ctg      545
Arg Lys Lys Arg Val Leu Gln Arg Arg Leu Lys Val Pro Pro Ala Leu
    140                 145                 150

aac cag ttc acg aag gtg ctg gac cgc gcg agc cga aac gag gcg ctg      593
Asn Gln Phe Thr Lys Val Leu Asp Arg Ala Ser Arg Asn Glu Ala Leu
155                 160                 165                 170

aag ctg att aag aag tac gcg ccg gag acc cgc aag gct cgc cgc gag      641
Lys Leu Ile Lys Lys Tyr Ala Pro Glu Thr Arg Lys Ala Arg Arg Glu
                175                 180                 185

cgc ctg cag aag gtt gcc gag gag aag aag aag gac ccg aag aag acg      689
Arg Leu Gln Lys Val Ala Glu Glu Lys Lys Lys Asp Pro Lys Lys Thr
            190                 195                 200

gta tcg acg aag gct ccc ctg gct gtt gtg acc ggt ctg cag gag gtg      737
Val Ser Thr Lys Ala Pro Leu Ala Val Val Thr Gly Leu Gln Glu Val
        205                 210                 215

acg cgc gcg atc gag aag aag cag gct cgc atg gtt gtg atc gcg aac      785
Thr Arg Ala Ile Glu Lys Lys Gln Ala Arg Met Val Val Ile Ala Asn
    220                 225                 230

aac gtg gac cct gtg gag ctc gtg ctg tgg atg ccg aac ctg tgc cgc      833
Asn Val Asp Pro Val Glu Leu Val Leu Trp Met Pro Asn Leu Cys Arg
235                 240                 245                 250

gcg aac aag atc ccg tat gcc atc gtg aag gac atg gcg cgc ctg ggc      881
Ala Asn Lys Ile Pro Tyr Ala Ile Val Lys Asp Met Ala Arg Leu Gly
                255                 260                 265

gat gcg atc ggg cgg aag acg gcg acg tgc gtt gcg ctc acc gac gtg      929
Asp Ala Ile Gly Arg Lys Thr Ala Thr Cys Val Ala Leu Thr Asp Val
            270                 275                 280

aac gcc gag gat gag gcg acg ctg aag aac ctg atc cgc tcc gtg aac      977
Asn Ala Glu Asp Glu Ala Thr Leu Lys Asn Leu Ile Arg Ser Val Asn
        285                 290                 295

gct cgc ttc ttg tcc cgc tcg gac gtg atc cgc cgc cag tgg ggt ggt     1025
Ala Arg Phe Leu Ser Arg Ser Asp Val Ile Arg Arg Gln Trp Gly Gly
    300                 305                 310

ctg cag ctg tct ctg cga tcc cgc gcg gag ctg cgc aag aag cat gcc     1073
Leu Gln Leu Ser Leu Arg Ser Arg Ala Glu Leu Arg Lys Lys His Ala
315                 320                 325                 330
```

-continued

```
cgc aac gct ggt gtg gac gcc gcg gcc atc atc cag taagccgctg         1119
Arg Asn Ala Gly Val Asp Ala Ala Ala Ile Ile Gln
                335                 340

tgctgtctcg gacacgatga cgttggtgtg ggtgcgtgtg tctgagagcg ttgtgtggcg   1179

gtcatggtgc tgcagccctg gtacgccgtt gatagtgttc tcatttggac gggagtgcag   1239

cccgcctcct ccacgtgacg ctcaatgacc cacccggtca ctggcgcaca acatccatgt   1299

cgtgaaaagc agatcgtcct ctctcgctct tttttctttc gtgtttgcgt gcaccgatgg   1359

gatgggccgc acctctcaac gcgagtgtgt gcgtgcgcgt gcgtctccgt gcaatcggtg   1419

catcgattct tttcgtttct gagtaacagg gataagaaca acaacaaaaa aaaaaaaaaa   1479

aaaaaaaaaa aaaaaaaaaa aaaaaa                                        1505


<210> SEQ ID NO 26
<211> LENGTH: 1883
<212> TYPE: DNA
<213> ORGANISM: Leishmania major
<220> FEATURE:
<221> NAME/KEY: CDS
<222> LOCATION: (1)..(1257)

<400> SEQUENCE: 26

atg tct cac tgc aag ttc gag cac ccc cgc cac ggc cat ctc ggc ttc       48
Met Ser His Cys Lys Phe Glu His Pro Arg His Gly His Leu Gly Phe
1               5                   10                  15

ctg ccg cgc aag cgc tcg cgc cag atc cgc ggc cgt gcg cgc gcg ttc       96
Leu Pro Arg Lys Arg Ser Arg Gln Ile Arg Gly Arg Ala Arg Ala Phe
            20                  25                  30

ccc aag gac gac gcg acg cag aag ccc cac ctg acg agc ttc atg gtg      144
Pro Lys Asp Asp Ala Thr Gln Lys Pro His Leu Thr Ser Phe Met Val
        35                  40                  45

ttc aag gcc ggt atg acg cac att gtg cgt gat gtc gat cgc cct gga      192
Phe Lys Ala Gly Met Thr His Ile Val Arg Asp Val Asp Arg Pro Gly
    50                  55                  60

tcg aag gtg aac aag aag gaa gtg gtg gag ccg gtg acg atc ctg gag      240
Ser Lys Val Asn Lys Lys Glu Val Val Glu Pro Val Thr Ile Leu Glu
65                  70                  75                  80

gcg ccg ccg atg gtg att gtc ggc att gtg ggc tac cgc caa acg ccg      288
Ala Pro Pro Met Val Ile Val Gly Ile Val Gly Tyr Arg Gln Thr Pro
                85                  90                  95

gtt ggc ctg aag acg atc ggc acc gtg tgg gcg cac cac acg agc gtc      336
Val Gly Leu Lys Thr Ile Gly Thr Val Trp Ala His His Thr Ser Val
            100                 105                 110

gag ttc cgc cgc cgc tac tac aag aac tgg aag cag tct gcg caa ctg      384
Glu Phe Arg Arg Arg Tyr Tyr Lys Asn Trp Lys Gln Ser Ala Gln Leu
        115                 120                 125

gcc ttc tcc cgc cag aag cag ttt gcg aac acg aag gag ggc aag gtc      432
Ala Phe Ser Arg Gln Lys Gln Phe Ala Asn Thr Lys Glu Gly Lys Val
    130                 135                 140

gcc gag gcg cgc acg ctg aac gcg ttc gcg aag aag gcg tcc gtc atc      480
Ala Glu Ala Arg Thr Leu Asn Ala Phe Ala Lys Lys Ala Ser Val Ile
145                 150                 155                 160

cgc gtg atc gcg cac acg cag ctg cgc aag ctt cgc aac cac cgc gtg      528
Arg Val Ile Ala His Thr Gln Leu Arg Lys Leu Arg Asn His Arg Val
                165                 170                 175

ggc gtg aag aag gcg cac gtg cag gag atc cag gtc aac ggc ggc agc      576
Gly Val Lys Lys Ala His Val Gln Glu Ile Gln Val Asn Gly Gly Ser
            180                 185                 190

gtt gcg gcg aag atc gcg ctg gcc aag tcc ctg ctg gag aag gag gtg      624
```

-continued

```
Val Ala Ala Lys Ile Ala Leu Ala Lys Ser Leu Leu Glu Lys Glu Val
        195                 200                 205

cgc gtc gac tcc gtg ttc cag cag tcc gag gcg tgc gac gtg tgc tcc      672
Arg Val Asp Ser Val Phe Gln Gln Ser Glu Ala Cys Asp Val Cys Ser
    210                 215                 220

gtc acg aaa ggc cac ggt acg gag ggc gtg gtg aag cgc tgg ggc gtt      720
Val Thr Lys Gly His Gly Thr Glu Gly Val Val Lys Arg Trp Gly Val
225                 230                 235                 240

gcc tgc ctg cca cgc aag acg cac cgc ggt ctg cgc aag gtt gcg tgc      768
Ala Cys Leu Pro Arg Lys Thr His Arg Gly Leu Arg Lys Val Ala Cys
                245                 250                 255

atc ggc gcg tgg cac cct gcc cgc gtc atg tac act gtc gcg cgc gcc      816
Ile Gly Ala Trp His Pro Ala Arg Val Met Tyr Thr Val Ala Arg Ala
            260                 265                 270

ggt cag cac ggt tac cac cac cgc acg cag ctg aac aag aag atc tac      864
Gly Gln His Gly Tyr His His Arg Thr Gln Leu Asn Lys Lys Ile Tyr
        275                 280                 285

cag atc ggc cgc tcc gtt gct gtg gag ccg aac cag gcg acg acg acc      912
Gln Ile Gly Arg Ser Val Ala Val Glu Pro Asn Gln Ala Thr Thr Thr
    290                 295                 300

tac gat ctg aca gcc aag acg atc acg ccc atg ggt ggc ttc gtc ggc      960
Tyr Asp Leu Thr Ala Lys Thr Ile Thr Pro Met Gly Gly Phe Val Gly
305                 310                 315                 320

tac ggt acg gtg cgc aac gac tac gtg atg ctg aag ggc tcc gtg tct     1008
Tyr Gly Thr Val Arg Asn Asp Tyr Val Met Leu Lys Gly Ser Val Ser
                325                 330                 335

ggc ccg cgc cgc cgt gtg atg acg ctg cgc cgc ccg atg gcg ccg cag     1056
Gly Pro Arg Arg Arg Val Met Thr Leu Arg Arg Pro Met Ala Pro Gln
            340                 345                 350

acg tcg cgc cag ctg aag gag aag atc gtg ctg aag ttc atc gac acg     1104
Thr Ser Arg Gln Leu Lys Glu Lys Ile Val Leu Lys Phe Ile Asp Thr
        355                 360                 365

agc tcg aag atc ggc cac ggc cgc ttc cag acg aag aag gag aag aac     1152
Ser Ser Lys Ile Gly His Gly Arg Phe Gln Thr Lys Lys Glu Lys Asn
    370                 375                 380

cag tgg ttc ggc ccg ctc aag aag gac cgc atc cgc cgc gag gag cgc     1200
Gln Trp Phe Gly Pro Leu Lys Lys Asp Arg Ile Arg Arg Glu Glu Arg
385                 390                 395                 400

ctg cgc aag gag cgc gct gcc cgc gcc gtg gag cgc aag gca aag gcc     1248
Leu Arg Lys Glu Arg Ala Ala Arg Ala Val Glu Arg Lys Ala Lys Ala
                405                 410                 415

gcg aag aag taagcatgcc aacgcatgca cgccttttcg tgtaccccag             1297
Ala Lys Lys

cctctgcctg accttctcgc gtctgccagc gtgcgtcttg ttccagcggt ggcgttggtt   1357

ctcttcgtgt ttcgtccgtg tcgctcgtgt gctcgttgtg cagggagtga tgcagtgtgt   1417

ggaagtgggt ggtggtacag atgccagaac ggtcttcttc gatagctgcc ctggcatccg   1477

cgcgtccctt gacgagagtg atctcgggta ctagtgtgaa tctgattttc tgttttttaa   1537

cgtgttttcg atttcatttc actgaacgaa aagaaaacga aagagtgagg tcggctgcgg   1597

agaagcatgt gaaccaacgt attgtccgtg ctggggcaga tccgcgacat cggctccttc   1657

cacggcggcg ttgttagcgt tcagcgagcg tatgccagag gaaccccgtt tcagttttta   1717

gtggttcgct acggtgccga gcactcctcc tttgctcctc gtcgttttgc gtgaagacgg   1777

caggttgtgc tgagcatgtc agtggaacct ctcaagtttc cttccactac atgtggactg   1837

tgaatctgca ggccaacatt atgcgcgaag caggcctcct agctgc                  1883
```

-continued

<210> SEQ ID NO 27
<211> LENGTH: 1155
<212> TYPE: DNA
<213> ORGANISM: Leishmania major

<400> SEQUENCE: 27

```
atggcgcagt gcgtgcgtcg gctggtgctc ggcgacgctc gccgctgcgg tggcgctgct      60

gctgtgcacg agcaggctcg ggtggcgcgt gctgctggga cgggcgactt cactgcggcg     120

cagcggacga acacgctggc ggtgctgcag gcgtttgggc gtgcgatccc taagcttggg     180

gagaagtggg cgggcaacga cttctgctcg tgggaggccg tcttgtgcaa tgcgccggac     240

gtgtacgtgt cgggaatcag tccgacgtat gccggcacgc tgccggagat gccagagaac     300

gtcgactaca ggcacgtcgt gatcaggcgg ctcgactttt ccgaaatggg gccggggctg     360

agcgggaccg tgcccgcctc atggcactcg atgacatctt tggagtcgtt gtcgattgaa     420

aagtgtgaaa gcatctccgg cagtgtgccc cccgagtggg gctcgatgac atcgctgagt     480

gttctcaatc tgcggggcac aggcatctcc ggcacgctgc cgccccagtg gagtgggatg     540

tcgaaggccc ggtccctgca gctgcaggac tgcgacctgt ccggcagtct gccctcttcg     600

tggtctgcga taccgatgct ggcttccgtc tctcttaagg gcaacaagtt ctgcgggtgt     660

gtgccggact cgtgggatca gaaggctggt cttgttgtgg acatcgagga caagcacaag     720

ggcagcgact gcttggctgc taaggactgc gcaacgacca ccactaagcc ctccgccacg     780

acagcgacca ccccgaacct cactaacttt ccccctacgc cgaggaccac gactgagccg     840

cttaccacaa ccagcactga ggcaccggct gaacccacaa ccaccactga ggcaccggct     900

gaacccacga ccactgctac cccaacaaac acgccgactc ctgcaccaga gacggagtgc     960

gaggtggatg ggtgtgaggt gtgcgagggg gactccgctg cgaggtgcgc gaggtgccgt    1020

gaggactact tcctgacgga cgagaagacg tgcctgaagc acaacgatgg cggtgttgct    1080

gctgtgtcga gcggagtggc agcagcagct gttgtgtgcg tggctgtgct gttcagcgtg    1140

gggctggcgg cctga                                                     1155
```

<210> SEQ ID NO 28
<211> LENGTH: 2315
<212> TYPE: DNA
<213> ORGANISM: Leishmania major
<220> FEATURE:
<221> NAME/KEY: CDS
<222> LOCATION: (89)..(1993)

<400> SEQUENCE: 28

```
tcactgcctc gcatcttttt ctgcctcgac atttgcgagc acattcaccc ttttcgcttt      60

gctttgcacg cttcctcctc tgaagccc atg ttt gct cgt cgt gtg tgc gga       112
                               Met Phe Ala Arg Arg Val Cys Gly
                               1               5

agc gct gcg gcg tcg gct gcg tgc ctg gcg cgc cac gag tcg cag aag      160
Ser Ala Ala Ala Ser Ala Ala Cys Leu Ala Arg His Glu Ser Gln Lys
    10                  15                  20

gtg cag ggc gac gtg att ggc gtg gac ctg ggc acg acg tac agc tgc      208
Val Gln Gly Asp Val Ile Gly Val Asp Leu Gly Thr Thr Tyr Ser Cys
25                  30                  35                  40

gtg gcg acg atg gac ggc gac aag gcg cgc gtg ctg gag aac tcg gag      256
Val Ala Thr Met Asp Gly Asp Lys Ala Arg Val Leu Glu Asn Ser Glu
                45                  50                  55

ggc ttc cgg acg acg ccg tct gtt gtg gcg ttc aag ggc agc gag aag      304
Gly Phe Arg Thr Thr Pro Ser Val Val Ala Phe Lys Gly Ser Glu Lys
            60                  65                  70
```

-continued

```
ctt gtg ggg ctt gcg gcg aag cgg cag gcg atc acg aac ccg cag tcg      352
Leu Val Gly Leu Ala Ala Lys Arg Gln Ala Ile Thr Asn Pro Gln Ser
        75                  80                  85

acg ttc tat gct gtg aag cgg ctg atc ggg cgc cgg ttc gag gac gag      400
Thr Phe Tyr Ala Val Lys Arg Leu Ile Gly Arg Arg Phe Glu Asp Glu
    90                  95                  100

cac atc cag aag gac atc aag aac gtg ccg tac aag atc gtg cgc gcg      448
His Ile Gln Lys Asp Ile Lys Asn Val Pro Tyr Lys Ile Val Arg Ala
105                 110                 115                 120

ggg aac ggt gac gcg tgg gtg cag gac ggg aac ggg aag cag tac tcg      496
Gly Asn Gly Asp Ala Trp Val Gln Asp Gly Asn Gly Lys Gln Tyr Ser
                125                 130                 135

ccg tcg cag atc ggc gcg ttc gtg ctg gag aag atg aag gag acg gcg      544
Pro Ser Gln Ile Gly Ala Phe Val Leu Glu Lys Met Lys Glu Thr Ala
            140                 145                 150

gag aac ttc ctg ggg cac aag gtg agc aac gcc gtc gtg acg tgc ccg      592
Glu Asn Phe Leu Gly His Lys Val Ser Asn Ala Val Val Thr Cys Pro
        155                 160                 165

gcg tac ttc aac gac gcg cag cgc cag gcg acg aag gac gcg ggg acg      640
Ala Tyr Phe Asn Asp Ala Gln Arg Gln Ala Thr Lys Asp Ala Gly Thr
    170                 175                 180

atc gcg ggc ctg aac gtg atc cgc gtg gtg aac gag ccg act gct gcg      688
Ile Ala Gly Leu Asn Val Ile Arg Val Val Asn Glu Pro Thr Ala Ala
185                 190                 195                 200

gcg ctt gcg tac ggc atg gac aag acg aag gac agc ctg atc gcg gtg      736
Ala Leu Ala Tyr Gly Met Asp Lys Thr Lys Asp Ser Leu Ile Ala Val
                205                 210                 215

tac gac ctc ggt ggc ggc acg ttc gat atc tcc gtg ctg gag atc gct      784
Tyr Asp Leu Gly Gly Gly Thr Phe Asp Ile Ser Val Leu Glu Ile Ala
            220                 225                 230

ggc ggc gtg ttc gag gtg aag gcg acg aac ggc gac acg cac ctt ggc      832
Gly Gly Val Phe Glu Val Lys Ala Thr Asn Gly Asp Thr His Leu Gly
        235                 240                 245

ggc gag gac ttt gac ctg gcg ctg tcg gac tac atc ctg gag gag ttc      880
Gly Glu Asp Phe Asp Leu Ala Leu Ser Asp Tyr Ile Leu Glu Glu Phe
    250                 255                 260

cgc aag acg agc ggg atc gac ctg agc aag gag cgg atg gcg ctg cag      928
Arg Lys Thr Ser Gly Ile Asp Leu Ser Lys Glu Arg Met Ala Leu Gln
265                 270                 275                 280

cgc gtg cgc gag gcc gcg gag aag gcg aag tgc gag ctg tcg tct gcg      976
Arg Val Arg Glu Ala Ala Glu Lys Ala Lys Cys Glu Leu Ser Ser Ala
                285                 290                 295

atg gag acg gag gtg aac ctg ccg ttc atc act gcg aac gcc gac ggc     1024
Met Glu Thr Glu Val Asn Leu Pro Phe Ile Thr Ala Asn Ala Asp Gly
            300                 305                 310

gcg cag cac atc cag atg cac atc agc cgt agc aag ttc gag ggc atc     1072
Ala Gln His Ile Gln Met His Ile Ser Arg Ser Lys Phe Glu Gly Ile
        315                 320                 325

acg cag cgg ctg atc gag cgg tcg att gcg ccg tgc aag cag tgc atg     1120
Thr Gln Arg Leu Ile Glu Arg Ser Ile Ala Pro Cys Lys Gln Cys Met
    330                 335                 340

aag gac gct ggt gtg gag ctg aag gag atc aac gac gtt gtg ctt gtt     1168
Lys Asp Ala Gly Val Glu Leu Lys Glu Ile Asn Asp Val Val Leu Val
345                 350                 355                 360

ggc ggc atg acg cgc atg ccg aag gtg gtg gag gag gtg aag aag ttc     1216
Gly Gly Met Thr Arg Met Pro Lys Val Val Glu Glu Val Lys Lys Phe
                365                 370                 375

ttc cag aag gac ccg ttc cgc ggc gtg aac ccc gac gag gct gtg gcg     1264
Phe Gln Lys Asp Pro Phe Arg Gly Val Asn Pro Asp Glu Ala Val Ala
```

-continued

```
            380                 385                 390

ctt ggt gcc gcg acg ctg ggc ggc gtg ctg cgg ggt aag gcg agt gac     1312
Leu Gly Ala Ala Thr Leu Gly Gly Val Leu Arg Gly Lys Ala Ser Asp
        395                 400                 405

ttg ata ctg gtg gac gtg aca ccg ctt tcg ctg ggc aca agt gtc gtc     1360
Leu Ile Leu Val Asp Val Thr Pro Leu Ser Leu Gly Thr Ser Val Val
    410                 415                 420

ggc gac gtg ttc acg cgc atg atc ccg aag aac acg acg atc ccg tgc     1408
Gly Asp Val Phe Thr Arg Met Ile Pro Lys Asn Thr Thr Ile Pro Cys
425                 430                 435                 440

atg cgg agc cat atc ttc aca acg gtg gac gat ggt cag aca gcc atc     1456
Met Arg Ser His Ile Phe Thr Thr Val Asp Asp Gly Gln Thr Ala Ile
                445                 450                 455

aaa ttc aag gtg ttc cag ggc gag cgc gaa atc gcc tcc gaa aac cag     1504
Lys Phe Lys Val Phe Gln Gly Glu Arg Glu Ile Ala Ser Glu Asn Gln
            460                 465                 470

ata agg ggt gag ttc gat ctt agc ggc atc ccg ccc gcg ccg cgt ggg     1552
Ile Arg Gly Glu Phe Asp Leu Ser Gly Ile Pro Pro Ala Pro Arg Gly
        475                 480                 485

gtg ccg cag atc gag gtg acg ttc gac atc gac gcg aac ggc atc tgc     1600
Val Pro Gln Ile Glu Val Thr Phe Asp Ile Asp Ala Asn Gly Ile Cys
    490                 495                 500

cac gtg acg gcg aag gac aag gcg acg ggc aag acg cag aac atc acg     1648
His Val Thr Ala Lys Asp Lys Ala Thr Gly Lys Thr Gln Asn Ile Thr
505                 510                 515                 520

atc acg gcg aac ggc ggg ctg tcg aag gag cag atc gag cag atg atc     1696
Ile Thr Ala Asn Gly Gly Leu Ser Lys Glu Gln Ile Glu Gln Met Ile
                525                 530                 535

cgc gac tcg gag cag cac gcg gag gcc gac cgc gtg aag cgc gag ctt     1744
Arg Asp Ser Glu Gln His Ala Glu Ala Asp Arg Val Lys Arg Glu Leu
            540                 545                 550

gtg gag gtg cgc aac aac gcg gag acg cag ctg aca acg gcg gag agg     1792
Val Glu Val Arg Asn Asn Ala Glu Thr Gln Leu Thr Thr Ala Glu Arg
        555                 560                 565

cag ctc ggc gag tgg aag tac gtg agc gat gcg gag aag gag aac gtg     1840
Gln Leu Gly Glu Trp Lys Tyr Val Ser Asp Ala Glu Lys Glu Asn Val
    570                 575                 580

aag acg ctg gtg gcg gag ctg cgc aag gcg atg gag aac ccg aac gtg     1888
Lys Thr Leu Val Ala Glu Leu Arg Lys Ala Met Glu Asn Pro Asn Val
585                 590                 595                 600

gcg aag gat gac ctt gcg gct gcg acg gac aag ctg cag aag gct gtg     1936
Ala Lys Asp Asp Leu Ala Ala Ala Thr Asp Lys Leu Gln Lys Ala Val
                605                 610                 615

atg gag tgc ggc cgc aca gag tac cag cag gct gcc gcg gcc aat tct     1984
Met Glu Cys Gly Arg Thr Glu Tyr Gln Gln Ala Ala Ala Ala Asn Ser
            620                 625                 630

ggc cag tgt tgattttgag agcgaggcaa cgatgtcgct gcgagcttgg             2033
Gly Gln Cys
        635

tgctcgtgta gatgcgggcc ttctttgttg ttggggaaaa ggacatggcg atagtgcaca   2093

gccctgtttc ttgtgcatgc tggtatcact gacgaagtgc tcgtcatgaa gaggggtaga   2153

cttcttcgtg tttcgggtgt tgtgtcggcg cggatgcctg tggcatcgag tcctgtgtct   2213

tctttcgcgc taggcaccgc cttacggtcg gctgacggcc aactgaatgg gatgcacctc   2273

acgtctaaaa ttatgaaagg ctcaactggc tcaccgtcag gt                      2315
```

<210> SEQ ID NO 29
<211> LENGTH: 1332

-continued

<212> TYPE: DNA
<213> ORGANISM: Leishmania major

<400> SEQUENCE: 29

```
atggcgacgt cgagggccgc tctctgcgct gttgcggttg tgtgcgtggt gcttgcggtt     60
gcctgcgcgc ccgcgcgcgc gatatacgtg ggcacgccgg ctgctgcgct gttcgaggag    120
ttcaagcgga cgtaccagcg cgcgtacggg acgctgaccg aggagcagca gcggctggcg    180
aacttcgagc gcaacctgga gctgatgcgc gagcatcagg cgaggaaccc acacgcgagg    240
ttcgggatca cgaagttctt tgacctgtcg gaggcggagt tcgccgcgcg ctacctgaac    300
ggcgccgcgt acttcgcagc ggcgaagcag cacgccggcc agcactaccg caaggcgcgc    360
gcggacctgt cggcggtgcc tgatgcggtg gactggcgcg agaagggcgc cgtgacgccg    420
gtgaagaatc agggtgcgtg cgggtcgtgc tgggcgttct cggcggtcgg caacatcgag    480
tcgcagtggg ccgttgccgg ccacaagctg gtgaggctgt cggagcagca gctggtgagc    540
tgcgatcacg tggacaatgg ttgcggcggc gggctgatgt tgcaggcatt cgagtgggtg    600
ctgcgaaaca tgaacgggac cgtgttcacg gagaagagct accccctacgt ctccggcaac    660
ggtgatgtgc ccgagtgctc gaacagcagt gaactcgctc ccggtgcgcg aatcgacggg    720
tacgtgtcga tggaaagcag cgaaagagtt atggctgcgt ggcttgcgaa gaatggcccc    780
atctcgattg cggtcgacgc cagctccttt atgtcttacc atagcggcgt cctgaccagc    840
tgcattggtg agcagctgaa ccatggcgtg ctgctcgttg ggtacaacat gactggtgag    900
gttccgtact gggtgatcaa gaactcgtgg ggtgaggact ggggcgagaa gggctacgtg    960
cgcgtgacca tgggggtgaa cgcgtgcctg ctcactgggt accccgtgtc cgtgcatgtg   1020
tcgcagagcc ccacccctgg cccaaacacg accaccacga cgcacgctcc taaacgggtg   1080
acggtgaagc agatcacctg cacggattat ttctgccgaa aggggtgcaa gacgacggtg   1140
atccccacga aagagtgcct gccgaacggg gcaggcggct cttttcagat ggagtgcggt   1200
gaccatcagg tgttgaagct cacctacacc tccatgaatt gcactggtga ggccaagtat   1260
acggtgacaa gggagggtaa gtgcgggata tcgtggtccg gctcgagcaa gagcatttgc   1320
cagtacgtgt ag                                                        1332
```

<210> SEQ ID NO 30
<211> LENGTH: 1413
<212> TYPE: DNA
<213> ORGANISM: Leishmania major
<220> FEATURE:
<221> NAME/KEY: CDS
<222> LOCATION: (55)..(1074)

<400> SEQUENCE: 30

```
ctttggcacg cgtacttgca ttgcttacca aaggtacacg tacacaggcg agag atg       57
                                                            Met
                                                            1

tca gct aac tgc gcg ggt ccc gca tca aca ccc gac gcg aag aag gcc      105
Ser Ala Asn Cys Ala Gly Pro Ala Ser Thr Pro Asp Ala Lys Lys Ala
            5                   10                  15

cga gtg gaa gcc gat gtg atc acg gag gcg gac cgc gtg ccg gcg ttt      153
Arg Val Glu Ala Asp Val Ile Thr Glu Ala Asp Arg Val Pro Ala Phe
        20                  25                  30

cct ctc ccg ccc acc gat gcc gct gcc tac gag cgt gaa cac gtg cac      201
Pro Leu Pro Pro Thr Asp Ala Ala Ala Tyr Glu Arg Glu His Val His
    35                  40                  45

aac gtg tac agc gcg att gcc gac cac ttc tct agc aca cgg tac aag      249
```

-continued

```
Asn Val Tyr Ser Ala Ile Ala Asp His Phe Ser Ser Thr Arg Tyr Lys
50                  55                  60                  65

gcg tgg cca cag gtc ggc gcc ttc ttg gag ggc cta ccg ccc ttt tcc      297
Ala Trp Pro Gln Val Gly Ala Phe Leu Glu Gly Leu Pro Pro Phe Ser
                70                  75                  80

ctc gtg gcg gat gtt ggc tgc gga aat ggg aag tac ttt tcg gca gca      345
Leu Val Ala Asp Val Gly Cys Gly Asn Gly Lys Tyr Phe Ser Ala Ala
            85                  90                  95

cag cgg ctt gcc ctc act gcc ccg tcg cat ccc atg acc aca tca ggc      393
Gln Arg Leu Ala Leu Thr Ala Pro Ser His Pro Met Thr Thr Ser Gly
        100                 105                 110

gct tct ctc gag atg aag tcg agg cag caa gca gag gcg cag ccg tcg      441
Ala Ser Leu Glu Met Lys Ser Arg Gln Gln Ala Glu Ala Gln Pro Ser
    115                 120                 125

ccg cct ctt gtc tcc ttt gca ccc gca cac cgc tac gtc ttg ggc ctc      489
Pro Pro Leu Val Ser Phe Ala Pro Ala His Arg Tyr Val Leu Gly Leu
130                 135                 140                 145

gac tat agt gag gag ctc ctg cgc tcc acg caa cgt cag ctg gtc gac      537
Asp Tyr Ser Glu Glu Leu Leu Arg Ser Thr Gln Arg Gln Leu Val Asp
                150                 155                 160

ccc aac atg cat cat gcg cag cgg cgt cgc cgc ctt agt ggc aag cgt      585
Pro Asn Met His His Ala Gln Arg Arg Arg Arg Leu Ser Gly Lys Arg
            165                 170                 175

gca aag aac gag gca gag gcg gtg gcg aca cct gtg tct gcg gag gag      633
Ala Lys Asn Glu Ala Glu Ala Val Ala Thr Pro Val Ser Ala Glu Glu
        180                 185                 190

ctc cca cga aca gat acg gtg cgc agc gac gct cta cgg tgc ccg ttg      681
Leu Pro Arg Thr Asp Thr Val Arg Ser Asp Ala Leu Arg Cys Pro Leu
    195                 200                 205

cgt agc ggc gtc ttc gac gcc gcc atc agt ata gcg gtg att cac cac      729
Arg Ser Gly Val Phe Asp Ala Ala Ile Ser Ile Ala Val Ile His His
210                 215                 220                 225

tac gcg agt cgc gag cgg cgg aga ctg gcg gtg cgc gag ctc ctc cgc      777
Tyr Ala Ser Arg Glu Arg Arg Arg Leu Ala Val Arg Glu Leu Leu Arg
                230                 235                 240

ctc gct cgg ccg cat ggt ggg cgt gta ctt atc tac gtg tgg gca cgt      825
Leu Ala Arg Pro His Gly Gly Arg Val Leu Ile Tyr Val Trp Ala Arg
            245                 250                 255

gag cag cga ggc cac aca aag cgt ctg gtc gac cca gaa acc ggc gac      873
Glu Gln Arg Gly His Thr Lys Arg Leu Val Asp Pro Glu Thr Gly Asp
        260                 265                 270

ggt ctc gtg cgg tgg gag cga aat cag aag tac gat ggg gca cag cag      921
Gly Leu Val Arg Trp Glu Arg Asn Gln Lys Tyr Asp Gly Ala Gln Gln
    275                 280                 285

gtg ttc cgc cgc tac tat cac ttt ttt gcg gag gga gag ctg gag cag      969
Val Phe Arg Arg Tyr Tyr His Phe Phe Ala Glu Gly Glu Leu Glu Gln
290                 295                 300                 305

ctg tgc aag gac gcg gcc agc gat gat ggg aca ggg tcg att ccg gtc     1017
Leu Cys Lys Asp Ala Ala Ser Asp Asp Gly Thr Gly Ser Ile Pro Val
                310                 315                 320

gca atc agg aaa tct tac tac gac aag gag aat tgg tgt gtg atg ctg     1065
Ala Ile Arg Lys Ser Tyr Tyr Asp Lys Glu Asn Trp Cys Val Met Leu
            325                 330                 335

gag cgc tgt tgacgtcgaa gtgaagggtg tggcgactcg aacgccgcct             1114
Glu Arg Cys
        340

gagatggaca acattgtgcc tgtgggtttt tgcatgcgcc tcttagcctt attcgtctac   1174

acccatctgc ttggcccttt catcttgagt aataagtagg tccacctcgt cttcacaggc   1234
```

-continued

```
gcattgtaaa gttgcgcgcg ggcattatcg gggaagccga cgtgtcatcg atgtcgaggc   1294

ttgcgttgac atcacccccct tccttctttg ccgcgccttc gcagacggtg acggggaatg   1354

gccaccgcta cgagagtgaa agaaggcagc agcagagccg agaaaaaaaa aaaaaaaaa    1413


<210> SEQ ID NO 31
<211> LENGTH: 481
<212> TYPE: DNA
<213> ORGANISM: Leishmania major
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (135)..(135)
<223> OTHER INFORMATION: a, c, t, g, unknown or other
<220> FEATURE:
<221> NAME/KEY: CDS
<222> LOCATION: (199)..(474)

<400> SEQUENCE: 31

naagaatttt ncaccagatc agtttctgta ctttattgaa gacctttgaa ccaacgctac     60

taaccaaagc acacacgtct actacttttt cttccttcca cgttttctgt ttgccctccg    120

attctcgctc aaggngcgta catcaccctc tcctttcacg cgctcgactt ttcctttcac    180

cccctccccg tgtaaacc atg gcc acc acg tac gag gag ttc tcg gcg aag      231
                    Met Ala Thr Thr Tyr Glu Glu Phe Ser Ala Lys
                    1               5                   10

ctg gac cgc ctg gat gag gag ttc aac agg aag atg cag gaa cag aac      279
Leu Asp Arg Leu Asp Glu Glu Phe Asn Arg Lys Met Gln Glu Gln Asn
            15                  20                  25

gcc aag ttc ttt gcg gac aag ccg gat gag tcg acg ctg tcg ccc gag      327
Ala Lys Phe Phe Ala Asp Lys Pro Asp Glu Ser Thr Leu Ser Pro Glu
        30                  35                  40

atg aag gag cac tac gag aag ttc gag cgc atg atc aag gag cac aca      375
Met Lys Glu His Tyr Glu Lys Phe Glu Arg Met Ile Lys Glu His Thr
    45                  50                  55

gag aag ttc aac aag aag atg cac gag cac tcg gag cac ttc aag cag      423
Glu Lys Phe Asn Lys Lys Met His Glu His Ser Glu His Phe Lys Gln
60                  65                  70                  75

aag ttc gcc gag ctg ctc gag cag cag aag gct gcg cag tac ccg tcc      471
Lys Phe Ala Glu Leu Leu Glu Gln Gln Lys Ala Ala Gln Tyr Pro Ser
                80                  85                  90

aag taagaca                                                          481
Lys


<210> SEQ ID NO 32
<211> LENGTH: 1000
<212> TYPE: DNA
<213> ORGANISM: Leishmania major
<220> FEATURE:
<221> NAME/KEY: CDS
<222> LOCATION: (35)..(481)

<400> SEQUENCE: 32

gtcaccccgg ttagagtgaa agcatcagcc catc atg ccc gct gac aag agc tac     55
                                      Met Pro Ala Asp Lys Ser Tyr
                                      1               5

gcg ctg aag cag gtg cag acc ttc ggc aag aag aag acg gca atc gcc      103
Ala Leu Lys Gln Val Gln Thr Phe Gly Lys Lys Lys Thr Ala Ile Ala
```

-continued

```
        10                  15                  20

gtg gcc acg gtc acc aag gct gcc cag tgc aac atc aag gtg aac ggt      151
Val Ala Thr Val Thr Lys Ala Ala Gln Cys Asn Ile Lys Val Asn Gly
    25                  30                  35

gtg ccg ctg cag cag atc ctg ccc gat acg ctg cgc gcg aag atc atg      199
Val Pro Leu Gln Gln Ile Leu Pro Asp Thr Leu Arg Ala Lys Ile Met
40                  45                  50                  55

gag gcc atc acc gtg gtg gga tcc aag tac tac tcg cgg ctg cgc atc      247
Glu Ala Ile Thr Val Val Gly Ser Lys Tyr Tyr Ser Arg Leu Arg Ile
                60                  65                  70

gat gtg gcg gtg cac ggt ggc ggc cag gtg tcg cag gcg tac gcc gcg      295
Asp Val Ala Val His Gly Gly Gly Gln Val Ser Gln Ala Tyr Ala Ala
            75                  80                  85

cgc cag gcg atc gcg aag ggc ctc att gcg ttc ttt cag aag tac cac      343
Arg Gln Ala Ile Ala Lys Gly Leu Ile Ala Phe Phe Gln Lys Tyr His
        90                  95                  100

aac gag gtg gag aag gcc gcg ctg aag gac aag ttc ctg gcg tac gac      391
Asn Glu Val Glu Lys Ala Ala Leu Lys Asp Lys Phe Leu Ala Tyr Asp
    105                 110                 115

aag ttc ctg ctc atc gcc gat ccc cgc cgc tgc gag ccg aag aag tgg      439
Lys Phe Leu Leu Ile Ala Asp Pro Arg Arg Cys Glu Pro Lys Lys Trp
120                 125                 130                 135

ggt cgc cac tct gcc cgc aca cgc ttc acc aag tcc tac cgg              481
Gly Arg His Ser Ala Arg Thr Arg Phe Thr Lys Ser Tyr Arg
                140                 145

taagctcatg tacgtctggg gtttgcatgc gcgtgcgcat gtgcatgcgt ctggctgctt    541

gctcgtgtgc ggctgatccg tcgatgctgc acggacaggg cacaacgcat tgccactgta    601

tgggacacac atgcgcacgc acatgcacct cgcacgctgc ttaggatgtg gagagatcgt    661

gcatggcagt catcgcggct gggtttttgt atgcgtctgt gcgcgagcgc gtgcgtgtgc    721

cagcggatcc gtgtcttgtt agccgtgacc agcatgcatc gctccgcatc ccctctccgc    781

acagacggtc cactgggtgc cacccgcaga ccgtcagtca gtcggttacg tacgggctct    841

tcgtaatttt cctttccctg acattatttt gttccgcaca taagcacatc acacagccta    901

cacacacaca cacctacacg catgatgtac gtgtgtgtgt gtgtgcgacg gaggcgtgcg    961

ctggcctagg cgtcagtgac ttcgtgcagc atgcgccat                          1000


<210> SEQ ID NO 33
<211> LENGTH: 1790
<212> TYPE: DNA
<213> ORGANISM: Leishmania major
<220> FEATURE:
<221> NAME/KEY: CDS
<222> LOCATION: (169)..(1515)

<400> SEQUENCE: 33

gcgccgcacc cctcctctgc accacctccg ccgcactctc ctctctctcc tctctgtcct     60

ctccctcggt ctctcctccc accaccggca cacgccgccc ccgcttgcct gcccgccgcg    120

cgcagataac cagctcgcta tctaacatca cgctctccgc tattcacc atg ggc aag     177
                                                     Met Gly Lys
                                                     1

gat aag gtg cac atg aac ctt gtg gtc gtc ggc cat gtc gac gcc ggc      225
Asp Lys Val His Met Asn Leu Val Val Val Gly His Val Asp Ala Gly
    5                   10                  15

aag tcc acc gcc act ggc cac ttg atc tac aag tgc ggt ggc atc gac      273
Lys Ser Thr Ala Thr Gly His Leu Ile Tyr Lys Cys Gly Gly Ile Asp
20                  25                  30                  35
```

-continued

```
aag cgc acg atc gag aag ttc gag aag gag gcc gcc gag atc ggc aag      321
Lys Arg Thr Ile Glu Lys Phe Glu Lys Glu Ala Ala Glu Ile Gly Lys
                40                  45                  50

gcg tcc ttc aag tac gcg tgg gtg ctc gac aag ctg aag gcg gag cgc      369
Ala Ser Phe Lys Tyr Ala Trp Val Leu Asp Lys Leu Lys Ala Glu Arg
            55                  60                  65

gag cgc ggc atc acg atc gac att gcg ctg tgg aag ttc gag tcg ccc      417
Glu Arg Gly Ile Thr Ile Asp Ile Ala Leu Trp Lys Phe Glu Ser Pro
        70                  75                  80

aag tcc gtg ttc acg atc atc gat gcg ccc ggc cac cgc gac ttc atc      465
Lys Ser Val Phe Thr Ile Ile Asp Ala Pro Gly His Arg Asp Phe Ile
    85                  90                  95

aag aac atg atc acg ggc acg tcg cag gcg gac gcc gcc att ctg atg      513
Lys Asn Met Ile Thr Gly Thr Ser Gln Ala Asp Ala Ala Ile Leu Met
100                 105                 110                 115

atc gac tcg acg cat ggc ggc ttc gag gct ggc atc tcg aag gac ggc      561
Ile Asp Ser Thr His Gly Gly Phe Glu Ala Gly Ile Ser Lys Asp Gly
                120                 125                 130

cag acc cgc gag cac gcg ctg ctt gcc ttc act ctt ggc gtg aag cag      609
Gln Thr Arg Glu His Ala Leu Leu Ala Phe Thr Leu Gly Val Lys Gln
            135                 140                 145

atg gtg gtg tgc tgc aac aag atg gac gac aag acg gtg acg tac gcg      657
Met Val Val Cys Cys Asn Lys Met Asp Asp Lys Thr Val Thr Tyr Ala
        150                 155                 160

cag tca cgc tac gat gag atc agc aag gag gtg ggc gcg tac ctg aag      705
Gln Ser Arg Tyr Asp Glu Ile Ser Lys Glu Val Gly Ala Tyr Leu Lys
    165                 170                 175

cgc gtg ggc tac aac ccg gag aag gtg cgc ttc atc ccg atc tcg ggc      753
Arg Val Gly Tyr Asn Pro Glu Lys Val Arg Phe Ile Pro Ile Ser Gly
180                 185                 190                 195

tgg cag ggc gac aac atg atc gag aag tcg gac aac atg ccg tgg tac      801
Trp Gln Gly Asp Asn Met Ile Glu Lys Ser Asp Asn Met Pro Trp Tyr
                200                 205                 210

aag ggt ccc acg ctg ctg gac gcg ctc ggc atg ctg gag ccg ccg gtg      849
Lys Gly Pro Thr Leu Leu Asp Ala Leu Gly Met Leu Glu Pro Pro Val
            215                 220                 225

cgc ccg gtg gac aag ccg ctg cgc ctg ccc ctg cag gac gtg tac aag      897
Arg Pro Val Asp Lys Pro Leu Arg Leu Pro Leu Gln Asp Val Tyr Lys
        230                 235                 240

atc ggc ggt atc ggg acg gtg ccc gtg ggc cgc gtg gag acc ggc atc      945
Ile Gly Gly Ile Gly Thr Val Pro Val Gly Arg Val Glu Thr Gly Ile
    245                 250                 255

atg aag ccg ggc gac gtg gtg acg ttc gcg ccc gcc aac gtg acg act      993
Met Lys Pro Gly Asp Val Val Thr Phe Ala Pro Ala Asn Val Thr Thr
260                 265                 270                 275

gag gtg aag tcg atc gag atg cac cac gag cag ctg gcg gag gcg cag     1041
Glu Val Lys Ser Ile Glu Met His His Glu Gln Leu Ala Glu Ala Gln
                280                 285                 290

ccc ggc gac aac gtc ggc ttc aac gtg aag aac gtg tcg gtg aag gac     1089
Pro Gly Asp Asn Val Gly Phe Asn Val Lys Asn Val Ser Val Lys Asp
            295                 300                 305

atc cgc cgt ggt aac gtg tgc ggc aac tcg aag aac gac ccg ccg aag     1137
Ile Arg Arg Gly Asn Val Cys Gly Asn Ser Lys Asn Asp Pro Pro Lys
        310                 315                 320

gag gcg gcc gac ttc acg gcg cag gtg atc gtg ctg aac cac ccc ggc     1185
Glu Ala Ala Asp Phe Thr Ala Gln Val Ile Val Leu Asn His Pro Gly
    325                 330                 335

cag atc agc aac ggc tat gcg ccg gtg ctg gac tgc cac acg agc cac     1233
Gln Ile Ser Asn Gly Tyr Ala Pro Val Leu Asp Cys His Thr Ser His
340                 345                 350                 355
```

-continued

```
att gcg tgc cgc ttc gcg gaa atc gag tcc aag atc gac cgc cgc tcc      1281
Ile Ala Cys Arg Phe Ala Glu Ile Glu Ser Lys Ile Asp Arg Arg Ser
                360                 365                 370

ggc aag gag ctg gag aag aac ccc aag gcg atc aag tct ggc gat gcc      1329
Gly Lys Glu Leu Glu Lys Asn Pro Lys Ala Ile Lys Ser Gly Asp Ala
            375                 380                 385

gcg atc gtg aag atg gtg ccg cag aag ccg atg tgc gtg gag gtg ttc      1377
Ala Ile Val Lys Met Val Pro Gln Lys Pro Met Cys Val Glu Val Phe
        390                 395                 400

aac gac tac gcg ccg ctg ggc cgc ttt gcc gtg cgc gac atg cgc cag      1425
Asn Asp Tyr Ala Pro Leu Gly Arg Phe Ala Val Arg Asp Met Arg Gln
    405                 410                 415

acg gtg gcc gtg ggc atc atc aag ggc gtg aac aag aag gag ggc agc      1473
Thr Val Ala Val Gly Ile Ile Lys Gly Val Asn Lys Lys Glu Gly Ser
420                 425                 430                 435

ggc ggt aag gtg acc aag gcg gcc gcg aag gct tcg aag aag              1515
Gly Gly Lys Val Thr Lys Ala Ala Ala Lys Ala Ser Lys Lys
                440                 445

taagcgtgcg gtgctccgcc gcccgcgccc cctccctcca ccccttcctt ttcgcttgta   1575

tccctccccc acgcgtcccg cggggcctct cctcttttcc cccaaaccca cgcacgccca   1635

cgcccacgcc cccctctctc tctctttcga tatatatgcg tgtgcgcttc agcgttatat   1695

aactcctgtt gttatgtgca cttaggtgtg gagaggcttt agctagtggc ctacgctgcg   1755

gtagaggtct cggtgtcgag tgctgtgttt gtggg                              1790


<210> SEQ ID NO 34
<211> LENGTH: 1878
<212> TYPE: DNA
<213> ORGANISM: Leishmania major
<220> FEATURE:
<221> NAME/KEY: CDS
<222> LOCATION: (25)..(1455)

<400> SEQUENCE: 34

ttccttttcg ttttgcaaag aaaa atg cag cgc tca ttc ctt gtt ttt gtt        51
                           Met Gln Arg Ser Phe Leu Val Phe Val
                           1               5

ctg tgc gcc ctt ctc ttc tgc gtc gcg tcc gca gag gtg cag gtg gcc       99
Leu Cys Ala Leu Leu Phe Cys Val Ala Ser Ala Glu Val Gln Val Ala
10                  15                  20                  25

act aag gac aac ttt gac aag gtc gta atc ggg gat ctc acg ttg gtc      147
Thr Lys Asp Asn Phe Asp Lys Val Val Ile Gly Asp Leu Thr Leu Val
                30                  35                  40

aag ttt tat gct ccg tgg tgc ggc cac tgc aag aca ctc gcc ccg gag      195
Lys Phe Tyr Ala Pro Trp Cys Gly His Cys Lys Thr Leu Ala Pro Glu
            45                  50                  55

ttt gta aag gcc gct gac atg ctg gcc ggc atc gcg acc ctt gca gag      243
Phe Val Lys Ala Ala Asp Met Leu Ala Gly Ile Ala Thr Leu Ala Glu
        60                  65                  70

gtc gat tgc acc aaa gaa gag agc ctt gct gag aag tac gaa atc aag      291
Val Asp Cys Thr Lys Glu Glu Ser Leu Ala Glu Lys Tyr Glu Ile Lys
    75                  80                  85

ggg ttc ccc acg ctg tac atc ttc cgt aac ggt gag aaa gtg aag atc      339
Gly Phe Pro Thr Leu Tyr Ile Phe Arg Asn Gly Glu Lys Val Lys Ile
90                  95                  100                 105

tac gat ggt ccc cgc act gcc gcc ggc atc gcg tcg tac atg aag gcg      387
Tyr Asp Gly Pro Arg Thr Ala Ala Gly Ile Ala Ser Tyr Met Lys Ala
                110                 115                 120

cat gtc ggt cca tcg atg aag gcc atc tca acg gct gaa gag ctg gag      435
```

-continued

```
His Val Gly Pro Ser Met Lys Ala Ile Ser Thr Ala Glu Glu Leu Glu
            125                 130                 135

gag ctc aag aag gag act ttc ccg gtg tgc gtg gtg aag aca gcg agc      483
Glu Leu Lys Lys Glu Thr Phe Pro Val Cys Val Val Lys Thr Ala Ser
        140                 145                 150

acc gac tcg gag atg gcg tcg atg ata acc aag gtg gcg gac tct ctc      531
Thr Asp Ser Glu Met Ala Ser Met Ile Thr Lys Val Ala Asp Ser Leu
    155                 160                 165

cgc tcg cag atg aac ttt gtg ctc gtg acg gat gcg gcc atc tct ccg      579
Arg Ser Gln Met Asn Phe Val Leu Val Thr Asp Ala Ala Ile Ser Pro
170                 175                 180                 185

aat gat gcc atg gag tcg gtt acg gtg tat cgc aag aat gcg gag cgc      627
Asn Asp Ala Met Glu Ser Val Thr Val Tyr Arg Lys Asn Ala Glu Arg
                190                 195                 200

gag gcg tac acc ggc gct aca cca atg acg gca gag tcg gtg aag agc      675
Glu Ala Tyr Thr Gly Ala Thr Pro Met Thr Ala Glu Ser Val Lys Ser
            205                 210                 215

ttt ctc acg agt gct gtg ttg gac tac ttt ggc gag ctc ggc cag gag      723
Phe Leu Thr Ser Ala Val Leu Asp Tyr Phe Gly Glu Leu Gly Gln Glu
        220                 225                 230

agc ttt cag aag tac atg gaa gcg aac aag gat aaa cct ctt ggg tgg      771
Ser Phe Gln Lys Tyr Met Glu Ala Asn Lys Asp Lys Pro Leu Gly Trp
    235                 240                 245

gtg ttc atc gac aag aac acg gat tct gcg ttg aag ggg tca ctt gtg      819
Val Phe Ile Asp Lys Asn Thr Asp Ser Ala Leu Lys Gly Ser Leu Val
250                 255                 260                 265

gcg gtg gcg gag aag tac cgc tcg cag gtg ttg cta acc tac att gac      867
Ala Val Ala Glu Lys Tyr Arg Ser Gln Val Leu Leu Thr Tyr Ile Asp
                270                 275                 280

ggc gat cag tac cgc ccc gtc tcg cgc cag ctg ggc att cct gag gat      915
Gly Asp Gln Tyr Arg Pro Val Ser Arg Gln Leu Gly Ile Pro Glu Asp
            285                 290                 295

gcg aag ttc ccg gcg ttt gtg gtc gat ttc gag cgc cgc cat cac gtg      963
Ala Lys Phe Pro Ala Phe Val Val Asp Phe Glu Arg Arg His His Val
        300                 305                 310

atg ggg acg gac acc cca gtc acc tcc gag tct gtc gct gcg ttt gtg     1011
Met Gly Thr Asp Thr Pro Val Thr Ser Glu Ser Val Ala Ala Phe Val
    315                 320                 325

gag aag tat gtc aag ggc gag acg aag cag acc gtg atg tcc gac gcg     1059
Glu Lys Tyr Val Lys Gly Glu Thr Lys Gln Thr Val Met Ser Asp Ala
330                 335                 340                 345

att ccc gct aag gag acg gtg aac ggc ctc aca acg gtg gtg ggt cag     1107
Ile Pro Ala Lys Glu Thr Val Asn Gly Leu Thr Thr Val Val Gly Gln
                350                 355                 360

act ttt gcg aag tac acg gac ggc aca caa aac gtg atg ctg ctc ttc     1155
Thr Phe Ala Lys Tyr Thr Asp Gly Thr Gln Asn Val Met Leu Leu Phe
            365                 370                 375

tac gcg ccg tgg tgc gga cac tgc aag aag ctg cac ccc gtc tac gat     1203
Tyr Ala Pro Trp Cys Gly His Cys Lys Lys Leu His Pro Val Tyr Asp
        380                 385                 390

aaa gta gcc aag agc ttc gag tct gag aat gtg atc att gcg aag atg     1251
Lys Val Ala Lys Ser Phe Glu Ser Glu Asn Val Ile Ile Ala Lys Met
    395                 400                 405

gat gcc acg acg aac gac ttt gac cgc gag aag ttt gag gtg tct gga     1299
Asp Ala Thr Thr Asn Asp Phe Asp Arg Glu Lys Phe Glu Val Ser Gly
410                 415                 420                 425

ttt cca acg att tac ttc atc cca gcc ggc aag ccg cca atc gtg tac     1347
Phe Pro Thr Ile Tyr Phe Ile Pro Ala Gly Lys Pro Pro Ile Val Tyr
                430                 435                 440
```

-continued

```
gag ggt ggc cgc acc gca gac gaa atc cag gtg ttt gtg aag tct cac     1395
Glu Gly Gly Arg Thr Ala Asp Glu Ile Gln Val Phe Val Lys Ser His
            445                 450                 455

ctg acc gcc tcc gcc gct cca tct ggc ggc cct tcc ggc aac agc gaa     1443
Leu Thr Ala Ser Ala Ala Pro Ser Gly Gly Pro Ser Gly Asn Ser Glu
        460                 465                 470

gag gaa gat ttg taggactgca agggatgtgg cgtttatagg ctgccctgcc         1495
Glu Glu Asp Leu
    475

ttcccttgct gtttctatga cggattaggc tttttttgt tatatgtggg gtggtcaaga   1555

gagtgccagg gctccttctt tatatccttg cgctttcttt tattttgctt ccttgtgttg   1615

acgtctatgc atgcgtgctg tcgacgactc tttgtcaacc tgcgtcctat ctagtagcat   1675

cgatgtgaaa agaagagtag agggaggtaa cgatgcgtgc gctggctgcc gttttcatgg   1735

gcgcaatttc gagaaggaaa atcggaaaat ggacaggata gcgaaattag cgcaacgaca   1795

aggtcgtgcg tctttctcta tcggtcatta aatttctggg ctttgtaaca atgaaagaag   1855

tcacacaaaa aaaaaaaaaa aaa                                           1878


<210> SEQ ID NO 35
<211> LENGTH: 577
<212> TYPE: PRT
<213> ORGANISM: Leishmania major

<400> SEQUENCE: 35

Met Asp Arg Glu Gly Ser Tyr Ser Ser His Ser Thr Arg Cys Ala Ser
1               5                   10                  15

Gly Ser Val Gly Asn Gln Arg Trp Ser Ala Ser Asn Arg Ser Ser Gly
            20                  25                  30

Thr Ala Val Gly Ala Thr Gly Glu Asp Phe Asn Ser Leu Ile Val Ala
        35                  40                  45

Phe Tyr Thr Arg Val Tyr Pro Ser Ala Asp Val Phe Ala Asp Asp Ala
    50                  55                  60

Ala Glu Phe Asp Leu Glu Asp Ile Ser Glu Ala Val Thr Glu Leu Ala
65                  70                  75                  80

Asn Glu Val Ser Ala Leu Gln Glu Glu Thr His Val Leu Gly Ser His
                85                  90                  95

Val Gln Thr Leu Gln Gln Arg Arg Pro Gly Gly Gly Ala Thr Val Ser
            100                 105                 110

Ile Pro Asn Ile Ser Glu Ser Ala Gly Ile Gln Leu Asp Ala Ala Asp
        115                 120                 125

Asn Ser Gly Ser Gly Ala Leu Ser Pro Val Asp Thr Thr Val Phe Leu
    130                 135                 140

Leu Gly Gly Asp Tyr Glu Leu Ser Met Gly Thr Ser Arg Thr Ser Gly
145                 150                 155                 160

Gly Gly Ala Ala Asp Thr Val Gly Ser Thr Ser Gly Thr Gly Arg Arg
                165                 170                 175

Gly Arg Ser Phe Arg Arg Arg Ser Leu Ala Asp Val Asp Ala Phe Met
            180                 185                 190

Arg Val Asp Asp Lys Ala Val Leu Leu Arg Gln Glu Thr Ala Arg Leu
        195                 200                 205

Arg Thr Gln Glu Glu Lys Ala Ala Lys Glu Ala Glu Gly Val His Glu
    210                 215                 220

Met Leu Val Ala Thr Val Glu Glu Ala Ile Arg Arg Arg Gln Glu Leu
225                 230                 235                 240
```

-continued

```
Arg Leu Glu Met Leu Gln Phe Glu Arg Glu Val Leu Arg Asn Gly Gly
                245                 250                 255

Ala Glu Asp Asp Thr Ala Glu Val Ser Ala His Arg Arg Asn Pro Leu
            260                 265                 270

Gly Asp Ala Lys Lys Leu Thr Val Ser Ser Ala Ala Val Ala Thr Thr
        275                 280                 285

Ala Asp Glu Leu Leu Arg Tyr Leu Glu Arg Arg His Ser Thr Gln Val
    290                 295                 300

Ser Tyr Leu Asp Lys Leu Glu Val Gln Cys Gln Ala Ala Glu Gln Asp
305                 310                 315                 320

Ile Ala Arg Ala Gln Gln Leu Val Arg Gln Arg Arg Ala Ala Gly Glu
                325                 330                 335

Ala Phe Gln Ala Val Asp Met Glu Gln Leu Arg Ile Glu His Lys Gln
            340                 345                 350

Phe Ser Glu Arg Met Glu Ala Lys Asn Lys Glu Leu Ala Glu Leu Lys
        355                 360                 365

Gly Thr Ser Thr Arg Thr Val Gln Gln Leu Asn His Leu Met Gly Gln
    370                 375                 380

Leu Asn Glu Leu Ala Ser Glu Gln Thr Arg Leu Lys Arg Glu Ala Lys
385                 390                 395                 400

Ser Arg Ser Glu Tyr Leu Ser Arg Cys Gly Lys Glu Ile Ala Thr Ala
                405                 410                 415

Thr Ala Glu Ala Val Gln Ala Glu Ser Lys His Met Thr Leu Lys Ala
            420                 425                 430

Gln Gln Glu Ala Val Lys Val Pro Lys Ile Glu Glu Tyr Met Ala Gln
        435                 440                 445

Lys Ala Glu Glu Val Glu Leu Gln Lys Ala Val Lys Asn Leu Glu Arg
    450                 455                 460

Lys Val Gln Ile Ala Glu Gly Gln Ala Ala Val Val Arg Gln Gln Ser
465                 470                 475                 480

Arg Arg Leu Gln Ala Gln Arg Ala Ser Ala Ile Lys Tyr Ala Asn Glu
                485                 490                 495

Lys His Leu Ser Arg Asn Ser Thr Thr Ser Arg Ala Thr Ala Ser Ala
            500                 505                 510

Gly Ala Thr Ala Ser Ser Arg Pro Ala Ala Gly Ser Ala Arg Gly Leu
        515                 520                 525

Leu Met Gln Arg Arg Gln Gln Arg Glu Gln Glu Gln Gln Pro Pro Ser
    530                 535                 540

Leu Pro Glu Ala Ser Thr Val Glu Gln Asp Gly Ser Ala Ala Ala Pro
545                 550                 555                 560

Ala Ala Asp Gln Pro Ala Ala Ala Ala Thr Thr Ala Thr Val Ser Ser
                565                 570                 575

Met


<210> SEQ ID NO 36
<211> LENGTH: 835
<212> TYPE: PRT
<213> ORGANISM: Leishmania major

<400> SEQUENCE: 36

Met Leu Phe Val Leu Gln Cys Thr Ala His Thr His Thr His Thr His
1               5                   10                  15

Thr Cys Arg Pro Gln His Leu Val Ala Pro Leu Ala Ser Leu Cys Arg
            20                  25                  30
```

-continued

```
Ser Leu Val Val Val Ser Ala Ser Leu Ser Pro Phe His Arg Pro Ser
        35                  40                  45

Leu Arg Val Gly His Thr Val Gln Cys Gln Ala Arg Ser His Val Ser
    50                  55                  60

Pro Leu Pro Thr His Leu Leu Phe Ser Ser Leu Ala Leu Ala Ala Cys
65                  70                  75                  80

Ala His Ala Arg Arg Ala Cys Arg Gly Ala Phe Ser Tyr Leu Thr Ala
                85                  90                  95

Thr Thr Ile Thr Ile Thr Val Thr Thr Thr Phe Thr Thr Phe Phe Leu
            100                 105                 110

Phe Ser Val Val Leu His Pro Arg Phe Asn Gly Asp Arg Ala Ala Lys
        115                 120                 125

Ala Lys Thr Gly Lys Lys Met Trp Arg Arg Ser Cys Cys Val Leu Ala
    130                 135                 140

Pro Ser Ile Pro Arg Ser Val Trp Asp Pro Ala His Tyr Asn Glu Asn
145                 150                 155                 160

Trp Val Asp Ser Tyr Ser Thr Ser Ile Ala Asp Arg Arg His Trp Pro
                165                 170                 175

Ala Lys Lys Trp Ser Ile Gly Leu Glu Pro Arg Thr Pro Arg Asp Trp
            180                 185                 190

Leu Arg Phe Ser Tyr Arg Asn Leu Ala Tyr Ala Tyr Asn Gly Ala Leu
        195                 200                 205

Arg Ala Cys Ala Thr Phe Pro Glu Met Leu Val Tyr Tyr Lys Glu Met
    210                 215                 220

Lys Gln Arg Gly Val Lys Val Asp Val Asp Thr Leu Asn Ala Leu Leu
225                 230                 235                 240

Ser Arg Ala Ala Arg Tyr Glu His Ile Gln Val Asp Asp Val Phe Leu
                245                 250                 255

Leu Phe Asp Glu Leu Thr Ala Leu Gly Ala Arg Pro Asp Ile Ala Ser
            260                 265                 270

Val Glu Thr Leu His Thr Val Leu Glu His Ala Ala His Gln Pro Pro
        275                 280                 285

Glu Trp Arg Glu Thr Arg Arg Arg Gln Leu Val Glu Leu Tyr Gln Tyr
    290                 295                 300

Leu Ala Leu Glu Glu Ile Glu Arg Leu Ala Pro His Arg Val Asp Ala
305                 310                 315                 320

Leu Leu Ser Ala Gln Ile Ala Arg Leu Arg Gly Asn Leu Lys Gln Leu
                325                 330                 335

Asn Ala Ser Leu Ser Pro Ser Val Tyr Arg Arg Tyr Phe Ala Ala Ile
            340                 345                 350

Asp Leu Gly Glu Thr Leu Ile Gln Glu Val His Asn Phe Leu Trp Glu
        355                 360                 365

Tyr Val Gly Ala Asp His Ala Ala Met Asp Val Pro Ser Leu Gln Leu
    370                 375                 380

Arg Ile Pro Phe Val Ala Ser Val Met Lys Arg Pro Leu Ala Thr Ala
385                 390                 395                 400

Asp Pro Ala Lys Val Lys Ala Thr Asp Phe Glu Asp Thr Asp Val Cys
                405                 410                 415

Ser Val Leu Leu Ala Ala Val Glu Arg Cys Val Asp Gly Asn Phe His
            420                 425                 430

Asp Arg Arg Pro Val Ser Glu Arg Arg Met Tyr Leu Ala Leu Leu Thr
        435                 440                 445

Met Leu Thr Ser Ser Gly Val Leu Tyr Thr Ala Asp Leu Met Ala Gln
```

-continued

```
    450                 455                 460

Met Met Asp Val Val Lys Tyr Ser Arg Asp Asp Arg Gly Arg Asp Arg
465                 470                 475                 480

Asp Ala Gln Arg Leu Leu Arg Tyr Ala Leu Arg Gly Ser Ser Ala Ala
                485                 490                 495

Asn Asp Ala Ala Tyr Arg Glu Leu Trp Arg Ala Val Ala Pro Pro Val
            500                 505                 510

Asp Ala Arg Val Val Gly Arg Tyr Leu Ala Ser Arg Asp Pro Trp Ser
        515                 520                 525

Pro Val His Ile Cys Tyr Asp Arg Ser Phe Gln Phe Arg Ala Phe Pro
    530                 535                 540

Ala Leu Gln Gln Ile Thr Gln Ser Gln Cys Ser Ser Ser Ser Ser Ser
545                 550                 555                 560

Ser Ser Ser Ser Ser Thr Asp Ala Ala Ala Val Ala Ala Ser Thr Ala
                565                 570                 575

Ala Gly Ala Gly Ser Ser Ser Thr Ala Ala Ala Ala Ala Glu Pro Asp
            580                 585                 590

Glu Ala Leu Glu Gly Val Ser Ala Gly Pro Pro Pro Gly Thr Val Ala
        595                 600                 605

Ala Lys Thr Ala Glu Ala Leu Gln Gln Arg Trp Asp Asp Val Arg Arg
    610                 615                 620

Leu Ile Asp Ile Thr Gly Val Leu Lys Pro Gly Ala Gly Leu Thr Ser
625                 630                 635                 640

Ala Arg Thr Gly Ser Ala Ala Pro Thr Gln Glu Ala Ala Gln Gln Ala
                645                 650                 655

Met Glu Val Phe Thr Gly Ala Ala Ala Phe Leu Arg Gly Val Ala Thr
            660                 665                 670

Gly Cys Arg Tyr Gly Glu Leu Ala Asp Ala Leu Ala Ile Gln Ala Val
        675                 680                 685

Gly Asp Gly Gln Gln Gln His His His Ala Pro Arg Ala Thr Pro Leu
    690                 695                 700

Gly Gly Ala Ala Ala Thr Ala Gly Ala Ala Arg Ser Ser Ser Gly Asn
705                 710                 715                 720

Val Asn Thr Glu Leu Tyr Ala Gly Gly Leu Asp Phe Asp Val Trp Gln
                725                 730                 735

Arg Leu Met Gln Cys Val Gln Gln Leu Arg Gln Asp Met Glu Gln Phe
            740                 745                 750

Met Ala Gln Gln Tyr Glu Ala His Gly Leu Gln Val Glu Pro Glu Phe
        755                 760                 765

Glu Cys Trp Glu Ala Met Leu Val Val Leu Arg Cys Ile Leu Asp Phe
    770                 775                 780

Cys Leu Val His Thr Gln Gln Tyr Gly Arg Thr Ala Gly Gly Gly Met
785                 790                 795                 800

Ala Glu Asn Leu Phe Leu Glu Ser Ala Gln Leu Arg Ala Gln Leu Val
                805                 810                 815

Glu Glu Ser Arg Thr Arg Phe Asn Gly Arg Met Arg Ile Leu Trp Leu
            820                 825                 830

Gln Glu Val
        835
```

<210> SEQ ID NO 37
<211> LENGTH: 340
<212> TYPE: PRT
<213> ORGANISM: Leishmania major

<400> SEQUENCE: 37

Met Ser Ala Asn Cys Ala Gly Pro Ala Ser Thr Pro Asp Ala Lys Lys
1 5 10 15

Ala Arg Val Glu Ala Asp Val Ile Thr Glu Ala Asp Arg Val Pro Ala
20 25 30

Phe Pro Leu Pro Pro Thr Asp Ala Ala Ala Tyr Glu Arg Glu His Val
35 40 45

His Asn Val Tyr Ser Ala Ile Ala Asp His Phe Ser Ser Thr Arg Tyr
50 55 60

Lys Ala Trp Pro Gln Val Gly Ala Phe Leu Glu Gly Leu Pro Pro Phe
65 70 75 80

Ser Leu Val Ala Asp Val Gly Cys Gly Asn Gly Lys Tyr Phe Ser Ala
85 90 95

Ala Gln Arg Leu Ala Leu Thr Ala Pro Ser His Pro Met Thr Thr Ser
100 105 110

Gly Ala Ser Leu Glu Met Lys Ser Arg Gln Gln Ala Glu Ala Gln Pro
115 120 125

Ser Pro Pro Leu Val Ser Phe Ala Pro Ala His Arg Tyr Val Leu Gly
130 135 140

Leu Asp Tyr Ser Glu Glu Leu Leu Arg Ser Thr Gln Arg Gln Leu Val
145 150 155 160

Asp Pro Asn Met His His Ala Gln Arg Arg Arg Arg Leu Ser Gly Lys
165 170 175

Arg Ala Lys Asn Glu Ala Glu Ala Val Ala Thr Pro Val Ser Ala Glu
180 185 190

Glu Leu Pro Arg Thr Asp Thr Val Arg Ser Asp Ala Leu Arg Cys Pro
195 200 205

Leu Arg Ser Gly Val Phe Asp Ala Ala Ile Ser Ile Ala Val Ile His
210 215 220

His Tyr Ala Ser Arg Glu Arg Arg Arg Leu Ala Val Arg Glu Leu Leu
225 230 235 240

Arg Leu Ala Arg Pro His Gly Gly Arg Val Leu Ile Tyr Val Trp Ala
245 250 255

Arg Glu Gln Arg Gly His Thr Lys Arg Leu Val Asp Pro Glu Thr Gly
260 265 270

Asp Gly Leu Val Arg Trp Glu Arg Asn Gln Lys Tyr Asp Gly Ala Gln
275 280 285

Gln Val Phe Arg Arg Tyr Tyr His Phe Phe Ala Glu Gly Glu Leu Glu
290 295 300

Gln Leu Cys Lys Asp Ala Ala Ser Asp Asp Gly Thr Gly Ser Ile Pro
305 310 315 320

Val Ala Ile Arg Lys Ser Tyr Tyr Asp Lys Glu Asn Trp Cys Val Met
325 330 335

Leu Glu Arg Cys
340

<210> SEQ ID NO 38
<211> LENGTH: 385
<212> TYPE: PRT
<213> ORGANISM: Leishmania major

<400> SEQUENCE: 38

Met Asn Phe Ala Asn Asn Ala Asn Gly Gly Cys Phe Gly Ser Leu Ser
1 5 10 15

-continued

```
Ala Ala Ala Ser Ala Ser Ala Ala Ala Ala Ala Pro Thr Ala Val Ser
            20                  25                  30

Gln Gly Ser Arg Leu Ala Ser Ser Gly Gln Ser Asn Ser His Ser Gly
        35                  40                  45

Ser Ala Thr Leu Asp Trp Ser Ala Ser Pro Pro Ser Ser Gly Gln Cys
    50                  55                  60

Pro Ser Gln Gln Lys His Ala Val Ser Gly Pro Ala Pro Phe Ser Tyr
65                  70                  75                  80

Tyr Tyr Gln Gly Thr Asp Val Ala Arg Pro Ser Ala Gln Val Arg His
                85                  90                  95

His Thr Ala Ala Ser Ala Ser Ala His Phe Asp Ile Thr Asn Arg Val
            100                 105                 110

Ala Ala Ser Val Ala Ala Val Ser Thr Ser Ala Asp Ala Gly Ala Glu
        115                 120                 125

Ser His Gln His Ala Ala Ser Thr Gln Gln Gln Gln Leu Pro Pro Val
    130                 135                 140

Ala Gly Thr Thr Val Gln Leu Thr Ser Pro Ser Ser Ser Thr Thr Arg
145                 150                 155                 160

Gly Ser Gly Ile Asn Val Asn Ala Gln Pro Tyr Tyr Tyr Val Ser Ser
                165                 170                 175

Arg Met Arg Lys Gln Gln Gln Gln Gln Ala Ala Ala Ala Ser Pro Ala
            180                 185                 190

Ser Val Asp Pro Ser Val Thr Arg Pro Gly Ser Asp Leu Ala Val Ala
        195                 200                 205

Gly Thr Thr Ser Thr Arg Thr Pro Ala Thr Ala Val Gly Thr Asp Asp
    210                 215                 220

Thr Val Ala Ala Val Gln Arg Ala Pro Leu Ser Thr Leu Glu Gly Gly
225                 230                 235                 240

Ser Asp Ala Arg Ser Pro Gly Ser Ser Phe Thr Ser Pro Ala Cys Val
                245                 250                 255

Asn Ser Leu Ala Arg Phe Ser Thr Tyr Ala Arg Thr Thr Thr Asp Ser
            260                 265                 270

Val Ala Gly His Ala Ser Gln Pro Ser Gly Phe Arg Ser Gly Ile Glu
        275                 280                 285

Thr Val Val Ser Ala Met Lys Met Ser Gly Ile Tyr Gly Gly Ser Gly
    290                 295                 300

Gly Gly Gly Asn Asn Gly Asn Ser Thr Ser Arg Ser Ser Ala His Pro
305                 310                 315                 320

His Thr Phe Pro Ser Arg Pro Ile Ala Arg Ser Gly Ala Asp Gly Gly
                325                 330                 335

Ser Gly Gly Glu Gln Ala Thr Leu Ala Arg Val Pro Arg Arg Ser Pro
            340                 345                 350

His Ala Asp His Gln Ala Pro Val His Arg Arg Ser Thr Phe Ala Ser
        355                 360                 365

Gln His Ser Leu Gly Lys Lys Arg Ser Lys Pro Asp Ser Tyr Lys Asp
    370                 375                 380

Tyr
385
```

<210> SEQ ID NO 39
<211> LENGTH: 201
<212> TYPE: PRT
<213> ORGANISM: Leishmania major -continued

<400> SEQUENCE: 39

```
Met Tyr His Ser Arg Thr Glu Thr Val Ser Arg Arg Asp Glu Gln Arg
1               5                   10                  15

His His Arg Ile Arg Gln Arg Thr Ala Thr Tyr Cys Met Cys Val Cys
            20                  25                  30

Arg Arg Ala Cys Leu Val Phe Asp Thr Pro Thr Phe Phe Phe Val Ser
        35                  40                  45

Val Tyr Ser His Ser Val Thr Cys Leu Arg Val Leu Leu Val Cys Val
    50                  55                  60

Cys Val Cys Val Ser Val Ser Leu Cys Gln Pro Leu Pro Pro Leu Phe
65                  70                  75                  80

Tyr Cys Ile Phe Phe Thr His Thr His Thr His Thr Glu Arg Lys Gln
                85                  90                  95

Leu Ala Arg Phe Ser Ser Cys Asn Val Ala Arg Ser Leu Ala Thr Cys
            100                 105                 110

Ser Leu Leu Leu Phe Cys Cys Phe Arg Val Gly Cys Leu Arg Val Cys
        115                 120                 125

Val Cys Ala Thr Thr Glu Ser Ile Tyr Met His Thr Ile Val Ser Phe
    130                 135                 140

Thr Val Leu Val Phe Met Ser Leu Lys Pro Asp Gly Gly Lys Gly Val
145                 150                 155                 160

His Thr Pro Leu Gly Ala Trp His Arg Arg Val Ser Arg Thr His Pro
                165                 170                 175

Pro Cys Gln Cys Gln Asn Arg Leu Trp Arg Trp Gln Ala Gln Val Pro
            180                 185                 190

Gly Met Cys Gly Gly Val Thr Ala Met
        195                 200
```

<210> SEQ ID NO 40
<211> LENGTH: 287
<212> TYPE: PRT
<213> ORGANISM: Leishmania major

<400> SEQUENCE: 40

```
Met Thr Ala Thr Gly Pro Leu Pro Arg Asp Val Arg Asp Val Ala Pro
1               5                   10                  15

Leu His Arg Trp Gln Thr Glu Gly Thr Ser Ser His Ser Glu Ala Gly
            20                  25                  30

Gly Asp Val Pro Ala Thr Cys Leu Phe Gln His Pro Val Val Ala Leu
        35                  40                  45

Leu Pro Ser Phe Pro Pro Leu Pro Phe Phe Leu Val Ala His Arg Thr
    50                  55                  60

Leu His Lys Cys Ala Leu Gly Cys Ala Pro Val Ala Phe Thr Trp Cys
65                  70                  75                  80

Thr Val Gln Phe Thr Trp Lys Arg Ser Pro Gln Leu Arg Cys Phe Gly
                85                  90                  95

Ser Ala Asn Leu Ala Asp Ile Ser Phe Gly Arg Gly Cys Asp Tyr Ser
            100                 105                 110

Ala Asn Met Leu Arg Cys Val Ser Arg Arg Leu Trp Tyr Gln Phe Lys
        115                 120                 125

Asp Leu Lys Ser Lys Val Ile Leu Glu Lys Leu Arg Asn Ser Lys Leu
    130                 135                 140

Gln Glu Gly Val His Pro Ser Asp Met Asp Met Glu Asp Leu Ala Arg
145                 150                 155                 160
```

-continued

```
Glu Ser Gly Ile Ala Pro Pro Ser Ser Val Asn Val Gln Asp Phe Val
                165                 170                 175

His Glu Lys Glu Ala Val Leu Glu Met Leu Gln Glu Gln Arg Leu Arg
            180                 185                 190

Arg Ile Ala Arg Arg Glu Ala Phe Leu Glu Trp Gln Ala Gly Gln Arg
        195                 200                 205

Glu Lys Gly Ala Ala His Arg Leu Val Arg Gln Ser Arg Lys Ala Glu
    210                 215                 220

Lys Tyr Lys Arg Arg His Tyr His Ala Thr Ser Gly Arg Met Leu Pro
225                 230                 235                 240

Ile Ser Leu Ser Pro Gly Gln Ala Pro Pro Asp His Arg Ala Pro Met
                245                 250                 255

Ser Met Pro Lys Ala Cys Val Ser Ser Thr Glu Phe Leu Arg Gly Gly
            260                 265                 270

Pro Ala Glu Asn Arg His Ala Ile His Leu Ser Leu Glu Lys Lys
        275                 280                 285


<210> SEQ ID NO 41
<211> LENGTH: 104
<212> TYPE: PRT
<213> ORGANISM: Leishmania major

<400> SEQUENCE: 41

Met Val Tyr Thr Arg Trp Lys Cys Asp Arg Ile Pro Val Leu Gln Leu
1               5                   10                  15

Lys Leu Phe Thr Gln Glu Tyr Asn Met Met Ala Val Val Gly Leu Leu
            20                  25                  30

Ser Met Val Phe Leu Phe Lys His Ala Ser Tyr Cys Ser Glu Glu Thr
        35                  40                  45

Glu Arg Lys Asn Gly Trp Trp Ala Gly Tyr Pro Tyr Trp Arg Asp Pro
    50                  55                  60

Ile Ala Arg Arg Asn Glu Ile Arg Tyr Lys Gln Leu Ile Asn Ser Asn
65                  70                  75                  80

Asp Val Asp Ile Thr Asp Pro Lys Trp Thr Gly Cys Ser Lys Glu Gln
                85                  90                  95

Leu Glu Arg Leu Arg Ala Ile Val
            100


<210> SEQ ID NO 42
<211> LENGTH: 1277
<212> TYPE: PRT
<213> ORGANISM: Leishmania major

<400> SEQUENCE: 42

Met Leu Ala Arg Tyr Leu Asp Pro Ser Val His Pro Leu Arg Val Gly
1               5                   10                  15

Gln Val Val Ala Tyr Asp Tyr Leu His Ala Ala Lys Thr Trp Gln Trp
            20                  25                  30

Thr Leu Gly Thr Val Arg Glu Ile Lys Asp Tyr Thr Ala Val Val Gln
        35                  40                  45

Gln Trp Gly Leu His Thr Gly Asp Ile Asp Thr Leu Arg Ser Ile Leu
    50                  55                  60

Leu Lys Glu Val Asp Thr Glu Asn Gly Arg Met Lys Asn Tyr His Asp
65                  70                  75                  80

Met Leu Ala Ile Ala Arg Glu Lys Leu Ala Ser Ile Arg Arg Ser Asn
                85                  90                  95
```

-continued

```
Glu Asp Arg Val Ser His Val Arg Gly His Phe Asp Lys Ala Arg Glu
            100                 105                 110

Lys Val Glu Leu Ile Asp Glu Val Asp Leu Arg Lys Val Thr Ala Gln
        115                 120                 125

Ala Ala Pro Ser Pro Val Ala Val Ala Val Leu Lys Ala Val Trp Ala
    130                 135                 140

Val Ala Lys Cys Asp Pro Thr Ala Val Glu Phe Tyr Glu Trp Ala Asp
145                 150                 155                 160

Val Gln Leu Glu Tyr Arg Lys Pro Ala Ala Leu Asp Glu Ile Ala Lys
                165                 170                 175

Thr Asp Val Leu Ala Lys Leu Tyr Pro Ser Ala Glu Ser Leu Gln Gln
            180                 185                 190

Ser Leu Glu Gln Asp Pro Lys Leu Asn Tyr Lys Ala Ala Ala Arg Asp
        195                 200                 205

Ser Pro Val Val Ala Ser Leu His Ala Trp Val Ile Thr Ala Leu Ala
    210                 215                 220

Tyr Gln Gln Ala Tyr Asn Leu Leu Ala His Asp Lys Arg Ile Gln Glu
225                 230                 235                 240

Gln Asn Asp Ala Ile Ala Ala Ala Ile Ala Gly Met Lys Ala Cys Arg
                245                 250                 255

Ala Lys Ile Ala Lys Leu Lys Asp Glu Leu Ser Ser Lys Asp Thr Ala
            260                 265                 270

Ala Leu Pro Gly Gln Val Thr Ser Phe Thr Arg Thr Ser Val Leu Val
        275                 280                 285

Thr Ile Pro Leu Ser Ala Val Ile Ser Pro Val Asn Val Asp Thr Asp
    290                 295                 300

Val Lys Arg Cys Val Leu Thr Lys Asp Glu Val Glu Gln Ile Pro Ile
305                 310                 315                 320

Asp Ala Lys Ile Thr Arg Tyr Ala Gln Lys Gln Lys Leu Ala Ile Thr
                325                 330                 335

Gly Ser His Leu Leu Asp Gln Tyr Ala Ala Ala Thr Thr Thr His Ile
            340                 345                 350

Tyr Val Thr Glu Leu Glu Asp Arg Leu Phe Phe Phe Gln His Tyr Met
        355                 360                 365

Ala Ser Ala Leu Arg Asp Ala Gln Thr Ala Ala Val Asp Ala His Gln
    370                 375                 380

Arg Leu Ala Val Ser Leu His Glu Leu Glu Ala Phe Arg Gln Lys Arg
385                 390                 395                 400

His Asp Ala Lys Lys Ala Arg Ala Ala Glu Pro Glu Leu Ala Asp Ala
                405                 410                 415

Asp Gly Val Glu Pro Ser Ser Gly Pro Thr Ser Ser Arg Ser Pro Thr
            420                 425                 430

Gly Arg Ala Ala Pro Arg Gly Gln Ser Ala Ala Pro Arg Gly Thr Ala
        435                 440                 445

Ser Gln Gln His Lys Leu Leu Gly Pro Ala Tyr Gln Ser Ile Asp Pro
    450                 455                 460

Ala Thr Ile Ala Asn Glu Pro Leu Tyr Ala Val Thr Ile Glu Glu Tyr
465                 470                 475                 480

Lys Ala Lys Asp Ala Ala Gly Glu Arg Ala Met Asp Glu Ala Glu Arg
                485                 490                 495

Met Ala Asp Glu Val Gln Arg Leu Ala Val Glu Leu Glu Asp Ala Lys
            500                 505                 510

Ala Ala Ala Asp Lys Leu Ala Glu Glu Leu Ala Ala Lys Asp Glu Glu
```

-continued

```
        515                 520                 525

Leu Ala Ala His Arg Gln Lys Arg His Asp Ala Arg Gln Ala Arg Ala
    530                 535                 540

Ser Asp Pro Ala Leu Ala Ala Ala Asp Ala Val Ala Pro Arg Ser Gly
545                 550                 555                 560

Lys Gly Ala Ala Ser Pro His Val Gly Ala Val Gln Arg Gln Ala Val
                565                 570                 575

Asp Pro Ala Thr Val Pro Val Ala Pro Ala Val Ile Ala Glu Glu Pro
            580                 585                 590

Leu Tyr Val Ala Thr Ala Glu Glu Leu Gln His Val Arg Asp Phe Ala
        595                 600                 605

Asp Gln Leu Ala Glu Glu Leu Glu Ala Phe Arg Gln Lys Arg His Asp
    610                 615                 620

Ala Lys Lys Ala Arg Ala Ala Glu Pro Glu Leu Ala Asp Ala Asp Gly
625                 630                 635                 640

Val Glu Pro Ser Ser Gly Pro Thr Ser Ser Arg Ser Pro Thr Gly Arg
                645                 650                 655

Ala Ala Pro Arg Gly Gln Ser Ala Ala Pro Arg Gly Thr Ala Ser Gln
            660                 665                 670

Gln His Lys Leu Leu Gly Pro Ala Tyr Gln Ser Ile Asp Pro Ala Thr
        675                 680                 685

Ile Ala Asn Glu Pro Leu Tyr Ala Val Thr Ile Glu Glu Tyr Lys Ala
    690                 695                 700

Lys Asp Ala Ala Gly Glu Arg Ala Met Asp Glu Ala Glu Arg Met Ala
705                 710                 715                 720

Asp Glu Val Gln Arg Leu Ala Val Glu Leu Glu Asp Ala Lys Ala Ala
                725                 730                 735

Ala Asp Lys Leu Ala Glu Glu Leu Ala Ala Lys Asp Glu Glu Leu Ala
            740                 745                 750

Ala His Arg Gln Lys Arg His Asp Ala Arg Gln Ala Arg Ala Ser Asp
        755                 760                 765

Pro Ala Leu Ala Ala Ala Asp Ala Val Ala Pro Arg Ser Gly Lys Gly
    770                 775                 780

Ala Ala Ser Pro His Val Gly Ala Val Gln Arg Gln Ala Val Asp Pro
785                 790                 795                 800

Ala Thr Val Pro Val Ala Pro Ala Val Ile Ala Glu Glu Pro Leu Tyr
                805                 810                 815

Val Ala Thr Ala Glu Glu Leu Gln His Val Arg Asp Phe Ala Asp Gln
            820                 825                 830

Leu Ala Glu Glu Leu Glu Ala Phe Arg Gln Lys Arg His Asp Ala Lys
        835                 840                 845

Lys Ala Arg Ala Ala Glu Pro Glu Leu Ala Asp Ala Asp Gly Val Glu
    850                 855                 860

Pro Ser Ser Gly Pro Thr Ser Ser Arg Ser Pro Thr Gly Arg Ala Ala
865                 870                 875                 880

Pro Arg Gly Gln Ser Ala Ala Pro Arg Gly Thr Ala Ser Gln Gln His
                885                 890                 895

Lys Leu Leu Gly Pro Ala Tyr Gln Ser Ile Asp Pro Ala Thr Ile Ala
            900                 905                 910

Asn Glu Pro Leu Tyr Ala Val Thr Ile Glu Glu Tyr Lys Ala Lys Asp
        915                 920                 925

Ala Ala Gly Glu Arg Ala Met Asp Glu Ala Glu Arg Met Ala Asp Glu
    930                 935                 940
```

-continued

```
Val Gln Arg Leu Ala Val Glu Leu Glu Asp Ala Lys Ala Ala Ala Asp
945                 950                 955                 960

Lys Leu Ala Glu Glu Leu Ala Ala Lys Asp Glu Glu Leu Ala Ala His
                965                 970                 975

Arg Gln Lys Arg His Asp Ala Arg Gln Ala Arg Ala Ser Asp Pro Ala
            980                 985                 990

Leu Ala Ala Ala Asp Ala Val Ala  Pro Arg Ser Gly Lys  Gly Ala Ala
        995                 1000                 1005

Ser Pro  His Val Gly Ala Val  Gln Arg Gln Ala Val  Asp Pro Ala
    1010                 1015                 1020

Thr Val  Pro Val Ala Pro Ala  Val Ile Ala Glu Glu  Pro Leu Tyr
1025                 1030                 1035

Val Ala  Thr Ala Glu Glu Leu  Gln His Val Arg Asp  Phe Ala Asp
1040                 1045                 1050

Gln Ala  Ala His Asp Ala Thr  Ala Arg Glu Ala Glu  Val Ala Gly
1055                 1060                 1065

Thr Val  Glu Asn Leu Arg Asn  Glu Leu Asp Asp Val  Arg Glu Met
1070                 1075                 1080

Asn Ala  Lys Leu Glu Asp Glu  Val Phe Ala Leu Lys  Glu Gln Leu
1085                 1090                 1095

Ser Asp  Ala Glu Asp Ala Tyr  Lys Lys Leu Ala Gly  Ala Leu Val
1100                 1105                 1110

Val Ala  Glu Asp Glu Arg Gln  Glu Leu Cys Asp Asp  Leu Glu Ala
1115                 1120                 1125

Ala Leu  Asp Glu Leu Glu Gln  Lys Lys Asp Glu Tyr  Asp Glu Leu
1130                 1135                 1140

Leu Gly  Asn Leu Glu Glu Val  Gln Gly Leu Leu Glu  Ala Ala Asp
1145                 1150                 1155

Val Ala  Gly Arg Thr Ala Val  Glu Ala Leu Glu Gln  Arg Asn Arg
1160                 1165                 1170

Asp Met  Ala Asp Leu Gln Gly  Glu Leu Ala Asn Ala  Leu Asp Ala
1175                 1180                 1185

Ser Lys  Glu Asn Glu Asn Leu  Arg Ala Leu Leu Asp  Ala Lys Glu
1190                 1195                 1200

Arg Glu  Ile Asp Arg Leu Lys  Glu Tyr Asn Ser Phe  Trp Thr Asp
1205                 1210                 1215

Thr Val  Gly Thr Gly Lys Gln  Lys Val Thr His Arg  Leu Thr Lys
1220                 1225                 1230

Ile Phe  Asp Gly Asp Trp Thr  Arg Leu Met Arg His  Arg Pro Glu
1235                 1240                 1245

Ala Leu  Lys Ala Ala Phe Val  Ile Asp Ser Ser Asn  Ala Cys His
1250                 1255                 1260

Val Pro  Gly Asp Gln Ile Val  Gln Val Asp Phe Asp  His Asp
1265                 1270                 1275
```

<210> SEQ ID NO 43
<211> LENGTH: 527
<212> TYPE: PRT
<213> ORGANISM: Leishmania major

<400> SEQUENCE: 43

```
Met Val Thr His Ala Leu His Glu Ser Leu Phe Pro Arg Asp Ala Ala
1               5                   10                  15

Ser Asp Ala Ala Gly Thr Ala Ala Thr Ser Leu Gln Val Ser Leu Pro
```

-continued

```
            20                  25                  30

Pro Ile Thr Val Ala Met Arg Arg Gly Ala Val Gln Met Arg Tyr Gly
        35                  40                  45

Leu Thr Tyr Leu Arg Thr Phe Pro Ala Ala Leu Arg Asp Ser Val Arg
    50                  55                  60

Val Leu Lys Thr Ala Met Ser Cys Asp Asp Gly Val Thr Arg Cys Pro
65                  70                  75                  80

Ser Tyr Met Ser Met Thr Gly Thr Leu Val Ser Ala Pro Leu Gly Leu
                85                  90                  95

Cys Cys Leu Cys Thr Ser Val Glu Cys Ala Leu Thr Ser Asp Leu Cys
            100                 105                 110

Asn Ala Ser Met Arg Ala His Phe Cys Phe Arg Thr Gly Ala Ala Gly
        115                 120                 125

Ile Thr Cys Val Gln Ser Glu Gly Ile Thr Tyr His Gly Trp Ala Val
    130                 135                 140

Gly Ser Ser Ser Pro Tyr Tyr Met Met His Leu Ser Ala Ser Gly Arg
145                 150                 155                 160

Gly Ile Ala Pro Thr Thr Leu Gln Leu Thr Thr Asp Ala Pro Glu Val
                165                 170                 175

Gln Lys Gly Ala Ser Ala Leu Gln Ile Leu Arg Ala Ser Gly Val Leu
            180                 185                 190

Pro Gly Glu Ser Asn Pro Thr Val Asp Ile Ser Gly Arg Val Leu Phe
        195                 200                 205

Val Pro Ser Ala Glu His Ser Ser Ala Ser Arg Ser Ile Ser Thr Gly
    210                 215                 220

Pro Val Arg Asp Asp Asp Pro Ala Glu Trp Leu Leu Leu Pro Ala Pro
225                 230                 235                 240

Leu Val Ser Val Ser Gly Asn Asp Cys Asp Lys Val Gly Ile Ser Pro
                245                 250                 255

Asp Tyr Phe Tyr Ser Leu Ser Ser Thr Lys Gln Cys Asn Ala Gln Lys
            260                 265                 270

Gly Thr Cys Val Arg His Gln Leu Ala Asp Tyr Arg Ala Ala Asp Leu
        275                 280                 285

Glu Gln Ile Ala Gln Gly Val Gly Gly Arg Tyr Ile Ala Ala Ser Leu
    290                 295                 300

Gly Thr Phe Thr Arg Gln Ala Met Arg Glu Gln Glu Phe Leu Leu Asp
305                 310                 315                 320

Ala Val Glu Arg Thr Gly Gly Ala Met Leu Arg Trp Thr Val Asn Ala
                325                 330                 335

Asp Gly Leu Val Phe Gln Pro Leu Pro Val His Gly Val Leu Asp Ala
            340                 345                 350

Ile Lys Phe Asp Ser Ser Thr Gly Ile Leu Tyr Val Thr Val Arg Asn
        355                 360                 365

Asn Asn Thr Tyr Gly Gly Leu Tyr Tyr Val Ala Val Gly Gln Cys Arg
    370                 375                 380

Gly Ala Arg Ala Ser Asn Cys Asp Ser Asp Gly Val Thr His Glu Cys
385                 390                 395                 400

Gly Arg Thr Ala Leu Val Ala Gly Ala Asn Thr Ser Ser Leu Leu Gln
                405                 410                 415

Phe Ser Met Val Ser Asp Leu Pro Glu Glu Val Gly Ser Thr Ala Ser
            420                 425                 430

Cys Thr Val Val Phe Arg Asp Ala Ala Ala Ala Leu Leu Ala Ser Ala
        435                 440                 445
```

-continued

```
Asn Ile Ser Trp Thr Val Glu His Thr Thr Thr Thr Pro Ala Pro Asn
    450                 455                 460

Ala Pro Lys Ala Glu Gln Cys Arg Arg Cys Ala Phe Arg Asp Leu Arg
465                 470                 475                 480

Cys Leu Phe Ser Thr Val Cys Glu Trp Gln Met Leu Leu Trp Thr Ala
                485                 490                 495

Val Ala Val Ala Val Thr Trp Thr Pro Tyr Ala Ile Leu Ala Tyr Trp
            500                 505                 510

Arg Met Ala Trp His Val Gly Ala Lys Leu Leu Ala Cys Leu Asn
        515                 520                 525


<210> SEQ ID NO 44
<211> LENGTH: 408
<212> TYPE: PRT
<213> ORGANISM: Leishmania major

<400> SEQUENCE: 44

Met Leu Glu Pro Thr Gly Arg Arg Gly Gly Pro Arg Leu Pro Thr Pro
1               5                   10                  15

Ala Arg Val Pro Val Arg Val His Trp Val Ala Ala Val Ala Gly Gly
            20                  25                  30

Trp Arg Trp Arg Cys Ala Ala Cys Cys Ala Ala Gly Ala Val Ala Ala
        35                  40                  45

Pro Ala Pro Ala Arg Ala Pro Ala Pro Thr Cys Val Cys His Gly Gly
    50                  55                  60

Gly Arg Pro Gly Val Val Ala Gly Met Leu Arg Trp Val Arg Gly Ser
65                  70                  75                  80

Leu Ala Ala Gly Glu His Thr Pro Ser Asp Ala Met Val Leu Asn Ala
                85                  90                  95

Met Ala Trp Leu Arg Ala Pro Arg Ser Arg Gly Val Gly Phe Pro Val
            100                 105                 110

Leu Cys Ala Cys Val Trp Leu Pro Pro Pro Val Pro Leu Arg Arg Ala
        115                 120                 125

Arg Gly Arg Phe Pro Val Arg Trp Cys Val Arg Val Arg Gly Pro Leu
    130                 135                 140

Ser Pro Ala Thr Arg Arg Leu Pro Val Lys Gly Val Trp Val Val Gly
145                 150                 155                 160

Val Gly Gly Trp Gly Ser Ser Ala Ala Thr Gly Arg Arg Gln Arg Leu
                165                 170                 175

Ala Cys Arg Gly Ala Cys Gly Arg Ala Ala Arg Gly Arg Pro Pro Ser
            180                 185                 190

Arg Gly Val Asp Gly Gly Gly Gly Cys Gly Gln Arg Thr Cys Trp Lys
        195                 200                 205

Thr Ala Leu Pro Arg Ala Thr Pro Arg Gly Thr Gly Ala Val Arg Thr
    210                 215                 220

Arg Cys Arg Ala Pro Leu Ala Trp Arg Ile Ala Pro Glu Gln Ser Lys
225                 230                 235                 240

Glu Arg Ser Ala Glu Gln Gly Arg Trp Thr Lys Arg Ser Arg Gly Tyr
                245                 250                 255

Ala Cys Glu Leu Ala Pro Pro Cys Val Cys Ala Ala Arg Pro Ala Ser
            260                 265                 270

Pro Arg Cys Gly Arg Val Cys Trp Arg Gly Ala Gly Ala Gly Ser Val
        275                 280                 285

Pro Arg Thr Pro Arg Val Thr Pro Ser Gly Pro Pro Asn Ser Gly Val
```

```
    290                 295                 300

Glu Ser His Arg Ala Val Leu Trp Gly Ala Val Ala Gly Gly Gly Glu
305                 310                 315                 320

Gln Gly Met His Ala Gly Cys Arg Val Trp Gly Gly Pro Gly Leu Arg
                325                 330                 335

Leu Ala Gly Phe Leu Ala Gly Leu Ile Arg His Ala Arg Ala Pro Pro
            340                 345                 350

Arg Gly Tyr Ser His Gly Gly Arg Arg Arg Phe Arg Pro Arg Ser Gly
        355                 360                 365

Ala Trp Met Arg Pro Ala Trp Val Gly Val Cys Gly Pro Pro Gly Val
    370                 375                 380

Cys Leu Ala Leu Ile Ala Trp Arg Val Ser Glu Glu Gly Ala Arg Thr
385                 390                 395                 400

Gly Lys Lys Gly Leu Leu Asp Ala
                405


<210> SEQ ID NO 45
<211> LENGTH: 478
<212> TYPE: PRT
<213> ORGANISM: Leishmania major

<400> SEQUENCE: 45

Met Pro Val Ile Gly Tyr Asn Cys Asp Ser Gly Ala Val Val Glu Val
1               5                   10                  15

Val Asn Pro Ala Ser Gly Ala Leu Gly Phe Ala Gly Lys Thr Val Ile
            20                  25                  30

Pro Gly Gly Ile Val Ser Ala Ala Ser Ala Gly Asp Gly Thr Leu Tyr
        35                  40                  45

Tyr Leu Pro Thr Ser Phe Pro Ser Met Leu His Arg Arg Asn Leu Glu
    50                  55                  60

Ser Gly Ala Asp Glu Met Val Glu Ser Leu Ala Arg Ala His Thr Gln
65                  70                  75                  80

Val Phe Phe His Arg Asn Lys Val Met Cys Ile Ser Ala Gly Ser Thr
                85                  90                  95

Glu Val Ala Val Tyr Asp Pro Leu Cys Ser Val Thr Glu Ile Ile Ser
            100                 105                 110

Leu Pro Tyr Arg Val Val Arg Ala Glu Pro Ala Asp His Gly Phe Val
        115                 120                 125

Phe Arg Ser Asp Cys Asn Arg Val Phe Gly Tyr Asp Phe Asn Lys Gly
    130                 135                 140

Leu Thr Glu Val Met Asn Gly Cys Ser Ile Thr Gly Phe Leu Gly His
145                 150                 155                 160

Tyr Lys Gln Tyr Ala Val Ala Leu Leu His Asp Gly Asp Glu Arg Val
                165                 170                 175

Val Gly Val Thr Glu Ala Gly Ser Ile Val Glu Leu Asp Ala Ala Leu
            180                 185                 190

Pro Cys Val Pro Phe Thr Ser Leu Asp Asp Val Val Leu Tyr Thr Ser
        195                 200                 205

Glu Asn Glu Val Val Ser Leu Lys Gly Gly Ser Ala Val Ser Pro Val
    210                 215                 220

Gly Glu Val His Leu Ser Ser Ser Gln Pro Thr Asp Ser Glu Val Leu
225                 230                 235                 240

Cys Thr Val Cys Leu Cys Glu Phe Asp Gly Asp Asp Gly Ile Thr Leu
                245                 250                 255
```

-continued

```
Asp Cys Gly His Tyr Phe His Lys Glu Cys Ile Glu Gln Trp Val Gly
            260                 265                 270

Asn Trp Met Asp Phe Ala Ala Lys Gly Glu His Val Lys Phe Thr Arg
        275                 280                 285

Ala Val Cys Pro Gly Gly Cys Lys His Leu Val Arg His Pro Leu Leu
    290                 295                 300

Ala Gln Ser Lys Gln Ile Ser Glu Leu Tyr Thr Glu Val Thr Ala Lys
305                 310                 315                 320

Lys Ala Glu Gln Leu Lys His Phe Asp Ala Thr Lys Ala Gln His Glu
                325                 330                 335

Phe Leu Phe Tyr Leu Cys Gly Arg Cys Gly Gly Val Phe Tyr Gly Gly
            340                 345                 350

Asp Gln Val Cys Ser Arg Met Gln Gly His Glu Pro Ser Ser Ser Pro
        355                 360                 365

Gln Glu Leu Val Cys Asp Thr Cys Ile Gly Lys Asp His Arg Thr Cys
    370                 375                 380

Asn Thr Leu Met Ala Val Phe Lys Cys Arg Tyr Cys Cys Asn Pro Ala
385                 390                 395                 400

Thr Gln Arg Ser Phe Gly Thr Arg Phe Met Cys Asp Arg Cys Ile Ala
                405                 410                 415

Arg Trp Asp Thr Ala Glu Pro Ala Leu Ile Pro Cys Pro Gly Ala Asp
            420                 425                 430

Ser Cys Pro Phe His Gly Asn His Pro Glu Pro Val Cys Asn Ile Ala
        435                 440                 445

Ala Cys Leu Thr Cys Leu Asp Pro Ala Met Val Ser His Ile Phe Asp
    450                 455                 460

Arg Val Ala Gly Val Ala Asp Gly Ala Gly Gly Gly Thr Asp
465                 470                 475


<210> SEQ ID NO 46
<211> LENGTH: 220
<212> TYPE: PRT
<213> ORGANISM: Leishmania major

<400> SEQUENCE: 46

Met Gly Gly Lys Arg Lys Lys Ser Asn Asn Gly Pro Val Lys Lys Glu
1               5                   10                  15

Ser Lys Tyr Lys Ile Pro Thr Arg Phe Asp Cys Pro Leu Cys Asp Ala
            20                  25                  30

Lys Ala Ser Ile Val Val Arg Met Phe Arg Ala Thr Ser Asp Ala Thr
        35                  40                  45

Val Gln Cys Arg Val Cys Gly Ala Gly Gly Thr Lys Arg Trp Asn Val
    50                  55                  60

Leu Arg Leu Glu Lys Pro Val Asp Val Phe Phe Arg Phe His Glu Ala
65                  70                  75                  80

Leu Val Gln Arg Asp His Ala Asp Leu Gln Gln Val Glu Met Gly Arg
                85                  90                  95

Glu Ala Arg Leu Ser Val Gly Ala Pro Asn Ala Val Leu Gly Gly Ser
            100                 105                 110

Gln Ser Ser Met Gly Lys Glu Ala Tyr Ser Pro Gly Asp Ala Ala Val
        115                 120                 125

Ala Gly Trp Ala Arg Leu Gly Ser Ser Ala Ala Ala Ala Ala Thr Ala
    130                 135                 140

Ser Gly Cys Ser His Ser Gln His Val Lys Ser Leu Gly Glu Leu Gln
145                 150                 155                 160
```

-continued

```
Arg Lys Leu Thr Met Pro Ala Trp Ser Gly Phe Ala Thr Ala Pro Thr
                165                 170                 175

Ala Ser Cys Ala Val Asp Leu Arg Asp Asp Tyr Glu Gly Glu Ala Glu
            180                 185                 190

Gly Ala Ala Ala His Tyr Phe Ala Pro Arg Gln Glu Val His Ser Ala
        195                 200                 205

Glu Asp Glu Asp Asp Glu Tyr Asp Gln Leu Phe Gln
    210                 215                 220


<210> SEQ ID NO 47
<211> LENGTH: 174
<212> TYPE: PRT
<213> ORGANISM: Leishmania major

<400> SEQUENCE: 47

Met Cys Ile Gly His Thr Arg Thr His Thr His Thr Arg Ala Arg Leu
1               5                   10                  15

Trp Val Ser Ala Ile Met Ala Ser Leu Gln Phe Ser Ala Phe Leu Leu
            20                  25                  30

Leu Pro Pro Phe Phe Phe His Arg Ala Pro Cys Arg Ala Ser Thr Thr
        35                  40                  45

Leu Thr Val Phe His Thr Ser Thr Gln Leu Leu Arg Tyr Pro Ile Thr
    50                  55                  60

Cys Lys Thr Arg Val Arg Thr Ala His Asn Thr Arg Phe Met Glu Val
65                  70                  75                  80

Phe Gly Met Leu Val Gln Ser Cys Thr Ser Ile Pro Ala His Val Arg
                85                  90                  95

Gln His Cys Arg Gly Val Gln Leu Pro Trp Ile Pro Pro Val Val Ser
            100                 105                 110

Val Leu Thr His Ser Val Glu Asp Gly Ser Ser Ser Lys Asp Glu Lys
        115                 120                 125

Arg Leu Lys Ala Glu Glu Pro His Gly Thr His Ala Val Met Arg Ala
    130                 135                 140

Cys Arg Glu Asp Arg Met Leu Gln Thr Asn Ser Leu Ala Leu Leu Pro
145                 150                 155                 160

Arg Pro Ala Ser Glu Cys Ala Ser Ala Pro Leu Gly Ser Asn
                165                 170


<210> SEQ ID NO 48
<211> LENGTH: 153
<212> TYPE: PRT
<213> ORGANISM: Leishmania major

<400> SEQUENCE: 48

Met Ser Leu Thr Leu Ile Pro Asp His Phe Gln His Ile Val Arg Leu
1               5                   10                  15

Leu Asn Thr Asn Val Glu Gly Lys Arg Lys Val Pro Phe Ala Leu Arg
            20                  25                  30

Met Val Lys Gly Val Gly Ile Arg Phe Ala Tyr Leu Val Cys Lys Lys
        35                  40                  45

Ala Gly Ile Asp Val Glu Arg Arg Ala Gly Thr Leu Thr Ala Glu Glu
    50                  55                  60

Leu Glu Lys Ile Ala Glu Ile Ile Ala Asp Pro Ala Lys Phe Lys Ile
65                  70                  75                  80

Pro Asp Trp Phe Leu Asn Arg Gln Arg Asp Pro Lys Thr Gly Lys Thr
                85                  90                  95
```

-continued

```
Glu His Leu Ser Ser Ser Met Val Asp Thr Arg Leu Arg Asp Asp Leu
            100                 105                 110

Glu Arg Leu Lys Lys Met Arg Ala His Arg Gly Val Arg His Ala Tyr
        115                 120                 125

Gly Leu Arg Val Arg Gly Gln His Thr Cys Thr Ser Gly Arg His Gly
    130                 135                 140

Lys Thr Val Gly Val Ser Arg Gly Lys
145                 150


<210> SEQ ID NO 49
<211> LENGTH: 134
<212> TYPE: PRT
<213> ORGANISM: Leishmania major

<400> SEQUENCE: 49

Met Thr Lys Phe Leu Lys Pro Gly Lys Val Val Ile Val Thr Ala Gly
1               5                   10                  15

Arg Tyr Ala Gly His Lys Ala Val Ile Val Gln Asn Ser Asp Val Val
            20                  25                  30

Thr Lys Glu Arg Pro Tyr Gly Arg Ala Leu Leu Ala Gly Ile Lys Lys
        35                  40                  45

Tyr Pro Lys Lys Val Val Arg Gly Met Ser Lys Gln Thr Ile Ala Arg
    50                  55                  60

Arg Ser Gln Val Gly Val Phe Leu Arg Val Val Asn His Lys His Phe
65                  70                  75                  80

Leu Pro Thr Arg Tyr Asn Val Asp Met Ser Lys Glu Leu Arg Gly Lys
                85                  90                  95

Ile Asn Val Ser Asp Ala Ser Lys Arg Ser Arg Ser Lys Arg Leu Val
            100                 105                 110

Arg His Val Phe Gln Ala Arg Tyr Asn Ala Gly Ser Ser Met Trp Phe
        115                 120                 125

Phe Gln Arg Leu Arg Phe
    130


<210> SEQ ID NO 50
<211> LENGTH: 575
<212> TYPE: PRT
<213> ORGANISM: Leishmania major

<400> SEQUENCE: 50

Met Ala Leu Leu Val Lys Leu Asp Ile Lys Asn Ser Glu Gly Asp Ala
1               5                   10                  15

Ile Gln Leu Leu Phe Glu Pro Tyr Val Ala Thr Met Arg Ser Glu Pro
            20                  25                  30

Arg Ala Phe Thr Met Leu Trp Arg Ala Ser Gln Ala Tyr Leu Leu Asp
        35                  40                  45

Val Ser Thr Leu Leu Glu His Val Ala Pro Lys Glu Val Leu Pro Leu
    50                  55                  60

Pro Ser Cys Val Ser Ser Ile Leu Gln Thr Phe Cys Lys Tyr His Leu
65                  70                  75                  80

Ser Glu Ser Arg Leu Leu Gly Ala Ser Ser Ser Ala Arg Thr Leu Thr
                85                  90                  95

Asp Ser Arg Ser Ser Leu Ala Gly Glu Thr Glu His Phe Leu His Ala
            100                 105                 110

Ser Thr Lys Pro Ser Ser Val Ser Asp Arg Ala Val Arg Glu Leu Ala
        115                 120                 125
```

-continued

```
Glu Arg Pro Asp Ala Ala Gln Trp Met Thr Ala Ala Gly Thr Arg Leu
    130                 135                 140

Ser Glu Glu Gly Leu Lys Ser Ser Glu Glu Leu Gln His Arg Arg Leu
145                 150                 155                 160

Pro Arg Val Val Arg Met Val Leu Glu Glu Asn Arg Thr Thr Leu Asn
                165                 170                 175

Thr Leu Leu His Trp Asp Gly Asn Leu Leu Lys Asp Ser Phe Ala Phe
            180                 185                 190

Leu Lys Tyr Glu Pro Asn Leu Ile Asp Phe Asn Phe Lys Leu Thr Asp
        195                 200                 205

Phe Arg Arg Arg Leu Gly Ser Arg Arg Gly Pro Asn Ile Leu Leu Arg
    210                 215                 220

Val Asn Arg Gln Thr Cys Leu Leu Asp Ser Phe Lys Glu Leu Gln Lys
225                 230                 235                 240

Val Lys Ser Phe Gly Gly Gln Leu His Ile Arg Phe His Gly Glu Glu
                245                 250                 255

Gly Ala Asp Ala Gly Gly Leu Thr Arg Glu Trp Leu Gln Leu Leu Ser
            260                 265                 270

Glu Ala Ile Val Asp Glu Arg Tyr Ala Leu Phe Ile His Ser Gln Asp
        275                 280                 285

Ser Ile Ser Phe Gln Pro Asn Pro Phe Ser Ser Val Asn Pro Asn His
    290                 295                 300

Leu Glu Tyr Phe Gln Phe Ala Gly Val Val Thr Gly Leu Ala Ile Ala
305                 310                 315                 320

His Asn Val Pro Ile Asp Ile His Phe Thr Arg Ala Phe Tyr Arg His
                325                 330                 335

Ile Ile Gly His Arg Pro Val Phe Ala Asp Leu Gln Ser Phe Asp Pro
            340                 345                 350

Glu Leu Tyr Thr Asn Leu Asn Trp Ile Met Glu Asn Asp Val Thr Asp
        355                 360                 365

Leu Gly Leu Thr Phe Ala Val Asn Tyr Asp Arg Phe Gly Ser Val Glu
    370                 375                 380

Glu Ala Glu Leu Glu Pro Asn Gly Gln Asn Thr Ala Val Thr Asn Ala
385                 390                 395                 400

Asn Lys Gln Gln Tyr Val Arg Leu Leu Cys Glu Phe Tyr Met Thr Lys
                405                 410                 415

Arg Thr Glu Asp Gln Leu Leu Arg Phe Leu Lys Gly Phe Tyr Ser Val
            420                 425                 430

Ile Pro Arg Arg Glu Ile Gln Cys Phe Thr Glu Lys Glu Leu Glu Leu
        435                 440                 445

Val Ile Ser Gly Met Pro Asn Ile Asp Val Glu Asp Leu Arg Thr His
    450                 455                 460

Thr Val Tyr Glu Gly Tyr Ser Ser Thr Ser Pro Gln Val Arg Trp Phe
465                 470                 475                 480

Trp Glu Ala Val Gly Ser Met Ser Lys Glu Asp Leu Ala Asn Leu Leu
                485                 490                 495

Gln Phe Thr Thr Gly Ser Ser Lys Val Pro His Gly Gly Phe Gly His
            500                 505                 510

Leu Glu Gly Ser Asn Gly Arg Ser Leu Pro Phe Thr Ile Ser Arg Trp
        515                 520                 525

Ala Val Thr Lys Glu Asp Leu Leu Pro Gln Ala His Thr Cys Phe Asn
    530                 535                 540
```

-continued

```
Lys Ile Asp Leu Pro Val Tyr Pro Ser Ala Ala Val Leu Lys Glu Lys
545                 550                 555                 560

Leu Met Leu Ala Ile Thr Tyr Gly Ser Met Gly Phe Thr Met Val
                565                 570                 575


<210> SEQ ID NO 51
<211> LENGTH: 546
<212> TYPE: PRT
<213> ORGANISM: Leishmania major

<400> SEQUENCE: 51

Met Gln Pro Lys Gln Lys Ala Ala Leu Gly Ile Asn Gly Thr Arg Thr
1               5                   10                  15

Ser Gly Ile Ala Val Arg Arg Glu Asn Val Ser Ala Ala Leu Ala Val
            20                  25                  30

Ala Asn Val Val Lys Ser Ser Leu Gly Pro Ile Gly Leu Asp Lys Met
        35                  40                  45

Leu Val Asp Asp Val Gly Asp Val Leu Val Thr Asn Asp Gly Ala Thr
    50                  55                  60

Ile Leu Lys Ser Leu Asp Val Glu His Pro Ala Ala Arg Leu Leu Val
65                  70                  75                  80

Asp Leu Ala Gln Leu Gln Asp Lys Glu Ile Gly Asp Gly Thr Thr Ser
                85                  90                  95

Val Val Ile Leu Ala Ala Glu Leu Leu Lys Arg Ala Gln Glu Leu Val
            100                 105                 110

Ser Gln Gly Ile His Ala Thr Ser Ile Ile Ala Gly Tyr Lys Leu Ala
        115                 120                 125

Met Arg Glu Ala Leu Arg Tyr Leu Asn Asp Asn Leu Gly Cys Ala Val
    130                 135                 140

Glu Ser Leu Gly Lys Asp Val Leu Leu Asn Val Ala Arg Thr Ser Met
145                 150                 155                 160

Ser Ser Lys Ile Leu Asn Asn Asp Ala Asp Leu Phe Ala Lys Ile Val
                165                 170                 175

Val Asp Ala Ile Met Ser Val Lys Thr Val Asn Asp Phe Gly Asp Val
            180                 185                 190

Ile Tyr Pro Arg Lys Ala Val Ser Ile Leu Leu Gln His Gly Arg Ser
        195                 200                 205

Leu His Glu Ser Arg Leu Val Gln Gly Phe Ala Met Asn Leu Ser Arg
    210                 215                 220

Ala Ala Gln Gly Met Pro Thr Ser Val Lys Asp Ala Lys Ile Ala Leu
225                 230                 235                 240

Ile Asp Phe Asp Leu Arg Ala Val Lys Met Lys Leu Gly Ile Asn Ile
                245                 250                 255

Thr Ile Thr Asp Pro Ser Lys Ala Glu Ala Ile Arg Gln Arg Glu Leu
            260                 265                 270

Asp Ile Thr Lys Glu Arg Ile Gln Lys Met Ile Ala Ala Gly Ala Asn
        275                 280                 285

Val Ile Met Thr Thr Trp Gly Ile Glu Asp Ser Met Met Lys Tyr Met
    290                 295                 300

Val Asp Asn Ser Val Leu Gly Val Arg Arg Val Lys Lys Asp Asp Ile
305                 310                 315                 320

Arg Arg Ile Ala Lys Thr Thr Gly Ala Gln Val Val His Thr Met Ser
                325                 330                 335

Asp Leu Glu Gly Glu Glu Val Phe Asp Pro Lys Trp Leu Gly Arg Ser
            340                 345                 350
```

-continued

```
Glu Lys Val Tyr Glu Glu Arg Ile Gly Asp Asp Asp Cys Ile Val Ile
        355                 360                 365

Ala Gly Thr Ser Asn Ala Val Cys Ala Thr Ile Val Cys Arg Gly Ala
    370                 375                 380

Asn Tyr Phe Met Leu Glu Glu Met Glu Arg Ala Leu Asn Asp Ala Leu
385                 390                 395                 400

Trp Ala Val Ala Arg Thr Cys Asp Ala Ser Cys Val Val Ala Gly Gly
                405                 410                 415

Gly Ser Val Glu Ala Ala Val Ser Val Tyr Leu Asp Asn Phe Ala Arg
            420                 425                 430

Thr Leu Ser Ser Arg Glu Gln Leu Ala Val Ala Glu Tyr Ala Glu Ala
        435                 440                 445

Leu Leu Val Ile Pro Lys Val Leu Ala Leu Asn Ala Ala Leu Asp Ala
    450                 455                 460

Thr Asp Leu Val Ala Lys Leu Arg Val Glu His Thr Gln Ala Gln Ser
465                 470                 475                 480

Ser Gly Gln Gln Thr Glu Ala Arg Phe Thr Gly Leu Asp Leu His Asn
                485                 490                 495

Gly Thr Leu Arg Asn Asn Ile Lys Ala Gly Val Leu Glu Pro Lys Pro
            500                 505                 510

Ser Lys Ile Lys Ser Leu Gln Phe Ala Thr Glu Ala Ala Val Thr Val
        515                 520                 525

Leu Arg Ile Asp Asp Cys Val Arg Leu Asn Pro Asp Glu Glu Asp Gln
    530                 535                 540

Gln Arg
545
```

<210> SEQ ID NO 52
<211> LENGTH: 144
<212> TYPE: PRT
<213> ORGANISM: Leishmania major

<400> SEQUENCE: 52

```
Met Asp Glu Glu Lys Arg Lys Lys Phe His Gly Val Gly Asn Thr Ala
1               5                   10                  15

Lys Asn Ser Arg Val Arg Gly Ala Thr Arg Ala Ser Leu Leu Lys Arg
            20                  25                  30

Thr Gly Arg Lys Pro Asp Ala Val Ser Met Glu Ala Thr Ile His Leu
        35                  40                  45

Ser Lys Leu Leu Lys Lys Lys Thr Phe Ser Lys Arg Ala Pro Leu Ala
    50                  55                  60

Ile Lys Arg Ile Lys Ala Phe Val Gly Arg Leu Met Lys Thr Lys Asp
65                  70                  75                  80

Asn Arg Ile Asp Ala Ser Leu Asn Thr Tyr Ile Trp His Lys Gly Val
                85                  90                  95

Lys Gly Val Pro Gly Arg Val Arg Val Leu Ile Gln Arg Lys Ser Glu
            100                 105                 110

Thr Thr Glu Gly Asn Lys His Lys His Phe Tyr Thr Val Ile Ser Asn
        115                 120                 125

Val Pro Val Ala Ser Phe Lys Gly Leu Thr Thr Lys Thr Val Glu Gln
    130                 135                 140
```

<210> SEQ ID NO 53
<211> LENGTH: 190
<212> TYPE: PRT

-continued

<213> ORGANISM: Leishmania major

<400> SEQUENCE: 53

Met Arg Asn Tyr Asn Asn Phe Asn Arg Val Trp Lys Ala Pro Arg Arg
1 5 10 15

Pro Phe Glu Lys Glu Arg Leu Asp Arg Glu Met Lys Leu Cys Gly Gln
20 25 30

Tyr Gly Leu Arg Cys Lys Arg Glu Ile Trp Arg Val Asn Met Thr Leu
35 40 45

Ser Lys Met Arg Arg Thr Ala Arg Leu Leu Leu Thr Leu Pro Glu Asn
50 55 60

His Pro Arg Arg Leu Leu Glu Gly Ser Ala Ile Met Arg Arg Cys His
65 70 75 80

Glu Tyr Gly Phe Leu Asp Glu Glu Lys Asp Lys Leu Asp Tyr Val Leu
85 90 95

Ser Leu Thr Val Pro Asp Ile Leu Glu Arg Arg Leu Gln Thr Ile Val
100 105 110

Phe Lys Ala Gly Leu Ala Lys Ser Val His His Ala Arg Val Leu Ile
115 120 125

Gln Gln Arg His Ile Ala Val Ala Lys Gln Ile Val Thr Ile Pro Ser
130 135 140

Phe Ile Val Arg Val Ser Ser Glu Arg His Ile Ala Phe Ala Asp Ala
145 150 155 160

Ser Pro Phe Gly Asn Gly Arg Ala Gly Arg Val Lys Arg Val Arg Ala
165 170 175

Lys Ala Ala Lys Arg His Ala Gly Gly Gly Asp Asp Asp Glu
180 185 190

<210> SEQ ID NO 54
<211> LENGTH: 195
<212> TYPE: PRT
<213> ORGANISM: Leishmania major

<400> SEQUENCE: 54

Met Ala Ala Thr Lys Ser Ala Val Ser Ala Ala Lys Arg Lys Ala Ala
1 5 10 15

Lys Lys Val Ser Arg Lys Ser Pro Glu Tyr Thr Thr Leu Arg Lys Ser
20 25 30

Cys Ala Pro Gly Ala Ile Ala Ile Ile Leu Ala Gly Arg Phe Arg Gly
35 40 45

Arg Arg Ala Val Ile Leu Lys Gln Leu Pro His Asn Gly Pro Leu Val
50 55 60

Val Ser Gly Pro Met Lys Tyr Asn Gly Val Pro Ile Arg Arg Ile Asp
65 70 75 80

Ser Arg Tyr Val Ile Ala Thr Ser Thr Thr Val Asp Ile Ser Ser Val
85 90 95

Asp Thr Ala Pro Ile Thr Ala Glu Val Phe Gln Arg Pro Lys Ala Glu
100 105 110

Lys Pro Thr Lys Ser Glu Gly Asp Phe Met Gly Asp Lys Gln Lys Ala
115 120 125

Lys Ala Glu Lys Ala Ala Lys Lys Thr Ser Lys Ala Gly Lys Lys Thr
130 135 140

Leu Val Ser Asp Ala Arg Ala Gln Leu Gln Lys Lys Ile Asp Ala Ala
145 150 155 160

Leu Ile Ala Ala Ile Lys Lys Asp Ala Gln Gly Lys Glu Lys Ala Gly

-continued

```
                165                 170                 175

Tyr Leu Arg Ser Val Phe Thr Val Lys Pro Gly Asp Ala Pro His Arg
            180                 185                 190

Trp Asn Trp
        195


<210> SEQ ID NO 55
<211> LENGTH: 179
<212> TYPE: PRT
<213> ORGANISM: Leishmania major

<400> SEQUENCE: 55

Met Val Lys Pro His Leu Arg His Tyr Gln Val Val Gly Arg Glu Ser
1               5                   10                  15

Pro Ser Glu Lys Asn Pro Glu Pro Thr Val Tyr Lys Phe Glu Val Phe
            20                  25                  30

Ala Pro Asn Phe Val Val Ala Lys Ser Arg Phe Trp Arg Met Met Arg
        35                  40                  45

Val Lys Asn Lys Val Lys Ala Thr His Gly Asp Val Leu Ser Cys Lys
    50                  55                  60

Val Val Lys Asp Ala Lys Leu Val Ala Arg Asn Tyr Leu Val Asp Ile
65                  70                  75                  80

Ala Tyr Tyr Ser Gln Arg Cys Gly Tyr Thr Arg Met Val Lys Glu Phe
                85                  90                  95

Arg Asp Val Ser Lys Thr Gly Ala Val Ser Gln Ala Tyr His Asp Leu
            100                 105                 110

Ala Ser Arg His Arg Ala Arg Tyr His Asn Ile Glu Val Leu Asn Val
        115                 120                 125

Lys Ser Ile Pro Asp His Glu Val Lys His Leu Ser Ile Ala Gln Tyr
    130                 135                 140

His Ala Pro Asn Leu Ser Phe Pro Leu Leu Gln Arg Arg Ile Lys Ala
145                 150                 155                 160

Ala Arg Lys Asp Arg Ala Ile Phe Val Lys Lys Asn Thr Lys Arg Ala
                165                 170                 175

Val Val Ala


<210> SEQ ID NO 56
<211> LENGTH: 394
<212> TYPE: PRT
<213> ORGANISM: Leishmania major

<400> SEQUENCE: 56

Met Met Arg Arg Thr Leu Leu Trp Leu Val Asn Phe Glu Pro Val Phe
1               5                   10                  15

Met Pro Ala Leu Ser Pro Ser Met Glu Thr Gly Thr Val Val Glu Trp
            20                  25                  30

Lys Lys Lys Ile Gly Glu Leu Val Lys Glu Ser Asp Val Phe Cys Thr
        35                  40                  45

Ile Gln Thr Asp Lys Ala Val Val Asp Tyr Thr Asn Thr Phe Glu Ser
    50                  55                  60

Gly Tyr Leu Ala Lys Ile Tyr Cys Gly Asn Gly Gln Ser Ala Pro Val
65                  70                  75                  80

Ala Lys Thr Ile Ala Val Met Val Ser Asp Ala Ala Asp Val Ser Lys
                85                  90                  95

Ala Asp Glu Tyr Thr Pro Glu Gly Glu Val Pro Ala Ala Glu Ala Glu
            100                 105                 110
```

-continued

```
Ala Pro Thr Ala Ala Ala Val Ala Ala Ala Pro Ala Ala Gly Gly Ala
        115                 120                 125

Ser Ser Lys Ala Pro Glu Gly Val Thr Cys Glu Pro Val Phe Met Pro
    130                 135                 140

Ala Leu Ser Pro Ser Met Glu Thr Gly Thr Val Val Glu Trp Lys Lys
145                 150                 155                 160

Lys Ile Gly Glu Leu Val Lys Glu Ser Asp Val Phe Cys Thr Ile Gln
                165                 170                 175

Thr Asp Lys Ala Val Val Asp Tyr Thr Asn Thr Phe Glu Ser Gly Tyr
            180                 185                 190

Leu Ala Lys Ile Tyr Cys Gly Asn Gly Gln Ser Ala Pro Val Ala Lys
        195                 200                 205

Thr Ile Ala Val Met Val Ser Asp Ala Ala Asp Val Glu Lys Val Ala
    210                 215                 220

Asn Tyr Tyr Pro Glu Asp Ala Val Gly Gly Pro Pro Ala Ser Ala Ala
225                 230                 235                 240

Asp Pro Ser Ala Ala Ala Ala Ala Ala Ala Ser Ala Arg Pro Ala Pro
                245                 250                 255

Ser Ala Ala Ser Ala Lys His Tyr Gly Gly Ser Leu Asp Ala Ala Val
            260                 265                 270

Ala Ala Ser Gly Pro Ser Val Ala Arg Ile Ala Ala Gly Leu Glu Thr
        275                 280                 285

Ser Thr Leu Ala Gly Ile Ala Pro Ser Gly Lys Gly Gly Arg Phe Leu
    290                 295                 300

Lys Ser Asp Phe Ser Gly Gln Pro Gly Phe Asp Tyr Asn Asp Thr Thr
305                 310                 315                 320

Pro Ala Arg Ala Met Gln Gln Lys Ala Ala Pro Ala Ala Ala Ala Asp
                325                 330                 335

Glu Ala Ser Lys Thr Ala Ala Lys Ser Ala Ala Pro Ala Ala Val Ser
            340                 345                 350

Gly Asp Ile Tyr Asn Val Val Leu Lys Pro Gly Pro Val Tyr Lys Ser
        355                 360                 365

Val Ser Asp Thr Ala Leu Leu Lys Lys Leu Met His Thr Met His Val
    370                 375                 380

Pro Lys Pro Lys Leu Lys Lys Ala Ala Glu
385                 390


<210> SEQ ID NO 57
<211> LENGTH: 438
<212> TYPE: PRT
<213> ORGANISM: Leishmania major

<400> SEQUENCE: 57

Met Gly Gln Asn Met Pro Lys Pro Pro Gly Ala Gly Lys Pro Glu Lys
1               5                   10                  15

Trp Glu Pro Pro Val Ala Pro Glu Ile Gly Lys Arg Lys Lys Lys Arg
            20                  25                  30

Gly Pro Asp Ala Ala Thr Arg Ile Pro Lys Val Tyr Pro Asn Arg Ala
        35                  40                  45

Cys Leu Leu Arg Lys Tyr Arg Leu Glu Arg Cys Lys Asp Tyr Leu Leu
    50                  55                  60

Leu Glu Glu Glu Phe Leu Arg Thr Ile Asn Ala Gln Arg Asp Ala Gln
65                  70                  75                  80

Ser Asn Leu Glu Glu Gly Ala Met Gly His Tyr Glu Ala Glu Leu Lys
```

-continued

```
                85                  90                  95

Arg Val Glu Asp Ile Arg Gly Thr Pro Leu Glu Val Ala Thr Leu Glu
            100                 105                 110

Glu Ala Val Asp Asp Ser His Ala Ile Val Ser Ile Ser Gly Thr Glu
        115                 120                 125

Tyr Tyr Val Pro Leu Met Ser Phe Val Asp Lys Glu Gln Leu Glu Leu
    130                 135                 140

Gly Cys Ser Val Leu Leu His Asp Arg Gln His Ser Ile Val Gly Val
145                 150                 155                 160

Leu Lys Asp Asp Val Asp Pro Leu Val Ser Val Met Lys Val Asp Lys
                165                 170                 175

Ala Pro Glu Asp Thr Tyr Ala Asp Ile Gly Gly Leu Glu Gln Gln Ile
            180                 185                 190

Gln Glu Ile Lys Glu Ala Val Glu Phe Pro Leu Ser His Pro Glu Leu
        195                 200                 205

Tyr Asp Glu Ile Gly Ile Lys Pro Pro Lys Gly Val Ile Leu Tyr Gly
    210                 215                 220

Val Pro Gly Thr Gly Lys Thr Leu Leu Ala Lys Ala Val Ala Asn Arg
225                 230                 235                 240

Thr Ser Ala Thr Phe Leu Arg Val Val Gly Ser Glu Leu Ile Gln Lys
                245                 250                 255

Tyr Ser Gly Glu Gly Pro Lys Leu Val Arg Glu Leu Phe Arg Val Ala
            260                 265                 270

Glu Glu His Ser Pro Ala Ile Val Phe Ile Asp Glu Ile Asp Ala Ile
        275                 280                 285

Gly Thr Lys Arg Tyr Asp Thr Asp Ser Ser Gly Thr Lys Glu Val Gln
    290                 295                 300

Arg Thr Met Leu Glu Leu Leu Thr Gln Leu Asp Gly Phe Asp Ser Ser
305                 310                 315                 320

Asn Asp Val Lys Val Ile Met Ala Thr Asn Arg Ile Asp Thr Leu Asp
                325                 330                 335

Pro Ala Leu Ile Arg Pro Gly Arg Ile Asp Arg Lys Ile Glu Phe Pro
            340                 345                 350

Phe Pro Asp Glu Lys Thr Lys Arg Arg Ile Phe Glu Ile His Thr Ser
        355                 360                 365

Arg Met Ser Leu Ala Glu Asp Val Asp Ile Ser Glu Phe Ile His Ala
    370                 375                 380

Lys Asp Glu Met Ser Gly Ala Asp Val Lys Ala Ile Cys Thr Glu Ala
385                 390                 395                 400

Gly Leu Leu Ala Leu Arg Glu Arg Arg Met Lys Val Cys Gln Ala Asp
                405                 410                 415

Phe Ile Lys Gly Lys Glu Asn Val Gln Tyr Arg Lys Asp Lys Ser Thr
            420                 425                 430

Phe Ser Arg Phe Tyr Leu
        435


<210> SEQ ID NO 58
<211> LENGTH: 113
<212> TYPE: PRT
<213> ORGANISM: Leishmania major

<400> SEQUENCE: 58

Met Pro Pro Lys Ala Arg Ala Pro Leu Pro Pro Gly Asp Val Glu Arg
1               5                   10                  15
```

-continued

```
Gly Glu Lys Leu Phe Lys Gly Arg Ala Ala Gln Cys His Thr Ala Thr
            20                  25                  30

Lys Gly Gly Ser Asn Gly Val Gly Pro Asn Leu Phe Gly Ile Val Asn
        35                  40                  45

Arg Pro Ser Gly Lys Val Glu Gly Phe Thr Tyr Ser Lys Ala Asn Ala
    50                  55                  60

Glu Ser Gly Val Ile Trp Thr Pro Glu Val Leu Asp Val Tyr Leu Glu
65                  70                  75                  80

Asn Pro Lys Lys Phe Met Pro Gly Thr Lys Met Ser Phe Ala Gly Ile
                85                  90                  95

Lys Lys Pro Gln Glu Arg Ala Asp Val Ile Ala Tyr Leu Glu Thr Leu
            100                 105                 110

Lys


<210> SEQ ID NO 59
<211> LENGTH: 342
<212> TYPE: PRT
<213> ORGANISM: Leishmania major

<400> SEQUENCE: 59

Met Tyr Met Tyr Leu Tyr Thr His Thr His Thr Ile Ala Trp Arg Val
1               5                   10                  15

Cys Val Ser Val Arg Cys Val Met Gly Cys Phe Val Leu Ala Phe His
            20                  25                  30

Pro Leu Ala Pro Ser Pro Ser Pro Pro Ser Pro Thr Thr Pro Trp Arg
        35                  40                  45

Pro Leu Tyr Asp Val His Arg Ser Arg Thr Pro Thr Arg Arg Asn Thr
    50                  55                  60

His Tyr Pro Arg Pro His Ala Gln Asp Val Cys Ile Cys Ser Met Pro
65                  70                  75                  80

Gly Lys Glu Val Lys Lys Val Thr Gln Pro Ala Lys Ala Ala Ser Pro
                85                  90                  95

Tyr Lys Lys Pro Ala Val Ala Ser His Phe Ala Ala Arg Pro Lys Asn
            100                 105                 110

Phe Gly Ile Gly Gln Asp Val Pro Tyr Ala Arg Asp Leu Ser Arg Phe
        115                 120                 125

Met Arg Trp Pro Thr Phe Val Thr Met Gln Arg Lys Lys Arg Val Leu
    130                 135                 140

Gln Arg Arg Leu Lys Val Pro Pro Ala Leu Asn Gln Phe Thr Lys Val
145                 150                 155                 160

Leu Asp Arg Ala Ser Arg Asn Glu Ala Leu Lys Leu Ile Lys Lys Tyr
                165                 170                 175

Ala Pro Glu Thr Arg Lys Ala Arg Arg Glu Arg Leu Gln Lys Val Ala
            180                 185                 190

Glu Glu Lys Lys Lys Asp Pro Lys Lys Thr Val Ser Thr Lys Ala Pro
        195                 200                 205

Leu Ala Val Val Thr Gly Leu Gln Glu Val Thr Arg Ala Ile Glu Lys
    210                 215                 220

Lys Gln Ala Arg Met Val Val Ile Ala Asn Asn Val Asp Pro Val Glu
225                 230                 235                 240

Leu Val Leu Trp Met Pro Asn Leu Cys Arg Ala Asn Lys Ile Pro Tyr
                245                 250                 255

Ala Ile Val Lys Asp Met Ala Arg Leu Gly Asp Ala Ile Gly Arg Lys
            260                 265                 270
```

-continued

```
Thr Ala Thr Cys Val Ala Leu Thr Asp Val Asn Ala Glu Asp Glu Ala
        275                 280                 285

Thr Leu Lys Asn Leu Ile Arg Ser Val Asn Ala Arg Phe Leu Ser Arg
    290                 295                 300

Ser Asp Val Ile Arg Arg Gln Trp Gly Gly Leu Gln Leu Ser Leu Arg
305                 310                 315                 320

Ser Arg Ala Glu Leu Arg Lys Lys His Ala Arg Asn Ala Gly Val Asp
                325                 330                 335

Ala Ala Ala Ile Ile Gln
            340


<210> SEQ ID NO 60
<211> LENGTH: 419
<212> TYPE: PRT
<213> ORGANISM: Leishmania major

<400> SEQUENCE: 60

Met Ser His Cys Lys Phe Glu His Pro Arg His Gly His Leu Gly Phe
1               5                   10                  15

Leu Pro Arg Lys Arg Ser Arg Gln Ile Arg Gly Arg Ala Arg Ala Phe
            20                  25                  30

Pro Lys Asp Asp Ala Thr Gln Lys Pro His Leu Thr Ser Phe Met Val
        35                  40                  45

Phe Lys Ala Gly Met Thr His Ile Val Arg Asp Val Asp Arg Pro Gly
    50                  55                  60

Ser Lys Val Asn Lys Lys Glu Val Val Glu Pro Val Thr Ile Leu Glu
65                  70                  75                  80

Ala Pro Pro Met Val Ile Val Gly Ile Val Gly Tyr Arg Gln Thr Pro
                85                  90                  95

Val Gly Leu Lys Thr Ile Gly Thr Val Trp Ala His His Thr Ser Val
            100                 105                 110

Glu Phe Arg Arg Arg Tyr Tyr Lys Asn Trp Lys Gln Ser Ala Gln Leu
        115                 120                 125

Ala Phe Ser Arg Gln Lys Gln Phe Ala Asn Thr Lys Glu Gly Lys Val
    130                 135                 140

Ala Glu Ala Arg Thr Leu Asn Ala Phe Ala Lys Lys Ala Ser Val Ile
145                 150                 155                 160

Arg Val Ile Ala His Thr Gln Leu Arg Lys Leu Arg Asn His Arg Val
                165                 170                 175

Gly Val Lys Lys Ala His Val Gln Glu Ile Gln Val Asn Gly Gly Ser
            180                 185                 190

Val Ala Ala Lys Ile Ala Leu Ala Lys Ser Leu Leu Glu Lys Glu Val
        195                 200                 205

Arg Val Asp Ser Val Phe Gln Gln Ser Glu Ala Cys Asp Val Cys Ser
    210                 215                 220

Val Thr Lys Gly His Gly Thr Glu Gly Val Val Lys Arg Trp Gly Val
225                 230                 235                 240

Ala Cys Leu Pro Arg Lys Thr His Arg Gly Leu Arg Lys Val Ala Cys
                245                 250                 255

Ile Gly Ala Trp His Pro Ala Arg Val Met Tyr Thr Val Ala Arg Ala
            260                 265                 270

Gly Gln His Gly Tyr His His Arg Thr Gln Leu Asn Lys Lys Ile Tyr
        275                 280                 285

Gln Ile Gly Arg Ser Val Ala Val Glu Pro Asn Gln Ala Thr Thr Thr
    290                 295                 300
```

-continued

```
Tyr Asp Leu Thr Ala Lys Thr Ile Thr Pro Met Gly Gly Phe Val Gly
305                 310                 315                 320

Tyr Gly Thr Val Arg Asn Asp Tyr Val Met Leu Lys Gly Ser Val Ser
                325                 330                 335

Gly Pro Arg Arg Arg Val Met Thr Leu Arg Arg Pro Met Ala Pro Gln
            340                 345                 350

Thr Ser Arg Gln Leu Lys Glu Lys Ile Val Leu Lys Phe Ile Asp Thr
        355                 360                 365

Ser Ser Lys Ile Gly His Gly Arg Phe Gln Thr Lys Lys Glu Lys Asn
    370                 375                 380

Gln Trp Phe Gly Pro Leu Lys Lys Asp Arg Ile Arg Arg Glu Glu Arg
385                 390                 395                 400

Leu Arg Lys Glu Arg Ala Ala Arg Ala Val Glu Arg Lys Ala Lys Ala
                405                 410                 415

Ala Lys Lys


<210> SEQ ID NO 61
<211> LENGTH: 384
<212> TYPE: PRT
<213> ORGANISM: Leishmania major

<400> SEQUENCE: 61

Met Ala Gln Cys Val Arg Arg Leu Val Leu Gly Asp Ala Arg Arg Cys
1               5                   10                  15

Gly Gly Ala Ala Ala Val His Glu Gln Ala Arg Val Ala Arg Ala Ala
            20                  25                  30

Gly Thr Gly Asp Phe Thr Ala Ala Gln Arg Thr Asn Thr Leu Ala Val
        35                  40                  45

Leu Gln Ala Phe Gly Arg Ala Ile Pro Lys Leu Gly Glu Lys Trp Ala
    50                  55                  60

Gly Asn Asp Phe Cys Ser Trp Glu Ala Val Leu Cys Asn Ala Pro Asp
65                  70                  75                  80

Val Tyr Val Ser Gly Ile Ser Pro Thr Tyr Ala Gly Thr Leu Pro Glu
                85                  90                  95

Met Pro Glu Asn Val Asp Tyr Arg His Val Val Ile Arg Arg Leu Asp
            100                 105                 110

Phe Ser Glu Met Gly Pro Gly Leu Ser Gly Thr Val Pro Ala Ser Trp
        115                 120                 125

His Ser Met Thr Ser Leu Glu Ser Leu Ser Ile Glu Lys Cys Glu Ser
    130                 135                 140

Ile Ser Gly Ser Val Pro Pro Glu Trp Gly Ser Met Thr Ser Leu Ser
145                 150                 155                 160

Val Leu Asn Leu Arg Gly Thr Gly Ile Ser Gly Thr Leu Pro Pro Gln
                165                 170                 175

Trp Ser Gly Met Ser Lys Ala Arg Ser Leu Gln Leu Gln Asp Cys Asp
            180                 185                 190

Leu Ser Gly Ser Leu Pro Ser Ser Trp Ser Ala Ile Pro Met Leu Ala
        195                 200                 205

Ser Val Ser Leu Lys Gly Asn Lys Phe Cys Gly Cys Val Pro Asp Ser
    210                 215                 220

Trp Asp Gln Lys Ala Gly Leu Val Val Asp Ile Glu Asp Lys His Lys
225                 230                 235                 240

Gly Ser Asp Cys Leu Ala Ala Lys Asp Cys Ala Thr Thr Thr Thr Lys
                245                 250                 255
```

-continued

```
Pro Ser Ala Thr Thr Ala Thr Thr Pro Asn Leu Thr Asn Phe Pro Pro
            260                 265                 270

Thr Pro Arg Thr Thr Thr Glu Pro Leu Thr Thr Thr Ser Thr Glu Ala
        275                 280                 285

Pro Ala Glu Pro Thr Thr Thr Thr Glu Ala Pro Ala Glu Pro Thr Thr
    290                 295                 300

Thr Ala Thr Pro Thr Asn Thr Pro Thr Pro Ala Pro Glu Thr Glu Cys
305                 310                 315                 320

Glu Val Asp Gly Cys Glu Val Cys Glu Gly Asp Ser Ala Ala Arg Cys
                325                 330                 335

Ala Arg Cys Arg Glu Asp Tyr Phe Leu Thr Asp Glu Lys Thr Cys Leu
            340                 345                 350

Lys His Asn Asp Gly Gly Val Ala Ala Val Ser Ser Gly Val Ala Ala
        355                 360                 365

Ala Ala Val Val Cys Val Ala Val Leu Phe Ser Val Gly Leu Ala Ala
    370                 375                 380


<210> SEQ ID NO 62
<211> LENGTH: 635
<212> TYPE: PRT
<213> ORGANISM: Leishmania major

<400> SEQUENCE: 62

Met Phe Ala Arg Arg Val Cys Gly Ser Ala Ala Ala Ser Ala Ala Cys
1               5                   10                  15

Leu Ala Arg His Glu Ser Gln Lys Val Gln Gly Asp Val Ile Gly Val
            20                  25                  30

Asp Leu Gly Thr Thr Tyr Ser Cys Val Ala Thr Met Asp Gly Asp Lys
        35                  40                  45

Ala Arg Val Leu Glu Asn Ser Glu Gly Phe Arg Thr Thr Pro Ser Val
    50                  55                  60

Val Ala Phe Lys Gly Ser Glu Lys Leu Val Gly Leu Ala Ala Lys Arg
65                  70                  75                  80

Gln Ala Ile Thr Asn Pro Gln Ser Thr Phe Tyr Ala Val Lys Arg Leu
                85                  90                  95

Ile Gly Arg Arg Phe Glu Asp Glu His Ile Gln Lys Asp Ile Lys Asn
            100                 105                 110

Val Pro Tyr Lys Ile Val Arg Ala Gly Asn Gly Asp Ala Trp Val Gln
        115                 120                 125

Asp Gly Asn Gly Lys Gln Tyr Ser Pro Ser Gln Ile Gly Ala Phe Val
    130                 135                 140

Leu Glu Lys Met Lys Glu Thr Ala Glu Asn Phe Leu Gly His Lys Val
145                 150                 155                 160

Ser Asn Ala Val Val Thr Cys Pro Ala Tyr Phe Asn Asp Ala Gln Arg
                165                 170                 175

Gln Ala Thr Lys Asp Ala Gly Thr Ile Ala Gly Leu Asn Val Ile Arg
            180                 185                 190

Val Val Asn Glu Pro Thr Ala Ala Ala Leu Ala Tyr Gly Met Asp Lys
        195                 200                 205

Thr Lys Asp Ser Leu Ile Ala Val Tyr Asp Leu Gly Gly Gly Thr Phe
    210                 215                 220

Asp Ile Ser Val Leu Glu Ile Ala Gly Gly Val Phe Glu Val Lys Ala
225                 230                 235                 240

Thr Asn Gly Asp Thr His Leu Gly Gly Glu Asp Phe Asp Leu Ala Leu
```

-continued

```
                245                 250                 255

Ser Asp Tyr Ile Leu Glu Glu Phe Arg Lys Thr Ser Gly Ile Asp Leu
            260                 265                 270

Ser Lys Glu Arg Met Ala Leu Gln Arg Val Arg Glu Ala Ala Glu Lys
        275                 280                 285

Ala Lys Cys Glu Leu Ser Ser Ala Met Glu Thr Glu Val Asn Leu Pro
    290                 295                 300

Phe Ile Thr Ala Asn Ala Asp Gly Ala Gln His Ile Gln Met His Ile
305                 310                 315                 320

Ser Arg Ser Lys Phe Glu Gly Ile Thr Gln Arg Leu Ile Glu Arg Ser
                325                 330                 335

Ile Ala Pro Cys Lys Gln Cys Met Lys Asp Ala Gly Val Glu Leu Lys
            340                 345                 350

Glu Ile Asn Asp Val Val Leu Val Gly Gly Met Thr Arg Met Pro Lys
        355                 360                 365

Val Val Glu Glu Val Lys Lys Phe Phe Gln Lys Asp Pro Phe Arg Gly
    370                 375                 380

Val Asn Pro Asp Glu Ala Val Ala Leu Gly Ala Ala Thr Leu Gly Gly
385                 390                 395                 400

Val Leu Arg Gly Lys Ala Ser Asp Leu Ile Leu Val Asp Val Thr Pro
                405                 410                 415

Leu Ser Leu Gly Thr Ser Val Val Gly Asp Val Phe Thr Arg Met Ile
            420                 425                 430

Pro Lys Asn Thr Thr Ile Pro Cys Met Arg Ser His Ile Phe Thr Thr
        435                 440                 445

Val Asp Asp Gly Gln Thr Ala Ile Lys Phe Lys Val Phe Gln Gly Glu
    450                 455                 460

Arg Glu Ile Ala Ser Glu Asn Gln Ile Arg Gly Glu Phe Asp Leu Ser
465                 470                 475                 480

Gly Ile Pro Pro Ala Pro Arg Gly Val Pro Gln Ile Glu Val Thr Phe
                485                 490                 495

Asp Ile Asp Ala Asn Gly Ile Cys His Val Thr Ala Lys Asp Lys Ala
            500                 505                 510

Thr Gly Lys Thr Gln Asn Ile Thr Ile Thr Ala Asn Gly Gly Leu Ser
        515                 520                 525

Lys Glu Gln Ile Glu Gln Met Ile Arg Asp Ser Glu Gln His Ala Glu
    530                 535                 540

Ala Asp Arg Val Lys Arg Glu Leu Val Glu Val Arg Asn Asn Ala Glu
545                 550                 555                 560

Thr Gln Leu Thr Thr Ala Glu Arg Gln Leu Gly Glu Trp Lys Tyr Val
                565                 570                 575

Ser Asp Ala Glu Lys Glu Asn Val Lys Thr Leu Val Ala Glu Leu Arg
            580                 585                 590

Lys Ala Met Glu Asn Pro Asn Val Ala Lys Asp Asp Leu Ala Ala Ala
        595                 600                 605

Thr Asp Lys Leu Gln Lys Ala Val Met Glu Cys Gly Arg Thr Glu Tyr
    610                 615                 620

Gln Gln Ala Ala Ala Ala Asn Ser Gly Gln Cys
625                 630                 635
```

<210> SEQ ID NO 63
<211> LENGTH: 443
<212> TYPE: PRT
<213> ORGANISM: Leishmania major -continued

<400> SEQUENCE: 63

```
Met Ala Thr Ser Arg Ala Ala Leu Cys Ala Val Ala Val Val Cys Val
1               5                   10                  15

Val Leu Ala Val Ala Cys Ala Pro Ala Arg Ala Ile Tyr Val Gly Thr
            20                  25                  30

Pro Ala Ala Ala Leu Phe Glu Glu Phe Lys Arg Thr Tyr Gln Arg Ala
        35                  40                  45

Tyr Gly Thr Leu Thr Glu Glu Gln Gln Arg Leu Ala Asn Phe Glu Arg
    50                  55                  60

Asn Leu Glu Leu Met Arg Glu His Gln Ala Arg Asn Pro His Ala Arg
65                  70                  75                  80

Phe Gly Ile Thr Lys Phe Phe Asp Leu Ser Glu Ala Glu Phe Ala Ala
                85                  90                  95

Arg Tyr Leu Asn Gly Ala Ala Tyr Phe Ala Ala Ala Lys Gln His Ala
            100                 105                 110

Gly Gln His Tyr Arg Lys Ala Arg Ala Asp Leu Ser Ala Val Pro Asp
        115                 120                 125

Ala Val Asp Trp Arg Glu Lys Gly Ala Val Thr Pro Val Lys Asn Gln
    130                 135                 140

Gly Ala Cys Gly Ser Cys Trp Ala Phe Ser Ala Val Gly Asn Ile Glu
145                 150                 155                 160

Ser Gln Trp Ala Val Ala Gly His Lys Leu Val Arg Leu Ser Glu Gln
                165                 170                 175

Gln Leu Val Ser Cys Asp His Val Asp Asn Gly Cys Gly Gly Gly Leu
            180                 185                 190

Met Leu Gln Ala Phe Glu Trp Val Leu Arg Asn Met Asn Gly Thr Val
        195                 200                 205

Phe Thr Glu Lys Ser Tyr Pro Tyr Val Ser Gly Asn Gly Asp Val Pro
    210                 215                 220

Glu Cys Ser Asn Ser Ser Glu Leu Ala Pro Gly Ala Arg Ile Asp Gly
225                 230                 235                 240

Tyr Val Ser Met Glu Ser Ser Glu Arg Val Met Ala Ala Trp Leu Ala
                245                 250                 255

Lys Asn Gly Pro Ile Ser Ile Ala Val Asp Ala Ser Ser Phe Met Ser
            260                 265                 270

Tyr His Ser Gly Val Leu Thr Ser Cys Ile Gly Glu Gln Leu Asn His
        275                 280                 285

Gly Val Leu Leu Val Gly Tyr Asn Met Thr Gly Glu Val Pro Tyr Trp
    290                 295                 300

Val Ile Lys Asn Ser Trp Gly Glu Asp Trp Gly Glu Lys Gly Tyr Val
305                 310                 315                 320

Arg Val Thr Met Gly Val Asn Ala Cys Leu Leu Thr Gly Tyr Pro Val
                325                 330                 335

Ser Val His Val Ser Gln Ser Pro Thr Pro Gly Pro Asn Thr Thr Thr
            340                 345                 350

Thr Thr His Ala Pro Lys Arg Val Thr Val Lys Gln Ile Thr Cys Thr
        355                 360                 365

Asp Tyr Phe Cys Arg Lys Gly Cys Lys Thr Thr Val Ile Pro Thr Lys
    370                 375                 380

Glu Cys Leu Pro Asn Gly Ala Gly Gly Ser Phe Gln Met Glu Cys Gly
385                 390                 395                 400

Asp His Gln Val Leu Lys Leu Thr Tyr Thr Ser Met Asn Cys Thr Gly
```

-continued

```
                405                 410                 415

Glu Ala Lys Tyr Thr Val Thr Arg Glu Gly Lys Cys Gly Ile Ser Trp
            420                 425                 430

Ser Gly Ser Ser Lys Ser Ile Cys Gln Tyr Val
        435                 440


<210> SEQ ID NO 64
<211> LENGTH: 340
<212> TYPE: PRT
<213> ORGANISM: Leishmania major

<400> SEQUENCE: 64

Met Ser Ala Asn Cys Ala Gly Pro Ala Ser Thr Pro Asp Ala Lys Lys
1               5                   10                  15

Ala Arg Val Glu Ala Asp Val Ile Thr Glu Ala Asp Arg Val Pro Ala
            20                  25                  30

Phe Pro Leu Pro Pro Thr Asp Ala Ala Ala Tyr Glu Arg Glu His Val
        35                  40                  45

His Asn Val Tyr Ser Ala Ile Ala Asp His Phe Ser Ser Thr Arg Tyr
    50                  55                  60

Lys Ala Trp Pro Gln Val Gly Ala Phe Leu Glu Gly Leu Pro Pro Phe
65                  70                  75                  80

Ser Leu Val Ala Asp Val Gly Cys Gly Asn Gly Lys Tyr Phe Ser Ala
                85                  90                  95

Ala Gln Arg Leu Ala Leu Thr Ala Pro Ser His Pro Met Thr Thr Ser
            100                 105                 110

Gly Ala Ser Leu Glu Met Lys Ser Arg Gln Gln Ala Glu Ala Gln Pro
        115                 120                 125

Ser Pro Pro Leu Val Ser Phe Ala Pro Ala His Arg Tyr Val Leu Gly
    130                 135                 140

Leu Asp Tyr Ser Glu Glu Leu Leu Arg Ser Thr Gln Arg Gln Leu Val
145                 150                 155                 160

Asp Pro Asn Met His His Ala Gln Arg Arg Arg Arg Leu Ser Gly Lys
                165                 170                 175

Arg Ala Lys Asn Glu Ala Glu Ala Val Ala Thr Pro Val Ser Ala Glu
            180                 185                 190

Glu Leu Pro Arg Thr Asp Thr Val Arg Ser Asp Ala Leu Arg Cys Pro
        195                 200                 205

Leu Arg Ser Gly Val Phe Asp Ala Ala Ile Ser Ile Ala Val Ile His
    210                 215                 220

His Tyr Ala Ser Arg Glu Arg Arg Arg Leu Ala Val Arg Glu Leu Leu
225                 230                 235                 240

Arg Leu Ala Arg Pro His Gly Gly Arg Val Leu Ile Tyr Val Trp Ala
                245                 250                 255

Arg Glu Gln Arg Gly His Thr Lys Arg Leu Val Asp Pro Glu Thr Gly
            260                 265                 270

Asp Gly Leu Val Arg Trp Glu Arg Asn Gln Lys Tyr Asp Gly Ala Gln
        275                 280                 285

Gln Val Phe Arg Arg Tyr Tyr His Phe Phe Ala Glu Gly Glu Leu Glu
    290                 295                 300

Gln Leu Cys Lys Asp Ala Ala Ser Asp Asp Gly Thr Gly Ser Ile Pro
305                 310                 315                 320

Val Ala Ile Arg Lys Ser Tyr Tyr Asp Lys Glu Asn Trp Cys Val Met
                325                 330                 335
```

-continued

Leu Glu Arg Cys
340

<210> SEQ ID NO 65
<211> LENGTH: 92
<212> TYPE: PRT
<213> ORGANISM: Leishmania major

<400> SEQUENCE: 65

Met Ala Thr Thr Tyr Glu Glu Phe Ser Ala Lys Leu Asp Arg Leu Asp
1 5 10 15

Glu Glu Phe Asn Arg Lys Met Gln Glu Gln Asn Ala Lys Phe Phe Ala
20 25 30

Asp Lys Pro Asp Glu Ser Thr Leu Ser Pro Glu Met Lys Glu His Tyr
35 40 45

Glu Lys Phe Glu Arg Met Ile Lys Glu His Thr Glu Lys Phe Asn Lys
50 55 60

Lys Met His Glu His Ser Glu His Phe Lys Gln Lys Phe Ala Glu Leu
65 70 75 80

Leu Glu Gln Gln Lys Ala Ala Gln Tyr Pro Ser Lys
85 90

<210> SEQ ID NO 66
<211> LENGTH: 149
<212> TYPE: PRT
<213> ORGANISM: Leishmania major

<400> SEQUENCE: 66

Met Pro Ala Asp Lys Ser Tyr Ala Leu Lys Gln Val Gln Thr Phe Gly
1 5 10 15

Lys Lys Lys Thr Ala Ile Ala Val Ala Thr Val Thr Lys Ala Ala Gln
20 25 30

Cys Asn Ile Lys Val Asn Gly Val Pro Leu Gln Gln Ile Leu Pro Asp
35 40 45

Thr Leu Arg Ala Lys Ile Met Glu Ala Ile Thr Val Val Gly Ser Lys
50 55 60

Tyr Tyr Ser Arg Leu Arg Ile Asp Val Ala Val His Gly Gly Gly Gln
65 70 75 80

Val Ser Gln Ala Tyr Ala Ala Arg Gln Ala Ile Ala Lys Gly Leu Ile
85 90 95

Ala Phe Phe Gln Lys Tyr His Asn Glu Val Glu Lys Ala Ala Leu Lys
100 105 110

Asp Lys Phe Leu Ala Tyr Asp Lys Phe Leu Leu Ile Ala Asp Pro Arg
115 120 125

Arg Cys Glu Pro Lys Lys Trp Gly Arg His Ser Ala Arg Thr Arg Phe
130 135 140

Thr Lys Ser Tyr Arg
145

<210> SEQ ID NO 67
<211> LENGTH: 449
<212> TYPE: PRT
<213> ORGANISM: Leishmania major

<400> SEQUENCE: 67

Met Gly Lys Asp Lys Val His Met Asn Leu Val Val Val Gly His Val
1 5 10 15

Asp Ala Gly Lys Ser Thr Ala Thr Gly His Leu Ile Tyr Lys Cys Gly

-continued

```
            20                  25                  30

Gly Ile Asp Lys Arg Thr Ile Glu Lys Phe Glu Lys Glu Ala Ala Glu
        35                  40                  45

Ile Gly Lys Ala Ser Phe Lys Tyr Ala Trp Val Leu Asp Lys Leu Lys
    50                  55                  60

Ala Glu Arg Glu Arg Gly Ile Thr Ile Asp Ile Ala Leu Trp Lys Phe
65                  70                  75                  80

Glu Ser Pro Lys Ser Val Phe Thr Ile Ile Asp Ala Pro Gly His Arg
                85                  90                  95

Asp Phe Ile Lys Asn Met Ile Thr Gly Thr Ser Gln Ala Asp Ala Ala
            100                 105                 110

Ile Leu Met Ile Asp Ser Thr His Gly Gly Phe Glu Ala Gly Ile Ser
        115                 120                 125

Lys Asp Gly Gln Thr Arg Glu His Ala Leu Leu Ala Phe Thr Leu Gly
    130                 135                 140

Val Lys Gln Met Val Val Cys Cys Asn Lys Met Asp Asp Lys Thr Val
145                 150                 155                 160

Thr Tyr Ala Gln Ser Arg Tyr Asp Glu Ile Ser Lys Glu Val Gly Ala
                165                 170                 175

Tyr Leu Lys Arg Val Gly Tyr Asn Pro Glu Lys Val Arg Phe Ile Pro
            180                 185                 190

Ile Ser Gly Trp Gln Gly Asp Asn Met Ile Glu Lys Ser Asp Asn Met
        195                 200                 205

Pro Trp Tyr Lys Gly Pro Thr Leu Leu Asp Ala Leu Gly Met Leu Glu
    210                 215                 220

Pro Pro Val Arg Pro Val Asp Lys Pro Leu Arg Leu Pro Leu Gln Asp
225                 230                 235                 240

Val Tyr Lys Ile Gly Gly Ile Gly Thr Val Pro Val Gly Arg Val Glu
                245                 250                 255

Thr Gly Ile Met Lys Pro Gly Asp Val Val Thr Phe Ala Pro Ala Asn
            260                 265                 270

Val Thr Thr Glu Val Lys Ser Ile Glu Met His His Glu Gln Leu Ala
        275                 280                 285

Glu Ala Gln Pro Gly Asp Asn Val Gly Phe Asn Val Lys Asn Val Ser
    290                 295                 300

Val Lys Asp Ile Arg Arg Gly Asn Val Cys Gly Asn Ser Lys Asn Asp
305                 310                 315                 320

Pro Pro Lys Glu Ala Ala Asp Phe Thr Ala Gln Val Ile Val Leu Asn
                325                 330                 335

His Pro Gly Gln Ile Ser Asn Gly Tyr Ala Pro Val Leu Asp Cys His
            340                 345                 350

Thr Ser His Ile Ala Cys Arg Phe Ala Glu Ile Glu Ser Lys Ile Asp
        355                 360                 365

Arg Arg Ser Gly Lys Glu Leu Glu Lys Asn Pro Lys Ala Ile Lys Ser
    370                 375                 380

Gly Asp Ala Ala Ile Val Lys Met Val Pro Gln Lys Pro Met Cys Val
385                 390                 395                 400

Glu Val Phe Asn Asp Tyr Ala Pro Leu Gly Arg Phe Ala Val Arg Asp
                405                 410                 415

Met Arg Gln Thr Val Ala Val Gly Ile Ile Lys Gly Val Asn Lys Lys
            420                 425                 430

Glu Gly Ser Gly Gly Lys Val Thr Lys Ala Ala Ala Lys Ala Ser Lys
        435                 440                 445
```

Lys

<210> SEQ ID NO 68
<211> LENGTH: 477
<212> TYPE: PRT
<213> ORGANISM: Leishmania major

<400> SEQUENCE: 68

```
Met Gln Arg Ser Phe Leu Val Phe Val Leu Cys Ala Leu Leu Phe Cys
1               5                   10                  15

Val Ala Ser Ala Glu Val Gln Val Ala Thr Lys Asp Asn Phe Asp Lys
            20                  25                  30

Val Val Ile Gly Asp Leu Thr Leu Val Lys Phe Tyr Ala Pro Trp Cys
        35                  40                  45

Gly His Cys Lys Thr Leu Ala Pro Glu Phe Val Lys Ala Ala Asp Met
    50                  55                  60

Leu Ala Gly Ile Ala Thr Leu Ala Glu Val Asp Cys Thr Lys Glu Glu
65                  70                  75                  80

Ser Leu Ala Glu Lys Tyr Glu Ile Lys Gly Phe Pro Thr Leu Tyr Ile
                85                  90                  95

Phe Arg Asn Gly Glu Lys Val Lys Ile Tyr Asp Gly Pro Arg Thr Ala
            100                 105                 110

Ala Gly Ile Ala Ser Tyr Met Lys Ala His Val Gly Pro Ser Met Lys
        115                 120                 125

Ala Ile Ser Thr Ala Glu Glu Leu Glu Glu Leu Lys Lys Glu Thr Phe
    130                 135                 140

Pro Val Cys Val Val Lys Thr Ala Ser Thr Asp Ser Glu Met Ala Ser
145                 150                 155                 160

Met Ile Thr Lys Val Ala Asp Ser Leu Arg Ser Gln Met Asn Phe Val
                165                 170                 175

Leu Val Thr Asp Ala Ala Ile Ser Pro Asn Asp Ala Met Glu Ser Val
            180                 185                 190

Thr Val Tyr Arg Lys Asn Ala Glu Arg Glu Ala Tyr Thr Gly Ala Thr
        195                 200                 205

Pro Met Thr Ala Glu Ser Val Lys Ser Phe Leu Thr Ser Ala Val Leu
    210                 215                 220

Asp Tyr Phe Gly Glu Leu Gly Gln Glu Ser Phe Gln Lys Tyr Met Glu
225                 230                 235                 240

Ala Asn Lys Asp Lys Pro Leu Gly Trp Val Phe Ile Asp Lys Asn Thr
                245                 250                 255

Asp Ser Ala Leu Lys Gly Ser Leu Val Ala Val Ala Glu Lys Tyr Arg
            260                 265                 270

Ser Gln Val Leu Leu Thr Tyr Ile Asp Gly Asp Gln Tyr Arg Pro Val
        275                 280                 285

Ser Arg Gln Leu Gly Ile Pro Glu Asp Ala Lys Phe Pro Ala Phe Val
    290                 295                 300

Val Asp Phe Glu Arg Arg His His Val Met Gly Thr Asp Thr Pro Val
305                 310                 315                 320

Thr Ser Glu Ser Val Ala Ala Phe Val Glu Lys Tyr Val Lys Gly Glu
                325                 330                 335

Thr Lys Gln Thr Val Met Ser Asp Ala Ile Pro Ala Lys Glu Thr Val
            340                 345                 350

Asn Gly Leu Thr Thr Val Val Gly Gln Thr Phe Ala Lys Tyr Thr Asp
        355                 360                 365
```

-continued

```
Gly Thr Gln Asn Val Met Leu Leu Phe Tyr Ala Pro Trp Cys Gly His
    370                 375                 380

Cys Lys Lys Leu His Pro Val Tyr Asp Lys Val Ala Lys Ser Phe Glu
385                 390                 395                 400

Ser Glu Asn Val Ile Ile Ala Lys Met Asp Ala Thr Thr Asn Asp Phe
                405                 410                 415

Asp Arg Glu Lys Phe Glu Val Ser Gly Phe Pro Thr Ile Tyr Phe Ile
            420                 425                 430

Pro Ala Gly Lys Pro Pro Ile Val Tyr Glu Gly Gly Arg Thr Ala Asp
        435                 440                 445

Glu Ile Gln Val Phe Val Lys Ser His Leu Thr Ala Ser Ala Ala Pro
    450                 455                 460

Ser Gly Gly Pro Ser Gly Asn Ser Glu Glu Glu Asp Leu
465                 470                 475


<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69

aattaaccct cactaaaggg                                                20


<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70

gtaatacgac tcactatagg gc                                             22
```